(12) United States Patent
Bhattacharya et al.

(10) Patent No.: US 7,820,648 B2
(45) Date of Patent: Oct. 26, 2010

(54) PYRIMIDINE DERIVATIVES FOR THE TREATMENT OF ABNORMAL CELL GROWTH

(75) Inventors: Samit Kumar Bhattacharya, Groton, CT (US); Michael Joseph Luzzio, Noank, CT (US); Donn Gregory Wishka, Mystic, CT (US); Gonghua Pan, Old Lyme, CT (US); Arthur Douglas Brosius, Niantic, CT (US); Joel Thomas Arcari, Groton, CT (US); James Alfred Southers, Jr., Norwich, CT (US); Kendra Louise Nelson, New London, CT (US); Jun Xiao, Waterford, CT (US)

(73) Assignees: Pfizer Inc, New York, NY (US); Pfizer Products Inc, New York, NY (US)

( * ) Notice: Subject to any disclaimer, the term of this patent is extended or adjusted under 35 U.S.C. 154(b) by 979 days.

(21) Appl. No.: 11/613,390

(22) Filed: Dec. 20, 2006

(65) Prior Publication Data
US 2008/0234303 A1 Sep. 25, 2008

Related U.S. Application Data

(60) Provisional application No. 60/752,708, filed on Dec. 21, 2005.

(51) Int. Cl.
*C07D 471/08* (2006.01)
*C07D 487/08* (2006.01)
*C07D 495/08* (2006.01)
*A61K 31/506* (2006.01)

(52) U.S. Cl. ............... 514/216; 514/235.8; 514/252.14; 514/252.19; 514/275; 540/581; 544/122; 544/295; 544/323; 544/324

(58) Field of Classification Search ............ 544/122, 544/295, 323, 324; 540/581; 514/216, 235.8, 514/252.14, 252.19, 275
See application file for complete search history.

(56) References Cited

U.S. PATENT DOCUMENTS

| | | |
|---|---|---|
| 6,593,326 B1 | 7/2003 | Bradbury et al. |
| 2003/0149266 A1 | 8/2003 | Pease et al. |
| 2003/0181474 A1 | 9/2003 | Pease et al. |
| 2004/0029902 A1 | 2/2004 | Singh et al. |
| 2004/0186118 A1 | 9/2004 | Bryant et al. |
| 2004/0220177 A1 | 11/2004 | Kath et al. |
| 2005/0124640 A1 | 6/2005 | Cardozo et al. |

FOREIGN PATENT DOCUMENTS

| | | |
|---|---|---|
| WO | 03030909 | 4/2003 |
| WO | 03078404 | 9/2003 |
| WO | 03095448 | 11/2003 |
| WO | 2004046118 | 6/2004 |

OTHER PUBLICATIONS

Simone, Oncology: Introduction, Cecil Textbook of Medicine, 20th Edition, pp. 1004-1010, 1996.*
Traxler, Protein Tyrosine Kinase Inhibitors in Cancer Treatment, Expert Opinion on Therapeutic Patents, 7(6):571-588, 1997.*

* cited by examiner

*Primary Examiner*—Deepak Rao
(74) *Attorney, Agent, or Firm*—Fariba Shoarinejad; Jeffrey H. Tidwell

(57) ABSTRACT

The present invention relates to a compound of the formula 1

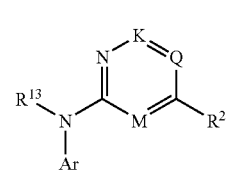

or a pharmaceutically acceptable salt thereof, wherein Ar is a group of formula

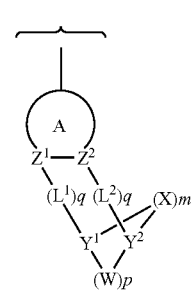

and $R^1$, $R^2$, $R^{13}$, A, K, M, $L^1$, $L^2$, X, $Y^1$, $Y^2$, Q, salt thereof, wherein $R^1$, $R^2$, $R^{13}$, A, K, $L^1$, $L^2$, W, X, $Z^1$, $Z^2$, $Y^1$, $Y^2$, $Z^1$, $Z^2$, M, Q, W, X, m, p and q are as defined herein. Such novel pyrimidine derivatives are useful in the treatment of abnormal cell growth, such as cancer, in mammals. The invention also relates to a method of using such compounds in the treatment of abnormal cell growth in mammals, especially humans, and to pharmaceutical compositions containing such compounds.

3 Claims, No Drawings

PYRIMIDINE DERIVATIVES FOR THE TREATMENT OF ABNORMAL CELL GROWTH

This application claims the benefit of U.S. Provisional Application No. 60/752,708, filed Dec. 21, 2005, the entire content of which is incorporated herein by reference.

BACKGROUND OF THE INVENTION

This invention relates to novel pyrimidine derivatives that are useful in the treatment of abnormal cell growth, such as cancer, in mammals. This invention also relates to a method of using such compounds in the treatment of abnormal cell growth in mammals, especially humans, and to pharmaceutical compositions containing such compounds.

It is known that a cell may become cancerous by virtue of the transformation of a portion of its DNA into an oncogene (i.e., a gene which, on activation, leads to the formation of malignant tumor cells). Many oncogenes encode proteins that are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are enzymes which span the cell membrane and possess an extracellular binding domain for growth factors such as epidermal growth factor, a transmembrane domain, and an intracellular portion which functions as a kinase to phosphorylate specific tyrosine residues in proteins and hence to influence cell proliferation. Other receptor tyrosine kinases include c-erbB-2, c-met, tie-2, PDGFr, FGFr, and VEGFR. It is known that such kinases are frequently aberrantly expressed in common human cancers such as breast cancer, gastrointestinal cancer such as colon, rectal or stomach cancer, leukemia, and ovarian, bronchial or pancreatic cancer. It has also been shown that epidermal growth factor receptor (EGFR), which possesses tyrosine kinase activity, is mutated and/or overexpressed in many human cancers such as brain, lung, squamous cell, bladder, gastric, breast, head and neck, oesophageal, gynecological and thyroid tumors.

Accordingly, it has been recognized that inhibitors of receptor tyrosine kinases are useful as selective inhibitors of the growth of mammalian cancer cells. For example, erbstatin, a tyrosine kinase inhibitor, selectively attenuates the growth in athymic nude mice of a transplanted human mammary carcinoma that expresses epidermal growth factor receptor tyrosine kinase (EGFR) but is without effect on the growth of another carcinoma that does not express the EGF receptor. Thus, selective inhibitors of certain receptor tyrosine kinases, are useful in the treatment of abnormal cell growth, in particular cancer, in mammals. In addition to receptor tyrosine kinases, selective inhibitors of certain non-receptor tyrosine kinases, such as FAK (focal adhesion kinase), lck, src, abl or serine/threonine kinases (e.g., cyclin dependent kinases), are useful in the treatment of abnormal cell growth, in particular cancer, in mammals. FAK is also known as Protein-Tyrosine Kinase 2, PTK2.

The below relates to FAK inhibitors:

Convincing evidence suggests that FAK, a cytoplasmic, non-receptor tyrosine kinase, plays an essential role in cell-matrix signal transduction pathways (Clark and Brugge 1995, *Science* 268: 233-239) and its aberrant activation is associated with an increase in the metastatic potential of tumors (Owens et al. 1995, *Cancer Research* 55: 2752-2755). FAK was originally identified as a 125 kDa protein highly tyrosine-phosphorylated in cells transformed by v-Src. FAK was subsequently found to be a tyrosine kinase that localizes to focal adhesions, which are contact points between cultured cells and their underlying substratum and sites of intense tyrosine phosphorylation. FAK is phosphorylated and, thus, activated in response to extracellular matrix (ECM)-binding to integrins. Recently, studies have demonstrated that an increase in FAK mRNA levels accompanied invasive transformation of tumors and attenuation of the expression of FAK (through the use of antisense oligonucleotides) include apoptosis in tumor cells (Xu et al. 1996, *Cell Growth and Diff.* 7: 413-418). In addition to being expressed in most tissue types, FAK is found at elevated levels in most human cancers, particularly in highly invasive metastases.

Various compounds, such as styrene derivatives, have also been shown to possess tyrosine kinase inhibitory properties. Five European patent publications, namely EP 0 566 226 A1 (published Oct. 20, 1993), EP 0 602 851 A1 (published Jun. 22, 1994), EP 0 635 507 A1 (published Jan. 25, 1995), EP 0 635 498 A1 (published Jan. 25, 1995), and EP 0 520 722 A1 (published Dec. 30, 1992), refer to certain bicyclic derivatives, in particular quinazoline derivatives, as possessing anti-cancer properties that result from their tyrosine kinase inhibitory properties.

Also, World Patent Application WO 92/20642 (published Nov. 26, 1992), refers to certain bis-mono and bicyclic aryl and heteroaryl compounds as tyrosine kinase inhibitors that are useful in inhibiting abnormal cell proliferation. World Patent Applications WO96/16960 (published Jun. 6, 1996), WO 96/09294 (published Mar. 6, 1996), WO 97/30034 (published Aug. 21, 1997), WO 98/02434 (published Jan. 22, 1998), WO 98/02437 (published Jan. 22, 1998), and WO 98/02438 (published Jan. 22, 1998), also refer to substituted bicyclic heteroaromatic derivatives as tyrosine kinase inhibitors that are useful for the same purpose. In addition, the following list of publications relate to bis-mono and bicyclic aryl and heteroaryl compounds that may optionally be used as tyrosine kinase inhibitors: WO 03/030909, WO 03/032997, US Patent Application NO. 2003/0181474, US Patent Application No. 2003/0162802, U.S. Pat. No. 5,863,924, WO 03/078404, U.S. Pat. No. 4,507,146, WO 99/41253, WO 01/72744, WO 02/48133, US Patent Application No. 2002/156087, WO 02/102783, and WO 03/063794.

U.S. patent application Ser. No. 10/734,039, filed Dec. 11, 2003 relates to a broad class of novel pyrimidine derivatives that are kinase inhibitors, and more specifically, inhibitors of FAK. Moreover, U.S. patent application Ser. No. 10/733,215, filed Dec. 11, 2003 relate more specifically to a subset of pyrimidine derivatives, i.e., those bearing a 5-aminooxindole, which are tyrosine kinase inhibitors, and more particularly, FAK inhibitors. Compounds such as these are useful in the treatment of abnormal cell growth.

The below relates to Aurora-2 inhibitors:

many kinases are involved in regulatory cascades for cells wherein their substrates may include other kinases whose activities are regulated by their phosphorylation state. Ultimately the activity of same downstream effector is modulated by phosphorylation resulting from activation of such a pathway.

The serine/threonine (S/T) kinase family includes members found at all steps of various signaling cascades, including those involved in controlling cell growth, migration, differentiation and secretion of hormones, phosphorylation of transcription factors resulting in altered gene expression, muscle contraction, glucose metabolism, control of cellular protein synthesis, and regulation of the cell cycle.

One family of mitotic serine/threonine kinases is the Aurora (AUR) kinase family. The AUR kinase family has been found to be essential for providing signals that initiate and advance mitosis. It has been found that the Aurora kinases are overexpressed in tumor types, including colon cancer, breast cancer, and leukemia. Two primary isoforms of Aurora kinases have been identified and designated as form A and B. Aurora A is also known as Aurora-2 (AUR2), STK6, ARK1, Aurora/IPL1-related kinase, while Aurora is also known as Aurora 1 or AUR1. The Aurora kinases have been characterized and identified in U.S. Pat. Nos. 5,962,312 and 5,972,676 (a divisional from the '312 patent) which relate to Aurora 1 (AUR-1) and Aurora-2 (AUR2) polypeptides, nucleic acids encoding such polypeptides, cells, tissues and animals containing such nucleic acids, antibodies to such polypeptides, assays utilizing such polypeptides, and methods relating to all of the foregoing The overexpression of Aurora kinases, especially Aurora-2, in tumor cells provides an attractive target for drug intervention and the potential for a significant opportunity for controlling cell division in many types of cancer, and in particular for colon cancer and breast cancer. Applicants have now identified novel heteroaromatic Aurora kinase inhibitors which are able to modulate (reduce) that activity of the Aurora kinases in cancer cells.

Accordingly, a need exists for additional selective inhibitors of certain receptor and non-receptor tyrosine kinases, useful in the treatment of abnormal cell growth, such as cancer, in mammals. The present invention provides novel pyrimidine derivatives that are kinase inhibitors and inhibitors of the non-receptor tyrosine kinases, e.g., FAK, Pyk, HgK, Aurora-1 and Aurora-2, and are useful in the treatment of abnormal cell growth.

SUMMARY OF THE INVENTION

The present invention relates to a compound of formula I:

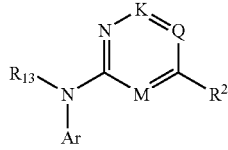

I wherein Ar is

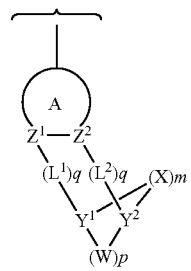

III or a pharmaceutically acceptable salt thereof, wherein
K is $C(R^1)$ or N
M is $C(H)$ or N;
Q is $C(D)$ or N;
D is a substituent selected from the group consisting of hydrogen, halogen, $-CF_3$, $-NO_2$, $-CN$, $-(C_1-C_6)$alkyl, $-(C_2-C_6)$alkenyl, $-(C_2-C_6)$alkynyl, $-(C_2-C_6)$perfluorinated alkyl, $-(C_2-C_6)$perfluorinated alkenyl, $-(C_3-C_6)$perfluorinated alkynyl, $-(C_3-C_7)$cycloalkyl, $-(C_5-C_{10})$cycloalkenyl, $-(C_6-C_{10})$bicycloalkyl, $-(C_6-C_{10})$bicycloalkenyl, $-(C_1-C_9)$heterocyclyl, $-(C_1-C_{10})$heterocycloalkenyl, $-(C_6-C_9)$heterocycloalkyl, $-(C_6-C_9)$heterobicycloalkenyl, $-(C_6-C_{10})$aryl, $-(C_1-C_9)$heteroaryl, $-(C_6-C_{10})$perfluorinated aryl, $-(C_1-C_9)$perfluorinated heteroaryl, $-NR^3R^4$, $-OR^5$, $-C(O)R^5$, $-CO_2R^5$, $-CONR^3R^4$, $-SR^6$, $-SOR^6$, $-SO_2R^6$, $-SO_2NR^3R^4$, $-NHCOR^5$, $-NR^3CONR^3R^4$, and $-NR^3SO_2R^6$, wherein said $-(C_1-C_6)$alkyl, $-(C_2-C_6)$alkenyl, $-(C_2-C_6)$alkynyl, $-(C_3-C_7)$cycloalkyl, $-(C_5-C_{10})$cycloalkenyl, $-(C_6-C_{10})$bicycloalkyl, $-(C_6-C_{10})$bicycloalkenyl, $-(C_1-C_9)$heterocyclyl, $-(C_1-C_{10})$heterocycloalkenyl, $-(C_6-C_9)$heterocycloalkyl, $-(C_6-C_9)$heterobicycloalkenyl, $-(C_6-C_{10})$aryl, $-(C_1-C_9)$heteroaryl, $-NR^3R^4$, $-OR^5$, $-C(O)R^5$, $-CO_2R^5$, $-CONR^3R^4$, $-SR^6$, $-SOR^6$, $-SO_2R^6$, $-SO_2NR^3R^4$, $-NHCOR^5$, $-NR^3CONR^3R^4$, and $-NR^3SO_2R^6$ D substituents are optionally substituted by one or three substituents independently selected from the group consisting of hydrogen, halogen, $-CF_3$, $-NO_2$, $-CN$, $-(C_1-C_6)$alkyl, $-(C_2-C_6)$alkenyl, $-(C_2-C_6)$alkynyl, $-CR^3=N-NR^3R^4$, $-CR^3=N-OR^5$, $-CR^3=N-NR^3C(O)R^3$, $-CR^3=N-NR^3C(O)OR^5$, $-NR^3R^4$, $-OR^5$, $-(C_3-C_7)$cycloalkyl, $-(C_2-C_9)$heterocyclyl, $-CO_2R^5$, $-CONR^3R^4$, $-SR^6$, $-SOR^6$, $-SO_2R^6$, $-SO_2NR^3R^4$, $-NHCOR^5$, $-NR^3CONR^3R^4$, and $-NR^3SO_2R^6$, and wherein each of said $-(C_1-C_6)$alkyl, $-(C_2-C_6)$alkenyl, $-(C_2-C_6)$alkynyl, $-(C_3-C_7)$cycloalkyl, $-(C_5-C_{10})$cycloalkenyl, $-(C_6-C_{10})$bicycloalkyl, $-(C_6-C_{10})$bicycloalkenyl, $-(C_1-C_9)$heterocyclyl, $-(C_1-C_{10})$heterocycloalkenyl, $-(C_6-C_9)$heterobicycloalkenyl, $-(C_6-C_9)$heterobicycloalkyl, $-(C_6-C_{10})$aryl, and $-(C_1-C_9)$heteroaryl substituents is optionally interrupted by one to three elements independently selected from the group consisting of $-C(R^3)=C(R^3)-$, $-C(O)-$, $-(C=N-R^3)-$, $-(C=N-NR^3R^4)-$, $-C=N-N-C(O)-R^5$, $-C=N-N-C(O)OR^3$, $-(C=CR^3R^4)-$, $-(C=C(R^3)C(O)-NR^3R^4))-$, $-(C=C(R^3)C(O)OR^6)-$, $-SO_2-$, $-S-$, $-O-$ and $-NR^3-$;

$R^1$ and $R^2$ are the same or different and are independently selected from the group consisting of hydrogen, halogen, $-CF_3$, $-NO_2$, $-CN$, $-(C_1-C_6)$alkyl, $-(C_2-C_6)$alkenyl, $-(C_2-C_6)$alkynyl, $-(C_2-C_6)$perfluorinated alkyl, $-(C_2-C_6)$perfluorinated alkenyl, $-(C_3-C_6)$perfluorinated alkynyl, $-(C_3-C_7)$cycloalkyl, $-(C_5-C_{10})$cycloalkenyl, $-(C_6-C_{10})$bicycloalkyl, $-(C_6-C_{10})$bicycloalkenyl, $-(C_2-C_9)$heterocyclyl, $-(C_2-C_{10})$heterocycloalkenyl, $-(C_6-C_9)$heterocycloalkyl, $-(C_6-C_9)$heterobicycloalkenyl, $-(C_6-C_{10})$aryl, $-(C_1-C_9)$heteroaryl, $-(C_6-C_{10})$perfluorinated aryl, $-(C_1-C_9)$perfluorinated heteroaryl, $-OR^5$, $-C(O)R^5$, $-CO_2R^5$, $-CONR^3R^4$, $-SR^6$, $-SOR^6$, $-SO_2R^6$, $-SO_2NR^3R^4$, $-NHCOR^5$, $-NR^3CONR^3R^4$, wherein said $-(C_1-C_6)$alkyl, $-(C_2-C_6)$alkenyl, $-(C_2-C_6)$alkynyl-, $-(C_3-C_7)$cycloalkyl, $-(C_5-C_{10})$cycloalkenyl, $-(C_6-C_{10})$bicycloalkyl, $-(C_6-C_{10})$bicycloalkenyl, $-(C_2-C_9)$heterocyclyl, $-(C_2-C_{10})$heterocycloalkenyl, $-(C_6-C_9)$heterocycloalkyl, $-(C_6-C_9)$heterobicycloalkenyl, $-(C_6-C_{10})$aryl, and $-(C_1-C_9)$heteroaryl may optionally be substituted with one to three moieties independently selected from $R^5$ and $R^6$, and

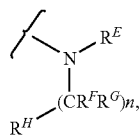

wherein n is an integer from 0 to 4;

$R^E$ is a substituent selected from the group consisting of hydrogen, —$(C_2-C_6)$perfluorinated alkyl, —$(C_2-C_6)$perfluorinated alkenyl, —$(C_3-C_6)$perfluorinated alkynyl, —$NR^3R^4$, —$OR^5$, —$C(O)R^5$, —$CO_2R^5$, —$CONR^3R^4$, —$SR^6$, —$SOR^6$, —$SO_2R^6$, —$SO_2NR^3R^4$, —$NHCOR^5$, —$NR^3CONR^3R^4$, —$NR^3SO_2R^6$, —$(C_3-C_7)$cycloalkyl, —$(C_5-C_{10})$cycloalkenyl, —$(C_6-C_{10})$bicycloalkyl, —$(C_6-C_{10})$bicycloalkenyl, —$(C_1-C_9)$heterocyclyl, —$(C_1-C_{10})$heterocycloalkenyl, —$(C_6-C_9)$heterobicycloalkyl, —$(C_6-C_9)$heterobicycloalkenyl, —$(C_6-C_{10})$aryl, —$(C_1-C_9)$heteroaryl, —$(C_6-C_{10})$perfluorinated aryl, —$(C_1-C_9)$perfluorinated heteroaryl; wherein said —$(C_1-C_6)$alkyl —$(C_3-C_7)$cycloalkyl, —$(C_5-C_{10})$cycloalkenyl, —$(C_6-C_{10})$bicycloalkyl, —$(C_6-C_{10})$bicycloalkenyl, —$(C_1-C_9)$heterocyclyl, —$(C_1-C_{10})$heterocycloalkenyl, —$(C_6-C_9)$heterobicycloalkyl, —$(C_6-C_9)$heterobicycloalkenyl, —$(C_6-C_{10})$aryl and —$(C_1-C_9)$heteroaryl $R^E$ substituents are optionally substituted by one to three moieties independently selected from the group consisting of hydrogen, halogen, —$(C_1-C_6)$alkyl, —CN, —$NR^3R^4$, —$OR^5$, —$(C_3-C_7)$cycloalkyl, —$(C_2-C_9)$heterocyclyl, —$CO_2R^5$, —$SO_2NR^3R^4$, —$NR^3SO_2R^6$, —$SO_2R^6$ and —$CONR^3R^4$;

each $R^F$ is a substituent independently selected from the group consisting of hydrogen, —$(C_1-C_6)$alkyl, —$(C_2-C_6)$perfluorinated alkyl, —$(C_2-C_6)$perfluorinated alkenyl, —$(C_3-C_6)$perfluorinated alkynyl, —$(C_3-C_7)$cycloalkyl, —$(C_5-C_{10})$cycloalkenyl, —$(C_6-C_{10})$bicycloalkyl, —$(C_6-C_{10})$bicycloalkenyl, —$(C_2-C_9)$heterocyclyl, —$(C_2-C_{10})$heterocycloalkenyl, —$(C_6-C_9)$heterobicycloalkyl, —$(C_6-C_9)$heterobicycloalkenyl, —$O(C_1-C_6)$alkyl, —$O(C_3-C_7)$cycloalkyl, —$O(C_1-C_9)$heterocyclyl, —$NR^3R^4$, —$SR^6$, —$SOR^6$, —$SO_2R^6$, —$CO_2R^5$, —$CONR^3R^4$, —$SO_2NR^3R^4$, —$NHCOR^5$, —$NR^3CONR^5R^4$, and —$NR^3SO_2R^6$; wherein said —$(C_1-C_6)$alkyl, —$(C_3-C_7)$cycloalkyl, —$(C_5-C_{10})$cycloalkenyl, —$(C_6-C_{10})$bicycloalkyl, —$(C_6-C_{10})$bicycloalkenyl, —$(C_2-C_9)$heterocyclyl, —$(C_2-C_{10})$heterocycloalkenyl, —$(C_6-C_9)$heterobicycloalkyl, —$(C_6-C_9)$heterobicycloalkenyl, —$O(C_1-C_6)$alkyl, —$O(C_3-C_7)$cycloalkyl, —$O(C_2-C_9)$heterocyclyl, —$NR^3R^4$, —$SR^6$, —$SOR^6$, —$SO_2R^6$, —$CO_2R^5$, —$CONR^3R^4$, —$SO_2NR^3R^4$, —$NHCOR^5$, —$NR^3CONR^3R^4$, and —$NR^5SO_2R^6$ $R^F$ substituents are optionally substituted by one to three moieties independently selected from the group consisting of hydrogen, halogen, —$CF_3$, —CN, —$(C_1-C_6)$alkyl, —$NR^3R^4$, —$OR^5$, —$(C_3-C_7)$cycloalkyl, —$(C_2-C_9)$heterocyclyl, —$CO_2R^5$, and —$CONR^3R^4$;

each $R^G$ is a substituent independently selected from the group consisting of hydrogen, —$(C_1-C_6)$alkyl, —$(C_2-C_6)$alkenyl, —$(C_2-C_6)$alkynyl, —$(C_2-C_6)$perfluorinated alkyl, —$(C_2-C_6)$perfluorinated alkenyl, —$(C_3-C_6)$perfluorinated alkynyl, —$(C_3-C_7)$cycloalkyl, —$(C_5-C_{10})$cycloalkenyl, —$(C_6-C_{10})$bicycloalkyl, —$(C_6-C_{10})$bicycloalkenyl, —$(C_2-C_9)$heterocyclyl, —$(C_2-C_{10})$heterocycloalkenyl, —$(C_6-C_9)$heterobicycloalkyl, —$(C_6-C_9)$, —$(C_6-C_9)$heterobicycloalkenyl, —$CO_2R^5$, and —$CONR^3R^4$, wherein said —$(C_1-C_6)$ alkyl, —$(C_2-C_6)$alkenyl, —$(C_2-C_6)$alkynyl, —$(C_3-C_7)$cycloalkyl, —$(C_5-C_{10})$cycloalkenyl, —$(C_6-C_{10})$bicycloalkyl, —$(C_6-C_{10})$bicycloalkenyl, —$(C_2-C_9)$heterocyclyl, —$(C_2-C_{10})$heterocycloalkenyl, —$(C_6-C_9)$heterobicycloalkyl, and —$(C_6-C_9)$heterobicycloalkenyl $R^G$ substituents, are optionally substituted by one to three moieties independently selected from the group consisting of hydrogen, halogen, —$CF_3$, —$NO_2$, —CN, —$(C_1-C_6)$alkyl, —$(C_2-C_6)$alkenyl, —$(C_2-C_6)$alkynyl, —$CR^3$=N—$NR^3R^4$, —$CR^3$=N—$OR^5$, —$CR^3$=N—$NR^3C(O)R^3$, —$CR^3$=N—$NR^3C(O)OR^5$, —$NR^3R^4$, —$OR^5$, —$(C_3-C_7)$cycloalkyl, —$(C_2-C_9)$heterocyclyl, —$CO_2R^5$, —$CONR^3R^4$, —$SR^6$, —$SOR^6$, —$SO_2R^6$, —$SO_2NR^3R^4$, —$NHCOR^5$, —$NR^3CONR^3R^4$, and —$NR^3SO_2R^6$, wherein said —$(C_1-C_6)$alkyl, —$(C_2-C_6)$alkenyl and —$(C_2-C_6)$alkynyl $R^G$ moieties may be optionally substituted by one to three $R^{10}$ groups;

$R^E$ and $R^H$ may be taken together with the atom(s) to which they are attached to form a —$(C_2-C_9)$heterocyclyl, —$(C_2-C_{10})$heterocycloalkenyl, —$(C_6-C_9)$heterobicycloalkyl, —$(C_6-C_9)$heterobicycloalkenyl, wherein said —$(C_2-C_9)$heterocyclyl, —$(C_{23}-C_{10})$heterocycloalkenyl, —$(C_5-C_{10})$heterobicycloalkyl and —$(C_6-C_{10})$heterobicycloalkenyl are optionally interrupted by one to three elements independently selected from the group consisting of —$C(R^3)$=$C(R^3)$—, —$C(O)$—, —$(C$=N—$R^3)$—, —$(C$=N—$NR^3R^4)$—, —$C$=N—N—$C(O)$—$R^5$, —$C$=N—N—$C(O)OR^5$, —$(C$=$CR^3R^4)$—, —$(C$=$C(R^3)C(O)$—$NR^3R^4)$)—, —$(C$=$C(R^3)C(O)OR^6)$—, —$SO_2$—, —S—, —O— and —$NR^3$—, and wherein said —$(C_2-C_9)$heterocyclyl, —$(C_2-C_{10})$heterocycloalkenyl, —$(C_5-C_{10})$heterobicycloalkyl and —$(C_6-C_{10})$heterobicycloalkenyl is optionally substituted by one to three moieties independently selected from the group consisting of hydrogen, halogen, —$CF_3$, —$NO_2$, —CN, —$(C_1-C_6)$alkyl, —$(C_2-C_6)$alkenyl, —$(C_2-C_6)$alkynyl, —$CR^3$=N—$NR^3R^4$, —$CR^3$=N—$OR^5$, —$CR^3$=N—$NR^3C(O)R^5$, —$CR^3$=N—$NR^3C(O)OR^5$, —$NR^3R^4$, —$OR^5$, —$(C_3-C_7)$cycloalkyl, —$(C_2-C_9)$heterocyclyl, —$CO_2R^5$, —$CONR^3R^4$, —$SR^6$, —$SOR^6$, —$SO_2R^6$, —$SO_2NR^3R^4$, —$NHCOR^5$, —$NR^3CONR^3R^4$, and —$NR^3SO_2R^6$;

$R^H$ is a substituent selected from the group consisting of:

(a) hydrogen;

(b) —$(C_6-C_{10})$aryl or —$(C_1-C_9)$heteroaryl, optionally substituted by one to three moieties independently selected from the group consisting of halogen, hydroxy, —$(C_1-C_6)$alkyl, —$(C_1-C_6)$alkyl-P(O)(O$(C_1-C_6)$alkyl)$_2$, —$(C_3-C_{10})$cycloalkyl, —$(C_6-C_{10})$aryl, —$(C_2-C_9)$heterocyclyl, —$(C_1-C_9)$heteroaryl, —$NR^3R^4$, —$NHSO_2(C_1-C_6)$alkyl, —$NHSO_2(C_3-C_6)$cycloalkyl, —$N((C_1-C_6)$alkyl)($SO_2$—$(C_1-C_6)$alkyl), —$N((C_1-C_6)$alkyl)($SO_2(C_3-C_6)$cycloalkyl), —$N((C_3-C_6)$($SO_2$—$(C_1-C_6)$alkyl), —$N((C_3-C_6)$cycloalkyl)($SO_2(C_3-C_6)$cycloalkyl), —$O(C_1-C_6)$alkyl, —O—$SO_2(C_1-C_6)$alkyl, —O—$SO_2(C_3-C_6)$cycloalkyl, —$C(O)(C_1-C_6)$alkyl, —$C(O)CF_3$, —$C(O)(C_3-C_{10})$cycloalkyl, —$C(O)(C_6-C_{10})$aryl, —$C(O)(C_2-C_9)$heterocyclyl, —$C(O)(C_1-C_9)$heteroaryl, —$C(O)O(C_1-C_6)$alkyl, —$C(O)O(C_3-C_{10})$cycloalkyl, —$C(O)O(C_6-C_{10})$aryl, —$C(O)O(C_2-C_9)$heterocyclyl, —$C(O)O(C_1-C_9)$heteroaryl, —$C(O)(C_1-C_6)$alkyl-O$(C_1-C_6)$alkyl, —$SO_2(C_1-C_6)$alkyl, —$SO_2(C_3-C_6)$cycloalkyl, —$SO_2CF_3$, —$SO_2NH_2$, —$SO_2NH(C_1-C_6)$alkyl, —$SO_2NH(C_3-C_6)$alkyl, —$SO_2N((C_1-C_6)$alkyl)$_2$, —$SO_2N((C_1-C_6)$alkyl)($(C_3-C_6)$cycloalkyl), —$SO_2N((C_3-C_6)$cycloalkyl)$_2$, and —$SO_2NR^3R^4$, wherein said —$(C_6-C_{10})$ aryl or —$(C_1-C_9)$ heteroaryl are optionally interrupted by one to three elements selected from the group consisting of —S—, —O—, —N—, —NH— and —$NR^{11}$, and wherein said —$(C_6-C_{10})$ aryl or —$C_1-C_9)$ heteroaryl are optionally fused to a —$(C_3-C_{10})$cycloalkyl or —$(C_2-C_9)$heterocyclyl moiety, and wherein said —($C_3$-$C_{10}$)cycloalkyl or —($C_2$-$C_9$)heterocyclyl moieties are optionally substituted by one to three elements selected from the group consisting of halogen, hydroxy, —($C_1$-$C_6$)alkyl, —($C_1$-$C_6$)alkyl-P(O)(O($C_1$-$C_6$)alkyl)$_2$, —($C_3$-$C_{10}$)cycloalkyl, —($C_6$-$C_{10}$)aryl, —($C_2$-$C_9$)heterocyclyl, —($C_1$-$C_9$)heteroaryl, —NR$^3$R$^4$, —NHSO$_2$($C_1$-$C_6$)alkyl, —NHSO$_2$($C_3$-$C_6$)cycloalkyl, —N(($C_1$-$C_6$)alkyl)(SO$_2$—($C_1$-$C_6$)alkyl), —N(($C_1$-$C_6$)alkyl)(SO$_2$($C_3$-$C_6$)cycloalkyl), —N(($C_3$-$C_6$)cycloalkyl)(SO$_2$-($C_1$-$C_6$)alkyl), —(($C_3$-$C_6$)cycloalkyl)(SO$_2$($C_3$-$C_6$)cycloalkyl), —O($C_1$-$C_6$)alkyl, —O—SO$_2$($C_3$-$C_6$)cycloalkyl, —C(O)($C_1$-$C_6$)alkyl, —C(O)CF$_3$, —C(O)($C_3$-$C_{10}$)cycloalkyl, —C(O)($C_6$-$C_{10}$)aryl, —C(O)($C_2$-$C_9$)heterocyclyl, —C(O)($C_1$-$C_9$)heteroaryl, —C(O)O($C_1$-$C_6$)alkyl, —C(O)O($C_3$-$C_{10}$)cycloalkyl, —C(O)O($C_6$-$C_{10}$)aryl, —C(O)O($C_2$-$C_9$)heterocyclyl, —C(O)O($C_1$-$C_9$)heteroaryl, —C(O)($C_1$-$C_6$)alkyl-O($C_1$-$C_6$)alkyl, —SO$_2$($C_1$-$C_6$)alkyl, —SO$_2$($C_3$-$C_6$)cycloalkyl, —SO$_2$CF$_3$, —SO$_2$NH$_2$, —SO$_2$NH($C_1$-$C_6$)alkyl, —SO$_2$NH($C_3$-$C_6$)cycloalkyl, —SO$_2$N(($C_1$-$C_6$)alkyl)$_2$, —SO$_2$N(($C_1$-$C_6$)alkyl(($C_3$-$C_6$)cycloalkyl), —SO$_2$N(($C_3$-$C_6$)cycloalkyl)$_2$ and —SO$_2$NR$^3$R$^4$;

(c) —($C_3$-$C_7$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocyclyl, —($C_2$-$C_{10}$)heterocycloalkenyl, —($C_6$-$C_9$)heterobicycloalkyl, —($C_6$-$C_9$)heterobicycloalkenyl and —($C_2$-$C_9$)heterocyclyl, optionally substituted by one to three moieties independently selected from the group consisting of halogen, hydroxy, —($C_1$-$C_6$)alkyl, —($C_1$-$C_6$)alkyl-P(O)(O($C_1$-$C_6$)alkyl)$_2$, —($C_3$-$C_{10}$)cycloalkyl, —($C_6$-$C_{10}$)aryl, —($C_2$-$C_9$)heterocyclyl, —($C_1$-$C_9$)heteroaryl, —NR$^3$R$^4$, —NSO$_2$($C_1$-$C_6$)alkyl, —NHSO$_2$($C_3$-$C_6$)cycloalkyl, —N(($C_1$-$C_6$)alkyl)(SO$_2$—($C_1$-$C_6$)alkyl), —N(($C_1$-$C_6$)alkyl)(SO$_2$($C_3$-$C_6$)cycloalkyl), —N(($C_3$-$C_6$)cycloalkyl)(SO$_2$—($C_1$-$C_6$)alkyl), —N(($C_3$-$C_6$)cycloalkyl)(SO$_2$($C_3$-$C_6$)cycloalkyl), —O($C_1$-$C_6$)alkyl, —O—SO$_2$($C_1$-$C_6$)alkyl, —O—SO$_2$($C_1$-$C_6$)alkyl, —O—SO$_2$($C_3$-$C_6$)cycloalkyl, —C(O)($C_1$-$C_6$)alkyl, —C(O)CF$_3$, —C(O)($C_3$-$C_{10}$)cycloalkyl, —C(O)($C_6$-$C_{10}$)aryl, —C(O)($C_2$-$C_9$)heterocyclyl, —C(O)($C_1$-$C_9$)heteroaryl, —C(O)O($C_1$-$C_6$)alkyl, —C(O)O($C_3$-$C_{10}$)cycloalkyl, —C(O)O($C_6$-$C_{10}$)aryl, —C(O)O($C_2$-$C_9$)heterocyclyl, —C(O)O($C_1$-$C_9$)heteroaryl, —C(O)($C_1$-$C_6$)alkyl-O($C_1$-$C_6$)alkyl, —SO$_2$($C_1$-$C_6$)cycloalkyl, —SO$_2$($C_3$-$C_6$)cycloalkyl, —SO$_2$CF$_3$, —SO$_2$NH$_2$, —SO$_2$NH($C_1$-$C_6$)alkyl, —SO$_2$NH($C_3$-$C_6$)cycloalkyl, —SO$_2$N(($C_1$-$C_6$)alkyl)$_2$, —SO$_2$N(($C_1$-$C_6$)alkyl)(($C_3$-$C_6$)cycloalkyl), —SO$_2$N(($C_3$-$C_6$)cycloalkyl)$_2$ and —SO$_2$NR$^3$R$^4$, wherein said —($C_3$-$C_7$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocyclyl, —($C_2$-$C_{10}$)heterocycloalkenyl, —($C_6$-$C_9$)heterobicycloalkyl, —($C_6$-$C_9$)heterobicycloalkenyl and —($C_2$-$C_9$)heterocyclyl are optionally interrupted by one to three elements selected from the group consisting of —C(R$^3$)═C(R$^3$)—, —C(O)—, —(C═N—R$^3$)—, —(C═N—NR$^3$R$^4$)—, —C═N—N—C(O)—R$^5$, —C═N—N—C(O)OR$^3$, —(C═CR$^3$R$^4$)—, —(C═C(R$^3$)C(O)—NR$^3$R$^4$))—, —(C═C(R$^3$)C(O)OR$^6$)—, —SO$_2$—, —S—, —O— and —NR$^3$—, and wherein said —($C_3$-$C_7$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocyclyl, —($C_2$-$C_{10}$)heterocycloalkenyl, —($C_6$-$C_9$)heterobicycloalkyl, —($C_6$-$C_9$)heterobicycloalkenyl substituents are optionally fused to a —($C_6$-$C_{10}$)aryl or —($C_1$-$C_9$)heteroaryl, optionally substituted by one to three moieties independently selected from the group consisting of halogen, hydroxy, —($C_1$-$C_6$)alkyl, —($C_1$-$C_6$)alkyl-P(O)(O($C_1$-$C_6$)alkyl)$_2$, —($C_3$-$C_{10}$)cycloalkyl, —($C_6$-$C_{10}$)aryl, —($C_2$-$C_9$)heterocyclyl, —($C_1$-$C_9$)heteroaryl, —NR$^3$R$^4$, —NHSO$_2$($C_1$-$C_6$)alkyl, —NHSO$_2$($C_3$-$C_6$)cycloalkyl, —N(($C_1$-$C_6$)alkyl)(SO$_2$—($C_1$-$C_6$)alkyl), —N(($C_1$-$C_6$)alkyl)(SO$_2$($C_3$-$C_6$)cycloalkyl), —N(($C_1$-$C_6$)alkyl)(SO$_2$—($C_1$-$C_6$)alkyl), —N(($C_3$-$C_6$)cycloalkyl)(SO$_2$—($C_1$-$C_6$)alkyl), —N(($C_3$-$C_6$)cycloalkyl)(SO$_2$($C_3$-$C_6$)cycloalkyl), —O($C_1$-$C_6$)alkyl, —O—SO$_2$($C_1$-$C_6$)alkyl, —O—SO$_2$($C_3$-$C_6$)cycloalkyl, —O($C_1$-$C_6$)alkyl, —C(O)CF$_3$, —C(O)($C_3$-$C_{10}$)cycloalkyl, —C(O)($C_6$-$C_{10}$)aryl, —C(O)($C_2$-$C_9$)heterocyclyl, —C(O)($C_1$-$C_9$)heteroaryl, —C(O)O($C_1$-$C_6$)alkyl, —C(O)O($C_3$-$C_{10}$)cycloalkyl, —C(O)O($C_6$-$C_{10}$)aryl, —C(O)O($C_2$-$C_9$)heterocyclyl, —C(O)O($C_1$-$C_9$)heteroaryl, —C(O)($C_1$-$C_6$)alkyl-O($C_1$-$C_6$)alkyl, —SO$_2$($C_1$-$C_6$)alkyl, —SO$_2$($C_3$-$C_6$)cycloalkyl, —SO$_2$CF$_3$, —SO$_2$NH$_2$, —SO$_2$NH($C_1$-$C_6$)alkyl, —SO$_2$NH($C_3$-$C_6$)cycloalkyl, —SO$_2$N(($C_1$-$C_6$)alkyl)$_2$, —SO$_2$N(($C_1$-$C_6$)alkyl)(($C_3$-$C_6$)cycloalkyl), —SO$_2$N(($C_3$-$C_6$)cycloalkyl)$_2$ and —SO$_2$NR$^3$R$^4$;

(d) —($C_1$-$C_6$)alkyl, —($C_2$-$C_6$)perfluorinated alkyl, —($C_2$-$C_6$)perfluorinated alkenyl, and —($C_3$-$C_6$)perfluorinated alkynyl, wherein said —($C_1$-$C_6$)alkyl is optionally substituted by one to three moieties selected from the group consisting of halogen, hydroxy, —($C_1$-$C_6$)alkyl, —($C_2$-$C_6$)alkenyl, —($C_2$-$C_6$)alkynyl, —($C_1$-$C_6$)alkyl-P(O)(O($C_1$-$C_6$)alkyl)$_2$, —NR$^3$R$^4$, —NHSO$_2$($C_1$-$C_6$)alkyl, —NHSO$_2$($C_3$-$C_6$)alkynyl, —N(($C_1$-$C_6$)alkyl)(SO$_2$—($C_1$-$C_6$)alkyl), —N(($C_1$-$C_6$)alkyl)(SO$_2$($C_3$-$C_6$)cycloalkyl), —N(($C_3$-$C_6$)cycloalkyl)(SO$_2$—($C_1$-$C_6$)alkyl), —N(($C_3$-$C_6$)cycloalkyl)(SO$_2$($C_3$-$C_6$)cycloalkyl), —NHC(O)($C_1$-$C_6$)alkyl, —NHC(O)($C_3$-$C_6$)cycloalkyl, —NHC(O)($C_2$-$C_9$)heterocyclyl, —NHC(O)($C_6$-$C_{10}$)aryl, —NHC(O)($C_1$-$C_9$)heteroaryl, —N(($C_1$-$C_6$)alkyl)C(O)($C_1$-$C_6$)alkyl, —N(($C_1$-$C_6$)alkyl)C(O)($C_3$-$C_6$)cycloalkyl, —N(($C_1$-$C_6$)alkyl)C(O)($C_2$-$C_9$)heterocyclyl, —N(($C_1$-$C_6$)alkyl)C(O)($C_6$-$C_{10}$)aryl, —N(($C_1$-$C_6$)alkyl)C(O)($C_1$-$C_9$)heteroaryl, —O($C_1$-$C_6$)alkyl, —O—SO$_2$($C_1$-$C_6$)alkyl, —O—SO$_2$($C_2$-$C_6$)cycloalkyl, —C(O)($C_1$-$C_6$)alkyl, —C(O)CF$_3$, —C(O)($C_3$-$C_{10}$)cycloalkyl, —C(O)($C_6$-$C_{10}$)aryl, —C(O)($C_2$-$C_9$)heterocyclyl, —C(O)($C_1$-$C_9$)heteroaryl, —C(O)O($C_1$-$C_6$)alkyl, —C(O)O($C_3$-$C_{10}$)cycloalkyl, —C(O)O($C_6$-$C_{10}$)aryl, —C(O)O($C_2$-$C_9$)heterocyclyl, —C(O)O($C_1$-$C_9$)heteroaryl, —C(O)($C_1$-$C_6$)alkyl-O($C_1$-$C_6$)alkyl, —SO$_2$($C_1$-$C_6$)alkyl, —SO$_2$($C_3$-$C_6$)cycloalkyl, —SO$_2$CF$_3$, —SO$_2$NH$_2$, —SO$_2$NH($C_1$-$C_6$)alkyl, —SO$_2$NH($C_3$-$C_6$)cycloalkyl, —SO$_2$N(($C_1$-$C_6$)alkyl)$_2$, —SO$_2$N(($C_1$-$C_6$)alkyl)(($C_3$-$C_6$)cycloalkyl), —SO$_2$N(($C_3$-$C_6$)cycloalkyl)$_2$ and —SO$_2$NR$^3$R$^4$, wherein said —($C_1$-$C_6$)alkyl is optionally interrupted by one to three elements independently selected from the group consisting of —C(O), —SO$_2$, —S—, —O—, and —NR$^{11}$;

and wherein each R$^H$ (b)-(d) substituent, moiety, or element is optionally substituted by one to three radicals independently selected from the group consisting of hydrogen, halogen, hydroxy, —CF$_3$, —NO$_2$, —CN, —($C_1$-$C_6$)alkyl, —($C_2$-$C_6$)alkenyl, —($C_2$-$C_6$)alkynyl, —($C_3$-$C_7$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterobicycloalkenyl, —($C_6$-$C_{10}$)aryl, —($C_1$-$C_9$)heteroaryl, —O($C_1$-$C_6$)alkyl, —O($C_3$-$C_7$)cycloalkyl, —O($C_2$-$C_9$)heterocyclyl, —CR$^3$═N—NR$^3$R$^4$, —CR$^3$═N—OR$^5$, —CR$^3$═N—NR$^3$C(O)R$^3$, —CR$^3$═N—NR$^3$C(O)OR$^5$, —NR$^3$R$^4$, —SR$^6$, —SOR$^6$, —SO$_2$R$^6$, —CO$_2$R$^5$, —CONR$^3$R$^4$, —SO$_2$NR$^3$R$^4$, —NHCOR$^5$, —NR$^3$CONR$^3$R$^4$, and —NR$^3$SO$_2$R$^6$;

A is a ring system selected from the group consisting of —($C_3$-$C_{10}$)cycloalkyl, —($C_5$-$C_{10}$)cycloalkenyl, —($C_2$-$C_{10}$)heterocyclyl, —($C_2$-$C_{10}$)heterocycloalkenyl, —($C_6$-$C_{10}$)aryl and —($C_2$-$C_9$)heteroaryl, wherein said —($C_3$-$C_{10}$)cycloalkyl, —($C_5$-$C_{10}$)cycloalkenyl, —($C_2$-$C_{10}$)heterocyclyl, —($C_2$-$C_{10}$)heterocycloalkenyl, —($C_6$-$C_{10}$)aryl and —($C_2$-$C_9$)heteroaryl of said A ring are optionally interrupted by one to three elements selected from the group consisting of —C($R^3$)=C($R^3$)—, —C(O)—, —(C=N—$R^3$)—, —(C=N—$NR^3R^4$)—, —C=N—N—C(O)—$R^5$, —C=N—N—C(O)O$R^3$, —(C=C$R^3R^4$)—, —C(=C($R^3$)C(O)—N$R^3R^4$))—, —(C=C($R^3$)C(O)O$R^6$)—, —SO$_2$—, —S—, —O— and —N$R^3$—, and wherein said A ring system is optionally substituted by one to three substituents independently selected from the group consisting of hydrogen, halogen, —CF$_3$, —NO$_2$, —CN, —($C_1$-$C_6$)alkyl, —($C_2$-$C_6$)alkenyl, —($C_2$-$C_6$)alkynyl, —C$R^3$=N—N$R^3R^4$, —C$R^3$=N—O$R^5$, —C$R^3$N—N$R^3$C(O)$R^3$, —C$R^3$=N—N$R^3$C(O)O$R^5$, —N$R^3R^4$, —O$R^5$, —($C_3$-$C_7$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocyclyl, —($C_2$-$C_{10}$)heterocycloalkenyl, —($C_6$-$C_9$)heterobicycloalkyl, —($C_6$-$C_9$)heterobicycloalkenyl, —($C_6$-$C_{10}$)aryl, —($C_1$-$C_9$)heteroaryl, —C(O)$R^5$, —CO$_2R^5$, —CON$R^3R^4$, —S$R^6$, —SO$R^6$, —SO$_2R^6$, —SO$_2$N$R^3R^4$, —NHCO$R^5$, —N$R^3$CON$R^3R^4$, and —N$R^3$SO$_2R^6$;

$Z^1$ and $Z^2$ are the same or different and are independently selected from the group consisting of —C—, —C$R^7$— and —N—, wherein each $R^7$ is the same or different;

$Y^1$ and $Y^2$ are the same or different and are independently selected from the group consisting of —C$R^7$— and —N—, wherein each $R^7$ is the same or different;

$L^1$ and $L^2$ are each independently a linker group selected from the group consisting of —C$R^8R^9$—, —C($R^3$)=C($R^3$)—, —C(O)—, —(C=N—$R^3$)—, —(C=N—N$R^3R^4$)—, —(C=N—NO$R^5$)—, —C=C$R^3R^4$—, —(C=C($R^3$)C(O)—N$R^3R^4$))—, —(C=C($R^3$)C(O)O$R^6$)—, —N—C(O)$R^6$—, —SO$_2$—, —S—, —O— and —N$R^3$, wherein $L^1$ is not —C($R^8$)=C($R^8$)— or —C≡C— when $Z^1$ or $Y^1$ is N, and $L^2$ is not —C($R^3$)=C($R^3$)— or —C≡C— when $Z^2$ or $Y^2$ is N;

q is an integer from 0 to 3;

$L^1$ and a substituent of A, or $L^2$ and a substituent of A can be taken together to form a —($C_5$-$C_7$)cycloalkyl, —($C_5$-$C_{10}$)cycloalkenyl, —($C_2$-$C_9$)heterocyclyl, —($C_2$-$C_{10}$)heterocycloalkenyl, —($C_6$-$C_{10}$)aryl and —($C_1$-$C_9$)heteroaryl, wherein each of said —($C_5$-$C_7$)cycloalkyl, —($C_5$-$C_{10}$)cycloalkenyl, —($C_2$-$C_9$)heterocyclyl, —($C_2$-$C_{10}$)heterocycloalkenyl, —($C_6$-$C_{10}$)aryl and —($C_1$-$C_9$)heteroaryl is optionally interrupted by one to three elements independently selected from the group consisting of —C($R^3$)=C($R^3$)—, —C(O)—, —(C=N—$R^3$)—, —(C=N—N$R^3R^4$)—, —(C=N—NO$R^5$)—, —(C=C$R^3$)—, —(C=C($R^3$)C(O)—N$R^3R^4$))—, —(C=C($R^3$)C(O)O$R^6$)—, —SO$_2$—, —S—, —O— and —N$R^3$—, and wherein each of said —($C_3$-$C_7$)cycloalkyl, —($C_3$-$C_{10}$)cycloalkenyl, —($C_2$-$C_9$)heterocyclyl and —($C_2$-$C_{10}$)heterocycloalkenyl is optionally substituted with one to three substituents independently selected from the group consisting of halogen, —CF$_3$, —CN, —NO$_2$, —($C_1$-$C_6$)alkyl, —O$R^{16}$, —C(O)O$R^{16}$, —OC(O)$R^{16}$, —OC(O)O$R^{16}$, —N($R^{16}$)$_2$, —N$R^{16}$C(O)$R^{16}$, —SO$_2R^{16}$, —SO$_2$N($R^{16}$)$_2$ and —N$R^{16}$SO$_2R^{16}$;

X and W are the same or different and are each independently selected from the group consisting of —C$R^8R^9$—, —N$R^{12}$—, —C(O)—, —(C=N$R^3$)—, —(C=N—N$R^3R^4$)—, —(C=N—N—O$R^5$)—, —(C=C$R^3R^4$)—, —(C=C($R^3$)C(O)—N$R^3R^4$))—, —(C=C($R^3$)C(O)O$R^6$)—, —S—, —S(O)—, —S(O)$_2$—, —S(O)(N$R^3R^4$)—, and —O—, wherein one or more adjacent carbon or heteroatoms selected from X, $Y^1$, $Y^2$, or W are optionally fused to a ring system selected from the group consisting of —($C_3$-$C_7$)cycloalkyl, —($C_2$-$C_9$)heterocyclyl, —($C_6$-$C_{10}$)aryl, and —($C_1$-$C_9$)heteroaryl, wherein each of said —($C_3$-$C_7$)cycloalkyl, —($C_2$-$C_9$)heterocyclyl, —($C_6$-$C_{10}$)aryl is optionally interrupted by one to three elements independently selected from the group consisting of —C($R^3$)=C($R^3$)—, —C(O)—, —(C=N—$R^3$)—, —(C=N—N$R^3R^4$)—, —(C=N—NO$R^5$)—, —(C=C$R^3$)—, —(C=C($R^3$)C(O)—N$R^3R^4$))—, —(C=C($R^3$)C(O)O$R^6$)—, —SO$_2$—, —S—, —O— and —N$R^3$, and wherein each of said —($C_3$-$C_7$)cycloalkyl, —($C_2$-$C_9$)heterocyclyl, —($C_6$-$C_{10}$)aryl, and —($C_1$-$C_9$)heteroaryl ring systems are optionally substituted by one to three substituents selected from the group consisting of hydrogen, hydroxyl, halogen, —CF$_3$, —CN, —NO$_2$, —($C_1$-$C_6$)alkyl, —NH($C_1$-$C_6$)alkyl, —NH($C_3$-$C_7$)cycloalkyl, —NH($C_2$-$C_9$)heterocyclyl, —NH($C_6$-$C_{10}$)aryl, —NH($C_1$-$C_9$)heteroaryl, —N(($C_1$-$C_6$)alkyl)$_2$, —N(($C_3$-$C_7$)cycloalkyl)$_2$, —N(($C_2$-$C_9$)heterocyclyl)$_2$, —N(($C_6$-$C_{10}$)aryl)$_2$, —N(($C_1$-$C_9$)heteroaryl)$_2$, —O($C_1$-$C_6$)alkyl, —O($C_3$-$C_7$)cycloalkyl, —O($C_2$-$C_9$)heterocyclyl, —O($C_6$-$C_{10}$)aryl, —O($C_1$-$C_9$)heteroaryl, —($C_3$-$C_7$)cycloalkyl, —($C_2$-$C_9$)heterocyclyl, —CO$_2$H, —C(O)(($C_1$-$C_6$)alkyl), —SO$_2$H, —SO$_2$(($C_1$-$C_6$)alkyl), —SO$_2$NH$_2$, —SO$_2$NH(($C_1$-$C_6$)alkyl), —SO$_2$N(($C_1$-$C_6$)alkyl)$_2$, —NHSO$_2$(($C_1$-$C_6$)alkyl, and —N(($C_1$-$C_6$)alkyl)SO$_2$(($C_1$-$C_6$)alkyl);

$Y^1$ together with W, $Y^2$ together with W, $Y^1$ together with X, $Y^2$ together with X, X together with W, or L together with Y can form a —($C_5$-$C_7$)cycloalkyl, —($C_5$-$C_{10}$)cycloalkenyl, —($C_2$-$C_9$)heterocyclyl and —($C_2$-$C_{10}$)heterocycloalkenyl, wherein each of said —($C_5$-$C_7$)cycloalkyl, —($C_5$-$C_{10}$)cycloalkenyl, —($C_2$-$C_9$)heterocyclyl and —($C_2$-$C_{10}$)heterocycloalkenyl is optionally interrupted by one to three elements independently selected from the group consisting of —C($R^3$)=C($R^3$)—, —C(O)—, —(C=N—$R^3$)—, —(C=N—N$R^3R^4$)—, —C=N—N—C(O)—$R^5$, —C=N—N—C(O)O$R^3$, —(C=C$R^3R^4$)—, —(C=C($R^3$)C(O)—N$R^3R^4$))—, —(C=C($R^3$)C(O)O$R^6$)—, —SO$_2$—, —S—, —O— and —N$R^3$—, and wherein each of said —($C_3$-$C_7$)cycloalkyl, —($C_3$-$C_{10}$)cycloalkenyl, —($C_2$-$C_9$)heterocyclyl and —($C_2$-$C_{10}$)heterocycloalkenyl is optionally substituted with one to three substituents independently selected from the group consisting of halogen, —CF$_3$, —CN, —NO$_2$, —($C_1$-$C_6$)alkyl, —O$R^{16}$, —C(O)O$R^{16}$, —OC(O)$R^{16}$, —OC(O)O$R^{16}$, —N($R^{16}$)$_2$, —N$R^{16}$C(O)$R^{16}$, —SO$_2R^{16}$, —SO$_2$N($R^{16}$)$_2$ and —N$R^{16}$SO$_2R^{16}$;

W together with another W, X together with another X, $L^1$ together with another $L^1$, or $L^2$ together with another $L^2$ can form a —($C_3$-$C_7$)cycloalkyl, —($C_5$-$C_{10}$)cycloalkenyl, —($C_2$-$C_9$)heterocyclyl, —($C_2$-$C_{10}$)heterocycloalkenyl, —($C_6$-$C_{10}$)aryl or —($C_1$-$C_9$)heteroaryl, wherein each of said —($C_3$-$C_7$)cycloalkyl, —($C_5$-$C_{10}$)cycloalkenyl, —($C_2$-$C_9$)heterocyclyl and —($C_2$-$C_{10}$)heterocycloalkenyl is optionally interrupted by one to three elements independently selected from the group consisting of —C($R^3$)=C($R^3$)—, —C(O)—, —(C=N—$R^3$)—, —(C=N—N$R^3R^4$)—, —C=N—N—C(O)—$R^5$, —C=N—N—C(O)O$R^3$, —(C=C$R^3R^4$)—, —(C=C($R^3$)C(O)—N$R^3R^4$))—, —(C=C($R^3$)C(O)O$R^6$)—, —SO$_2$—, —S—, —O— and —N$R^3$—, and wherein each of said —($C_3$-$C_7$)cycloalkyl, —($C_3$-$C_{10}$)cycloalkenyl, —($C_6$-$C_{10}$)bicycloalkyl, —($C_6$-$C_{10}$)bicycloalkenyl, —($C_2$-$C_9$)heterocyclyl —($C_2$-$C_{10}$)heterocycloalkenyl, —($C_5$-$C_{10}$)heterobicycloalkyl, —($C_6$-$C_{10}$)heterobicycloalkenyl, —($C_6$-$C_{10}$)aryl and —($C_1$-$C_9$)heteroaryl is optionally substituted with one to three substituents independently selected from the group consisting of halogen, —CF$_3$, —CN, —NO$_2$, —($C_1$-$C_6$)alkyl, —O$R^{16}$, —C(O)O$R^{16}$, —OC(O)$R^{16}$, —OC(O)O$R^{16}$, —N($R^{16}$)$_2$, —N$R^{16}$C(O)$R^{16}$, —SO$_2R^{16}$, —SO$_2$N($R^{16}$)$_2$ and —N$R^{16}$SO$_2R^{16}$;

$R^3$ and $R^4$ are each independently a substituent selected from the group consisting of hydrogen, —($C_1$-$C_6$)alkyl, —($C_3$-$C_7$)cycloalkyl, —($C_5$-$C_{11}$)bicycloalkyl, —($C_2$-$C_9$)heterocyclyl, —($C_6$-$C_{10}$)aryl, —($C_1$-$C_9$)heteroaryl, —CO$_2$H, —C(O)((C$_1$-C$_6$)alkyl), —C(O)((C$_2$-C$_9$)heterocycloalkyl), —C(O)OR$^8$, —C(O)NR$^8$R$^9$, and —SO$_2$((C$_1$-C$_6$)alkyl); wherein said —(C$_1$-C$_6$)alkyl, —(C$_3$-C$_7$)cycloalkyl, —(C$_5$-C$_{11}$)bicycloalkyl, —(C$_2$-C$_9$)heterocyclyl, —(C$_6$-C$_{10}$)aryl, —(C$_1$-C$_9$)heteroaryl, —C(O)((C$_1$-C$_6$)alkyl), —C(O)((C$_2$-C$_9$ heterocycloalkyl) and —SO$_2$((C$_1$-C$_6$)alkyl) substituents are optionally substituted by one to three moieties independently selected from the group consisting of amino, hydrogen, hydroxyl, halogen, —CF$_3$, —CN, —NO$_2$, =O, =S, =NR$^8$, —C(O)NR$^5$R$^6$, —(C$_1$-C$_6$)alkyl, —NH(C$_1$-C$_6$)alkyl, NR$^8$C(O)R$^9$, —NR$^8$CONR$^8$R$^9$ —NH(C$_3$-C$_7$)cycloalkyl, —NH(C$_2$-C$_9$)heterocyclyl, —NH(C$_6$-C$_{10}$)aryl, —NH(C$_1$-C$_9$)heteroaryl, —N((C$_1$-C$_6$)alkyl)$_2$, —N((C$_3$-C$_7$)cycloalkyl)$_2$, —N((C$_2$-C$_9$)heterocyclyl)$_2$, —N((C$_6$-C$_{10}$)aryl)$_2$, —N((C$_1$-C$_9$)heteroaryl)$_2$, —O(C$_1$-C$_6$)alkyl, —O(C$_3$-C$_7$)cycloalkyl, —O(C$_2$-C$_9$)heterocyclyl, —O(C$_6$-C$_{10}$)aryl, —O(C$_1$-C$_9$)heteroaryl, —(C$_3$-C$_7$)cycloalkyl, —(C$_2$-C$_9$)heterocyclyl, —CO$_2$H, —C(O)((C$_1$-C$_6$)alkyl), —SO$_2$H, —SO$_2$(C$_1$-C$_6$)alkyl, —SO$_2$NH$_2$, —SO$_2$NH((C$_1$-C$_6$)alkyl), —SO$_2$N((C$_1$-C$_6$)alkyl)$_2$, —NHSO$_2$((C$_1$-C$_6$)alkyl), —N((C$_1$-C$_6$)alkyl)SO$_2$((C$_1$-C$_6$)alkyl), —NHSO$_2$NR$^8$R$^9$, wherein R$^3$ and R$^4$ when attached to the same nitrogen atom may form a —(C$_2$-C$_9$)heterocyclyl optionally substituted by one to three substituents independently selected from the group consisting of hydrogen, halogen, —CF$_3$, —NO$_2$, —CN, —(C$_1$-C$_6$)alkyl, —(C$_2$-C$_6$)alkenyl, —(C$_2$-C$_6$)alkynyl, —CR$^5$=N—NR$^5$R$^6$, —CR$^5$=N—OR$^{10}$, —CR$^5$=N—NR$^5$C(O)R$^{10}$, —CR$^5$=N—NR$^5$C(O)OR$^{10}$, —NR$^5$R$^6$, —OR$^5$, —(C$_3$-C$_7$)cycloalkyl, —(C$_2$-C$_9$)heterocyclyl, —CO$_2$R$^5$, —CONR$^5$R$^6$, —SR$^6$, —SOR$^6$, —SO$_2$R$^6$, —SO$_2$NR$^5$R$^6$, —NHCOR$^5$, —NR$^5$CONR$^5$R$^6$ and —NR$^5$SO$_2$R$^6$;

R$^5$ is a substituent selected from the group consisting of hydrogen, —(C$_1$-C$_6$)alkyl, —(C$_2$-C$_6$)alkenyl, —(C$_3$-C$_7$)cycloalkyl, —(C$_5$-C$_7$)cycloalkenyl, —(C$_2$-C$_9$)heterocyclyl, —(C$_6$-C$_{10}$)aryl, —(C$_1$-C$_9$)heteroaryl, —CO$_2$H, —C((O)((C$_1$-C$_6$)alkyl), and —P(O)(OR$^{16}$)$_2$, wherein said —(C$_1$-C$_6$)alkyl, —(C$_3$-C$_7$)cycloalkyl, —(C$_2$-C$_9$)heterocyclyl, —(C$_6$-C$_{10}$)aryl, —(C$_1$-C$_9$)heteroaryl, —C(O)((C$_1$-C$_6$)alkyl), and substituents are optionally substituted by one to three moieties independently selected from the group consisting of hydrogen, hydroxyl, halogen, —CF$_3$, —CN, —NO$_2$, —(C$_1$-C$_6$)alkyl, —NH(C$_1$-C$_6$)alkyl, —NH(C$_3$-C$_7$)cycloalkyl, —NH(C$_2$-C$_9$)heterocyclyl, —NH(C$_6$-C$_{10}$)aryl, —NH(C$_1$-C$_9$)heteroaryl, —N((C$_1$-C$_6$)alkyl)$_2$, —N((C$_3$-C$_7$)cycloalkyl)$_2$, —N((C$_2$-C$_9$)heterocyclyl)$_2$, —N((C$_6$-C$_{10}$)aryl)$_2$, —N((C$_1$-C$_9$)heteroaryl)$_2$, —O(C$_1$-C$_6$)alkyl, —O(C$_3$-C$_7$)cycloalkyl, —O(C$_2$-C$_9$)heterocyclyl, —O(C$_6$-C$_{10}$)aryl, —O(C$_1$-C$_9$)heteroaryl, —(C$_3$-C$_7$)cycloalkyl, —(C$_2$-C$_9$)heterocyclyl, —CO$_2$H, —C(O)((C$_1$-C$_6$)alkyl), —SO$_2$H, —SO$_2$((C$_1$-C$_6$)alkyl), —SO$_2$NH$_2$, —SO$_2$NH((C$_1$-C$_6$)alkyl), —SO$_2$N((C$_1$-C$_6$)alkyl)$_2$, —NHSO$_2$((C$_1$-C$_6$)alkyl), and —N((C$_1$-C$_6$)alkyl)SO$_2$((C$_1$-C$_6$)alkyl;

R$^6$ is a substituent selected from the group consisting of hydrogen, —(C$_1$-C$_6$)alkyl, —(C$_3$-C$_7$)cycloalkyl, —(C$_2$-C$_9$)heterocyclyl, —(C$_6$-C$_{10}$)aryl, —(C$_1$-C$_9$)heteroaryl, —CO$_2$H, —C(O)((C$_1$-C$_6$)alkyl), and —SO$_2$((C$_1$-C$_6$)alkyl), wherein said —(C$_1$-C$_6$)alkyl, —(C$_3$-C$_7$)cycloalkyl, —(C$_2$-C$_9$)heterocyclyl, —(C$_6$-C$_{10}$)aryl, —(C$_1$-C$_9$)heteroaryl, —C(O)((C$_1$-C$_6$)alkyl), and —SO$_2$((C$_1$-C$_6$)alkyl) substituents are optionally substituted by one to three moieties independently selected from the group consisting of hydrogen, hydroxyl, halogen, —CF$_3$, —CN, —NO$_2$, —(C$_1$-C$_6$)alkyl, —NH(C$_1$-C$_6$)alkyl, —NH(C$_3$-C$_7$)cycloalkyl, —NH(C$_2$-C$_9$)heterocyclyl, —NH(C$_6$-C$_{10}$)aryl, —NH(C$_1$-C$_9$)heteroaryl, —N((C$_1$-C$_6$)alkyl)$_2$, —N((C$_3$-C$_7$)cycloalkyl)$_2$, —N((C$_2$-C$_9$)heterocyclyl)$_2$, —N((C$_6$-C$_{10}$)aryl)$_2$, —N((C$_1$-C$_9$)hetero aryl)$_2$, —O(C$_1$-C$_6$)alkyl, —O(C$_3$-C$_7$)cycloalkyl, —O(C$_2$-C$_9$)heterocyclyl, —O(C$_6$-C$_{10}$)aryl, —O(C$_1$-C$_9$)heteroaryl, —(C$_3$-C$_7$)cycloalkyl, —(C$_2$-C$_9$)heterocyclyl, —CO$_2$H, —C(O)((C$_1$-C$_6$)alkyl), —SO$_2$H, —SO$_2$((C$_1$-C$_6$)alkyl, —SO$_2$NH$_2$, —SO$_2$NH((C$_1$-C$_6$)alkyl, —SO$_2$N((C$_1$-C$_6$)alkyl)$_2$, —NHSO$_2$((C$_1$-C$_6$)alkyl), and —N((C$_1$-C$_6$)alkyl) SO$_2$((C$_1$-C$_6$)alkyl);

R$^7$ is a substituent selected from the group consisting of hydrogen, halogen, —NO$_2$, —CF$_3$, —CN, —NR$^{10}$R$^{10}$, —C(O)NR$^{10}$R$^{10}$, —OR$^{10}$, —CO$_2$R$^{10}$, —C(O)R$^{10}$, —SR$^{10}$, —SOR$^{10}$, —SO$_2$R$^{10}$, —SO$_2$NR$^{10}$R$^{10}$, —NHCOR$^{10}$, —NR$^{10}$CONR$^{10}$R$^{10}$, —NR$^{10}$SO$_2$R$^{10}$, —P(O)(OR$^{16}$)$_2$, —(C$_1$-C$_6$)alkyl, —(C$_1$-C$_6$)alkyl, —(C$_2$-C$_6$)alkenyl, —(C$_2$-C$_6$)alkynyl, —(C$_2$-C$_6$)perfluorinated alkyl, —(C$_2$-C$_6$)perfluorinated alkenyl, —(C$_3$-C$_6$)perfluorinated alkynyl, —(C$_3$-C$_7$)cycloalkyl, —(C$_3$-C$_{10}$)cycloalkenyl, —(C$_6$-C$_{10}$)bicycloalkyl, —(C$_6$-C$_{10}$)bicycloalkenyl, —(C$_2$-C$_9$)heterocyclyl, —(C$_2$-C$_{10}$)heterocycloalkenyl, —(C$_5$-C$_{10}$)heterobicycloalkyl, —(C$_6$-C$_{10}$)heterobicycloalkenyl, —(C$_6$-C$_{10}$)aryl, —(C$_1$-C$_9$)heteroaryl, —(C$_6$-C$_{10}$)perfluorinated aryl, —(C$_1$-C$_9$)perfluorinated heteroaryl, wherein said —(C$_1$-C$_6$)alkyl, —(C$_2$-C$_6$)alkenyl, —(C$_2$-C$_6$)alkynyl, —(C$_3$-C$_7$)cycloalkyl, —(C$_3$-C$_{10}$)cycloalkenyl, —(C$_6$-C$_{10}$)bicycloalkyl, —(C$_6$-C$_{10}$)bicycloalkenyl, —(C$_2$-C$_9$)heterocyclyl, —(C$_2$-C$_{10}$)heterocycloalkenyl, —(C$_5$-C$_{10}$)heterobicycloalkyl, —(C$_6$-C$_{10}$)heterobicycloalkenyl, and —(C$_6$-C$_{10}$)aryl, —(C$_1$-C$_9$)heteroaryl substituents are optionally substituted by one to three moieties independently selected from the group consisting of hydrogen, hydroxyl, halogen, —CF$_3$, —CN, —NO$_2$, —(C$_1$-C$_6$)alkyl, —NH(C$_1$-C$_6$)alkyl, —NH(C$_3$-C$_7$)cycloalkyl, —NH(C$_2$-C$_9$)heterocyclyl, —NH(C$_6$-C$_{10}$)aryl, —NH(C$_1$-C$_9$)heteroaryl, —N((C$_1$-C$_6$)alkyl)$_2$, —N((C$_3$-C$_7$)cycloalkyl)$_2$, —N((C$_2$-C$_9$)heterocyclyl)$_2$, —N((C$_6$-C$_{10}$)aryl)$_2$, —N((C$_1$-C$_9$)heteroaryl)$_2$, —O(C$_1$-C$_6$)alkyl, —O(C$_3$-C$_7$)cycloalkyl, —O(C$_2$-C$_9$)heterocyclyl, —O(C$_6$-C$_{10}$)aryl, —O(C$_1$-C$_9$)heteroaryl, —(C$_3$-C$_7$)cycloalkyl, —(C$_2$-C$_9$)heterocyclyl, —CO$_2$H, —C(O)((C$_1$-C$_6$)alkyl), —SO$_2$H, —SO$_2$((C$_1$-C$_6$)alkyl, —SO$_2$NH$_2$, —SO$_2$NH((C$_1$-C$_6$)alkyl, —SO$_2$N((C$_1$-C$_6$)alkyl)$_2$, —NHSO$_2$ ((C$_1$-C$_6$)alkyl), and —N((C$_1$-C$_6$)alkyl)SO$_2$((C$_1$-C$_6$)alkyl);

R$^8$ and R$^9$ are each independently a substituent selected from the group consisting of hydrogen, halogen, —(C$_1$-C$_6$)alkyl, —(C$_2$-C$_6$)perfluorinated alkyl, —(C$_3$-C$_7$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocyclyl, —(C$_2$-C$_{10}$)heterocycloalkenyl, —(C$_5$-C$_{10}$)heterobicycloalkyl, —(C$_6$-C$_9$)heterobicycloalkenyl, —(C$_6$-C$_{10}$)aryl, —(C$_1$-C$_9$)heteroaryl, —(C$_6$-C$_{10}$)perfluorinated aryl, —(C$_1$-C$_9$)perfluorinated heteroaryl, —CO$_2$H, —C(O)((C$_1$-C$_6$)alkyl), —OR$^{10}$, —SO$_2$((C$_1$-C$_6$)alkyl) and —P(O)(OR$^{16}$)$_2$, wherein said —(C$_1$-C$_6$)alkyl, —(C$_3$-C$_7$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocyclyl, —(C$_2$-C$_{10}$)heterocycloalkenyl, —(C$_6$-C$_9$)heterobicycloalkyl, —(C$_6$-C$_9$)heterobicycloalkenyl, —(C$_6$-C$_{10}$)aryl, —(C$_1$-C$_9$)heteroaryl, —C(O)((C$_1$-C$_6$)alkyl), and —SO$_2$((C$_1$-C$_6$)alkyl) substituents are optionally substituted by one to three moieties independently selected from the group consisting of hydrogen, hydroxyl, halogen, —CF$_3$, —CN, —NO$_2$, —(C$_1$-C$_6$)alkyl, —NH(C$_1$-C$_6$)alkyl, —NH(C$_3$-C$_7$)cycloalkyl, —NH(C$_2$-C$_9$)heterocyclyl, —NH(C$_6$-C$_{10}$)aryl, —NH(C$_1$-C$_9$)heteroaryl, —N((C$_1$-C$_6$)alkyl)$_2$, —N((C$_3$-C$_7$)cycloalkyl)$_2$, —N((C$_2$-C$_9$)heterocyclyl)$_2$, —N((C$_6$-C$_{10}$)aryl)$_2$, —N((C$_1$-C$_9$)heteroaryl)$_2$, —O(C$_1$-C$_6$)alkyl, —O(C$_3$-C$_7$)cycloalkyl, —O(C$_2$-C$_9$)heterocyclyl, —O(C$_6$-C$_{10}$)aryl, —O(C$_1$-C$_9$)heteroaryl, —(C$_3$-C$_7$)cycloalkyl, —(C$_2$-C$_9$)heterocyclyl, —CO$_2$H, —C(O)((C$_1$-C$_6$)alkyl), —SO$_2$H, —SO$_2$((C$_1$-C$_6$)alkyl, —SO$_2$NH$_2$, —SO$_2$NH((C$_1$-C$_6$)alkyl, —SO$_2$N((C$_1$-C$_6$)alkyl)$_2$, —NHSO$_2$((C$_1$-C$_6$)alkyl), and —N((C$_1$-C$_6$)alkyl)SO$_2$((C$_1$-C$_6$)alkyl);

R$^8$ and R$^9$ when joined to the same carbon atom can join to form a —(C$_3$-C$_7$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocyclyl, —(C$_2$-C$_{10}$)heterocycloalkenyl, —(C$_6$-C$_9$)heterobicycloalkyl, —(C$_6$-C$_9$)heterobicycloalkenyl, —(C$_6$-C$_{10}$)aryl, or —(C$_1$-C$_9$)heteroaryl, wherein each of the foregoing —(C$_3$-C$_7$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocyclyl, —(C$_2$-C$_{10}$)heterocycloalkenyl, —(C$_6$-C$_9$)heterobicycloalkyl, —(C$_6$-C$_9$)heterobicycloalkenyl, —(C$_6$-C$_{10}$)aryl and —(C$_1$-C$_9$)heteroaryl is optionally substituted with one to three substituents independently selected from the group consisting of halogen, —CF$_3$, —CN, —NO$_2$, —(C$_1$-C$_6$)alkyl, —OR$^{16}$, —C(O)OR$^{16}$, —OC(O)R$^{16}$, —OC(O)OR$^{16}$, —N(R$^{16}$)$_2$, —NR$^{16}$C(O)R$^{16}$, —SO$_2$R$^{16}$, —SO$_2$N(R$^{16}$)$_2$ and —NR$^{16}$SO$_2$R$^{16}$;

R$^{10}$ and R$^{11}$ are each independently a substituent selected from the group consisting of hydrogen, —(C$_1$-C$_6$)alkyl, —(C$_2$-C$_6$)perfluorinated alkyl, —(C$_3$-C$_7$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocyclyl, —(C$_2$-C$_{10}$)heterocycloalkenyl, —(C$_6$-C$_9$)heterobicycloalkyl, —(C$_6$-C$_9$)heterobicycloalkenyl, —(C$_6$-C$_{10}$)aryl, —(C$_1$-C$_9$)heteroaryl, —(C$_6$-C$_{10}$)perfluorinated aryl, —(C$_1$-C$_9$)perfluorinated heteroaryl, —CO$_2$H, —C(O)((C$_1$-C$_6$)alkyl), —SO$_2$((C$_1$-C$_6$)alkyl) and —P(O)(OR$^{16}$)$_2$, wherein said —(C$_1$-C$_6$)alkyl, —(C$_3$-C$_7$)cycloalkyl, —(C$_2$-C$_9$)heterocyclyl, —(C$_6$-C$_{10}$)aryl, —(C$_1$-C$_9$)heteroaryl, —C(O)((C$_1$-C$_6$)alkyl), and —SO$_2$((C$_1$-C$_6$)alkyl) substituents are optionally substituted by one to three moieties independently selected from the group consisting of hydrogen, hydroxyl, halogen, —CF$_3$, —CN, —NO$_2$, —(C$_1$-C$_6$)alkyl, —NH(C$_1$-C$_6$)alkyl, —NH(C$_3$-C$_7$)cycloalkyl, —NH(C$_2$-C$_9$)heterocyclyl, —NH(C$_6$-C$_{10}$)aryl, —NH(C$_1$-C$_9$)heteroaryl, —N((C$_1$-C$_6$)alkyl)$_2$, —N((C$_3$-C$_7$)cycloalkyl)$_2$, —N((C$_2$-C$_9$)heterocyclyl)$_2$, —N((C$_6$-C$_{10}$)aryl)$_2$, —N((C$_1$-C$_9$)heteroaryl)$_2$, —O(C$_1$-C$_6$)alkyl, —O(C$_3$-C$_7$)cycloalkyl, —O(C$_2$-C$_9$)heterocyclyl, —O(C$_6$-C$_{10}$)aryl, —O(C$_1$-C$_9$)heteroaryl, —(C$_3$-C$_7$)cycloalkyl, —(C$_2$-C$_9$)heterocyclyl, —CO$_2$H, —C(O)((C$_1$-C$_6$)alkyl), —SO$_2$H, —SO$_2$((C$_1$-C$_6$)alkyl), —SO$_2$NH$_2$, —SO$_2$NH((C$_1$-C$_6$)alkyl), —SO$_2$N((C$_1$-C$_6$)alkyl)$_2$, —NHSO$_2$((C$_1$-C$_6$)alkyl), and —N((C$_1$-C$_6$)alkyl)SO$_2$((C$_1$-C$_6$)alkyl);

R$^{12}$ is a substituent selected from a group consisting of hydrogen, —(C$_1$-C$_6$)alkyl, —(C$_3$-C$_7$)cycloalkyl, —(C$_2$-C$_9$)heterocyclyl, —(C$_6$-C$_{10}$)aryl, —(C$_1$-C$_9$)heteroaryl, —C(O)R$^{15}$, —C(O)OR$^{15}$, —C(O)N(R$^{15}$)$_2$, —C(O)NR$^{15}$C(O)NR$^{15}$ and —SO$_2$(R$^{15}$)$_2$, wherein said —(C$_1$-C$_6$)alkyl, —(C$_3$-C$_7$)cycloalkyl, —(C$_2$-C$_9$)heterocyclyl, —(C$_6$-C$_{10}$)aryl and —(C$_1$-C$_9$)heteroaryl substituents are optionally substituted by one to three moieties independently selected from the group consisting of halogen, —CF$_3$, —CN, —NO$_2$, —(C$_1$-C$_6$)alkyl, —OR$^{16}$, —C(O)OR$^{16}$, —OC(O)R$^{16}$, —OC(O)OR$^{16}$, —N(R$^{16}$)$_2$, —NR$^{16}$C(O)R$^{16}$, —SO$_2$R$^{16}$, —SO$_2$N(R$^{16}$)$_2$ and —NR$^{16}$SO$_2$R$^{16}$;

R$^{13}$ is a substituent selected from the group consisting of hydrogen, —(C$_1$-C$_6$)alkyl, —C(O)H, —C(O)(C$_1$-C$_6$)alkyl), —(C$_1$-C$_6$)alkyl)OR$^{14}$, —(C$_1$-C$_6$)alkyl)N(R$^{16}$)$_2$ and —P(O)(OR$^{16}$)$_2$;

R$^{14}$ is a substituent selected from the group consisting of hydrogen, —(C$_1$-C$_6$)alkyl) and —P(O)(OR$^{16}$)$_2$;

R$^{15}$ is a substituent independently selected from the group consisting of hydrogen, —(C$_1$-C$_6$)alkyl, —(C$_3$-C$_7$)cycloalkyl, —(C$_2$-C$_9$)heterocyclyl, —(C$_6$-C$_{10}$)aryl, and —(C$_1$-C$_9$)heteroaryl, wherein said —(C$_1$-C$_6$)alkyl, —(C$_3$-C$_7$)cycloalkyl, —(C$_2$-C$_9$)heterocyclyl, —(C$_6$-C$_{10}$)aryl, and —(C$_1$-C$_9$)heteroaryl, are optionally substituted by one to three moieties independently selected from the group consisting of halogen, —CF$_3$, —CN, —NO$_2$, —(C$_1$-C$_6$)alkyl, —OR$^{16}$, —C(O)(R$^{16}$)$_2$, —C(O)OR$^{16}$, —OC(O)R$^{16}$, —N(R$^{16}$)$_2$, —NR$^{16}$C(O)R$^{16}$, —SO$_2$R$^{16}$, —SO$_2$N(R$^{16}$)$_2$ and —NR$^{16}$SO$_2$R$^{16}$;

two R$_{15}$ groups when attached to the same nitrogen atom may form a —(C$_2$-C$_9$)heterocyclyl optionally substituted by one to three substituents independently selected from the group consisting of hydrogen, halogen, —CF$_3$, —NO$_2$, —CN, —(C$_1$-C$_6$)alkyl, —(C$_2$-C$_6$)alkenyl, —(C$_2$-C$_6$)alkynyl, —CR$^{16}$=N—N(R$^{16}$)$_2$, —CR$^{16}$=N—OR$^{16}$, —CR$^{16}$=N—NR$^{16}$C(O)R$^{16}$, —CR$^3$=N—NR$^{16}$C(O)OR$^{16}$, —N(R$^{16}$)$_2$, —OR$^{16}$, —(C$_3$-C$_7$)cycloalkyl, —(C$_2$-C$_9$)heterocyclyl, —CO$_2$R$^{16}$, —CON(R$^{16}$)$_2$, —SR$^{16}$, —SOR$^{16}$, —SO$_2$R$^{16}$, —SO$_2$N(R$^{16}$)$_2$, —NHCOR$^{16}$, —NR$^{16}$CON(R$^{16}$)$_2$ and —NR$^{16}$SO$_2$R$^{16}$;

R$^{16}$ is a substituent independently selected from the group consisting of hydrogen, —(C$_1$-C$_6$)alkyl, —(C$_3$-C$_7$)cycloalkyl, —(C$_2$-C$_9$)heterocyclyl, —(C$_6$-C$_{10}$)aryl, and —(C$_1$-C$_9$)heteroaryl;

two R$_{16}$ groups when attached to the same nitrogen atom may form a —(C$_2$-C$_9$)heterocyclyl optionally substituted by one to three substituents independently selected from the group consisting of halogen, —CF$_3$, —NO$_2$, —CN, —(C$_1$-C$_6$)alkyl, —(C$_3$-C$_7$)cycloalkyl, —(C$_2$-C$_9$)heterocyclyl, —(C$_6$-C$_{10}$)aryl, and —(C$_1$-C$_9$)heteroaryl;

m is an integer from 1 to 4; and p is an integer from 1 to 4.

The present invention also relates to a compound of formula II

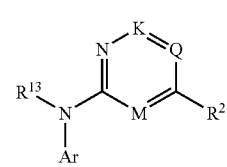

wherein Ar is a fused bicyclic ring system comprising at least one bridged ring fused to at least one saturated, unsaturated or aromatic ring selected from the group consisting of —(C$_3$-C$_{10}$)cycloalkyl, —(C$_5$-C$_{10}$)cycloalkenyl, —(C$_2$-C$_{10l}$)heterocyclyl, —(C$_2$-C$_{10}$)heterocycloalkenyl, —(C$_6$-C$_{10}$)aryl and —(C$_2$-C$_9$)heteroaryl, wherein Ar is optionally substituted by one to five substituents independently selected from the group consisting of hydrogen, halogen, —CF$_3$, —NO$_2$, —CN, —(C$_1$-C$_6$)alkyl, —(C$_2$-C$_6$)alkenyl, —(C$_2$-C$_6$)alkynyl, —CR$^3$=N—NR$^3$R$^4$, —CR$^3$=N—OR$^5$, —CR$^3$=N—NR$^3$C(O)R$^3$, —CR$^3$=N—NR$^3$C(O)OR$^5$, —NR$^3$R$^4$, —OR$^5$, —(C$_3$-C$_7$)cycloalkyl, —(C$_2$-C$_9$)heterocyclyl, —C(O)R$^5$, —CO$_2$R$^5$, —CONR$^3$R$^4$, —SR$^6$, —SOR$^6$, —SO$_2$R$^6$, —SO$_2$NR$^3$R$^4$, —NHCOR$^{15}$, —NR$^3$CONR$^3$R$^4$, and —NR$^3$SO$_2$R$^6$;

and one or more adjacent carbon or heteroatoms of said bridged ring or said saturated, unsaturated or aromatic ring are optionally fused to a ring system selected from the group consisting of —(C$_3$-C$_7$)cycloalkyl, —(C$_2$-C$_9$)heterocyclyl, —(C$_6$-C$_{10}$)aryl, and —(C$_1$-C$_9$)heteroaryl, wherein said —(C$_3$-C$_7$)cycloalkyl, —(C$_2$-C$_9$)heterocyclyl, —(C$_6$-C$_{10}$)aryl, and —(C$_1$-C$_9$)heteroaryl ring systems are optionally substituted by one to three substituents selected from the group consisting of hydrogen, hydroxyl, halogen, —CF$_3$, —CN, —NO$_2$, —(C$_1$-C$_6$)alkyl, —NH(C$_1$-C$_6$)alkyl, —NH(C$_3$-C$_7$)cycloalkyl, —NH(C$_2$-C$_9$)heterocyclyl, —NH(C$_6$-

$C_{10}$)aryl, —NH($C_1$-$C_9$)heteroaryl, —N(($C_1$-$C_6$)alkyl)$_2$, —N(($C_3$-$C_7$)cycloalkyl)$_2$, —N(($C_2$-$C_9$)heterocyclyl)$_2$, —N(($C_6$-$C_{10}$)aryl)$_2$, —N(($C_1$-$C_9$)heteroaryl)$_2$, —O($C_1$-$C_6$) alkyl, —O($C_3$-$C_7$)cycloalkyl, —O($C_2$-$C_9$)heterocyclyl, —O($C_6$-$C_{10}$)aryl, —O($C_1$-$C_9$)heteroaryl, —($C_3$-$C_7$)cycloalkyl, —($C_2$-$C_9$)heterocyclyl, —CO$_2$H, —C(O)(($C_1$-$C_6$) alkyl), —SO$_2$H, —SO$_2$(($C_1$-$C_6$)alkyl), —SO$_2$NH$_2$, —SO$_2$NH(($C_1$-$C_6$)alkyl), —SO$_2$N(($C_1$-$C_6$)alkyl)$_2$, —NHSO$_2$(($C_1$-$C_6$)alkyl), and —N(($C_1$-$C_6$)alkyl)SO$_2$(($C_1$-$C_6$)alkyl); and K, M and Q are as defined above;
$R^1$ to $R^{16}$ are as defined above;
$Z^1$ and $Z^2$ are as defined above;
$Y^1$ and $Y^2$ are as defined above;
$L^1$ and $L^2$ are as defined above;
q is as defined above;
X is as defined above;
W is as defined above;
m is as defined above;
n is as defined above; and
p is as defined above.

Unless stated otherwise, the compounds of formula I and II are referred to hereinafter collectively as "the compounds of the invention."

In one embodiment, M in N.

In another embodiment, Q is C(D).

In another embodiment, at least one bridged ring is selected from the group consisting of a 2.1.1, 2.2.1, 2.2.2, 3.2.1, 3.2.2 and 3.3.2 ring system.

In another embodiment, Q is C(D) and D is selected from the group consisting of hydrogen, halogen, —OR$^5$, —CF$_3$, —NO$_2$, —CN, —($C_1$-$C_6$)alkyl, —($C_2$-$C_6$)alkenyl, —($C_2$-$C_6$)alkynyl, —($C_2$-$C_6$)perfluorinated alkyl, —($C_2$-$C_6$)perfluorinated alkenyl, —($C_3$-$C_6$)perfluorinated alkynyl, wherein said —($C_1$-$C_6$)alkyl, —($C_2$-$C_6$)alkenyl, —($C_2$-$C_6$)alkynyl, D substituents are optionally substituted by one to three substituents independently selected from the group consisting of hydrogen, halogen, —CF$_3$, —NO$_2$, —CN, —($C_1$-$C_6$)alkyl, —($C_2$-$C_6$)alkenyl, —($C_2$-$C_6$)alkynyl, —CR$^3$=N—NR$^3$R$^4$, —CR$^3$=N—OR$^5$, —CR$^3$=N—NR$^3$C(O)R$^3$, —CR$^3$=N—NR$^3$C(O)OR$^5$, —NR$^3$R$^4$, —OR$^5$, —($C_3$-$C_7$)cycloalkyl, —($C_2$-$C_9$)heterocyclyl, —CO$_2$R$^5$, —CONR$^3$R$^4$, —SR$^6$, —SOR$^6$, —SO$_2$R$^6$, —SO$_2$NR$^3$R$^4$, —NHCOR$^5$, —NR$^3$CONR$^3$R$^4$, and —NR$^3$SO$_2$R$^6$.

In another embodiment, Q is C(D) and D is selected from the group consisting of —($C_3$-$C_7$)cycloalkyl, —($C_5$-$C_{10}$)cycloalkenyl, —($C_6$-$C_{10}$)bicycloalkyl, —($C_6$-$C_{10}$)bicycloalkenyl, —($C_1$-$C_9$)heterocyclyl, —($C_1$-$C_{10}$)heterocycloalkenyl, —($C_6$-$C_9$)heterobicycloalkyl, —($C_6$-$C_9$)heterobicycloalkenyl, —($C_6$-$C_{10}$)aryl, and —($C_1$-$C_9$)heteroaryl, wherein said —($C_3$-$C_7$)cycloalkyl, —($C_5$-$C_{10}$)cycloalkenyl, —($C_6$-$C_{10}$)bicycloalkyl, —($C_6$-$C_{10}$)bicycloalkenyl, —($C_1$-$C_9$)heterocyclyl, —($C_1$-$C_{10}$)heterocycloalkenyl, —($C_6$-$C_9$)heterobicycloalkyl, —($C_6$-$C_9$)heterobicycloalkenyl, —($C_6$-$C_{10}$)aryl, and —($C_1$-$C_9$)heteroaryl D substituents are optionally substituted by one to three substituents independently selected from the group consisting of hydrogen, halogen, —CF$_3$, —NO$_2$, —CN, —($C_1$-$C_6$)alkyl, —($C_2$-$C_6$)alkenyl, —($C_2$-$C_6$)alkynyl, —CR$^3$=N—NR$^3$R$^4$, —CR$^3$=N—OR$^5$, —CR$^3$=N—NR$^3$C(O)R$^3$, —CR$^3$=N—NR$^3$C(O)OR$^5$, —NR$^3$R$^4$, —OR$^5$, —($C_3$-$C_7$)cycloalkyl, —($C_2$-$C_9$)heterocyclyl, —CO$_2$R$^5$, —CONR$^3$R$^4$, —SR$^6$, —SOR$^6$, —SO$_2$R$^6$, —SO$_2$NR$^3$R$^4$, —NHCOR$^5$, —NR$^3$CONR$^3$R$^4$, and —NR$^3$SO$_2$R$^6$.

In another embodiment, Q is C(D) and D is selected from the group consisting of —NR$^3$R$^4$, —OR$^5$, —C(O)R$^5$, —CO$_2$R$^5$, —CONR$^3$R$^4$, —SR$^6$, —SOR$^6$, —SO$_2$R$^6$, —SO$_2$NR$^3$R$^4$, —NHCOR$^5$, —NR$^3$CONR$^3$R$^4$, and —NR$^3$SO$_2$R$^6$, wherein said —NR$^3$R$^4$, —OR$^5$, —C(O)R$^5$, —CO$_2$R$^5$, —CONR$^3$R$^4$, —SR$^6$, —SOR$^6$, —SO$_2$R$^6$, —SO$_2$NR$^3$R$^4$, —NHCOR$^5$, —NR$^3$CONR$^3$R$^4$, and —NR$^3$SO$_2$R$^6$ D substituents are optionally substituted by one to three substituents independently selected from the group consisting of hydrogen halogen, —CF$_3$, —NO$_2$, —CN, —($C_1$-$C_6$)alkyl, —($C_2$-$C_6$)alkenyl, —($C_2$-$C_6$)alkynyl, —CR$^3$=N—NR$^3$R$^4$, —CR$^3$=N—OR$^5$, —CR$^3$=N—NR$^3$C(O)R$^3$, —CR$^3$=N—NR$^3$C(O)OR$^5$, —NR$^3$R$^4$, —OR$^5$, —($C_3$-$C_7$)cycloalkyl, —($C_2$-$C_9$)heterocyclyl, —CO$_2$R$^5$, —CONR$^3$R$^4$, —SR$^6$, —SOR$^6$, —SO$_2$R$^6$, —SO$_2$NR$^3$R$^4$, —NHCOR$^5$, —NR$^3$CONR$^3$R$^4$, and —NR$^3$SO$_2$R$^6$.

In another embodiment, Q is C(D) and D is selected from the group consisting of hydrogen, halogen, hydroxy, —CF$_3$, —NO$_2$, —CN, and —($C_1$-$C_6$)alkyl, wherein said —($C_1$-$C_6$) alkyl D substituent is optionally substituted by one to three substituents independently selected from the group consisting of hydrogen, halogen, hydroxy, —CF$_3$, —NO$_2$, —CN, and —($C_1$-$C_6$)alkyl.

In another embodiment, Q is C(D) and D is selected from the group consisting of hydrogen, halogen, hydroxy, —CF$_3$, —NO$_2$, and —CN.

In another embodiment, Q is C(D) and D is —($C_1$-$C_6$)alkyl optionally substituted by one to three substituents independently selected from the group consisting of hydrogen, halogen, hydroxy, —CF$_3$, —NO$_2$, —CN, and —($C_1$-$C_6$)alkyl.

In a preferred embodiment, Q is C(D) and D is selected from the group consisting of halogen, —CF$_3$, and —NO$_2$.

In another preferred embodiment, Q is C(D) and D is —($C_1$-$C_6$)alkyl optionally substituted by one to three halogen substituents.

In a more preferred embodiment, Q is C(D) and D is —CF$_3$.

In another embodiment, K is C(R$^1$).

In another embodiment, K is C(R$^1$) and R$^1$ is selected from the group consisting of hydrogen, halogen, —CF$_3$, —NO$_2$, —CN, —($C_1$-$C_6$)alkyl, —($C_2$-$C_6$)alkenyl, —($C_2$-$C_6$)alkynyl, —($C_2$-$C_6$)perfluorinated alkyl, —($C_2$-$C_6$)perfluorinated alkenyl, —($C_3$-$C_6$)perfluorinated alkynyl, —($C_3$-$C_7$)cycloalkyl, —($C_2$-$C_9$)heterocyclyl, —($C_6$-$C_{10}$)aryl, —($C_1$-$C_9$)heteroaryl, —OR$^5$, —C(O)R$^5$, —CO$_2$R$^5$, —CONR$^3$R$^4$, —SR$^6$, —SOR$^6$, —SO$_2$R$^6$, —SO$_2$NR$^3$R$^4$, —NHCOR$^5$, —NR$^3$CONR$^3$R$^4$, —NR$^3$SO$_2$R$^6$, and

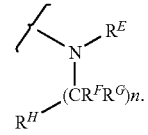

In another embodiment, K is C(R$^1$) and R$^1$ is selected from the group consisting of —($C_1$-$C_6$)alkyl, —($C_2$-$C_6$)alkenyl, —($C_2$-$C_6$)alkynyl, —($C_2$-$C_6$)perfluorinated alkyl, —($C_2$-$C_6$) perfluorinated alkenyl, —($C_3$-$C_6$)perfluorinated alkynyl, —($C_3$-$C_7$)cycloalkyl, —($C_2$-$C_9$)heterocyclyl, —($C_6$-$C_{10}$) aryl, and —($C_1$-$C_9$)heteroaryl.

In another embodiment, K is C(R$^1$) and R$^1$ is selected from the group consisting of —OR$^5$, —C(O)R$^5$, —CO$_2$R$^5$, —CONR$^3$R$^4$, —SR$^6$, —SOR$^6$, —SO$_2$R$^6$, —SO$_2$NR$^3$R$^4$, —NHCOR$^5$, —NR$^3$CONR$^3$R$^4$, and —NR$^3$SO$_2$R$^6$.

In another embodiment, K is C(R$^1$) and R$^1$ is

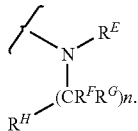

In another embodiment, K is C(R$^1$) and R$^1$ is selected from the group consisting of hydrogen, halogen, hydroxy, —CF$_3$, —NO$_2$, —CN.

In another embodiment, K is C(R$^1$) and R$^1$ is hydrogen.

In another embodiment, M is N, K is C(H) and K is C(H).

In another embodiment, M is N, K is C(H), and Q is C(CF3) and K is C(H).

In another embodiment, R$^2$ is selected from the group consisting of hydrogen, halogen, —CF$_3$, —NO$_2$, —CN, —(C$_1$-C$_6$)alkyl, —(C$_2$-C$_6$)alkenyl, —(C$_2$-C$_6$)alkynyl, —(C$_3$-C$_7$)cycloalkyl, —(C$_2$-C$_9$)heterocyclyl, —(C$_6$-C$_{10}$)aryl, —(C$_1$-C$_9$)heteroaryl, —NR$^3$R$^4$, OR$^5$, —C(O)R$^5$, —CO$_2$R$^5$, —CONR$^3$R$^4$, —SR$^6$, —SOR$^6$, —SO$_2$R$^6$, —SO$_2$NR$^3$R$^4$, —NHCOR$^5$, —NR$^3$CONR$^3$R$^4$, —NR$^3$SO$_2$R$^6$, and

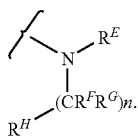

In another embodiment, R$^2$ is selected from the group consisting of —(C$_1$-C$_6$)alkyl, —(C$_2$-C$_6$)alkenyl, —(C$_2$-C$_6$)alkynyl, —(C$_3$-C$_7$)cycloalkyl, —(C$_2$-C$_9$)heterocyclyl, —(C$_6$-C$_{10}$)aryl, and —(C$_1$-C$_9$)heteroaryl, wherein said —(C$_1$-C$_6$)alkyl, —(C$_2$-C$_6$)alkenyl, —(C$_2$-C$_6$)alkynyl, —(C$_3$-C$_7$)cycloalkyl, —(C$_5$-C$_{10}$)cycloalkenyl, —(C$_6$-C$_{10}$)aryl, and —(C$_1$-C$_9$)heteroaryl may optionally be substituted with one to three moieties independently selected from R$^5$ and R$^6$.

In another embodiment, R$^2$ is selected from the group consisting of —NR$^3$R$^4$, OR$^5$, —C(O)R$^5$, —CO$_2$R$^5$, —CONR$^3$R$^4$, —SR$^6$, —SOR$^6$, —SO$_2$R$^6$, —SO$_2$NR$^3$R$^4$, —NHCOR$^5$, —NR$^3$CONR$^3$R$^4$, and —NR$^3$SO$_2$R$^6$.

In another embodiment, R$^2$ is

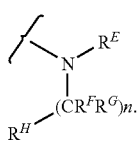

In a more preferred embodiment R$^2$ is

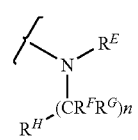

In another preferred embodiment, R$^2$ is

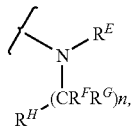

R$^E$ is hydrogen, and n is 0.

In another preferred embodiment, R$^2$ is

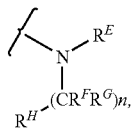

R$^E$ is hydrogen, n is 0, and R$^H$ is —(C$_3$-C$_7$)cycloalkyl.

In another embodiment, R$^H$ is selected from the group consisting of —(C$_3$-C$_7$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocyclyl, —(C$_2$-C$_{10}$)heterocycloalkenyl, —(C$_6$-C$_9$)heterobicycloalkyl, —(C$_6$-C$_9$)heterobicycloalkenyl and —(C$_2$-C$_9$)heterocyclyl.

In another embodiment, R$^H$ is selected from the group consisting of -cyclopropyl, -cyclobutyl, -cyclopentyl and -cyclohexyl.

In another embodiment, R$^H$ is -cyclopropyl.
In another embodiment, R$^H$ is -cyclobutyl.
In another embodiment, R$^H$ is -cyclopentyl.
In another embodiment, R$^H$ is -cyclohexyl.
In another embodiment, n is 0.
In another preferred embodiment, R$^2$ is

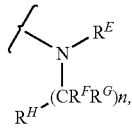

R$^E$ is hydrogen, n is 0, and R$^H$ is selected from the group consisting of -cyclopropyl, -cyclobutyl, -cyclopentyl and -cyclohexyl.

In another embodiment, A is a —(C$_6$-C$_{10}$)aryl, optionally substituted by one to three substituents independently selected from the group consisting of hydrogen, halogen, —CF$_3$, —NO$_2$, —CN, —(C$_1$-C$_6$)alkyl, —(C$_2$-C$_6$)alkenyl, —(C$_2$-C$_6$)alkynyl, —CR$^3$=N—NR$^3$R$^4$, —CR$^3$=N—OR$^5$, —CR$^3$=N—NR$^3$C(O)R$^3$, —CR$^3$=N—NR$^3$C(O)OR$^5$, —NR$^3$R$^4$, —OR$^5$, —(C$_3$-C$_7$)cycloalkyl, —(C$_2$-C$_9$)heterocyclyl, —C(O)R$^5$, —CO$_2$R$^5$, —CONR$^3$R$^4$, —SR$^6$, —SOR$^6$, —SO$_2$R$^6$, —SO$_2$NR$^3$R$^4$, —NHCOR$^{15}$, —NR$^3$CONR$^3$R$^4$, and —NR$^3$SO$_2$R$^6$.

In another embodiment, A is —(C$_3$-C$_{10}$)cycloalkyl, optionally substituted by one to three substituents independently selected from the group consisting of hydrogen, halogen, —CF$_3$, —NO$_2$, —CN, —(C$_1$-C$_6$)alkyl, —(C$_2$-C$_6$)alkenyl, —(C$_2$-C$_6$)alkynyl, —CR$^3$=N—NR$^3$R$^4$, —CR$^3$=N—OR$^5$, —CR$^3$=N—NR$^3$C(O)R$^3$, —CR$^3$=N—NR$^3$C(O)OR$^5$, —NR$^3$R$^4$, —OR$^5$, —(C$_3$-C$_7$)cycloalkyl, —(C$_2$-C$_9$)heterocyclyl, —C(O)R$^5$, —CO$_2$R$^5$, —CONR$^3$R$^4$, —SR$^6$, —$SOR^6$, —$SO_2R^6$, —$SO_2NR^3R^4$, —$NHCOR^{15}$, —$NR^3CONR^3R^4$, and —$NR^3SO_2R^6$.

In another embodiment, A is selected from the group consisting of cyclopropyl, cyclobutyl, cyclopentyl, cyclohexyl, cycloheptyl, cyclooctyl, cyclononyl, and cyclodecyl, optionally substituted by one to three substituents independently selected from the group consisting of hydrogen, halogen, —$CF_3$, —$NO_2$, —CN, —$(C_1$-$C_6)$alkyl, —$(C_2$-$C_6)$alkenyl, —$(C_2$-$C_6)$alkynyl, —$CR^3$=N—$NR^3R^4$, —$CR^3$=N—$OR^5$, —$CR^3$=N—$NR^3C(O)R^3$, —$CR^3$=N—$NR^3C(O)OR^5$, —$NR^3R^4$, —$OR^5$, —$(C_3$-$C_7)$cycloalkyl, —$(C_2$-$C_9)$heterocyclyl, —$C(O)R^5$, —$CO_2R^5$, —$CONR^3R^4$, —$SR^6$, —$SOR^6$, —$SO_2R^6$, —$SO_2NR^3R^4$, —$NHCOR^{15}$, —$NR^3CONR^3R^4$, and —$NR^3SO_2R^6$.

In another embodiment, A is —$(C_5$-$C_{10})$cycloalkenyl, optionally substituted by one to three substituents independently selected from the group consisting of hydrogen, halogen, —$CF_3$, —$NO_2$, —CN, —$(C_1$-$C_6)$alkyl, —$(C_2$-$C_6)$alkenyl, —$(C_2$-$C_6)$alkynyl, —$CR^3$=N—$NR^3R^4$, —$CR^3$=N—$OR^5$, —$CR^3$=N—$NR^3C(O)R^3$, —$CR^3$=N—$NR^3C(O)OR^5$, —$NR^3R^4$, —$OR^5$, —$(C_3$-$C_7)$cycloalkyl, —$(C_2$-$C_9)$heterocyclyl, —$C(O)R^5$, —$CO_2R^5$, —$CONR^3R^4$, —$SR^6$, —$SOR^6$, —$SO_2R^6$, —$SO_2NR^3R^4$, —$NHCOR^{15}$, —$NR^3CONR^3R^4$, and —$NR^3SO_2R^6$.

In another embodiment, A is selected from the group consisting of cyclopentenyl, cyclohexenyl, cycloheptenyl, cyclooctenyl, cyclononenyl, and cyclodecenyl, optionally substituted by one to three substituents independently selected from the group consisting of hydrogen, halogen, —$CF_3$, —$NO_2$, —CN, —$(C_1$-$C_6)$alkyl, —$(C_2$-$C_6)$alkenyl, —$(C_2$-$C_6)$alkynyl, —$CR^3$=N—$NR^3R^4$, —$CR^3$=N—$OR^5$, —$CR^3$=N—$NR^3C(O)R^3$, —$CR^3$=N—$NR^3C(O)OR^5$, —$NR^3R^4$, —$OR^5$, —$(C_3$-$C_7)$cycloalkyl, —$(C_2$-$C_9)$heterocyclyl, —$C(O)R^5$, —$CO_2R^5$, —$CONR^3R^4$, —$SR^6$, —$SOR^6$, —$SO_2R^6$, —$SO_2NR^3R^4$, —$NHCOR^{15}$, —$NR^3CONR^3R^4$, and —$NR^3SO_2R^6$.

In another embodiment, A is —$(C_2$-$C_{10})$heterocyclyl, optionally substituted by one to three substituents independently selected from the group consisting of hydrogen, halogen, —$CF_3$, —$NO_2$, —CN, —$(C_1$-$C_6)$alkyl, —$(C_2$-$C_6)$alkenyl, —$(C_2$-$C_6)$alkynyl, —$CR^3$=N—$NR^3R^4$, —$CR^3$=N—$OR^5$, —$CR^3$=N—$NR^3C(O)R^3$, —$CR^3$=N—$NR^3C(O)OR^5$, —$NR^3R^4$, —$OR^5$, —$(C_3$-$C_7)$cycloalkyl, —$(C_2$-$C_9)$heterocyclyl, —$C(O)R^5$, —$CO_2R^5$, —$CONR^3R^4$, —$SR^6$, —$SOR^6$, —$SO_2R^6$, —$SO_2NR^3R^4$, —$NHCOR^{15}$, —$NR^3CONR^3R^4$, and —$NR^3SO_2R^6$.

In another embodiment, A is —$(C_2$-$C_{10})$heterocycloalkenyl, optionally substituted by one to three substituents independently selected from the group consisting of hydrogen, halogen, —$CF_3$, —$NO_2$, —CN, —$(C_1$-$C_6)$alkyl, —$(C_2$-$C_6)$alkenyl, —$(C_2$-$C_6)$alkynyl, —$CR^3$=N—$NR^3R^4$, —$CR^3$=N—$OR^5$, —$CR^3$=N—$NR^3C(O)R^3$, —$CR^3$=N—$NR^3C(O)OR^5$, —$NR^3R^4$, —$OR^5$, —$(C_3$-$C_7)$cycloalkyl, —$(C_2$-$C_9)$heterocyclyl, —$C(O)R^5$, —$CO_2R^5$, —$CONR^3R^4$, —$SR^6$, —$SOR^6$, —$SO_2R^6$, —$SO_2NR^3R^4$, —$NHCOR^{15}$, —$NR^3CONR^3R^4$, and —$NR^3SO_2R^6$.

In another embodiment, A is —$(C_1$-$C_9)$heteroaryl, optionally substituted by one to three substituents independently selected from the group consisting of hydrogen, halogen, —$CF_3$, —$NO_2$, —CN, —$(C_1$-$C_6)$alkyl, —$(C_2$-$C_6)$alkenyl, —$(C_2$-$C_6)$alkynyl, —$CR^3$=N—$NR^3R^4$, —$CR^3$=N—$OR^5$, —$CR^3$=N—$NR^3C(O)R^3$, —$CR^3$=N—$NR^3C(O)OR^5$, —$NR^3R^4$, —$OR^5$, —$(C_3$-$C_7)$cycloalkyl, —$(C_2$-$C_9)$heterocyclyl, —$C(O)R^5$, —$CO_2R^5$, —$CONR^3R^4$, —$SR^6$, —$SOR^6$, —$SO_2R^6$, —$SO_2NR^3R^4$, —$NHCOR^{15}$, —$NR^3CONR^3R^4$, and —$NR^3SO_2R^6$.

In another embodiment, A is selected from the group consisting of oxazole, imidazole, thiazole, furyl, thienyl, pyrrolo, pyridyl, pyrazyl, pyrimidyl, quinoline, isoquinoline, isoquinazoline, benzimidazole, and pyridopyrimidine, wherein each of said oxazole, imidazole, thiazole, furyl, thienyl, pyrrolo, pyridyl, pyrazyl, pyrimidyl, quinoline, isoquinoline, isoquinazoline, benzimidazole, and pyridopyrimidine groups is optionally interrupted by one to three elements independently selected from the group consisting of —$C(R^3)$=$C(R^3)$—, —$C(O)$—, —$(C$=N—$R^3)$—, —$(C$=N—$NR^3R^4)$—, —$(C$=N—$NOR^5)$—, —$(C$=$CR^3)$—, —$(C$=$C(R^3)C(O)$—$NR^3R^4))$—, —$(C$=$C(R^3)C(O)OR^6)$—, —$SO_2$—, —S—, —O— and —$NR^3$—.

In another embodiment, A is selected from the group consisting of phenyl and naphthyl optionally substituted by one to three substituents independently selected from the group consisting of hydrogen, halogen, —$CF_3$, —$NO_2$, —CN, —$(C_1$-$C_6)$alkyl, —$(C_2$-$C_6)$alkenyl, —$(C_2$-$C_6)$alkynyl, —$CR^3$=N—$NR^3R^4$, —$CR^3$=N—$OR^5$, —$CR^3$=N—$NR^3C(O)R^3$, —$CR^3$=N—$NR^3C(O)OR^5$, —$NR^3R^4$, —$OR^5$, —$(C_3$-$C_7)$cycloalkyl, —$(C_2$-$C_9)$heterocyclyl, —$C(O)R^5$, —$CO_2R^5$, —$CONR^3R^4$, —$SR^6$, —$SOR^6$, —$SO_2R^6$, —$SO_2NR^3R^4$, —$NHCOR^{15}$, —$NR^3CONR^3R^4$, and —$NR^3SO_2R^6$.

In a more preferred embodiment, A is phenyl.

In one embodiment, $Z^1$ and $Z^2$ are —$CR^7$—.

In another embodiment, $Y^1$ and $Y^2$ are each —CH—.

In another embodiment, $L^1$ and $L^2$ are each independently —$CR^8R^9$—.

In a preferred embodiment, q is 0.

In another preferred embodiment, X and W are the same or different and are each independently selected from the group consisting of —$CR^8R^9$— and —$NR^{12}$—.

In another embodiment, X is selected from the group consisting of —S—, —S(O)—, —$S(O)_2$— and —$S(O)NR^3$—.

In another embodiment, X is —$CR^8R^9$—.

In another embodiment, X is —$C(O)$—.

In another embodiment, X is —$C$(=$NR^3$—.

In another embodiment, X is —O—.

In a preferred embodiment, X is —$NR^{12}$—.

In another preferred embodiment, X is —$NR^{12}$— and n is 1.

In another embodiment, $R^{12}$ is —$C(O)R^{15}$—.

In another preferred embodiment, X is —$NR^{12}$, m is 1, $R^{12}$ is —$C(O)R^{15}$, and $R^{15}$ is a —$(C_1$-$C_6)$alkyl optionally substituted by one to three moieties independently selected from the group consisting of halogen, —$CF_3$, —CN, —$NO_2$, —$(C_1$-$C_6)$alkyl, —$OR^{16}$, —$C(O)(R^{16})_2$, —$C(O)OR^{16}$, —$OC(O)R^{16}$, —$N(R^{16})_2$, —$NR^{16}C(O)R^{16}$, —$SO_2R^{16}$, —$SO_2N(R^{16})_2$ and —$NR^{16}SO_2R^{16}$.

In another preferred embodiment, X is —$NR^{12}$, m is 1, $R^{12}$ is —$C(O)R^{15}$, and $R^{15}$ is a —$(C_1$-$C_6)$alkyl optionally substituted by one to three moieties independently selected from the group consisting of halogen, —$CF_3$, —CN and —$NO_2$.

In another preferred embodiment, X is —$NR^{12}$, m is 1, $R^{12}$ is —$C(O)R^{15}$, and $R^{15}$ is a —$(C_1$-$C_6)$alkyl optionally substituted by one to three moieties independently selected from the group consisting of —$OR^{16}$, —$C(O)(R^{16})_2$, —$C(O)OR^{16}$, and —$OC(O)R^{16}$.

In another preferred embodiment, X is —$NR^{12}$, m is 1, $R^{12}$ is —$C(O)R^{15}$, and $R^{15}$ is a —$(C_1$-$C_6)$alkyl optionally substituted by one to three moieties independently selected from the group consisting of —$N(R^{16})_2$, —$NR^{16}C(O)R^{16}$, —$SO_2R^{16}$, —$SO_2N(R^{16})_2$ and —$NR^{16}SO_2R^{16}$.

In another preferred embodiment, X is —$NR^{12}$, m is 1, $R^{12}$ is —$C(O)R^{15}$, and $R^{15}$ is a —$(C_1$-$C_6)$alkyl substituted by —$N(R^{16})_2$.

In another preferred embodiment, X is —NR$^{12}$, m is 1, R$^{12}$ is —C(O)R$^{15}$, and R$^{15}$ is a —(C$_1$-C$_6$)alkyl substituted by —NR$^{16}$C(O)R$^{16}$.

In another preferred embodiment, X is —NR$^{12}$, m is 1, R$^{12}$ is —C(O)R$^{15}$, and R$^{15}$ is a —(C$_1$-C$_6$)alkyl substituted by —SO$_2$R$^{16}$.

In another preferred embodiment, X is —NR$^{12}$, m is 1, R$^{12}$ is —C(O)R$^{15}$, and R$^{15}$ is a —(C$_1$-C$_6$)alkyl substituted by —SO$_2$N(R$^{16}$)$_2$.

In another preferred embodiment, X is —NR$^{12}$, m is 1, R$^{12}$ is —C(O)R$^{15}$, and R$^{15}$ is a —(C$_1$-C$_6$)alkyl substituted by —NR$^{16}$SO$_2$R$^{16}$.

In another embodiment, W is selected from the group consisting of —S—, —S(O)—, —S(O)$_2$, and —S(O)NR$^3$—.

In another embodiment, W is —CR$^8$R$^9$—.

In another embodiment, W is —C(O)—.

In another embodiment, W is —C=NR$^3$—.

In another embodiment, W is —O—.

In a preferred embodiment, another embodiment, W is —NR$^{12}$—.

In a most preferred embodiment, W is —CR$^8$R$^9$— and p is 2.

In another embodiment, W is —CH$_2$— and p is 2.

In another preferred embodiment, Ar is selected from the group consisting of —(C$_6$-C$_{10}$)aryl and —(C$_1$-C$_9$)heteroaryl.

In another embodiment, Ar is selected from the group consisting of:

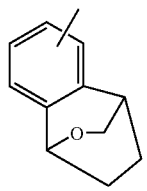 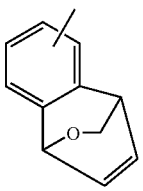

and

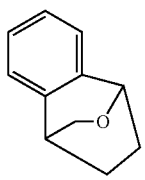 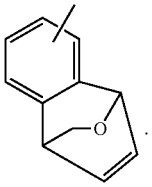

In another embodiment, Ar is selected from the group consisting of:

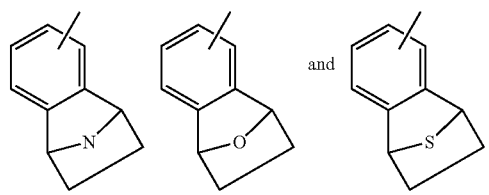

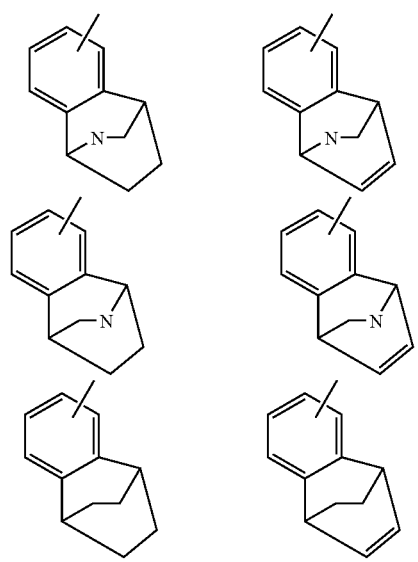

In another embodiment, Ar is selected from the group consisting of:

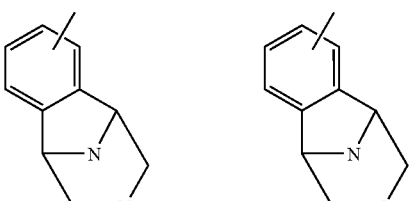

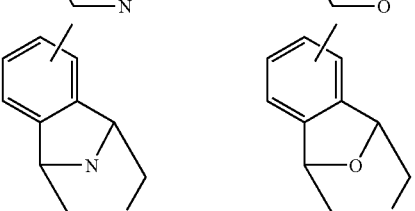

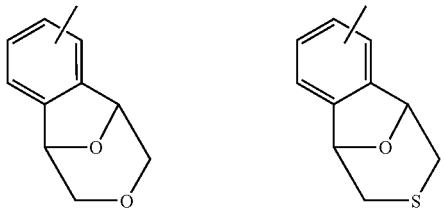

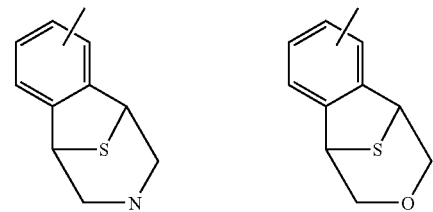

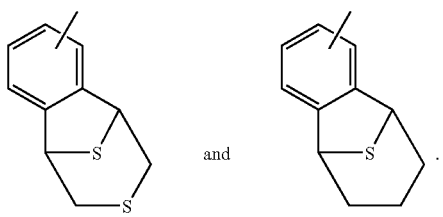

In another embodiment, Ar is selected from the group consisting of:

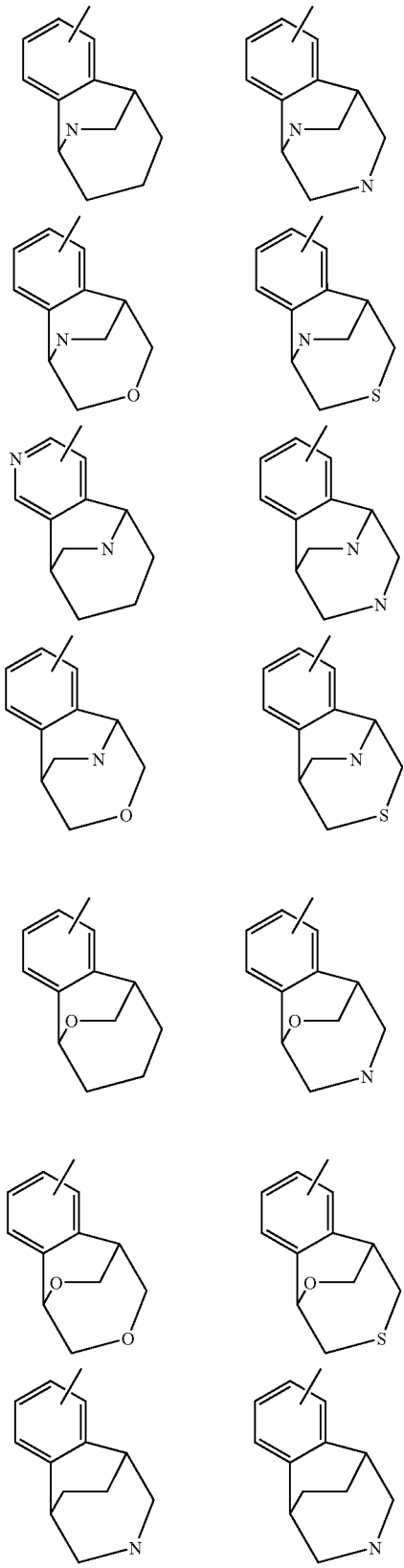

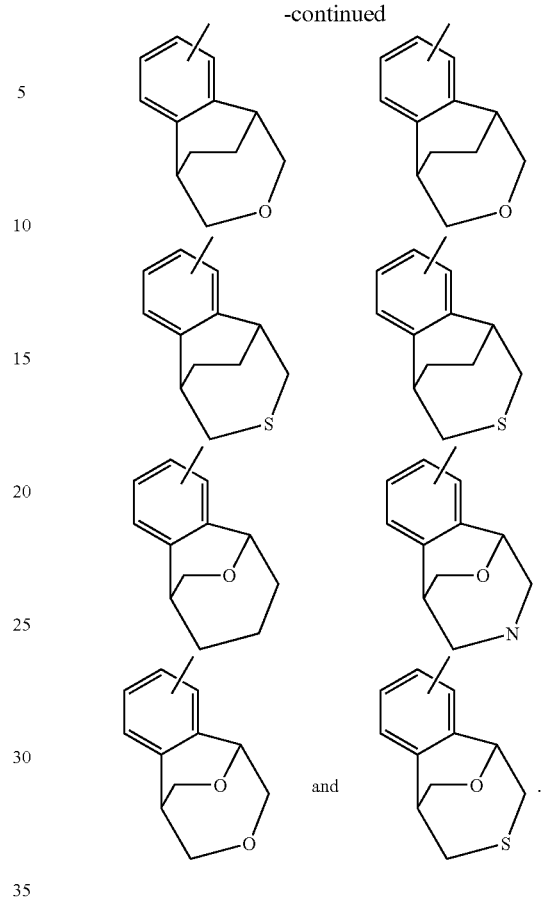

In another preferred embodiment, $Z^1$ and $Z^2$ are each —$CR^7$—.

In a more another preferred embodiment, $Y^1$ and $Y^2$ are each —$CR^7$—, each $R^7$ is the same or different, and each $R^7$ is independently selected from the group consisting of hydrogen, halogen, —$CF_3$, —$NO_2$, —CN, —$(C_1$-$C_6)$alkyl, —$(C_2$-$C_6)$alkynyl, —$(C_3$-$C_7)$cycloalkyl, —$(C_2$-$C_9)$heterocyclyl, —$(C_6$-$C_{10})$aryl, —$(C_1$-$C_9)$heteroaryl, —$NR^3R^4$, —$OR^5$, —$COR^5$, —$CO_2R^5$, —$CONR^3R^4$, —$SR^6$, —$SOR^6$, —$SO_2R^6$, —$SO_2NR^3R^4$, —$NHCOR^5$, —$NR^5CONR^3R^4$, and —$NR^3SO_2R^6$.

In one embodiment, the invention relates to a compound selected from the group consisting of compounds 1 through 409 as described in the Examples section of this application, or pharmaceutically acceptable salt thereof.

In a preferred embodiment, the compound is selected from the group consisting of:

N-(3-{[2-(12,12-Dioxo-12$\lambda^6$-thia-tricyclo[6.3.1.0$^{2.7}$] dodeca-2(7),3,5-trien-4-ylamino-5-trifluoromethyl-pyrimidin-4-ylamino]-methyl}-pyridin-2-yl)-N-methyl-methanesulfonamide;

N-(3-{[2-(10-Methanesulfonyl-10-aza-tricyclo[6.3.1.0$^{2.7}$] dodeca-2(7),3,5-trien-4-ylamino)-5-trifluoromethyl-pyrimidin-4-ylamino]-methyl}-pyridin-2-yl)-N-methyl-methanesulfonamide;

N-Methyl-N-(3-{[2-(10-trifluoroacetyl-10-aza-tricyclo [6.3.1.0$^{2.7}$]dodeca-2(7),3,5-trien-4-ylamino)-5-trifluoromethyl-pyrimidin-4-ylamino]-methyl}-pyridin-2-yl)-methanesulfonamide;

N-(3-{[2-(10-Aza-tricyclo[6.3.1.0$^{2.7}$]dodeca-2(7),3,5-trien-4-ylamino)-5-trifluoromethyl-pyrimidin-4-ylamino]-methyl}-pyridin-2-yl)-N-methyl-methanesulfonamide;

N-Methyl-N-(3-{[2-(9-trifluoroacetyl-1,2,3,4-tetrahydro-1,
  4-epiazano-naphthalen-6-ylamino)-5-trifluoromethyl-py-
  rimidin-4-ylamino]-methyl}-pyridin-2-yl)-methane-
  sulfonamide
N-Methyl-N-(3-{[2-(1,2,3,4-tetrahydro-1,4-epiazano-naph-
  thalen-6-ylamino)-5-trifluoromethyl-pyrimidin-4-
  ylamino]-methyl}-pyridin-2-yl)-methanesulfonamide;
N-(3-{[2-(9-Methanesulfonyl-1,2,3,4-tetrahydro-1,4-epia-
  zano-naphthalen-6-ylamino)-5-trifluoromethyl-pyrimi-
  din-4-ylamino]-methyl}-pyridin-2-yl)-N-methyl-meth-
  anesulfonamide,
and pharmaceutically acceptable salts thereof of each of the foregoing compounds.

In another preferred embodiment, the compound of the invention is selected from the group consisting of:
N-{(1R,2R)-2-[2-(9-Acetyl-(1S,4R)-1,2,3,4-tetrahydro-1,4-
  epiazano-naphthalen-6-ylamino)-5-trifluoromethyl-pyri-
  midin-4-ylamino]-methyl}-acetamide,
(+/−)-6-(4-Cyclobutylamino-5-trifluoromethyl-pyrimidin-2-
  ylamino)-1,2,3,4-tetrahydro-1,4-epiazano-naphthalene-9-
  carboxylic acid isopropylamide,
[(1S,4R)-6-(4-Cyclobutylamino-5-trifluoromethyl-pyrimi-
  din-2-ylamino)-1,2,3,4-tetrahydro-1,4-epiazano-naphtha-
  len-9-yl]-cyclopropyl-methanone,
N-{2-[6-(4-Cyclopropylamino-5-trifluoromethyl-pyrimi-
  din-2-ylamino)-(1S,4R)-1,2,3,4-tetrahydro-1,4-epiazano-
  naphthalen-9-yl]-2-oxo-ethyl}-N-methyl-acetamide,
1-[6-(4-Methylamino-5-trifluoromethyl-pyrimidin-2-
  ylamino)-(1R,4S)-1,2,3,4-tetrahydro-1,4-epiazano-naph-
  thalen-9-yl]-ethanone,
(+/−)-1-[-6-(4-Methoxy-5-trifluoromethyl-pyrimidin-2-
  ylamino)-1,2,3,4-tetrahydro-1,4-epiazano-naphthalen-9-
  yl]-ethanone,
(+/−)-1-[6-(4-Cyclopropylamino-5-trifluoromethyl-pyrimi-
  din-2-ylamino)-1,2,3,4-tetrahydro-1,4-epiazano-naphtha-
  len-9-yl]-ethanone,
(+/−)-N4-Cyclobutyl-N2-(9-methanesulfonyl-1,2,3,4-tet-
  rahydro-1,4-epiazano-naphthalen-6-yl)-5-trifluorom-
  ethyl-pyrimidine-2,4-diamine,
(+/−)-1-[6-(4-Cyclobutylamino-5-trifluoromethyl-pyrimi-
  din-2-ylamino)-1,2,3,4-tetrahydro-1,4-epiazano-naphtha-
  len-9-yl]-2-methylamino-ethanone,
Cyclopropyl-[6-(4-cyclopropylamino-5-trifluoromethyl-py-
  rimidin-2-ylamino)-(1R,4S)-1,2,3,4-tetrahydro-1,4-epia-
  zano-naphthalen-9-yl]-methanone,
1-[6-(4-Cyclopropylamino-5-trifluoromethyl-pyrimidin-2-
  ylamino)-(1S,4R)-1,2,3,4-tetrahydro-1,4-epiazano-naph-
  thalen-9-yl]-2-methoxy-ethanone,
(+/−)-N2-(9-Ethyl-1,2,3,4-tetrahydro-1,4-epiazano-naph-
  thalen-6-yl)-N4-methyl-5-trifluoromethyl-pyrimidine-2,
  4-diamine,
(+/−)-N4-Cyclopropyl-N2-(9-ethyl-1,2,3,4-tetrahydro-1,4-
  epiazano-naphthalen-6-yl)-5-trifluoromethyl-pyrimidine-
  2,4-diamine,
(+/−)-Acetic acid 2-[6-(4-cyclobutylamino-5-trifluorom-
  ethyl-pyrimidin-2-ylamino)-1,2,3,4-tetrahydro-1,4-epia-
  zano-naphthalen-9-yl]-2-oxo-ethyl ester,
2-Methyl-1-[-6-(4-propylamino-5-trifluoromethyl-pyrimi-
  din-2-ylamino)-(1S,4R)-1,2,3,4-tetrahydro-1,4-epiazano-
  naphthalen-9-yl]-propan-1-one,
(+/−)-N4-Cyclobutyl-N2-1,2,3,4-tetrahydro-1,4-epiazano-
  naphthalen-6-yl-5-trifluoromethyl-pyrimidine-2,4-di-
  amine,
6-(4-Cyclopropylamino-5-trifluoromethyl-pyrimidin-2-
  ylamino)-(1S,4R)-1,2,3,4-tetrahydro-1,4-epiazano-naph-
  thalene-9-carboxylic acid isopropylamide,
(+/−)-1-[6-(4-Cyclobutylamino-5-trifluoromethyl-pyrimi-
  din-2-ylamino)-1,2,3,4-tetrahydro-1,4-epiazano-naphtha-
  len-9-yl]-ethanone,
2-Hydroxy-1-[-6-(4-cyclobutylamino-5-trifluoromethyl-py-
  rimidin-2-ylamino)-(1S,4R)-1,2,3,4-tetrahydro-1,4-epia-
  zano-naphthalen-9-yl]-ethanone,
1-[-6-(4-Ethylamino-5-trifluoromethyl-pyrimidin-2-
  ylamino)-(1S,4R)-1,2,3,4-tetrahydro-1,4-epiazano-naph-
  thalen-9-yl]-2-methylamino-ethanone,
1-[-6-(4-Cyclobutylamino-5-trifluoromethyl-pyrimidin-2-
  ylamino)-(1S,4R)-1,2,3,4-tetrahydro-1,4-epiazano-naph-
  thalen-9-yl]-2-methylamino-ethanone,
1-[6-(4-Cyclopropylamino-5-trifluoromethyl-pyrimidin-2-
  ylamino)-(1S,4R)-1,2,3,4-tetrahydro-1,4-epiazano-naph-
  thalen-9-yl]-2-methylamino-ethanone,
(+/−)-2-Amino-1-[-6-(4-cyclobutylamino-5-trifluorom-
  ethyl-pyrimidin-2-ylamino)-1,2,3,4-tetrahydro-1,4-epia-
  zano-naphthalen-9-yl]-ethanone,
2-Fluoro-1-{6-[4-Cyclopropylamino-5-trifluoromethyl-py-
  rimidin-2-ylamino]-(1S,4R)-1,2,3,4-tetrahydro-1,4-epia-
  zano-naphthalen-9-yl}-ethanone,
N-{2-[-6-(4-Cyclobutylamino-5-trifluoromethyl-pyrimidin-
  2-ylamino)-(1S,4R)-1,2,3,4-tetrahydro-1,4-epiazano-
  naphthalen-9-yl]-2-oxo-ethyl}-N-methyl-acetamide,
2-Hydroxy-1-[-6-(4-cyclobutylamino-5-trifluoromethyl-py-
  rimidin-2-ylamino)-(1R,4S)-1,2,3,4-tetrahydro-1,4-epia-
  zano-naphthalen-9-yl]-ethanone,
N-{2-[6-(4-Ethylamino-5-trifluoromethyl-pyrimidin-2-
  ylamino)-(1S,4R)-1,2,3,4-tetrahydro-1,4-epiazano-naph-
  thalen-9-yl]-2-oxo-ethyl}-acetamide,
2-Amino-1-[-6-(4-ethylamino-5-trifluoromethyl-pyrimidin-
  2-ylamino)-(1S,4R)-1,2,3,4-tetrahydro-1,4-epiazano-
  naphthalen-9-yl]-ethanone,
2-Amino-1-[-6-(4-cyclobutylamino-5-trifluoromethyl-pyri-
  midin-2-ylamino)-(1S,4R)-1,2,3,4-tetrahydro-1,4-epia-
  zano-naphthalen-9-yl]-ethanone,
(+/−)-2-Hydroxy-1-[-6-(4-cyclobutylamino-5-trifluorom-
  ethyl-pyrimidin-2-ylamino)-(1S,4R)-1,2,3,4-tetrahydro-
  1,4-epiazano-naphthalen-9-yl]-ethanone,
2-Fluoro-1-[6-(4-Ethylamino-5-trifluoromethyl-pyrimidin-
  2-ylamino)-(1S,4R)-1,2,3,4-tetrahydro-1,4-epiazano-
  naphthalen-9-yl]-ethanone,
6-[4-(2-Methoxy-ethylamino)-5-trifluoromethyl-pyrimidin-
  2-ylamino]-(1S,4R)-1,2,3,4-tetrahydro-1,4-epiazano-
  naphthalene-9-carboxylic acid isopropylamide,
2-Fluoro-1-{6-[4-(2-methoxy-ethylamino)-5-trifluorom-
  ethyl-pyrimidin-2-ylamino]-1,2,3,4-tetrahydro-1,4-epia-
  zano-naphthalen-9-yl}-ethanone,
6-(4-Cyclopropylamino-5-trifluoromethyl-pyrimidin-2-
  ylamino)-(1R,4S)-1,2,3,4-tetrahydro-1,4-epiazano-naph-
  thalene-9-carboxylic acid isopropyl amide,
2-Amino-1-[-6-(4-cyclobutylamino-5-trifluoromethyl-pyri-
  midin-2-ylamino)-(1R,4S)-1,2,3,4-tetrahydro-1,4-epia-
  zano-naphthalen-9-yl]-ethanone,
1-[6-(4-Ethylamino-5-trifluoromethyl-pyrimidin-2-
  ylamino)-(1S,4R)-1,2,3,4-tetrahydro-1,4-epiazano-naph-
  thalen-9-yl]-2-methoxy-ethanone,
1-[-6-(4-Cyclobutylamino-5-trifluoromethyl-pyrimidin-2-
  ylamino)-(1S,4R)-1,2,3,4-tetrahydro-1,4-epiazano-naph-
  thalen-9-yl]-2-methoxy-ethanone,
(+/−)-1-{6-[4-(1,3-Dihydro-pyrrolo[3,4-c]pyridin-2-yl)-5-
  trifluoromethyl-pyrimidin-2-ylamino]-1,2,3,4-tetrahydro-
  1,4-epiazano-naphthalen-9-yl}-ethanone,
6-(4-Methylamino-5-trifluoromethyl-pyrimidin-2-
  ylamino)-(1S,4R)-1,2,3,4-tetrahydro-1,4-epiazano-naph-
  thalene-9-carboxylic acid isopropylamide, 6-(4-Ethylamino-5-trifluoromethyl-pyrimidin-2-ylamino)-(1S,4R)-1,2,3,4-tetrahydro-1,4-epiazano-naphthalene-9-carboxylic acid isopropylamide, (+/−)-1-[6-(4-Cyclopropylamino-5-methyl-pyrimidin-2-ylamino)-1,2,3,4-tetrahydro-1,4-epiazano-naphthalen-9-yl]-ethanone, 1-{6-[4-(2-Methoxy-ethylamino)-5-trifluoromethyl-pyrimidin-2-ylamino]-(1S,4R)-1,2,3,4-tetrahydro-1,4-epiazano-naphthalen-9-yl}-ethanone, 1-[6-(4-Ethylamino-5-trifluoromethyl-pyrimidin-2-ylamino)-(1S,4R)-1,2,3,4-tetrahydro-1,4-epiazano-naphthalen-9-yl]-ethanone, 2-Methyl-1-[6-(4-methylamino-5-trifluoromethyl-pyrimidin-2-ylamino)-(1S,4R)-1,2,3,4-tetrahydro-1,4-epiazano-naphthalen-9-yl]-propan-1-one, 6-(4-Cyclobutylamino-5-trifluoromethyl-pyrimidin-2-ylamino)-(1S,4R)-1,2,3,4-tetrahydro-1,4-epiazano-naphthalene-9-carboxylic acid methyl ester, 2-Methoxy-1-[6-(4-methylamino-5-trifluoromethyl-pyrimidin-2-ylamino)-(1S,4R)-1,2,3,4-tetrahydro-1,4-epiazano-naphthalen-9-yl]-ethanone, 2-Methoxy-1-{6-[4-(2-methoxy-ethylamino)-5-trifluoromethyl-pyrimidin-2-ylamino]-(1S,4R)-1,2,3,4-tetrahydro-1,4-epiazano-naphthalen-9-yl}-ethanone, and pharmaceutically acceptable salts thereof of each of the foregoing compounds.

In another preferred embodiment, the compound of the invention is selected from the group consisting of:

1-[6-(4-Cyclobutylamino-5-trifluoromethyl-pyrimidin-2-ylamino)-(1S,4R)-1,2,3,4-tetrahydro-1,4-epiazano-naphthalen-9-yl]-2-hydroxy-ethanone, 2-Amino-1-[6-(4-cyclobutylamino-5-trifluoromethyl-pyrimidin-2-ylamino)-(1S,4R)-1,2,3,4-tetrahydro-1,4-epiazano-naphthalen-9-yl]-ethanone, 1-[6-(5-Chloro-4-cyclobutylamino-pyrimidin-2-ylamino)-(1S,4R)-1,2,3,4-tetrahydro-1,4-epiazano-naphthalen-9-yl]-ethanone, N-{2-[6-(4-Cyclobutylamino-5-trifluoromethyl-pyrimidin-2-ylamino)-(1S,4R)-1,2,3,4-tetrahydro-1,4-epiazano-naphthalen-9-yl]-2-oxo-ethyl}-acetamide, 6-(4-Cyclobutylamino-5-trifluoromethyl-pyrimidin-2-ylamino)-(1S,2R)-1,2,3,4-tetrahydro-1,4-epiazano-naphthalene-9-carboxylic acid ethyl-amide, 1-[6-(4-Cyclobutylamino-5-trifluoromethyl-pyrimidin-2-ylamino)-(1S,4R)-1,2,3,4-tetrahydro-1,4-epiazano-naphthalen-9-yl]-2-methoxy-ethanone,

[6-(4-Cyclobutylamino-5-trifluoromethyl-pyrimidin-2-ylamino)-(1S,4R)-1,2,3,4-tetrahydro-1,4-epiazano-naphthalen-9-yl]-cyclopropyl-methanone, 1-[6-(4-Cyclobutylamino-5-trifluoromethyl-pyrimidin-2-ylamino)-(1S,4R)-1,2,3,4-tetrahydro-1,4-epiazano-naphthalen-9-yl]-ethanone, N4-Cyclobutyl-N2-[(1S,4R)-1,2,3,4-tetrahydro-1,4-epiazano-naphthalen-6-yl)-5-trifluoromethyl-pyrimidine-2,4-diamine, (+/−)-1-[6-(4-Cyclopropylamino-5-trifluoromethyl-pyrimidin-2-ylamino)-1,2,3,4-tetrahydro-1,4-epiazano-naphthalen-9-yl]-ethanone, 1-[6-(4-Cyclopropylamino-5-methyl-pyrimidin-2-ylamino)-(1S,4R)-1,2,3,4-tetrahydro-1,4-epiazano-naphthalen-9-yl]-ethanone, 1-[6-(4-Cyclopropylamino-5-fluoro-pyrimidin-2-ylamino)-(1S,4R)-,2,3,4-tetrahydro-1,4-epiazano-naphthalen-9-yl]-ethanone, 1-[6-(4-Ethylamino-5-methyl-pyrimidin-2-ylamino)-(1S,4R)-1,2,3,4-tetrahydro-1,4-epiazano-naphthalen-9-yl]-ethanone, 1-[6-(4-Ethylamino-5-fluoro-pyrimidin-2-ylamino)-(1S,4R)-1,2,3,4-tetrahydro-1,4-epiazano-naphthalen-9-yl]-ethanone, 1-[6-(4-ethylamino-5-chloro-pyrimidin-2-ylamino)-(1S,4R)-1,2,3,4-tetrahydro-1,4-epiazano-naphthalen-9-yl]-ethanone, 1-{6-[5-Fluoro-4-((S)-2-methoxymethyl-pyrrolidin-1-yl)-pyrimidin-2-ylamino]-(1S,4R)-1,2,3,4-tetrahydro-1,4-epiazano-naphthalen-9-yl}-ethanone, N4-Cyclobutyl-N2-[(1R,4S)-1,2,3,4-tetrahydro-1,4-epiazano-naphthalen-6-yl]-5-trifluoromethyl-pyrimidine-2,4-diamine, 1-[6-(4-Cyclobutylamino-5-methyl-pyrimidin-2-ylamino)-(1R,4S)-1,2,3,4-tetrahydro-1,4-epiazano-naphthalen-9-yl]-ethanone, 1-[6-(4-Cyclobutylamino-5-fluoro-pyrimidin-2-ylamino)-(1R,4S)-1,2,3,4-tetrahydro-1,4-epiazano-naphthalen-9-yl]-ethanone, N-{2-[6-(4-Cyclobutylamino-5-trifluoromethyl-pyrimidin-2-ylamino)-(1R,4S)-1,2,3,4-tetrahydro-1,4-epiazano-naphthalen-9-yl]-2-oxo-ethyl}-acetamide,

[6-(4-Cyclobutylamino-5-trifluoromethyl-pyrimidin-2-ylamino)-(1R,4S)-1,2,3,4-tetrahydro-1,4-epiazano-naphthalen-9-yl]-acetic acid methyl ester,

[6-(4-Cyclobutylamino-5-trifluoromethyl-pyrimidin-2-ylamino)-(1R,4S)-1,2,3,4-tetrahydro-1,4-epiazano-naphthalen-9-yl]-ethanone,

[6-(4-Cyclobutylamino-5-trifluoromethyl-pyrimidin-2-ylamino)-(1R,4S)-1,2,3,4-tetrahydro-1,4-epiazano-naphthalen-9-yl]-cyclopropyl-methanone, 1-[6-(4-Cyclobutylamino-5-trifluoromethyl-pyrimidin-2-ylamino)-(1R,4S)-1,2,3,4-tetrahydro-1,4-epiazano-naphthalen-9-yl]-2-methoxy-ethanone, 6-(4-Ethylamino-5-trifluoromethyl-pyrimidin-2-ylamino)-(1R,4S)-1,2,3,4-tetrahydro-1,4-epiazano-naphthalene-9-carboxylic acid isopropyl-amide, 1-[6-(4-Cyclobutylamino-5-trifluoromethyl-pyrimidin-2-ylamino)-(1R,4S)-1,2,3,4-tetrahydro-1,4-epiazano-naphthalen-9-yl]-2-methylamino-ethanone, 1-[6-(5-Chloro-4-cyclobutylamino-pyrimidin-2-ylamino)-(1R,4S)-1,2,3,4-tetrahydro-1,4-epiazano-naphthalen-9-yl]-ethanone, 1-[6-(4-Cyclobutylamino-5-fluoro-pyrimidin-2-ylamino)-(1R,4S)-1,2,3,4-tetrahydro-1,4-epiazano-naphthalen-9-yl]-ethanone, 1-[6-(4-Cyclobutylamino-5-ethyl-pyrimidin-2-ylamino)-(1R,4S)-1,2,3,4-tetrahydro-1,4-epiazano-naphthalen-9-yl]-ethanone, 1-[6-(4-Cyclobutylamino-5-methyl-pyrimidin-2-ylamino)-(1R,4S)-1,2,3,4-tetrahydro-1,4-epiazano-naphthalen-9-yl]-ethanone, N4-Cyclopropyl-N2-(1R,4S)-1,2,3,4-tetrahydro-1,4-epiazano-naphthalen-6-yl-5-trifluoromethyl-pyrimidine-2,4-diamine, N4-Cyclopropyl-N2-[(1R,4S)-9-methanesulfonyl-1,2,3,4-tetrahydro-1,4-epiazano-naphthalen-6-yl]-5-trifluoromethyl-pyrimidine-2,4-diamine, 1-[6-(4-Cyclopropylamino-5-trifluoromethyl-pyrimidin-2-ylamino)-(1R,4S)-1,2,3,4-tetrahydro-1,4-epiazano-naphthalen-9-yl]-2-methoxy-ethanone, (+/−)-1-{6-[4-(2-Methoxy-ethylamino)-5-trifluoromethyl-pyrimidin-2-ylamino]-1,2,3,4-tetrahydro-1,4-epiazano-naphthalen-9-yl}-ethanone, (+/−)-2-[6-(4-Cyclobutylamino-5-trifluoromethyl-pyrimidin-2-ylamino)-1,2,3,4-tetrahydro-1,4-epiazano-naphthalen-9-yl]-N,N-dimethyl-acetamide, and pharmaceutically acceptable salts thereof of each of the foregoing compounds.

The present invention also includes isotopically-labeled compounds, which are identical to those recited in formulae 1 and 2, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as, but not limited to, $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of the invention. Certain isotopically-labeled compounds of the present invention, for example those into which radioactive isotopes such as $^{3}$H and $^{14}$C are incorporated, are useful in drug and/or substrate tissue distribution assays. Tritiated, i.e., $^{3}$H, and carbon-14, i.e., $^{14}$C, isotopes are particularly preferred for their ease of preparation and detectability. Further, substitution with heavier isotopes such as deuterium, i.e., $^{2}$H, can afford certain therapeutic advantages resulting from greater metabolic stability, for example increased in vivo half-life or reduced dosage requirements and, hence, may be preferred in some circumstances. Isotopically-labeled compounds of this invention and prodrugs thereof can generally be prepared by carrying out the procedures disclosed in the Schemes and/or in the Examples and Preparations below, by substituting a readily available isotopically-labeled reagent for a non-isotopically-labeled reagent.

The present invention also related to the pharmaceutically acceptable acid addition salts of compounds of the invention. The acids which are used to prepare the pharmaceutically acceptable acid addition salts of the aforementioned base compounds of this invention are those which form non-toxic acid addition salts, i.e., salts containing pharmacologically acceptable anions, such as, but not limited to, the chloride, bromide, iodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)] salts.

The invention also relates to base addition salts of the compounds of the invention. The chemical bases that may be used as reagents to prepare pharmaceutically acceptable base salts of those compounds of the compounds of the invention that are acidic in nature are those that form non-toxic base salts with such compounds. Such non-toxic base salts include, but are not limited to those derived from such pharmacologically acceptable cations (e.g., calcium and magnesium), ammonium or water-soluble amine addition salts such as N-methylglucamine-(meglumine), and the lower alkanoammonium and other base salts of pharmaceutically acceptable organic amines.

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include a basic moiety, such as an amino group, may form pharmaceutically acceptable salt with various amino acids, in addition to the acids mentioned above.

This invention also encompasses pharmaceutical compositions containing prodrugs of compounds of the compounds of the invention. Compounds of the compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of the invention. The amino acid residues include the 20 naturally occurring amino acids commonly designated by three letter symbols and also include, 4-hydroxyproline, hydroxylysine, demosine, isodemosine, 2-methylhistidine, norvalin, beta-alanine, gamma-aminobutyric acid, citruline, homocysteine, homoserine, ornithine and methionine sulfone. Prodrugs also include compounds wherein carbonates, carbamates, amides and alkyl esters are covalently bonded to the above substituents of the compounds of the invention through the carbonyl carbon prodrug sidechain.

This invention also encompasses compounds of the invention containing protective groups. One skilled in the art will also appreciate that compounds of the invention can also be prepared with certain protecting groups that are useful for purification or storage and can be removed before administration to a patient. The protection and deprotection of functional groups is described in "Protective Groups in Organic Chemistry", edited by J. W. F. McOmie, Plenum Press (1973) and "Protective Groups in Organic Synthesis", 3rd edition, T. W. Greene and P. G. M. Wuts, Wiley-Interscience (1999).

The compounds of this invention include all stereoisomers (e.g., cis and trans isomers) and all optical isomers of compounds of the invention (e.g., R and S enantiomers), as well as racemic, diastereomeric and other mixtures of such isomers.

The compounds, salts and prodrugs of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds.

The present invention also includes atropisomers of the present invention Atropisomers refer to compounds of the invention that can be separated into rotationally restricted isomers.

The compounds of the invention may contain olefin-like double bonds. When such bonds are present, the compounds of the invention exist as cis and trans configurations and as mixtures thereof.

A "suitable substituent" is intended to mean a chemically and pharmaceutically acceptable functional group i.e., a moiety that does not negate the biological activity of the inventive compounds. Such suitable substituents may be routinely selected by those skilled in the art. Illustrative examples of suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—C(O)— groups, amino groups, alkyl- and dialkylamino groups, carbamoyl groups, alkylcarbonyl groups, alkoxycarbonyl groups, alkylaminocarbonyl groups dialkylamino carbonyl groups, arylcarbonyl groups, aryloxycarbonyl groups, alkylsulfonyl groups, arylsulfonyl groups and the like. Those skilled in the art will appreciate that many substituents can be substituted by additional substituents. Further examples of suitable substituents include those recited in the definition of compounds of the invention, the $R^1$ through $R^{12}$, as defined hereinabove.

The term "interrupted by" refers to compounds in which an element selected from the group consisting of —C($R^3$)=C($R^3$)—, —C(O)—, —(C=N—$R^3$)—, —(C=N—N$R^3R^4$)—, —C=N—N—C(O)—$R^5$, —C=N—N—C(O)O$R^3$, —(C=C$R^3R^4$)—, —(C=C($R^3$)C(O)—N$R^3R^4$))—, —(C=C($R^3$)C(O)O$R^6$)—, —SO$_2$—, —S—, —O— and —N$R^3$— is inserted into, e.g., an acyclic system or a ring system. For example, if a substituent is a heterocyclic group, such as an azetidine group:

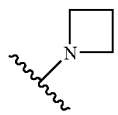

the ring may be interrupted by, e.g., a —C(O)— to form a pyrrolidinone group:

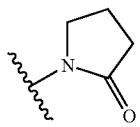

such that two ring atoms of the azetidine group are interrupted by the —C(O)— group. Compounds of the invention can accommodate up to three such replacements or interruptions.

As used herein, the term "alkyl," as well as the alkyl moieties of other groups referred to herein (e.g., alkoxy), may be linear or branched (such as methyl, ethyl, n-propyl, isopropyl, n-butyl, iso-butyl, secondary-butyl, tertiary-butyl); optionally substituted by 1 to 3 suitable substituents as defined above such as fluoro, chloro, trifluoromethyl, —($C_1$-$C_6$)alkoxy, —($C_6$-$C_{10}$)aryloxy, trifluoromethoxy, difluoromethoxy or —($C_1$-$C_6$)alkyl. The phrase "each of said alkyl" as used herein refers to any of the preceding alkyl moieties within a group such alkoxy, alkenyl or alkylamino. Preferred alkyls include ($C_1$-$C_6$)alkyl, more preferred are ($C_1$-$C_4$)alkyl, and most preferred are methyl and ethyl.

As used herein, the term "halogen" includes fluoro, chloro, bromo or iodo or fluoride, chloride, bromide or iodide.

As used herein, the term "alkenyl" means straight or branched chain unsaturate radicals of 2 to 6 carbon atoms, including, but not limited to ethenyl, 1-propenyl, 2-propenyl (allyl), iso-propenyl, 2-methyl-1-propenyl, 1-butenyl, 2-butenyl, and the like; optionally substituted by 1 to 3 suitable substituents as defined above such as fluoro, chloro, trifluoromethyl, —($C_1$-$C_6$)alkoxy, —($C_6$-$C_{10}$)aryloxy, trifluoromethoxy, difluoromethoxy or —($C_1$-$C_6$)alkyl.

As used herein, the term "alkynyl" is used herein to mean straight or branched hydrocarbon chain radicals having one triple bond including, but not limited to, ethynyl, propynyl, butynyl, and the like; optionally substituted by 1 to 3 suitable substituents as defined above such as fluoro, chloro, trifluoromethyl, —($C_1$-$C_6$)alkoxy, —($C_6$-$C_{10}$)aryloxy, trifluoromethoxy, difluoromethoxy or —($C_1$-$C_6$)alkyl.

The term "perfluorinated" refers to a compound containing 4 or more fluorine groups.

As used herein, the term "carbonyl" or "C(O)" (as used in phrases such as alkylcarbonyl, alkyl-C(O)— or alkoxycarbonyl) refers to the joinder of the >C=O moiety to a second moiety such as an alkyl or amino group (i.e. an amido group). Alkoxycarbonylamino (i.e. alkoxy-C(O)—NH—) refers to an alkyl carbamate group. The carbonyl group is also equivalently defined herein as C(O). Alkylcarbonylamino refers to groups such as acetamide.

As used herein, the term "cycloalkyl" refers to a mono-carboxylic ring (e.g., cyclopropyl, cyclobutyl, cyclopentyl, cyclohexyl, cycloheptyl, cyclooctyl, cyclononyl, cyclopentenyl, cyclohexenyl); optionally substituted by 1 to 3 suitable substituents as defined above such as fluoro, chloro, trifluoromethyl, —($C_1$-$C_6$)alkoxy, —($C_6$-$C_{10}$)aryloxy, trifluoromethoxy, difluoromethoxy or —($C_1$-$C_6$)alkyl.

As used herein, the term "cycloalkenyl" refers to a cycloalkyl as defined above and further containing 1 or 2 double bonds.

As used herein, the term "bicycloalkyl" refers to a cycloalkyl as defined above which is bridged to a second carboxylic ring (e.g., bicyclo[2.2.1]heptanyl, bicyclo[3.2.1]octanyl and bicyclo[5.2.0]nonanyl, etc.).

As used herein, the term "bicycloalkenyl" refers to a bicycloalkyl as defined above and further containing 1 or 2 double bonds.

As used herein, the term "aryl" means aromatic radicals such as phenyl, naphthyl, tetrahydronaphthyl, indanyl and the like; optionally substituted by 1 to 3 suitable substituents as defined above.

As used herein, the term "heteroaryl" refers to an aromatic heterocyclic group usually with one heteroatom selected from O, S and N in the ring. In addition to said heteroatom, the aromatic group may optionally have up to four N atoms in the ring. For example, heteroaryl group includes pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like; optionally substituted by 1 to 3 suitable substituents as defined above such as fluoro, chloro, trifluoromethyl, —($C_1$-$C_6$)alkoxy, —($C_6$-$C_{10}$)aryloxy, trifluoromethoxy, difluoromethoxy or —($C_1$-$C_6$)alkyl.

As used herein, the term heteroatom refers to an atom or group selected from N, O, S(O)$_n$ or NR, where n is an integer from 0 to 2 and R is a substituent group.

The term "heterocyclic" as used herein refers to a cyclic group containing 1-9 carbon atoms and 1 to 4 hetero atoms. Examples of such rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl, and the like. Examples of said monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-tetrahydrodiazin-1-yl, 1,4-oxazin-2-yl, 1,2,5-oxathiazin-4-yl and the like; optionally containing 1 or 2 double bonds and optionally substituted by 1 to 3 suitable substitutents as defined above such as fluoro, chloro, trifluoromethyl, $-(C_1-C_6)$alkoxy, $-(C_6-C_{10})$aryloxy, trifluoromethoxy, difluoromethoxy or $-(C_1-C_6)$alkyl.

As used herein, the term "heterobicycloalkyl" refers to a bicycloalkyl as defined above, wherein at least one of the carbon ring atoms has been replaced by at least one heteroatom (e.g. tropane).

As used herein, the term "heterobicycloalkenyl" refers to a heterobicycloalkyl as defined above and further containing 1 or 2 double bonds.

Nitrogen heteroatoms as used herein refers to N=, >N and —NH; wherein —N= refers to a nitrogen double bond, >N refers to a nitrogen containing two bond connections and —N refers to a nitrogen containing one bond.

"Embodiment" as used herein refers to specific groupings of compounds or uses into discrete subgenera. Such subgenera may be cognizable according to one particular substituent such as a specific $R^1$ or $R^3$ group. Other subgenera are cognizable according to combinations of various substituents, such as all compounds wherein $R^2$ is hydrogen and $R^1$ is $-(C_1-C_6)$alkyl.

The term "perfluorinated" or "perfluoro" refer to a compound having 4 or more fluorine groups.

The invention also relates to methods of making the compounds of the invention.

In one embodiment, the invention relates to a method for making a compound of formula 1 comprising allowing a compound of formula

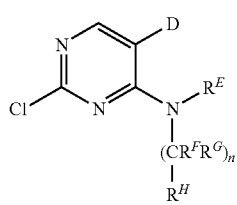

to react with a compound of formula

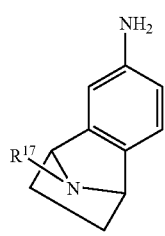

to provide the compounds of the invention; wherein $R^{17}$ is selected from the group consisting of $R^{12}$ as defined above and a protecting group.

In another embodiment, the invention relates to a method for making the compounds of the invention comprising allowing a compound of formula

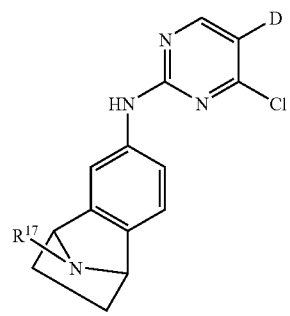

to react with a compound of formula

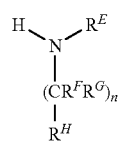

to provide the compounds of the invention wherein $R^{17}$ is as defined above.

When preparing compounds of the invention in accordance with the invention, it is open to a person skilled in the art to routinely select the form of the intermediate compound which provides the best combination of features for this purpose. Such features include the melting point, solubility, processability and yield of the intermediate form and the resulting ease with which the product may be purified on isolation.

The invention also relates to methods for making intermediate compounds that are useful for making the compounds of the invention.

As noted above, invention also relates to the pharmaceutically acceptable salts of the compounds of the invention. Pharmaceutically acceptable salts of the compounds of the invention include the acid addition and base salts thereof. Suitable acid addition salts are formed from acids which form non-toxic slats. Non-limiting examples of suitable acid addition salts include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Non-limiting examples of suitable base salts include the aluminum, arginine, benzathine, calcium, choline, diethylamine, diolamine, glycine, lysine, magnesium, meglumine, olamine, potassium, sodium, tromethamine and zinc salts.

Hemisalts of acids and bases my also be formed, for example, hemisulphate and hemicalcium salts.

For a review on suitable salts, see *Handbook of Pharmaceutical Salts: Properties, Selection, and Use* by Stahl and Wermuth (Wiley-VCH, 200). Methods for making pharmaceutically acceptable salts of compounds of the invention are known to one skill in the art.

The compounds of the invention may also exist in unsolvated and solvated forms. Accordingly, the invention also relates to the hydrates and solvates of the compounds of the invention.

The term "solvate" is used herein to describe a molecular complex comprising the compound of the invention and one or more pharmaceutically acceptable solvent molecules, for example, ethanol.

The term 'hydrate' is employed when said solvent is water. A currently accepted classification system for organic hydrates is one that defines isolated site, channel, or metal-ion coordinated hydrates—see Polymorphism in Pharmaceutical Solids by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The invention also relates to prodrugs of the compounds of the invention. Thus certain derivatives of compounds of the invention which may have little or no pharmacological activity themselves can, when administered into or onto the body, be converted into compounds of the invention having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of the invention with certain moieties known to those skilled in the art as 'pro-moieties' as described, for example, in Design of Prodrugs by H. Bundgaard (Elsevier, 1985).

Some non-limiting examples of prodrugs in accordance with the invention include (i) where the compound of the invention contains a carboxylic acid functionality (—COOH), an ester thereof, for example, a compound wherein the hydrogen of the carboxylic acid functionality of the compound of formula (I) is replace by $(C_1-C_6)$alkyl;

(ii) where the compound of the invention contains an alcohol functionality (—OH), an ether thereof, for example, a compound wherein the hydrogen of the alcohol functionality of the compound of the invention is replaced by $(C_1-C_6)$ alkanoyloxymethyl; and (iii) where the compound of the invention contains a primary or secondary amino functionality (—$NH_2$ or —NHR where R≠H), an amide thereof, for example, a compound wherein, as the case may be, one or both hydrogens of the amino functionality of the compound of the invention is/are replaced by $(C_1-C_6)$alkanoyl.

Further examples of replacement groups in accordance with the foregoing examples and examples of other prodrug types may be found in the aforementioned references.

Moreover, certain compounds of the invention may themselves act as prodrugs of other compounds of the invention.

Also includes within the scope of the invention are metabolites of compounds of the invention, that is, compounds formed in vivo upon administration of the drug. Some examples of metabolites in accordance with the invention include:

(i) where the compound of the invention contains a methyl group, an hydroxymethyl derivatives thereof (e.g., —CH→—$CH_2OH$);

(ii) where the compound of the invention contains an alkoxy group, an hydroxy derivative thereof (e.g., —$OR^7$→—OH);

(iii) where the compound of the invention contains a tertiary amino group, a secondary amino derivative thereof (e.g., —$NR^3R^4$→—$NHR^3$ or —$NHR^4$);

(iv) where the compound of the invention contains a secondary amino group, a primary derivative thereof (e.g., —$NHR^3$→—$NH_2$);

(v) where the compound of the invention contains a phenyl moiety, a phenol derivative thereof (e.g., -Ph→PhOH); and (vi) where the compound of the invention contains a secondary amide group, a carboxylic acid derivative thereof (e.g., —$CONH_2$→COOH).

Compounds of the invention containing one or more asymmetric carbon atoms can exist as two or more stereoisomers. Where a compound of the invention contains an alkenyl or alkenylene group, geometric cis/trans (or Z/E) isomers are possible. Where structural isomers are interconvertible via a low energy barrier, tautomeric isomerism ("tautomerism") can occur. This can take the form of proton tautomerism in compounds of the invention containing, for example, an amino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of the invention, including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of the invention contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0% to 50% by volume of an alcoholic solvent such as isopropanol, typically from 2% to 20%, and from 0 to 5% by volume of an alkylamine, typically 0.1% diethylamine. Concentration of the eluate affords the enriched mixture.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, Stereochemistry of Organic Compounds by E. L. Eliel and S. H. Wilen (Wiley, 1994).

The invention also relates to methods for the treatment of abnormal cell growth in a mammal. In one embodiment, the invention relates to a method for the treatment of abnormal cell growth in a mammal comprising administering to said mammal an amount of a compound of the invention that is effective in treating abnormal cell growth.

In another embodiment, the abnormal cell growth is cancer.

In another embodiment, the cancer is selected from the group consisting of lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, beast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers.

The invention also relates to methods for the treatment of cancer solid tumors in a mammal. In one embodiment, the invention relates to the treatment of cancer solid tumor in a mammal comprising administering to said mammal an amount of a compound of the invention that is effective in treating said cancer solid tumor.

In another embodiment, the cancer solid tumor is breast, lung, colon, brain, prostate, stomach, pancreatic, ovarian, skin (melanoma), endocrine, uterine, testicular, or bladder.

In another embodiment, the invention relates to a method for the treatment of abnormal cell growth in a mammal which comprises administering to said mammal an amount of a compound of the invention that is effective in treating abnormal cell growth in combination with an anti-tumor agent selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

In still another embodiment, the invention relates to a pharmaceutical composition comprising an effective amount of the compound of the invention, and a pharmaceutically acceptable carrier.

In another embodiment, the invention relates to a pharmaceutical composition useful for treating abnormal cell growth in a mammal comprising an effective amount of the compound of the invention, and a pharmaceutically acceptable carrier.

A particular aspect of this invention is directed to methods for treating or preventing a condition that presents with low bone mass in a mammal (including a human being) which comprise administering to a mammal in need of such treatment a condition that presents with low bone mass treating amount of a compound of the invention or a pharmaceutically acceptable salt of said compound of the invention.

This invention is particularly directed to such methods wherein the condition that presents with low bone mass is osteoporosis, frailty, an osteoporotic fracture, a bone defect, childhood idiopathic bone loss, alveolar bone loss, mandibular bone loss, bone fracture, osteotomy, periodontitis or prosthetic ingrowth.

A particular aspect of this invention is directed to methods for treating osteoporosis in a mammal (including a human being) which comprise administering to a mammal in need of such treatment an osteoporosis treating amount of a compound of the invention or a pharmaceutically acceptable salt of said compound.

Another aspect of this invention is directed to methods for treating a bone fracture or an osteoporotic fracture in a mammal which comprise administering to a mammal in need of such treatment a bone fracture treating or an osteoporotic fracture treating amount of a compound of the invention or a pharmaceutically acceptable salt of said compound.

The term "osteoporosis" includes primary osteoporosis, such as senile, postmenopausal and juvenile osteoporosis, as well as secondary osteoporosis, such as osteoporosis due to hyperthyroidism or Cushing syndrome (due to corticosteroid use), acromegaly, hypogonadism, dysosteogenesis and hypophospatasemia.

DETAILED DESCRIPTION OF THE INVENTION

The compounds of the invention can be prepared by the following general methods and by methods described in the Experimental Section.

Synthesis of 2,4-diamino Pyrimidines

Two non-limiting methods for making the 2,4-diamino pyrimidines of the invention are depicted in Schemes 1 and 2. Scheme 1 shows a method for preparing 2,4-diamino pyrimidines where D is a group other than a trifluoromethyl group.

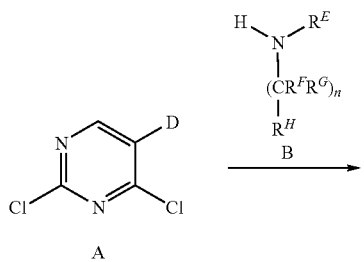

-continued

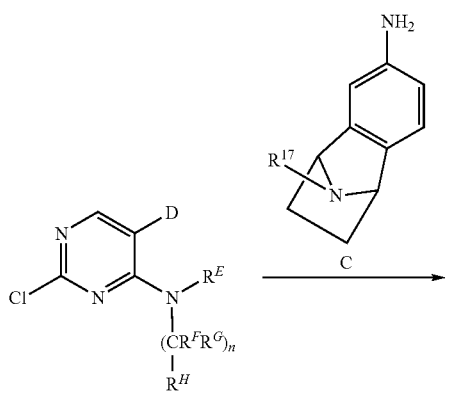

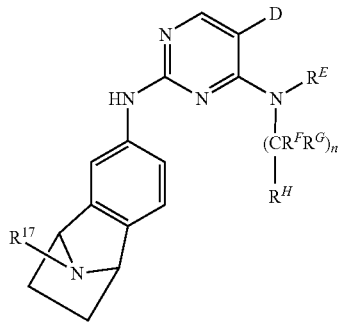

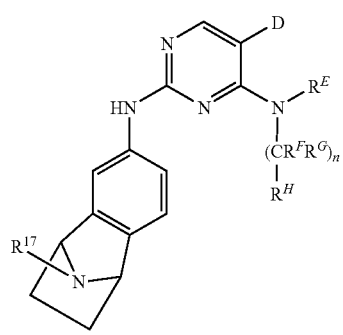

Scheme 2 shows a method for preparing 2,4-diamino-5-trifluoromethyl pyrimidines where the C-5 pyrimidine position is substituted with a trifluoromethyl group.

Scheme 2

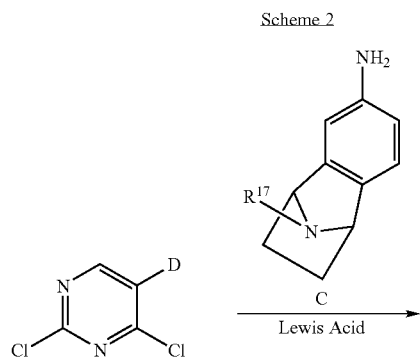

wherein said "$R^{17}$" can be either an $R^{12}$ group as defined above or a protecting group. Non limiting examples of protecting groups such as tert-butoxy carbonyl—(BOC), benzyloxy carbonyl—(CBZ), trifluoroacetamido—(TFA), or benzyl (Bn) may be employed as protecting groups as described by Green and Wuts, "Protective Groups in Organic Synthesis" Third Edition, Wiley Interscience. The protecting group can be removed at the appropriate time within the synthetic sequence such that the revealed unprotected atom can be further functionalized to prepare the compounds of depicted in Scheme 3, where $R^{17}$ can be an $R^{12}$ group as defined above or another group which can be further modified to provide $R^{12}$.

Scheme 3

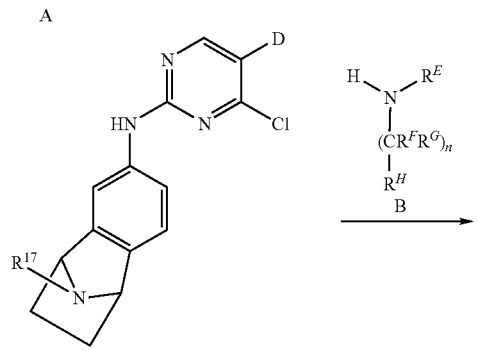

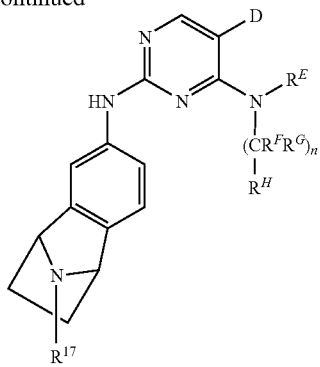

The compounds of general formulae A, B and C are commercially available or can be prepared by known methods (See, e.g., WO 2004056786, WO 2004056807; WO 2005023780; Angewandte Chemie, International Edition, 41(22), (200); Angewandte Chemie, International Edition, 43(33), 4364-4366 (2004); Archiv der Pharmazie (Weinheim, Germany), 314(1), 26-34 (1981); Bulletin of the Chemical Society of Japan, 59(12), 3988-90 (1986); Chemical & Pharmaceutical Bulletin, 33(6), 2313-22 (1985); Chemical Communications, 5, 143 (1966); Journal of Medicinal Chemistry, 31(2), 433-44 (1988); Journal of Organic Chemistry, 49(21), 4025-9 (1984); Journal of Organic Chemistry, 67(23), 8043 (2002); Journal of Organic Chemistry, 55(2), 405-6 (1990); Journal of Organic Chemistry, 60(21), 6904-11 (1995); Journal of the American Chemical Society, 109(18), 5393-403 (1987); Journal of the American Chemical Society, 125(49), 15191-15199 (2003); Journal of the Chemical Society, Perkin Transactions 1: Organic and Bio-Organic Chemistry (1972-1999), (15), 1647-54 (1976); Journal of the Chemical Society, Perkin Transactions 1: Organic and Bio-Organic Chemistry (1972-1999), (8), 2013-16; (1979); Journal of the Chemical Society, Perkins Transactions I, 1981, 1846; March and Smith, Text Book on Organic Chemistry; Monatshefte fuer Chemie, 128(3), 271-280 (1997); New Journal of Chemistry 29(1), 42-56 (2005); Organic & Biomolecular Chemistry, 1(21), 3787-3798 (2003); Synlett, (1), 58-60 (1998); Synlett, (7), 1103-1105 (1999); Synthesis, (11), 1755-1758 (2004); Synthesis Communications, 20(12), 1877-84 (1990); Tetrahedron, 60 (16), 3611 (2004); U.S. Pat. No. 4,761,713; U.S. Pat. No. 6,605,610; Journal of the American Chemical Society 91(24), 6775-8 (1969); Journal of the American Chemical Society, 91(5), 1170-5 (1969); Journal of the American Chemical Society, 88(18), 4289-90 (1966); and references cited within the foregoing references).

These compounds depicted in Schemes 1-3 are also useful for the preparation of other similar ring systems and also both larger and smaller rings for the compounds of formula C described below:

[2.2.1] Ring Systems

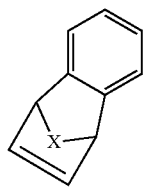

where X is (CH$_2$): 1,4-Dihydro-1,4-methano-naphthalene where X is Oxygen: 11-Oxa-tricyclo[6.2.1.0$^{2.7}$]undeca-2,4,6,9-tetraene where X is N—H: 1,4-Dihydro-1,4-epiazano-naphthalene where X is Sulfur: 11-Thia-tricyclo[6.2.1.0$^{2.7}$]undeca-2,4,6,9-tetraene

[2.2.2] Ring Systems

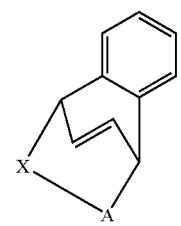

where both X and A are CH$_2$: Tricyclo[6.2.2.0$^{2.7}$]dodeca-2,4,6,9-tetraene where X is N-Boc, A is CH$_2$: 9-Aza-tricyclo[6.2.2.0$^{2.7}$]dodeca-2,4,6,11-tetraene-9-carboxylic acid methyl ester where X is N, A is C═O: 9-Aza-tricyclo[6.2.2.0$^{2.7}$]dodeca-2,4,6,11-tetraene-10-one As noted above, compounds of the general formula C can be prepared by known methods following the general procedure depicted in Scheme 4. Based upon chemistry that the compounds of the general structural formula C.

Scheme 4

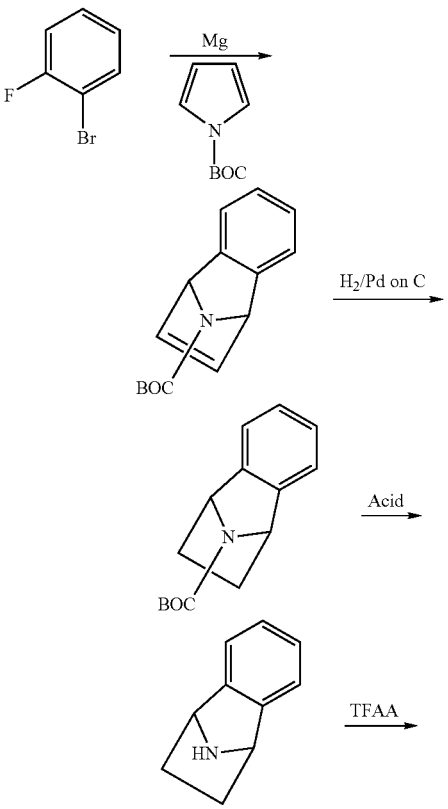

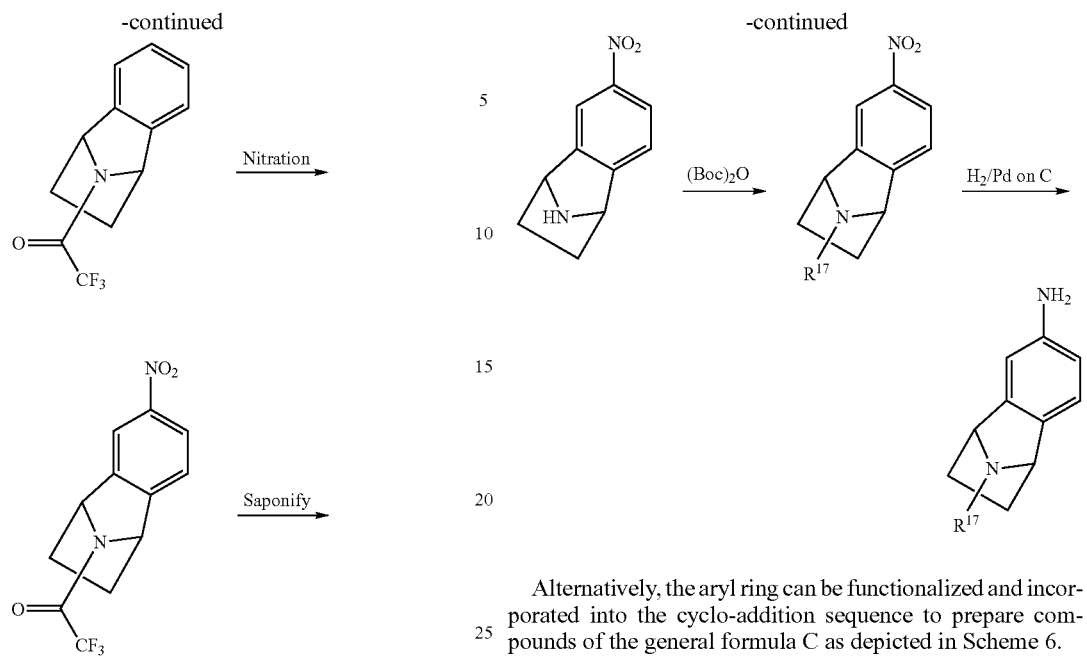

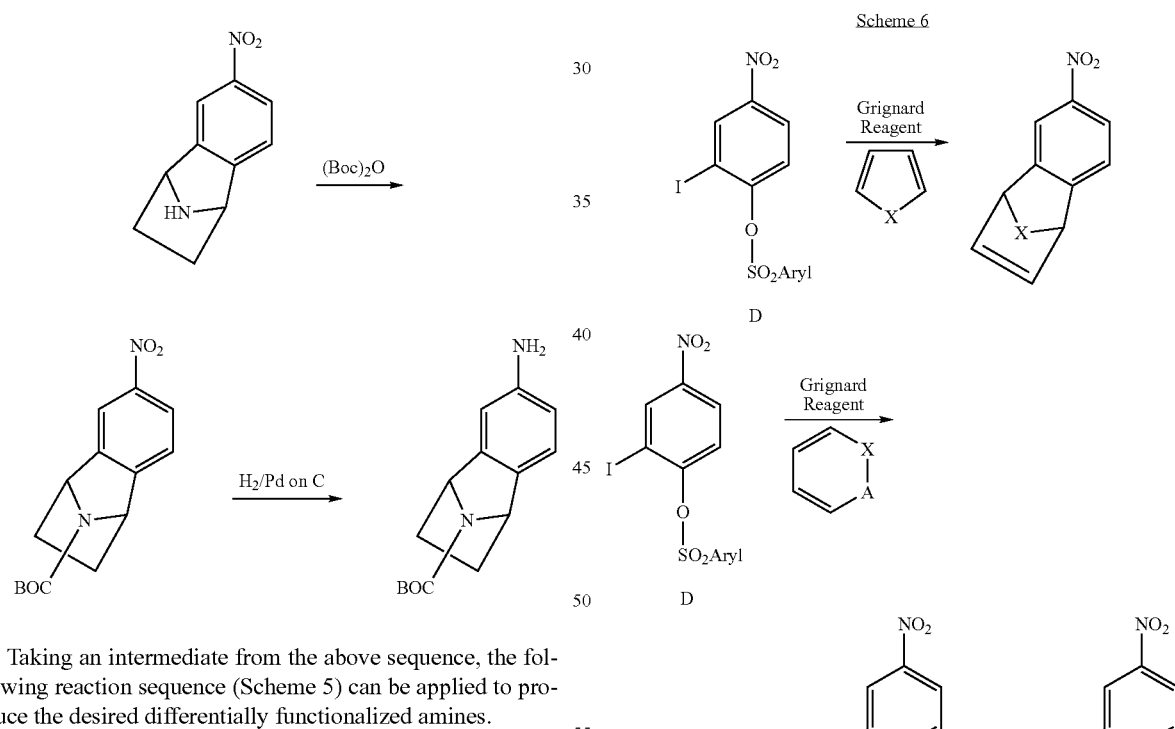

Taking an intermediate from the above sequence, the following reaction sequence (Scheme 5) can be applied to produce the desired differentially functionalized amines.

Alternatively, the aryl ring can be functionalized and incorporated into the cyclo-addition sequence to prepare compounds of the general formula C as depicted in Scheme 6.

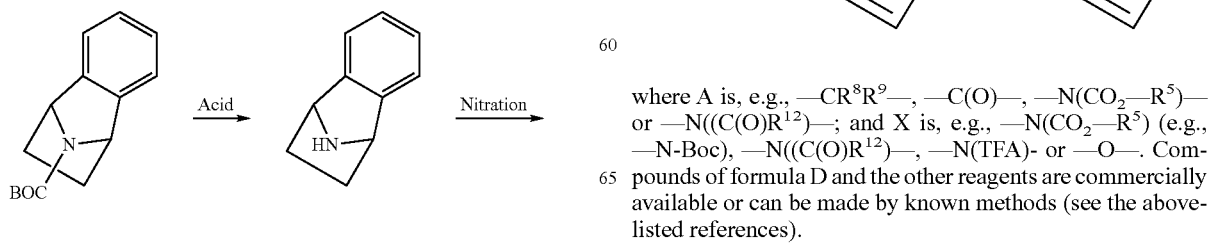

where A is, e.g., —CR$^8$R$^9$—, —C(O)—, —N(CO$_2$—R$^5$)— or —N((C(O)R$^{12}$)—; and X is, e.g., —N(CO$_2$—R$^5$) (e.g., —N-Boc), —N((C(O)R$^{12}$)—, —N(TFA)- or —O—. Compounds of formula D and the other reagents are commercially available or can be made by known methods (see the above-listed references).

Alternatively, the following reaction schemes (Schemes 7a and 7b) can be used to prepare compounds of general formula C (see the above-listed references):

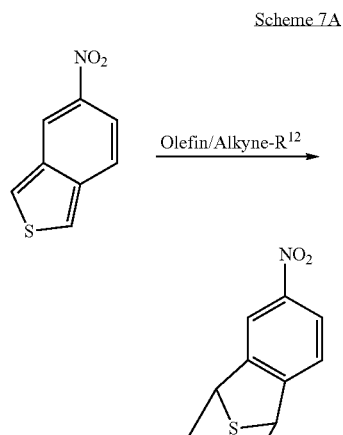

Scheme 7A

Scheme 7B

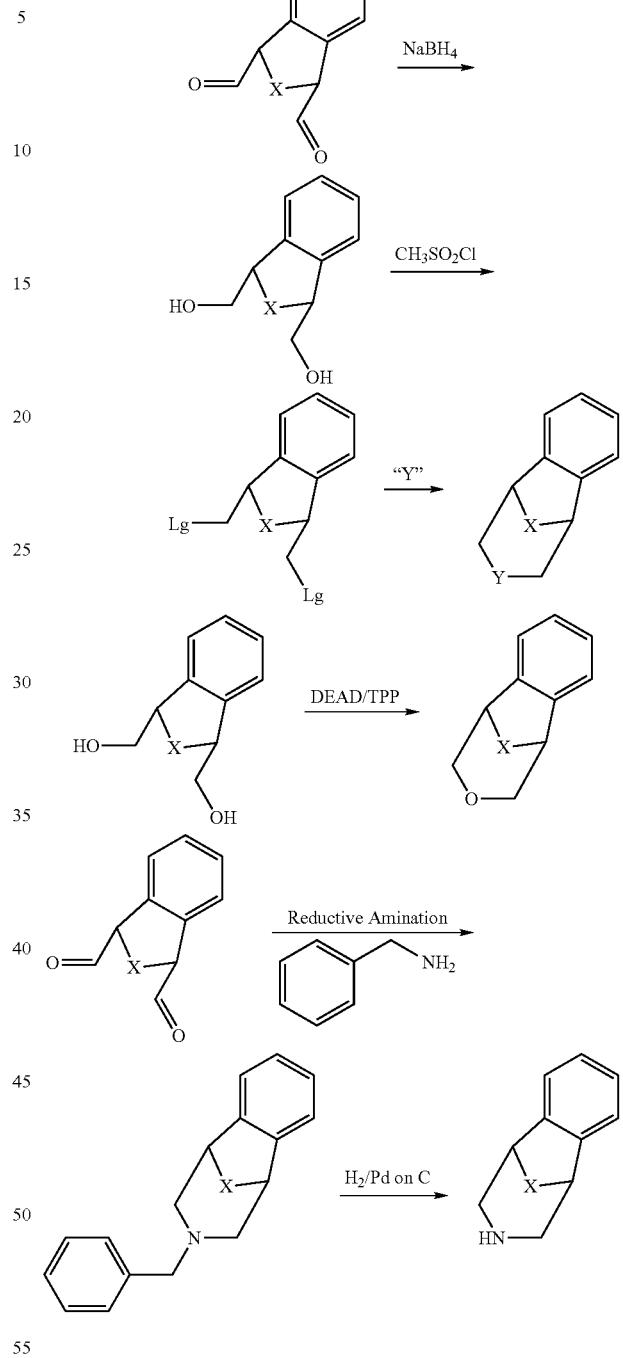

wherein an "Olefin" is defined as a group containing either a double bond or triple bond and $R^{17}$ is as defined above. The number of groups on the olefin can vary from 1 to 4 depending on the dienophile used. Non-limiting examples of useful ethylenic olefins are acyclic un-functionalized olefins, cyclic functionalized olefins, cyclic un-functionalized olefins, and cyclic functionalized olefins. Non-limiting examples of useful acetylenic olefins include substituted acetylenes and non-substituted acetylenes.

Compounds of the general formula C can also be prepared by ring expansion starting with a heterocycle by known methods (see the above-listed references) as depicted in Scheme 8:

Scheme 8

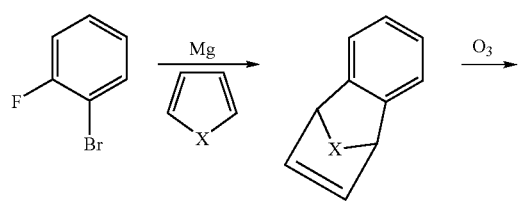

where X=N-Boc, N-TFA, or oxygen; "Y"=Na$_2$S or H$_2$N-Benzyl; Y=Sulfur or N—R; Lg=leaving group (such as mesylate, tosylate); O=oxygen; DEAD=diethyl azodicarboxylate; and TPP=triphenyl phosphine.

Alternatively, the compounds of general formula C can be prepared by known methods (see the above-listed references) starting with a heteroalkane by ring expansion according to known methods as depicted in Scheme 8:

Scheme 9

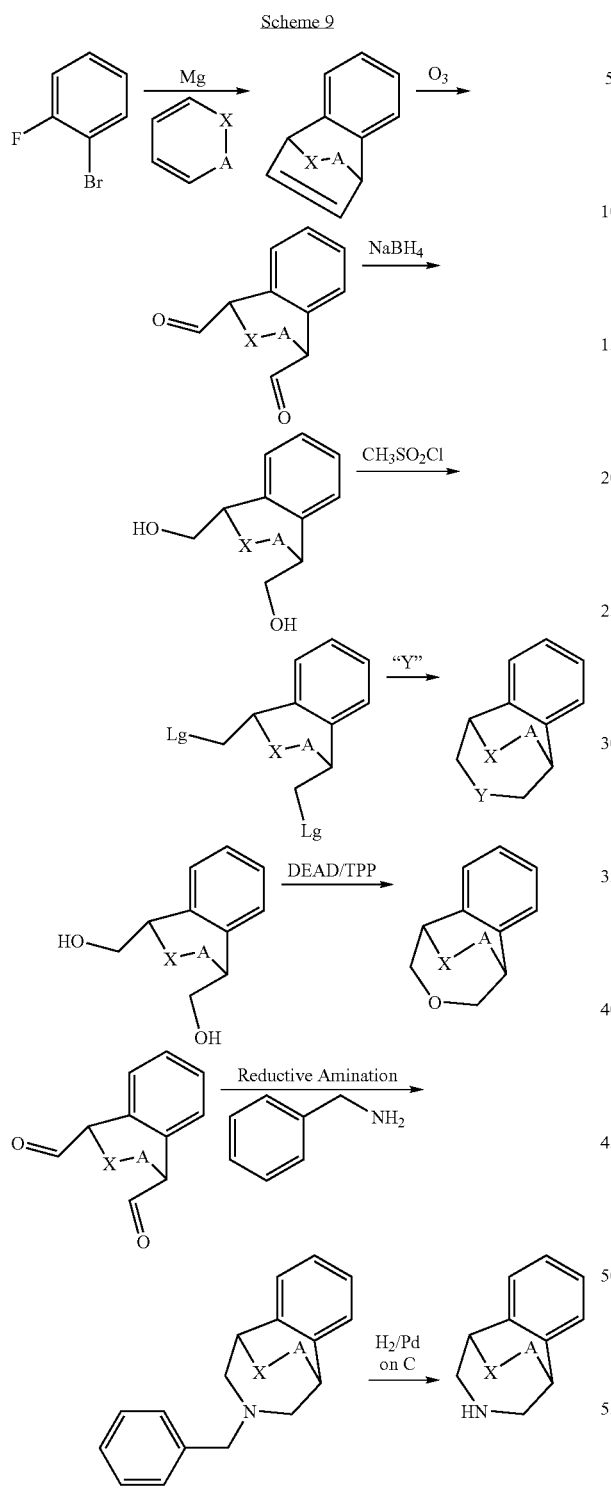

where X=N-Boc, N—CO$_2$R or N-TFA; A=CH$_2$, C=O or N—CO$_2$R; "Y"=Na$_2$S or H$_2$N-Benzyl; Y=sulfur or N—R; Lg=leaving group (such as mesylate, tosylate); O=oxygen; DEAD=diethyl azodicarboxylate; and TPP=triphenyl phosphine.

Non-limiting methods for functionalizing olefins include 2-3 dipole cycloaddition reaction, aziridination, cyclopropanation, decarboxylation reactions, Dieckmann condensation, Diels-Alder reaction, ene reaction, epoxidation, Favorskii reaction, Friedel Crafts reaction, halogenation, Heck reaction (to add additional carbon functionality), hetero-ene reaction, hydride reductions (e.g., of aldehydes, ketones, esters amides), hydroboration-oxidation of the olefin (to install a hydroxy group), Michael reaction, olefin metathasis, osmylation of the olefin to install cis diols, oxidation of the installed hydroxy group to ketone, and reductive amination of ketones with amines. The general method for functionalizing the olefinic groups are depicted in Scheme 10 (where FG is a functional group) and are described in, e.g., the above-listed references.

Scheme 10

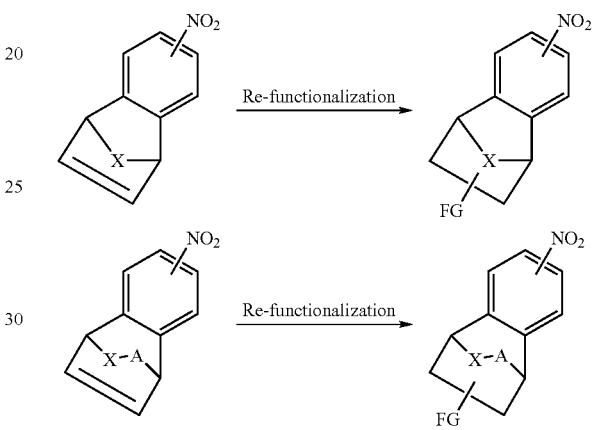

Alternatively, compounds of the invention, where either L$^1$=an atom linker and L$^2$=a bond or L$^1$=bond and L$^2$=an atom linker, can be prepared by forming a compound of general formula C followed by reaction with the appropriate 5-substituted-2,4-diamino pyrimidine as depicted in Schemes 11 or 12.

Scheme 11

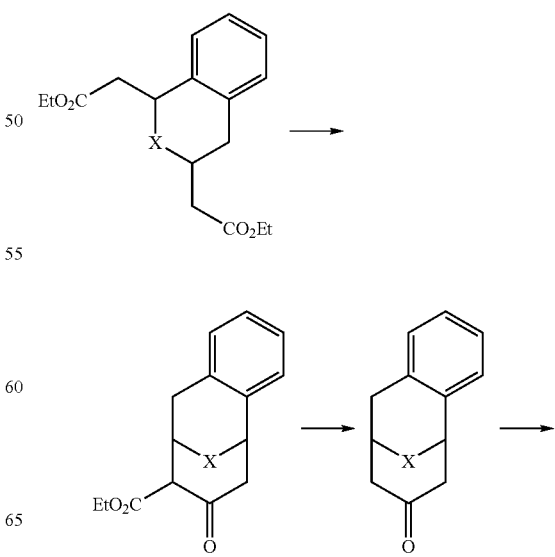

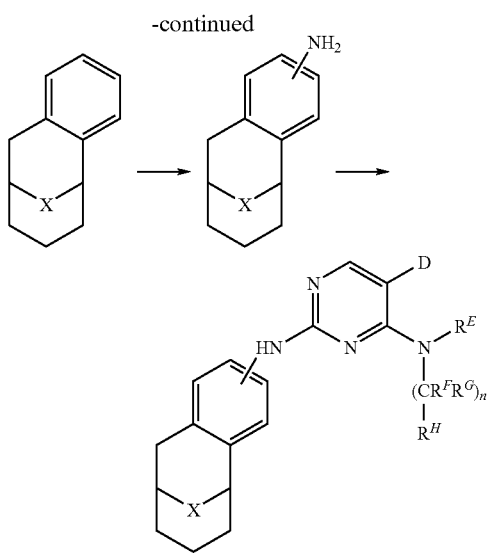

where X can be —S—, —SO$_2$—, —O—, —NR$^{17}$— or —CR$^8$R$^9$— as defined above.

Scheme 12

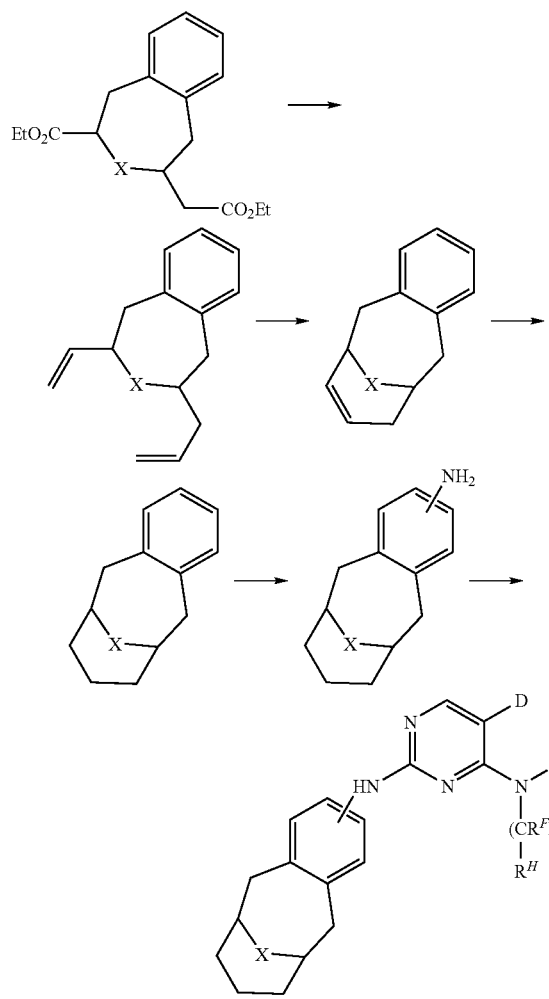

where X can be —S—, —SO$_2$—, —O—, —NR$^{17}$— or —CR$^8$R$^9$— as defined above.

In Vitro and In Vivo Assays

As noted above, the compounds of the invention are useful as inhibitors of non-receptor tyrosine kinases such as, e.g., FAK, Aurora-1, Aurora-2, HgK and Pyk. Methods for determining the in vitro and in vivo activity of these compounds inhibitors of non-receptor tyrosine kinases are described below:

In-Vitro Activity of FAK:

The in vitro activity of the compounds of the compounds of the invention may be determined by the following procedure. More particularly, the following assay provides a method to determine whether compounds of the compounds of the invention inhibit the tyrosine kinase activity of the catalytic construct FAK(410-689). The assay is an ELISA-based format, measuring the inhibition of poly-glu-tyr phosphorylation by FAK(410-689).

The assay protocol has three parts:
  I. Purification and cleavage of His-FAK(410-689)
  II. FAK410-689 (a.k.a. FAKcd) Activation
  III. FAKcd Kinase ELISA Materials:
  Ni-NTA agarose (Qiagen)
  XK-16 column (Amersham-Pharmacia)
  300 mM Imidizole
  Superdex 200 HiLoad 16/60 prep grade column (Amersham Biotech.)
  Antibody: Anti-Phosphotyrosine HRP-Conjugated Py20 (Transduction labs)
  FAKcd: Purified and activated in house
  TMB Microwell Peroxidase Substrate (Oncogene Research Products #CL07)
  BSA: Sigma #A3294
  Tween-20: Sigma #P1379
  DMSO: Sigma #D-5879
  D-PBS: Gibco #14190-037

Reagents for Purification:
  Buffer A: 50 mM HEPES pH 7.0
  500 mM NaCl
  0.1 mM TCEP
  Complete™ protease inhibitor cocktail tablets (Roche)
  Buffer B: 25 mM HEPES pH 7.0
  400 mM NaCl
  0.1 mM TCEP
  Buffer C: 10 mM HEPES pH 7.5
  200 mM Ammonium Sulfate
  0.1 mM TCEP Reagents for Activation
  FAK(410-689): 3 tubes of frozen aliquots at 150 ul/tube for a total of 450 ul at 1.48 mg/ml (660 ug)
  His-Src(249-524): ~0.74 mg/ml stock in 10 mM HEPES, 200 mM (NH4)2SO4
  Src reaction buffer (Upstate Biotech):
  100 mM Tris-HCl pH7.2
  125 mM MgCl2
  25 mM MnCl2
  2 mM EDTA
  250 um Na3VO4
  2 mM DTT
  Mn2+/ATP cocktail (Upstate Biotech)
  75 mM MnCl2
  500 um ATP
  20 mM MOPS pH 7.2

1 mM Na3VO4
25 mM glycerol phosphate
5 mM EGTA
1 mM DTT
ATP: 150 mM stock
$MgCl_2$: 1 M Stock
DTT: 1M stock Reagents for FAKcd Kinase ELISA
Phosphorylation Buffer:
50 mM HEPES, pH 7.5
125 mM NaCl
48 mM MgCl2
Wash Buffer: TBS+0.1% Tween-20.
Blocking Buffer:
Tris Buffer Saline
3% BSA
0.05% Tween-20, filtered
Plate Coating Buffer:
50 mg/ml Poly-Glu-Tyr (Sigma #P0275) in Phosphate buffer Saline (DPBS).
ATP: 0.1M ATP in H2O or HEPES, pH7
Note: ATP Assay Buffer:
Make up as 75 uM ATP in PBS, so that 80 ul in 120 ul reaction volume=50 uM final ATP concentration.

I. Purification of His-FAKcd(410-689)

1. Resuspended 130 g baculovirus cell paste containing the over expressed His-FAKcd410-689 recombinant protein in 3 volumes (400 ml) of Buffer A.
2. Lyse cells with one pass on a microfluidizer.
3. Remove cell debris by centrifugation at 4° C. for 35 minutes at 14,000 rpm in a Sorval SLA-1500 rotor.
4. Transfer the supernatant to a clean tube and add 6.0 ml of Ni-NTA agarose (Qiagen).
5. Incubate the suspension with gentle rocking at 4° C. for 1 hour.
6. Centrifuge suspension at 700×g in a swinging bucket rotor.
7. Discard the supernatant and resuspend the agarose beads in 20.0 ml of Buffer A.
8. Transfer the beads to an XK-16 column (Amersham-Pharmacia) connected to a FPLC™.
9. Wash the agarose-beads with 5 column volumes of a Buffer A and elute off the column with a step gradient of a Buffer A containing 300 mM Imidizole.
10. Perform a buffer exchange of the eluted fractions into Buffer B.
11. Following buffer exchange, pool the fractions and add thrombin at a 1:300 (w/w) ratio and incubated overnight at 13° C. to remove the N-terminal His-tag (His-FAK410-698→FAK410-689 (a.k.a. FAKcd)).
12. Add the reaction mixture back into the Ni-NTA column equilibrated with Buffer A and collect the flow-through.
13. Concentrate the flow-through down to 1.7 ml and load directly onto a Superdex 200 HiLoad 16/60 prep grade column equilibrated with Buffer C. The desired protein elutes between 85-95 ml.
14. Aliquot the FAKcd protein and store frozen at −80° C.

II. FAK Activation

1. To 450 ul of FAK(410-689) at 1.48 mg/ml (660 ug) add the following:
   30 ul of 0.037 mg/ml (1 uM) His-Src(249-524)
   30 ul of 7.5 mM ATP
   12 ul of 20 mM MgCl2
   10 ul Mn2+/ATP cocktail (UpState Biotech.)
   4 ul of 6.7 mM DTT
   60 ul Src Reaction Buffer (UpState Biotech.)
2. Incubate Reaction for at least 3 hours at room temperature At time $t_0$, almost all of the FAK(410-689) is singly phosphorylated. The second phosphorylation is slow. At $t_{120}$ (t=120 minutes), add 10 ul of 150 mM ATP.

$T_0$=(Start) 90% singly phosphorylated FAK(410-689) (1 PO4)
$T_{43}$=(43 min) 65% singly phosphorylated (1 PO4), 35% doubly phosphorylated (2 PO4)
$T_{90}$=(90 min) 45% 1 PO4, 55% 2 PO4
$T_{150}$=15% 1 PO4, 85% 2 PO4
$T_{210}$=<10% 1 PO4, >90% 2 PO4 desalted sample 3. Add 180 ul aliquots of the desalted material to NiNTA spin column and incubate on spin column
4. Spin at 10 k rpm (microfuge), for 5 minutes to isolate and collect flow through (Activated FAK(410-689)) and remove His-Src (captured on column)

III. FAKcd Kinase ELISA

1. Coat 96-well Nunc MaxiSorp plates with poly-glu-tyr (pGT) at 10 ug/well: Prepare 10 ug/ml of pGT in PBS and aliquot 100 ul/well. Incubate the plates at 37° C. overnight, aspirate the supernatant, wash the plates 3 times with Wash Buffer, and flick to dry before storing at 4° C.
2. Prepare compound stock solutions of 2.5 mM in 100% DMSO. The stocks are subsequently diluted to 60× of the final concentration in 100% DMSO, and diluted 1:5 in Kinase Phosphorylation Buffer.
3. Prepare at 75 uM working ATP solution in Kinase phosphorylation buffer. Add 80 ul to each well for a final ATP concentration of 50 uM.
4. Transfer 10 ul of the diluted compounds (0.5 log serial dilutions) to each well of the pGT assay plate, running each compound in triplicates on the same plate.
5. Dilute on ice, FAKcd protein to 1:1000 in Kinase Phosphorylation Buffer. Dispense 30 ul per well.
6. Note: Linearity and the appropriate dilution must be pre-determined for each batch of protein. The enzyme concentration selected should be such that quantitation of the assay signal will be approximately 0.8-1.0 at OD450, and in the linear range of the reaction rate.
7. Prepare both a No ATP control (noise) and a No Compound Control (Signal):
8. (Noise) One blank row of wells receives 10 ul of 1:5 diluted compounds in DMSO, 80 ul of Phosphorylation buffer (minus ATP), and 30 ul FAKcd solution.
9. (Signal) Control wells receive 10 ul of 1:5 diluted DMSO (minus Compound) in Kinase phosphorylation buffer, 80 ul of 75 uM ATP, and 30 ul of 1:1000 FAKcd enzyme.
10. Incubate reaction at room temperature for 15 minutes with gentle shaking on a plate shaker.
11. Terminate the reaction by aspirating off the reaction mixture and washing 3 times with wash buffer.
12. Dilute phospho-tyrosine HRP-conjugated (pY20HRP) antibody to 0.250 ug/ml (1:1000 of Stock) in blocking buffer. Dispense 100 ul per well, and incubate with shaking for 30 minutes at R. T.
13. Aspirate the supernatant and wash the plate 3 times with wash buffer.
14. Add 100 ul per well of room temperature TMB solution to initiate color development. Color development is terminated after approximately 15-30 sec. by the addition of 100 ul of 0.09M H2SO4 per well.

15. The signal is quantitated by measurement of absorbance at 450 nm on the BioRad microplate reader or a microplate reader capable of reading at OD450.

16. Inhibition of tyrosine kinase activity would result in a reduced absorbance signal. The signal is typically 0.8-1.0 OD units. The values are reported as $IC_{50s}$, uM concentration.

FAK Inducible Cell-Based ELISA: Final Protocol

Materials:

Reacti-Bind Goat Anti-Rabbit Plates 96-well (Pierce Product#15135ZZ @115.00 USD)

FAKpY397 rabbit polyclonal antibody (Biosource #44624 @315.00 USD)

ChromePure Rabbit IgG, whole molecule (Jackson Laboratories #001-000-003 @60/25 mg USD)

UBI αFAK clone 2A7 mouse monoclonal antibody (Upstate#05-182 @ 289.00 USD)

Peroxidase-conjugated AffiniPure Goat Anti-Mouse IgG (Jackson labs #115-035-146 @95/1.5 ml USD)

SuperBlock TBS (Pierce Product#37535ZZ @99 USD)

Bovine Serum Albumin (Sigma #A-9647 @117.95/100 g USD)

TMB Peroxidase substrate (Oncogene Research Products #CL07-100 ml @40.00 USD)

Na3VO4 Sodium Orthovanadate (Sigma #S6508 @43.95/50 g USD)

MTT substrate (Sigma #M-2128 @25.95/500 mg USD)

Growth Media: DMEM+10% FBS, P/S, Glu, 750 ug/ml Zeocin and 50 ug/ml Hygromycin (Zeocin InVitrogen #R250-05 @ 725 USD and Hygromycon InVitrogen #R220-05 @ 150 USD)

Mifepristone InVitrogen # H110-01 @ 125 USD

Complete™ EDTA-free Protease Inhibitor pellet Boehringer Mannheim #1873580

FAK cell-based Protocol for selectivity of kinase-dependent phosphoFAKY397

Procedure:

An inducible FAK cell-based assay in ELISA format for the screening of chemical matter to identify tyrosine kinase specific inhibitors was developed. The cell-based assay exploits the mechanism of the GeneSwitch™ system (InVitrogen) to exogenously control the expression and phosphorylation of FAK and the kinase-dependent autophosphorylation site at residue Y397.

Inhibition of the kinase-dependent autophosphorylation at Y397 results in a reduced absorbance signal at OD450. The signal is typically 0.9 to 1.5 OD450 units with the noise falling in the range of 0.08 to 0.1 OD450 units. The values are reported as IC50s, uM concentration.

On day 1, grow A431•FAKwt in T175 flasks. On the day prior to running the FAK cell-assay, seed A431•FAKwt cells in growth media on 96-well U-bottom plates. Allow cells to sit at 37° C., 5% CO2 for 6 to 8 hours prior to FAK induction. Prepare Mifepristone stock solution of 10 uM in 100% Ethanol. The stock solution is subsequently diluted to 10× of the final concentration in Growth Media. Transfer 10 ul of this dilution (final concentration of 0.1 nM Mifepristone) into each well. Allow cells to sit at 37° C., 5% CO2 overnight (12 to 16 hours). Also, prepare control wells without Mifepristone induction of FAK expression and phosphorylation.

On day 2, coat Goat Anti-Rabbit plate(s) with 3.5 ug/ml of phosphospecific FAKpY397 polyclonal antibody prepared in SuperBlock TBS buffer, and allow plate(s) to shake on a plate shaker at room temperature for 2 hours. Optionally, control wells may be coated with 3.5 ug/ml of control Capture antibody (Whole Rabbit IgG molecules) prepared in SuperBlock TBS. Wash off excess FAKpY397 antibody 3 times using buffer. Block Anti-FAKpY397 coated plate(s) with 200 ul per well of 3% BSA/0.5% Tween Blocking buffer for 1 hour at room temperature on the plate shaker. While the plate(s) are blocking, prepare compound stock solutions of 5 mM in 100% DMSO. The stock solutions are subsequently serially diluted to 100× of the final concentration in 100% DMSO. Make a 1:10 dilution using the 100× solution into growth media and transfer 10 ul of the appropriate compound dilutions to each well containing either the FAK induced or uninduced control A431 cells for 30 minutes 37° C., 5% CO2. Prepare RIPA lysis buffer (50 mM Tris-HCl, pH7.4, 1% NP-40, 0.25% Na-deoxycholate, 150 mM NaCl, 1 mM EDTA, 1 mM Na3VO4, 1 mM NaF, and one Complete™ EDTA-free protease inhibitor pellet per 50 ml solution). At the end of 30 minutes compound treatment, wash off compound 3 times using TBS-T wash buffer. Lyse cells with 100 ul/well of RIPA buffer.

To the coated plate, remove blocking buffer and wash 3 times using TBS-T wash buffer. Using a 96-well automated microdispenser, transfer 100 ul of whole cell-lysate (from step 6) to the Goat Anti-Rabbit FAKpY397 coated plate(s) to capture phosphoFAKY397 proteins. Shake at room temperature for 2 hours. Wash off unbound proteins 3 times using TBS-T wash buffer. Prepare 0.5 ug/ml (1:2000 dilution) of UBI αFAK detection antibody in 3% BSA/0.5% Tween blocking buffer. Dispense 100 ul of UBI αFAK solution per well and shake for 30 minutes at room temperature. Wash of excess UBI αFAK antibody 3 times using TBS-T wash buffer. Prepare 0.08 ug/ml (1:5000 dilution) of secondary Anti-Mouse Peroxidase (Anti-2MHRP) conjugated antibody. Dispense 100 ul per well of the Anti-2MHRP solution and shake for 30 minutes at room temperature. Wash off excess Anti-2MHRP antibody 3 times using TBS-T wash buffer. Add 100 ul per well of room temperature TMB substrate solution to allow for color development. Terminate the TMB reaction with 100 ul per well of TMB stop solution (0.09M H2SO4) and quantitate the signal by measurement of absorbance at 450 nm on the BioRad microplate reader.

Additional FAK cell assays are hereby incorporated by reference from 60/412,078 entitled "INDUCIBLE FOCAL ADHESION KINASE CELL ASSAY".

In a preferred embodiment, the compounds of the present invention have an in vitro activity as determined by a kinase assay, e.g., such as that described herein, of less than 500 nM. Preferably, the compounds have an $IC_{50}$ of less than 25 nM in the kinase assay, and more preferably less than 10 nM. In a further preferred embodiment, the compounds exhibit an $IC_{50}$ in a FAK cell based assay, e.g., such as that described herein, of less than 1 µM, more preferably less than 100 nM, and most preferably less than 25 nM.

In-Vitro Activity of Aurora-2:

The in vitro activity of the compounds of The invention may be determined by the following procedure.

This assay measures the activity of recombinant Aurora-2 (AUR2) kinase, specifically the phosphorylation of a peptide substrate, and the potency of inhibitors of Aurora-2 kinase. Product (phosphorylated peptide) is measured by use of a scintillation proximity assay (SPA). The peptide substrate is incubated with gamma 33P-ATP and enzyme and after the designated time the peptide is captured on a streptavidin SPA bead and the extent of phosphorylation is measured by scintillation counting. Inhibition is evaluated based on the ability of inhibitor to reduce phosphorylation relative to the reaction without inhibitor.

The Aurora-2 kinase used in the assay is full length human protein incorporating a $His_6$ sequence at the N-terminus to facilitate purification. The gene coding this sequence was incorporated into a baculovirus and the virus used to infect SF9 insect cells in culture. The recombinant protein was purified by nickel-agarose affinity chromatography by standard methods.

The reactions are performed in a volume of 50 µL consisting of 25 ng Aurora 2 protein, 50 mM Tris pH8, 10 mM MgCl$_2$, 1 mM dithiothreitol, 0.1 mM NaVO$_4$, 0.02% bovine serum albumin, 10 µM ATP, 0.03 µCi $^{33}$P-ATP, and 2 µMJ biotin-(LRRWSLG)$_4$ in wells of a 96 well nonbinding surface clear bottom microplate (Wallac Isoplate Cat 1450-514). Compounds are initially dissolved in DMSO, then diluted in 50 mM Tris pH8, 10 mM MgCl$_2$, 1 mM dithiothreitol, 0.1 mM NaVO$_4$, 0.02% bovine serum albumin such that 5 µL addition to each well yields the desired final concentration. The reaction is conducted at room temperature for 45 min with gentle shaking, then terminated by addition of 30 µL of Stop Buffer (0.3 mg Streptavidin SPA beads (Amersham), 1:1 water: phosphate buffered saline (0.2 g/L KCl, 0.2 g/L KH$_2$PO$_4$, 8 g/L NaCl, 1.15 g/L Na$_2$HPO$_4$), 0.5% Triton-X, 75 mM EDTA, 375 µM ATP). Cesium chloride (100 µL, 7.5M) is added to each well, the beads are allowed to settle overnight and scintillation counts performed on a Wallac Microbeta Trilux counter. A background correction is made for each based on a zero time reaction. Compound potency is determined as the concentration of inhibitor that produces 50% inhibition relative to the control reaction (without compound), i.e., IC$_{50}$.

In-Vitro Activity Towards HgK:

The in vitro activity of the compounds of the invention toward HgK may be determined by the following procedure using purified recombinant GST-HGK (produced via baculovirus expression in insect cells) and with peptide #1345, KRTLRRKRTLRRKRTLRR produced by Sugen and New England Peptide (without biotin tag) as a substrate. The following reagents were also used:

100 mM Tris
5 mM MnCl2
5 mM MgCl2
200 mM NaCl
0.8 mM CHAPS
1 mM DTT
10 mM NaF
10% glycerol
ATP/Peptide Mix in HGK Buffer:
ATP 2 uM (1 uM final assay conc.)
Peptide 1345A 40 uM (20 uM final assay conc.)

1. Add 10 ul/well of a Whatman 384-well white plate (#7701-3100) using a Titertek Multi-drop.
2. Add 0.5 ul of drug from HTS compressed drug plate using a Tomtec liquid handler.
3. Prepare HGK enzyme in HGK buffer, 400 nM (final assay conc. 200 nM). Add 10 ul per well using
4. Apricot Soken. (Add only blank buffer to control wells G and H 13-18)
5. Incubate at 37 C for one hour, or until assay has progressed 70% at room temp. Add 10 ul pro-mega
6. Luciferase reagent which has been diluted 1:3 in a 100 mM Tris, 5 mM MgCl2 buffer, and is at room temp.
7. Read luminescence in an LJL Analyst (Molecular Devices, Sunnyvale, Calif.).

In-Vitro Activity to Inhibit Osteoporosis and/or Low Bone Mass:

Still further, the following assay(s) may be used to assess the ability of a compound of the present invention to inhibit osteoporosis and/or low bone mass, as described above.

(1) Effect of test Compound on Body Weight, Body Composition and Bone Density in the Aged Intact and Ovariectomized Female Rat This assay may be used to test the effects of a test compound in aged intact or ovanectomized (OVX) female rat model.

Study Protocol

Sprague-Dawley female rats are sham-operated or OVX at 18 months of age, while a group of rats is necropsied at day 0 to serve as baseline controls. One day post-surgery, the rats are treated with either vehicle or test compound. The vehicle or test compound is administered twice a week (Tuesday and Friday) by subcutaneous injection (s.c.), with the test compound being administered at an average dose of 10 milligrams per kilogram of body weight per day (10 mg/kg/day).

All rats are given s.c. injection of 10 mg/kg of calcein (Sigma, St. Louis, Mo.) for fluorescent bone label 2 and 12 days before necropsy. On the day of necropsy, all rats under ketamine/xylazine anesthesia are weighed and undergo dual-energy X-ray absorptiometry (DXA, QDR-4500/W, Hologic Inc., Waltham, Mass.) equipped with Rat Whole Body Scan software for lean and fat body mass determination. The rats femoral metaphysis and femoral shafts from each rat are analyzed by peripheral quantitative computerized tomography (pQCT), and volumetric total, trabecular and cortical bone mineral content and density are determined.

Peripheral Quantitative Computerized Tomography (pQCT) Analysis: Excised femurs are scanned by a pQCT X-ray machine (Stratec XCT research M, Norland Medical Systems, Fort Atkinson, Wis.) with software version 5.40. A 1 millimeter (mm) thick cross section of the femur metaphysis is taken at 5.0 mm (proximal femoral metaphysis, a primary cancellous bone site) and 13 mm (femoral shafts, a cortical bone site) proximal from the distal end with a voxel size of 0.10 mm. Cortical bone is defined and analyzed using contour node 2 and cortical mode 4. An outer threshold setting of 340 mg/cm$^3$ is used to distinguish the cortical shell from soft tissue and an inner threshold of 529 mg/cm$^3$ to distinguish cortical bone along the endocortical surface. Trabecular bone is determined using peel mode 4 with a threshold of 655 mg/cm$^3$ to distinguish (sub)cortical from cancellous bone. An addition concentric peel of 1% of the defined cancellous bone is used to ensure that (sub)cortical bone is eliminated from the analysis. Volumetric content, density, and area are determined for both trabecular and cortical bone (Jamsa T. et al., *Bone* 23:155-161, 1998; Ke H. Z., et al., *Journal of Bone and Mineral Research,* 16:765-773, 2001).

Vaginal histology: Vaginal tissue is fixed and embedded in paraffin. Five micron sections are cut and stained with Alcian Blue staining. Histology examination of vaginal luminal epithelial thickness and mucopolysaccharide (secreted cells) is performed.

The experimental groups for the protocol are as follows:
Group I: Baseline controls
Group II: Sham+Vehicle
Group III: OVX+Vehicle
Group IV: OVX+Test Compound at 10 mg/kg/day (in Vehicle)

(2) Fracture Healing Assays (a) Assay for Effects on Fracture Healing after Systemic Administration Fracture Technique: Sprague-Dawley rats at 3 months of age are anesthetized with Ketamine. A 1 cm incision is made on the anteromedial aspect of the proximal part of the right tibia or femur. The following describes the tibial surgical technique. The incision is carried through to the bone, and a 1 mm hole is drilled 4 mm proximal to the distal aspect of the tibial tuberosity 2 mm medial to the anterior ridge. Intramedullary nailing is performed with a 0.8 mm stainless steel tube (maximum load 36.3 N, maximum stiffness 61.8 N/mm, tested under the same conditions as the bones). No reaming of the medullary canal is performed. A standardized closed fracture is produced 2 mm above the tibiofibular junction by three-point bending using specially designed adjustable forceps with blunt jaws. To minimize soft tissue damage, care is taken not to displace the fracture. The skin is closed with monofilament nylon sutures. The operation is performed under sterile conditions. Radiographs of all fractures are taken immediately after nailing, and rats with fractures outside the specified diaphyseal area or with displaced nails are excluded. The remaining animals are divided randomly into the following groups with 10-12 animals per each subgroup per time point for testing the fracture healing. The first group receives daily gavage from 0.01 to 100 mg/kg/day of the compound to be tested (1 ml/rat) for 10, 20, 40 and 80 days.

At 10, 20, 40 and 80 days, 10-12 rats from each group are anesthetized with Ketamine and sacrificed by exsanguination. Both tibiofibular bones are removed by dissection and all soft tissue is stripped. Bones from 5-6 rats for each group are stored in 70% ethanol for histological analysis, and bones from another 5-6 rats for each group are stored in a buffered Ringer's solution (+4° C., pH 7.4) for radiographs and biomechanical testing which is performed.

Histological Analysis: The methods for histologic analysis of fractured bone have been previously published by Mosekilde and Bak (The Effects of Growth Hormone on Fracture Healing in rats: A Histological Description. Bone, 14:19-27, 1993). Briefly, the fracture site is sawed 8 mm to each side of the fracture line, embedded undecalcified in methymethacrylate, and cut frontals sections on a Reichert-Jung Polycut microtome in 8 µm thick. Masson-Trichrome stained mid-frontal sections (including both tibia and fibula) are used for visualization of the cellular and tissue response to fracture healing with and without treatment. Sirius red stained sections are used to demonstrate the characteristics of the callus structure and to differentiate between woven bone and lamellar bone at the fracture site. The following measurements are performed: (1) fracture gap—measured as the shortest distance between the cortical bone ends in the fracture, (2) callus length and callus diameter, (3) total bone volume area of callus, (4) bony tissue per tissue area inside the callus area, (5) fibrous tissue in the callus, and (6) cartilage area in the callus.

Biometrical Analysis: The methods of biometrical analysis have been previously published by Bak and Andreassen (The Effects of Aging on Fracture healing in rats. Calcif Tissue Int 45:229-297, 1989). Briefly, radiographs of all fractures are taken prior to the biochemical test. The mechanical properties of the healing fractures are analyzed by a destructive three- or four-point bending procedure. Maximum load, stiffness, energy at maximum load, deflection at maximum load, and maximum stress are determined.

(a) Assay for Effects on Fracture Healing after Local Administration

Fracture Technique: Female or male beagle dogs at approximately 2 years of age are used under anesthesia in the study. Transverse radial fractures are produced by slow continuous loading in three-point bending as described by Lenehan et al. (Lenehan, T. M.; Balligand, M.; Nunamaker, D. M.; Wood, F. E.: Effects of EHDP on Fracture Healing in Dogs. J Orthop Res 3:499-507; 1985). A wire is pulled through the fracture site to ensure complete anatomical disruption of the bone. Thereafter, local delivery of prostaglandin agonists to the fracture site is achieved by slow release of compound delivered by slow release pellets or by administration of the compounds in a suitable formulation such as a paste gel solution or suspension for 10, 15, or 20 weeks.

Histological Analysis: The methods for histologic analysis of fractured bone have been previously published by Peter et al. (Peter, C. P.; Cook, W. O.; Nunamaker, D. M.; Provost, M. T.; Seedor, J. G.; Rodan, G. A. Effects of alendronate on fracture healing and bone remodeling in dogs. J. Orthop. Res. 14:74-70, 1996) and Mosekilde and Bak (The Effects of Growth Hormone on Fracture Healing in Rats: A Histological Description. Bone, 14:19-27, 1993). Briefly, after sacrifice, the fracture site is sawed 3 cm to each side of the fracture line, embedded undecalcified in methymethacrylate, and cut on a Reichert-Jung Polycut microtome in 8 µm thick of frontal sections. Masson-Trichrome stained mid-frontal sections (including both tibia and fibula) are used for visualization of the cellular and tissue response to fracture healing with and without treatment. Sirius red stained sections are used to demonstrate the characteristics of the callus structure and to differentiate between woven bone and lamellar bone at the fracture site. The following measurements are performed: (1) fracture gap—measured as the shortest distance between the cortical bone ends in the fracture, (2) callus length and callus diameter, (3) total bone volume area of callus, (4) bony tissue per tissue area inside the callus area, (5) fibrous tissue in the callus, (6) cartilage area in the callus.

Biomechanical Analysis: The methods for biomechanical analysis have been previously published by Bak and Andreassen (The Effects of Aging on Fracture Healing in Rats. Calcif Tissue Int 45:292-297, 1989) and Peter et al. (Peter, C. P.; Cook, W. O.; Nunamaker, D. M.; Provost, M. T.; Seedor, J. G.; Rodan, G. A. Effects of Alendronate On Fracture Healing And Bone Remodeling In Dogs J. Orthop. Res. 14:74-70, 1996). Briefly, radiographs of all fractures are taken prior to the biomechanical test. The mechanical properties of the healing fractures are analyzed by a destructive three- or four-point bending procedures. Maximum load, stiffness, energy at maximum load, deflection at maximum load, and maximum stress are determined.

Methods for Treating Abnormal Cell Growth in a Mammal

This invention also relates to a method for the treatment of abnormal cell growth in a mammal, including a human, comprising administering to said mammal an amount of a compound of the invention, as defined above, or a pharmaceutically acceptable salt, solvate or prodrug thereof, that is effective in treating abnormal cell growth. In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In one embodiment the method comprises comprising administering to a mammal an amount of a compound of the invention that is effective in treating said cancer solid tumor. In one preferred embodiment the solid tumor is breast, lung, colon, brain, prostate, stomach, pancreatic, ovarian, skin (melanoma), endocrine, uterine, testicular, and bladder cancer.

In another embodiment of said method, said abnormal cell growth is a benign proliferative disease, including, but not limited to, psoriasis, benign prostatic hypertrophy or restinosis.

This invention also relates to a method for the treatment of abnormal cell growth in a mammal which comprises administering to said mammal an amount of a compound of the invention, or a pharmaceutically acceptable salt, solvate or prodrug thereof, that is effective in treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

This invention also relates to a pharmaceutical composition for the treatment of abnormal cell growth in a mammal, including a human, comprising an amount of a compound of the invention, as defined above, or a pharmaceutically acceptable salt, solvate or prodrug thereof, that is effective in treating abnormal cell growth, and a pharmaceutically acceptable carrier. In one embodiment of said composition, said abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

This invention also relates to a method for the treatment of abnormal cell growth in a mammal which comprises administering to said mammal an amount of a compound of the invention, or pharmaceutically acceptable salt, solvate or prodrug thereof, that is effective in treating abnormal cell growth in combination with another anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens. The invention also contemplates a pharmaceutical composition for treating abnormal cell growth wherein the composition includes a compound of the invention, as defined above, or a pharmaceutically acceptable salt, solvate or prodrug thereof, that is effective in treating abnormal cell growth, and another anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

This invention also relates to a method for the treatment of a disorder associated with angiogenesis in a mammal, including a human, comprising administering to said mammal an amount of a compound of the invention, as defined above, or a pharmaceutically acceptable salt, solvate or prodrug thereof, that is effective in treating said disorder in combination with one or more anti-tumor agents listed above. Such disorders include cancerous tumors such as melanoma; ocular disorders such as age-related macular degeneration, presumed ocular histoplasmosis syndrome, and retinal neovascularization from proliferative diabetic retinopathy; rheumatoid arthritis; bone loss disorders such as osteoporosis, Paget's disease, humoral hypercalcemia of malignancy, hypercalcemia from tumors metastatic to bone, and osteoporosis induced by glucocorticoid treatment; coronary restinosis; and certain microbial infections including those associated with microbial pathogens selected from adenovirus, hantaviruses, *Borrelia burgdorferi, Yersinia* spp., *Bordetella pertussis*, and group A *Streptococcus*.

This invention also relates to a method of (and to a pharmaceutical composition for) treating abnormal cell growth in a mammal which comprise an amount of a compound of the invention, or pharmaceutically acceptable salt, solvate or prodrug thereof, in combination with an amount of one or more substances selected from anti-angiogenesis agents, signal transduction inhibitors, and antiproliferative agents, which amounts are together effective in treating said abnormal cell growth.

Anti-angiogenesis agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with a compound of the invention in the methods and pharmaceutical compositions described herein. Examples of useful COX-II inhibitors include CELEBREX™ (celecoxib), Bextra (valdecoxib), paracoxib, Vioxx (rofecoxib), and Arcoxia (etoricoxib). Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 937,788 (published Jul. 28, 1999), WO 90/05719 (published may 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in combination with the compounds of the present invention are AG-3340, RO 32-3555, RS 13-0830, and the compounds recited in the following list:

3-[[4-(4-fluoro-phenoxy)-benzenesulfonyl]-(1-hydroxycarbamoyl-cyclopentyl)-amino]-propanoic acid;

3-exo-3-[4-(4-fluoro-phenoxy)-benzenesulfonylamino]-8-oxa-bicyclo[3.2.1]octane-3-carboxylic acid hydroxyamide;

(2R,3R) 1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonylamino]-tetrahydro-pyran-4-carboxylic acid hydroxyamide;

3-[[4-(4-fluoro-phenoxy)-benzenesulfonyl]-(1-hydroxycarbamoyl-cyclobutyl)-amino]-propionic acid;

4-[4-(4-chloro-phenoxy)-benzenesulfonylamino]-tetrahydro-pyran-4-carboxylic acid hydroxyamide;

3-[4-(4-chloro-phenoxy)-benzenesulfonylamino]-tetrahydro-pyran-4-carboxylic acid hydroxyamide;

(2R,3R) 1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1-methyl-ethyl))-amino]-propanoic acid;

3-[[4-(4-fluoro-phenoxy)-benzenesulfonyl]-(1-hydroxycarbamoyl-tetrahydro-pyran-4-yl)-amino]-propionic acid;

3-exo-3-[4-(4-chloro-phenoxy)-benzenesulfonylamino]-8-oxa-bicyclo[3.2.1]octane-3-carboxylic acid hydroxyamide;

3-endo-3-[4-(4-fluoro-phenoxy)-benzenesulfonylamino]-8-oxa-bicyclo[3.2.1]octane-3-carboxylic acid hydroxamide; and 3-[4-(4-fluoro-phenoxy)-benzenesulfonylamino]-tetrahydro-furan-3-carboxylic acid hydroxamide;

and pharmaceutically acceptable salts, solvates and prodrugs of said compounds.

VEGF inhibitors, for example, SU-11248, SU-5416 and SU-6668 (Sugen Inc. of South San Francisco, Calif., USA), can also be combined with a compound of the invention. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), U.S. Pat. No. 6,653,308 (issued Nov. 25, 2003), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); Avastin, an anti-VEGF monoclonal antibody of Genentech, Inc. of South San Francisco, Calif.; and angiozyme, a synthetic ribozyme from Ribozyme (Boulder, Co.) and Chiron (Emeryville, Calif.).

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), may be administered in combination with a compound of the invention. Such erbB2 inhibitors include Herceptin, 2C4, and pertuzumab. Such erbB2 inhibitors include those described in WO 98/02434 (published Jan. 22, 1998), WO 99/35146 (published Jul. 15, 1999) WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued mar. 2, 1999), each of which is herein incorporated by reference in its entirety. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are herein incorporated by reference in its entirety. Other erbb2 receptor inhibitors include TAK-165 (Takeda) and GW-572016 (Glaxo-Wellcome).

Various other compounds, such as styrene derivatives, have also been shown to possess tyrosine kinase inhibitory properties, and some of tyrosine kinase inhibitors have been identified as erbB2 receptor inhibitors. More recently, five European patent publications, namely EP 0 566 226 A1 (published Oct. 20, 1993), EP 0 602 851 A1 (published Jun. 22, 1994), EP 0 635 507 A1 (published Jan. 25, 1995), EP 0 635 498 A1 (published Jan. 25, 1995), and EP 0 502 722 A1 (published Dec. 30, 1992), refer to certain bicyclic derivatives, in particular quinazoline derivatives, as processing anti-cancer properties that result from their tyrosine kinase inhibitory properties. Also, World Patent Application WO 92/20642 (published Nov. 26, 1992), refers to certain bis-mono and bicyclic aryl and heteroaryl compounds as tyrosine kinase inhibitors that are useful in inhibiting abnormal cell proliferation. World Patent Applications WO96/16960 (published Jun. 6, 1996), WO 96/09294 (published mar. 6, 1996), WO 97/30034 (published Aug. 21, 1997), WO 98/02434 (published Jan. 22, 1998), also refer to substituted bicyclic heteroaromatic derivatives as tyrosine kinase inhibitors that are useful for the same purpose. Other patent applications that refer to anti-cancer compounds are World Patent Application WO00/44728 (published Aug. 3, 2000), EP 1029853A1 (published Aug. 23, 2000), and WO01/98277 (published Dec. 12, 2001) all of which are incorporated herein by reference in their entirety.

Other antiproliferative agents that may be used with the compounds of the present invention include inhibitors of the enzyme farnesyl protein transferase and inhibitors of the receptor tyrosine kinase PDGFr, including the compounds disclosed and claimed in the following U.S. patent application Ser. No. 09/221,946 (filed Dec. 28, 1998); Ser. No. 09/454,058 (filed Dec. 2, 1999); Ser. No. 09/501,163 (filed Feb. 9, 2000); 09/539,930 (filed Mar. 31, 2000); Ser. No. 09/202,796 (filed May 22, 1997); Ser. No. 09/384,339 (filed Aug. 26, 1999); and Ser. No. 09/383,755 (filed Aug. 26, 1999); and the compounds disclosed and claimed in the following U.S. provisional patent applications 60/168,207 (filed Nov. 30, 1999); 60/170,119 (filed Dec. 10, 1999); 60/177,718 (filed Jan. 21, 2000); 60/168,217 (filed Nov. 30, 1999), and 60/200,834 (filed May 1, 2000). Each of the foregoing patent applications and provisional patent applications is herein incorporated by reference in their entirety.

A compound of the invention may also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the farnesyl protein transferase inhibitors described in the references cited in the "Background" section, supra. Specific CTLA4 antibodies that can be used in the present invention include those described in U.S. Provisional Application 60/113,647 (filed Dec. 23, 1998) which is herein incorporated by reference in its entirety.

A compound of the invention may be applied as a sole therapy or may involve one or more other anti-tumor substances, for example those selected from, for example, mitotic inhibitors, for example vinblastine; alkylating agents, for example cis-platin, oxaliplatin, carboplatin and cyclophosphamide; anti-metabolites, for example 5-fluorouracil, capecitabine, cytosine arabinoside and hydroxyurea, or, for example, one of the preferred anti-metabolites disclosed in European Patent Application No. 239362 such as N-(6-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex (tamoxifen) or, for example anti-androgens such as Casodex (4'-cyano-3-(4-fluorophenylsulphonyl)-2-hydroxy-2-methyl-3'-(trifluoromethyl)propionanilide).

The compounds of the present invention may be used alone or in combination with one or more of a variety of anti-cancer agents or supportive care agents. For example, the compounds of the present invention may be used with cytotoxic agents, e.g., one or more selected from the group consisting of a camptothecin, irinotecan HCl (Camptosar), edotecarin, SU-11248, epirubicin (Ellence), docetaxel (Taxotere), paclitaxel, rituximab (Rituxan) bevacizumab (Avastin), imatinib mesylate (Gleevac), Erbitux, gefitinib (Iressa), and combinations thereof. The invention also contemplates the use of the compounds of the present invention together with hormonal therapy, e.g., exemestane (Aromasin), Lupron, anastrozole (arimidex), tamoxifen citrate (Nolvadex), Trelstar, and combinations thereof. Further, the invention provides a compound of the present invention alone or in combination with one or more supportive care products, e.g., a product selected from the group consisting of Filgrastim (Neupogen), ondansetron (Zofran), Fragmin, Procrit, Aloxi, Emend, or combinations thereof. Such conjoint treatment may be achieved by way of the simultaneous, sequential or separate dosing of the individual components of the treatment.

The compounds of the invention may be used with antitumor agents, alkylating agents, antimetabolites, antibiotics, plant-derived antitumor agents, camptothecin derivatives, tyrosine kinase inhibitors, antibodies, interferons, and/or biological response modifiers. In this regard, the following is a non-limiting list of examples of secondary agents that may be used with the compounds of the invention.

Alkylating agents include, but are not limited to, nitrogen mustard N-oxide, cyclophosphamide, ifosfamide, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustin, glufosfamide, ifosfamide, KW-2170, mafosfamide, and mitolactol; platinum-coordinated alkylating compounds include but are not limited to, cisplatin, carboplatin, eptaplatin, lobaplatin, nedaplatin, oxaliplatin or satrplatin;

Antimetabolites include but a re not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, gemcitabine, fludarabin, 5-azacitidine, capecitabine, cladribine, clofarabine, decitabine, eflornithine, ethynylcytidine, cytosine arabinoside, hydroxyurea, TS-1, melphalan, nelarabine, nolatrexed, ocfosfate, disodium premetrexed, pentostatin, pelitrexol, raltitrexed, triapine, trimetrexate, vidarabine, vincristine, vinorelbine; or for example, one of the preferred anti-metabolitie disclosed in European Patent Application No. 239362 such as N-(5-[N-(3,4-dihydro-2-methyl-4-oxoquinazolin-6-ylmethyl)-N-methylamino]-2-thenoyl)-L-glutamic acid;

Antibiotics include but are not limited to: aclarubicin, actinomycin D, amrubicin, annamycin, bleomycin, daunorubicin, doxorubicin, elsamitrucin, epirubicin, galarubicin, idarubicin, mitomycin C, memorubicin, neocarzinostatin, peplomycin, pirarubicin, rebeccamycin, stimalamer, srteptozocin, valrubicin or zinostatin;

Hormonal therapy agents, e.g., exemestane (Aromasin), Lupron, anastrozole (Arimidex), doxercalciferol, fadrozole, formestane, anti-estrogens such as tamoxifen citrate (Nolvadex) and fulvestrant, Trelstar, toremifene, raloxifene, lasofoxifene, letrozole (Femara), or anti-androgens such as bicalutamide, flutamide, mifepristone, nilutamide, Casodex® (4'-cyano-3-(4-fluorophenylsulphonyl)-2-hydroxy-2-methyl-3'-(trifluoromethyl)propionanilide) and combinations thereof;

Plant derived anti-tumor substances include for example those selected from mitotic inhibitors, for example vinblastine, docetaxel (Taxotere) and paclitaxel;

Cytotoxic topoisomerase inhibiting agents include one or more agents selected from the group consisting of aclarubicin, amonafide, belotecan, camptothecin, 10-hydroxycamptothecin, 9-aminocamptothecin, diflomotecan, irinotecan HCl (Camptosar), edotecarin, epirubicin (Ellence), etoposide, exatecan, gimatecan, lurtotecan, mitoxantrone, pirarubicin, pixantrone, rubitecan, sobuzoxane, SN-38, tafluposide, and topotecan, and combinations thereof;

Immunologicals including interferons and numerous other immune enhancing agents. Interferons include interferon alpha, interferon alpha-2a, interferon, alpha-2b, interferon beta, interferon gamma-1a or interferon gamma-n1. Other agents include PF3512676, filgrastim, lentinan, sizofilan, TheraCys, ubenimex, WF-10, aldesleukin, alemfuzumab, BAM-002, dacarbazine, daclizumab, denileukin, gemtuzumab ozogamicin, ibritumomab, imiquimod, lenograstim, lentinan, melanoma vaccine (Corixa), melgramostinm, OncoVAX-CL, sargramostim, tasonermin, tecleukin, thymalasin, tositumomab, Virulizin, Z-100, epratuzumab, mitumomab, oregovomab, pemtumomab, Provenge;

Biological response modifiers are agents that modify defense mechanisms of living organisms or biological responses, such as survival, growth, or differentiation of tissue cells to direct them to have anti-tumor activity. Such agents include krestin, lentinan, sizofiran, picibanil, or ubenimex;

Other anticancer agents include alitretinoin, ampligen, atrasentan bexarotene, bortezomib, Bosentan, calcitrol, exisulind, finasteride, fotemustine, ibandronic acid, miltefosine, mitoxantrone, l-asparaginase, procarbazine, dacarbazine, hydroxycarbamide, pegaspargase, pentostatin, tazarotne, TLK-286, Velcade, Tarceva, or tretinoin;

Other anti-angiogenic compounds include acitretin, fenretinide, thalidomide, zoledronic acid, angiostatin, aplidine, cilengtide, combretastatin A-4, endostatin, halofuginone, rebimastat, removab, Revlimid, squalamine, ukrain and Vitaxin;

Platinum-coordinated compounds include but are not limited to, cisplatin, carboplatin, nedaplatin, or oxaliplatin;

Camptothecin derivatives include but are not limited to camptothecin, 10-hydroxycamptothecin, 9-aminocamptothecin, irinotecan, SN-38, edotecarin, and topotecan;

Tyrosine kinase inhibitors are Iressa or SU5416;

Antibodies include Herceptin, Erbitux, Avastin, or Rituximab;

Interferons include interferon alpha, interferon alpha-2a, interferon, alpha-2b, interferon beta, interferon gamma-1a or interferon gamma-n1;

Biological response modifiers are agents that modify defense mechanisms of living organisms or biological responses, such as survival, growth, or differentiation of tissue cells to direct them to have anti-tumor activity. Such agents include krestin, lentinan, sizofiran, picibanil, or ubenimex; and Other antitumor agents include mitoxantrone, l-asparaginase, procarbazine, dacarbazine, hydroxycarbamide, pentostatin, or tretinoin.

"Abnormal cell growth", as used herein, unless otherwise indicated, refers to cell growth that is independent of normal regulatory mechanisms (e.g., loss of contact inhibition). This includes the abnormal growth of: (1) tumor cell (tumors) that proliferate by expressing a mutated tyrosine kinase or overexpression of a receptor tyrosine kinase; (2) benign and malignant cells of other proliferative diseases in which aberrant tyrosine kinase activation occurs; (4) any tumors that proliferate by receptor tyrosine kinase; (5) any tumors that proliferate by aberrant serine/threonine kinase activation; and (6) benign and malignant cells of other proliferative diseases in which aberrant serine/threonine kinase activation occurs.

The compounds of the present invention are potent inhibitors of the FAK, Aurora-1, Aurora-2 and HgK protein tyrosine kinases, and thus are all adapted to therapeutic use as antiproliferative agents (e.g., anticancer), antitumor (e.g., effective against solid tumors), antiangiogenesis (e.g., stop or prevent proliferation of blood vessels) in mammals, particularly in humans. In particular, the compounds of the present invention are useful in the prevention and treatment of a variety of human hyperproliferative disorders such as malignant and benign tumors of the liver, kidney, bladder, breast, gastric, ovarian, colorectal, prostate, pancreatic, lung, vulval, thyroid, hepatic carcinomas, sarcomas, glioblastomas, head and neck, and other hyperplastic conditions such as benign hyperplasia of the skin (e.g., psoriasis) and benign hyperplasia of the prostate (e.g., BPH). It is, in addition, expected that a compound of the present invention may possess activity against a range of leukemias and lymphoid malignancies.

In one preferred embodiment of the present invention cancer is selected from lung cancer, bone cancer, pancreatic cancer, gastric, skin cancer, cancer of the head or neck, cutaneous or intraocular melanoma, uterine cancer, ovarian cancer, gynecological, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, squamous cell, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain, pituitary adenoma, or a combination of one or more of the foregoing cancers.

In a more preferred embodiment cancer is selected a solid tumor, such as, but not limited to, breast, lung, colon, brain (e.g., glioblastoma), prostate, stomach, pancreatic, ovarian, skin (melanoma), endocrine, uterine, testicular, and bladder.

The compounds of the present invention may also be useful in the treatment of additional disorders in which aberrant expression ligand/receptor interactions or activation or signalling events related to various protein tyrosine kinases, are involved. Such disorders may include those of neuronal glial, astrocytal, hypothalamic, and other glandular, macrophagal, epithelial, stromal, and blastocoelic nature in which aberrant function, expression, activation or signalling of the erbB tyrosine kinases are involved. In addition, the compounds of the present invention may have therapeutic utility in inflammatory, angiogenic and immunologic disorders involving both identical and as yet unidentified tyrosine kinases that are inhibited by the compounds of the present invention.

A particular aspect of this invention is directed to methods for treating or preventing a condition that presents with low bone mass in a mammal (including a human being) which comprise administering to a mammal in need of such treatment a condition that presents with low bone mass treating amount of a compound of the invention or a pharmaceutically acceptable salt of said compound.

This invention is particularly directed to such methods wherein the condition that presents with low bone mass is osteoporosis, frailty, an osteoporotic fracture, a bone defect, childhood idiopathic bone loss, alveolar bone loss, mandibular bone loss, bone fracture, osteotomy, periodontitis or prosthetic ingrowth.

A particular aspect of this invention is directed to methods for treating osteoporosis in a mammal (including a human being) which comprise administering to a mammal in need of such treatment an osteoporosis treating amount of a compound of the invention or a pharmaceutically acceptable salt of said compound.

Another aspect of this invention is directed to methods for treating a bone fracture or an osteoporotic fracture in a mammal which comprise administering to a mammal in need of such treatment a bone fracture treating or an osteoporotic fracture treating amount of a compound of the invention or a pharmaceutically acceptable salt of said compound.

The term "osteoporosis" includes primary osteoporosis, such as senile, postmenopausal and juvenile osteoporosis, as well as secondary osteoporosis, such as osteoporosis due to hyperthyroidism or Cushing syndrome (due to corticosteroid use), acromegaly, hypogonadism, dysosteogenesis and hypophosphatasemia.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The present invention also provides a pharmaceutical composition comprising a compound of formula (I), or a pharmaceutically acceptable salt or solvate thereof, as hereinabove defined in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined with a pharmaceutically acceptable adjuvant, diluent or carrier.

For the above-mentioned therapeutic uses the dosage administered will, of course, vary with the compound employed, the mode of administration, the treatment desired and the disorder indicated. The daily dosage of the compound of formula (I)/salt/solvate (active ingredient) may be in the range from 1 mg to 1 gram, preferably 1 mg to 250 mg, more preferably 10 mg to 100 mg.

The present invention also encompasses sustained release compositions.

Methods for Administering the Compounds of the Invention

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumour substances, for example those selected from, for example, mitotic inhibitors, for example vinblastine; alkylating agents, for example cisplatin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex® (tamoxifen) or, for example anti-androgens such as Casodex® (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository, The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral centers, unless otherwise noted, exist as a racemic mixture of diastereomers. Single enantiomers/diastereomers may be obtained by methods known to those skilled in the art.

EXAMPLES

Where HPLC chromatography is referred to the preparations and examples below, the general conditions used, unless otherwise indicated, are as follows. The column used is a ZORBAX™ RXC18 column (manufactured by Hewlett Packard) of 150 mm distance and 4.6 mm interior diameter. The samples are run on a Hewlett Packard-1100 system. A gradient solvent method is used running 100 percent ammonium acetate/acetic acid buffer (0.2 M) to 100 percent acetonitrile over 10 minutes. The system then proceeds on a wash cycle with 100 percent acetonitrile for 1.5 minutes and then 100 percent buffer solution for 3 minutes. The flow rate over this period is a constant 3 mL/minute.

Examples

General Methods

HPLC Methods

Where HPLC chromatography is referred to in the preparations and examples, the general conditions used, unless otherwise indicated, are as follows. The column used is a ZORBAX™ Eclipse XDB-C8 column (manufactured by Agilent) of 150 mm distance and 4.6 mm interior diameter. The samples are run on a Agilent 1100 series system. A gradient solvent method is used running 100 percent ammonium acetate/acetic acid buffer (0.2M) to a mixture of 15 percent ammonium acetate/acetic acid buffer (0.2M) and 85 percent acetonitrile over 8 minutes and then to 100 percent acetonitrile over 1 minute. The system then proceeds on a wash cycle running 100 percent acetonitrile to 100 percent buffer solution for 2 minutes. The flow rate over this period is a constant 3 mL/minute.

Other specific methods follow.

Method A1

HPLC analyses were obtained using a Reliasil BDX-C18 column (4.6×100 mm) with UV detection at 223 nm (Method A) or a Symmetry C18 column (4.6×250 mm) with UV detection at 254 nm (Method B) using a standard solvent gradient program.

| Time (min) | Flow (mL/min) | % A | % B |
|---|---|---|---|
| 0.0 | 1.5 | 90.0 | 10.0 |
| 25.0 | 1.5 | 10.0 | 90.0 |
| 30.0 | 1.5 | 10.0 | 90.0 |

A = Water with 0.05% v/v Trifluoroacetic Acid,
B = Acetonitrile with 0.05% v/v Trifluoroacetic Acid Method B1

| Time (min) | Flow (mL/min) | % A | % B |
|---|---|---|---|
| 0.0 | 1.0 | 90.0 | 10.0 |
| 20.0 | 1.0 | 10.0 | 90.0 |
| 35.0 | 1.0 | 10.0 | 90.0 |

A = Water with 0.05% v/v Trifluoroacetic Acid,
B = Acetonitrile with 0.05% v/v Trifluoroacetic Acid Method A: Column: Xterra MS C 18 (4.6×50 mm, 3.5 um). Gradient: $H_2O/CH_3CN/2\%$ $NH_4OH$ in $H_2O$ from 85:10:5 at 0 min to 0:95:5 at 5 min at 2 ml/min.

Method B: Column: Atlantis dC18 (4.6×50 mm, 5 um). Gradient: $H_2O/CH_3CN/1\%$ TFA in $H_2O$ from 85/10/5 to 25/70/5 within 5 min at 2 ml/min.

Method C: Column: Xterra MS C8 (4.6×50 mm, 3.5 um). Gradient: $H_2O/CH_3CN/2\%$ $NH_4OH$ in $H_2O$ from 90/5/5 to 35/60/5 within 5 min at 2 ml/min.

Method D: Column: Waters Symmetry C8 (4.6×50 mm, 4.6 um). Gradient: $H_2O/CH_3CN/1\%$ TFA in $H_2O$ from 94:5:1 at 0 min to 4:95:1 at 3.5 min, from 4:95:1 at 3.5 min to 4:95:1 at 4 min at 2 ml/min.

Method E: Where HPLC chromatography is referred to in the preparations and examples, the general conditions used, unless otherwise indicated, are as follows. The column used is a ZORBAX™ Eclipse XDB-C8 column (manufactured by Agilent) of 150 mm distance and 4.6 mm interior diameter. The samples are run on a Agilent 1100 series system. A gradient solvent method is used running 100 percent ammonium acetate/acetic acid buffer (0.2M) to a mixture of 15 percent ammonium acetate/acetic acid buffer (0.2M) and 85 percent acetonitrile over 8 minutes and then to 100 percent acetonitrile over 1 minute. The system then proceeds on a wash cycle running 100 percent acetonitrile to 100 percent buffer solution for 2 minutes. The flow rate over this period is a constant 3 mL/minute.

Method F: Where LCMS chromatography is referred to in the preparations and examples, the general conditions used, unless otherwise indicated, are as follows. The Gilson™ 215 liquid handler is used, fitted with a Varian C8 column and Gilson HPLC pump. The chromatography system uses binary solvent system consisting of and an acidic solution (composed of 98 percent water, 1.99 percent acetonitrile and 0.01 percent formic acid) and an acetonitrile solution (composed of 99.995 percent acetonitrile and 0.005 percent formic acid). A gradient solvent method is used running a mixture of 95 percent of the acidic solution and 5 percent of the acetonitrile solution to a mixture of 80 percent acid solution and 20 percent acetonitrile solution over 1 minute, continuing to a mixture of 50 percent acidic solution and 50 percent acetonitrile solution over a period of 1.3 minutes and continuing to 100 percent acetonitrile solution over 1.2 minutes. The system then proceeds on an equilibration cycle running 100 percent acetonitrile solution to a mixture of 95 percent acidic solution and 5 percent acetonitrile over 0.2 minutes. The flow rate during this period is a constant 1 mL/minute.

Method G: The reactions were purified on Shimadzu prep HPLC, using a waters SunFire C18, 5 um, 3.0×5.0 mm steel column. The mobile phase, flow rate 18.0 ml/min, water (gradient 95-0%) and acetonitrile (gradient 5-100%) using 1% trifluoroacetic acid in water (2.0 mL/min) as a modifier.

Example 1

(+/−) N-(3-{[2-(12,12-Dioxo-12λ$^6$-thia-tricyclo [6.3.1.0$^{2.7}$]dodeca-2(7),3,5-trien-4-ylamino)-5-trifluoromethyl-pyrimidin-4-ylamino]-methyl}-pyridin-2-yl)-N-methyl-methanesulfonamide (1)

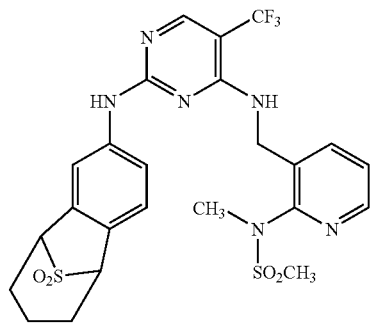

1

Step 1. (+/−) 4-Nitro-12-thia-tricyclo[6.3.1.0$^{2.7}$]dodeca-2 (7),3,5-triene 12,12-dioxide (C4): 12-Thia-tricyclo [6.3.1.0$^{2.7}$]dodeca-2(7),3,5-triene 12,12-dioxide (C3) (see *J. Chem. Soc., Perk. Trans. I*, 1981(7), 1845) (407 mg, 1.96 mmol) was carefully dissolved into 6.00 mL cold $H_2SO_4$, and the resultant solution was chilled to −10° C. (NaCl/ice bath). The resultant brown solution was treated portion wise with $KNO_3$ (198 mg, 1.96 mmol) such that the internal reaction temperature never exceeded −8° C. The reaction mixture was stir at about −10° C. for an additional five minutes and poured onto ice. The resultant turbid ice mixture was stirred until all of the ice had melted, and the resultant aqueous mixture was washed with EtOAc. The combined organic layers were dried over $MgSO_4$ and concentrated under reduced pressure to provide C4 as a pale yellow solid (397 mg, 1.56 mmol, 80% yield). $C_{11}H_{11}NO_4S$. GC/MS r.t.=5.07 min.; m/z 237, 189 (bp), 174, 161, 141, 128, 115. $^1$H NMR (CDCl$_3$) δ 8.30 (d, J=8.3 Hz, 1H), 7.25 (s, 1H), 7.56 (d, J=8.3 Hz, 1H), 4.26 (dd, J=10.7, 4.9 Hz, 2H), 2.68-2.60 (m, 2H), 2.11-2.03 (m, 2H), 1.57-1.52 (m, 1H), 0.87-0.74 (m, 1H) ppm.

Step 2. (+/−) 12,12-Dioxo-12$\lambda^6$-thia-tricyclo[6.1.3.0$^{2.7}$] dodeca-2(7),3,5-trien-4-ylamine (C5): A mixture of C4 (397 mg (1.56 mmol)), EtOH (3.00 mL) and cyclohexene (790 mL, 7.80 mmol) was carefully treated with palladium on carbon (832 mg, 0.780 mmol) and heated to 60° C. After three hours, the reaction mixture was allowed to cool to 25° C. and concentrated under reduced pressure. The resulting residue was purified over silica (40% EtOAc in hexanes) to provide C5 as a white solid (78 mg, 0.358 mmol, 23%). $C_{11}H_{13}NO_2S$ GC/MS r.t.=2.94 min. m/z 159 (bp), 144, 130; $^1$H NMR (CDCl$_3$) δ 6.69-6.67 (m, 2H), 4.06 (d, J=5.2 Hz, 1H), 4.02 (d, J=4.7 Hz, 1H), 2.56-2.51 (m, 2H), 2.00-1.95 (m, 2H), 1.48-1.44 (m, 1H), 1.00-0.93 (m, 1H) ppm.

Step 3. (+/−) (4-Chloro-5-trifluoromethyl-pyrimidin-2-yl)-(12,12-dioxo-12$\lambda^{2.7}$-thia-tricyclo[6.3.1.0$^{2.7}$]dodeca-2(7), 3,5-trien-4-yl)-amine (C6): A solution of 2,4-dichloro-5-trifluoromethyl pyrimidine (78 mg, 0.358 mmol) and 1/1 (vol:vol) mixture of t-BuOH and dichloroethane (400 mL) was cooled to 0° C., treated with a solution of ZnCl$_2$ solution (715 mL (0.715 mmol, 1.0 Molar in Et$_2$O), and stirred at 0° C. for 30 minutes. The mixture was treated with slurry of C5 in 1/1 tBuOH/CH$_2$Cl$_2$ (800 mL) then dropwise with diisopropyl ethylamine (125 mL, 0.715 mmol). After five minutes was heated to 50° C. After 4 hours the reaction mixture was allowed to cool to ambient 25° C. and concentrated under reduced pressure. The resultant residue was triturated with MeOH, and the resulting was collected by filtrated to provide C6 as a white solid (52 mg, 0.129 mmol, 36%). $C_{16}H_{13}ClF_3N_3O_2S$ LC/MS (Method F) m/z 402/404 (MH$^+$); $^1$H NMR (D$_6$-DMSO) δ 10.8 (s, 1H), 8.81 (s, 1H), 7.69 (s, 1H), 7.68 (d, J=8.3 Hz, 1H), 7.41 (d, J=8.3 Hz, 1H), 4.42-4.37 (m, 2H), 2.39-2.24 (m, 2H), 1.94-1.90 (m, 2H), 1.38-1.34 (m, 1H), 0.79-0.60 (m, 1H) ppm.

Step 4. A mixture of C6 (51 mg; 0.126 mmol) and 1:1 (vol:vol) t-BuOH/dichloroethane (500 μL) was added to a mixture of N-(3-Aminomethyl-pyridin-2-yl)-N-methyl-methanesulfonamide (38 mg, 0.139 mmol) and diisopropyl ethylamine (66 μL, 0.378 mmol). The reaction mixture was heated to 85° C. in a sealed vial. After two hours, the hot reaction mixture was loaded directly onto silica under reduced pressure, purified via chromatography (99:1:0.1 CHCl$_3$:CH$_3$OH:NH$_4$OH), and concentrated under reduced pressure to provide 1 as a white solid (13 mg, 0.0223 mmol, 18%). LC/MS (Method F) r.t.=2.26 min.; m/z 583.2. HPLC r.t.=6.40 min.

Example 2

N-(3-{[2-(10-Methanesulfonyl-10-aza-tricyclo [6.3.1.0$^{2.7}$]dodeca-2(7),2,5-trien-4-ylamino-5-trifluoromethyl-pyrimidin-4-ylamino]-methyl}-pyridin-2-yl)-N-methyl-methanesulfonamide (2)

Step 1. (+/−)10-Methanesulfonyl-4-nitro-10-aza-tricyclo [6.3.1.0$^{2.7}$]dodeca-2,4,6-triene (C7): 4-Nitro-10-aza-tricyclo [6.3.1.0$^{2.7}$]dodeca-2,4,6-triene (150 mg, 0.734 mmol) (see International Publication No. WO01/062736) was combined with pyridine (3.00 mL) and chilled to −10° C. in a NaCl/ice bath. Methane sulfonyl chloride (74 μL, 0.954 mmol) was slowly added and the mixture allowed to equilibrate to ambient temperature. (A color change to orange was noted.) After two hours, the reaction mixture was cooled to 0° C. and water (500 μL) was carefully added. The mixture was concentrated under reduced pressure, and the resultant orange solid was combined with a minimum amount of 99:1:0.1 CHCl$_3$:CH$_3$OH:NH$_4$O. The resultant orange mixture was filtered and the solid phase collected to provide C7 as a crystalline white solid (56 mg, 0.230 mmol, 31% yield). The filtrates were purified over silica gel (99:1:0.1 CHCl$_3$:CH$_3$OH:NH$_4$OH) to provide additional C7. $C_{12}H_{14}N_2O_4S$ GC/MS r.t.=5.53 min., m/z 282 (MI), 128, 122 (bp). $^1$H NMR (D$_6$-DMSO) δ 8.16 (s, 1H), 8.10 (D, J=7.9 Hz, 1H), 7.54 (d, J=7.9 Hz, 1H), 3.48-3.38 (m, 5H), 3.24-3.19 (m, 2H), 2.54 (s, 3H), 2.27-2.21 (m, 1H) ppm.

Step 2. (+/−)10-Methanesulfonyl-10-aza-tricyclo [6.3.1.0$^{2.7}$]dodeca-2,4,6-trien-4-ylamine (C8): A mixture of C7 (207 mg, 0.734 mmol) and 5:4:3 (vol:vol) dioxane/EtOH/H$_2$O (5.00 mL) was treated sequentially with NH$_4$Cl (157 mg, 2.94 mmol) and powdered iron (205 mg, 3.67 mmol). The resultant mixture was heated to 80° C. under a gentle flow of nitrogen. After three hours, the reaction mixture was allowed to cool to 25° C., diluted with EtOAc and H$_2$O, and filtered through diatomaceous earth. The resultant organic phase was collected, dried over MgSO$_4$, and concentrated under reduced pressure to provide C8. This compound was used without further purification. $C_{12}H_{16}N_2O_2S$ LC/MS (Method F) 253.1 (MH$^+$); $^1$H NMR (D$_6$-DMSO) δ 6.89 (d, J=7.8 Hz, 1H), 6.50 (s, 1H), 6.36 (d, J=7.8 Hz, 1H), 4.92 (bs, 2H), 3.40-3.31 (m, 2H), 3.18-3.13 (m, 2H), 3.02 (bs, 2H), 2.50 (s, 3H), 2.10-2.08 (m, 1H), 1.72-1.67 (d, J=10.9 Hz, 1H) ppm.

Step 3: N-{3-[(2-Chloro-5-trifluoromethyl-pyrimidin-4-ylamino)-methyl]-pyridin-2-yl}-N-methyl-methanesulfonamide (247 mg, 0.624 mmol) (see WO 2005023780) was combined with dioxane (1.00 mL) and C8 (158 g, 0.624 mmol) and diisopropyl ethylamine (255 mL, 1.47 mmol) and heated to 110° C. under a gentle flow of nitrogen. After sixteen hours the mixture was concentrated under reduced pressure, and the resultant residue was purified over silica (95:5:0.5 CHCl$_3$:CH$_3$OH:NH$_4$OH) to 2 as a white foam (61 mg, 0.0997 mmol, 16%). $C_{25}H_{28}F_3N_7O_4S_2$ LC/MS (Method F) m/z 612.3 (MH$^+$); $^1$H NMR (D$_6$-DMSO) δ 8.22 (s, 1H) ppm.

Example 3

(+/−) N-Methyl-N-(3-{[2-(10-trifluoroacetyl-10-aza-tricyclo[6.3.1.0$^{2.7}$]dodeca-2(7),3,5-trien-4-ylamino)-5-trifluoromethyl-pyrimidin-4-ylamino]-methyl}-pyridin-2-yl)-methanesulfonamide (3)

A mixture of 1-(4-Amino-10-aza-tricyclo[6.3.1.0$^{2.7}$] dodeca-2,4,6-trien-10-yl)-2,2,2-trifluoro-ethanone (158 g, 0.624 mmol) (see International Publication Nos. WO01/076576A2, WO01/062736A1, WO99/35131 and European Patent No. EP 1078637), 1,4-dioxane (1.00 mL), N-{3-[(2-Chloro-5-trifluoromethyl-pyrimidin-4-ylamino)-methyl]-pyridin-2-yl}-N-methyl-methanesulfonamide (247 mg, 0.624 mmol) and DIAE (255 mL, 1.47 mmol) was heated to 110° C. under a gentle flow of nitrogen. After sixteen hours, the mixture was concentrated, and the resulting residue was purified over silica (95:5:0.5 CHCl$_3$:CH$_3$OH:NH$_4$OH) to provide (+/−) N-Methyl-N-(3-{[2-(10-trifluoroacetyl-10-aza-tricyclo[6.3.1.0$^{2.7}$]dodeca-2(7),3,5-trien-4-ylamino)-5-trifluoromethyl-pyrimidin-4-ylamino]-methyl}-pyridin-2-yl)-methanesulfonamide (3) as a white foam (78 mg, 0.124 mmol, 20%). $C_{26}H_{25}F_6N_7O_3S$ LC/MS (Method F) 630.3 (MH$^+$); $^{19}$F NMR (D$_6$-DMSO) δ −60.38, −67.99 (1:1 ratio) ppm.

Example 4

(+/−) N-(3-{[2-(10-Aza-tricyclo[6.3.1.0$^{2.7}$]dodeca-2 (7),3,5-trien-4-ylamino)-5-trifluoromethyl-pyrimidin-4-ylamino]-methyl}-pyridin-2-yl)-methanesulfonamide (4)

A solution 3 and tetrahydrofuran (2.00 mL) was treated with three crystals of benzyl triethyl ammonium chloride and 40% aqueous NaOH (2.00 mL), and the resultant bi-phasic reaction was heated to 70° C. under nitrogen. After sixteen hours, the mixture was allowed to cool to 25° C. The organic phase was collected and the aqueous layer was washed with EtOAc. The combined organic phases were dried over MgSO$_4$, concentrated under reduced pressure, and purified over silica (92:8:0.8 CHCl$_3$:CH$_3$OH: NH$_4$OH) to provide 32 g of 4 as a yellow foam). The yellow foam was dissolved in a minimum amount of CH$_2$Cl$_2$ at ° C., and 15 μL (0.0600 mmol) of 4.0 M HCl in 1,4-dioxane was slowly added. The resultant white slurry was stirred under a gentle flow of nitrogen for one hour and filtered to provide the hydrochloride salt from of 4 as a white solid (25 mg, 0.0474 mmol, 38%). C$_{24}$H$_{26}$F$_3$N$_7$O$_2$S HPLC r.t.=5.10 min.; LC/MS (Method F) m/z 534.4 (MH$^+$).

Example 5

M-Methyl-N-(3-{[2-(9-trifluoroacetyl-1,2,3,4-tetrahydro-1,4-epiazano-naphthalen-6-ylamino)-5-trifluoromethyl-pyrimidin-4-ylamino]-methyl}-pyridin-2-yl)-methanesulfonamide (5)

Step 1. 2,2,2-Trifluoro-1-(1,2,3,4-tetrahydro-1,4-epiazano-naphthalen-9-yl)-ethanone (C11): A solution of 1,2,3,4-tetrahydro-1,4-epiazano-naphthalene (see JOC, 1966(31), 764) in dry CH$_2$Cl$_2$ (40.0 mL) and DIAE (1.92 mL, 11.0 mmol) was cooled to 0° C. and treated with trifluoroacetic anhydride (1.55 mL (11.0 mmol). The reaction mixture was allowed to slowly equilibrate to 25° C. under nitrogen atmosphere. After five hours, the resultant green reaction mixture was cooled to 0° C. and treated with 2.00 mL water to quench any remaining anhydride. Aqueous NaOH (1N) was added and the phases separated. The aqueous layer was washed with CH$_2$Cl$_2$, and the combined organics were dried over MgSO$_4$ and concentrated under reduced pressure. The resultant dark oil was treated with EtOAc, stirred with activated charcoal, filtered through diatomaceous earth, and concentrated under reduced pressure to provide C11 as a brown oil (1.65 g, 6.80 mmol, 68% yield). GC/MS r.t.=2.22 min, m/z 241 (MI), 213 (bp), 116; $^{19}$F NMR (D$_6$-DMSO) δ −71.50 ppm.

Step 2. (+/−) 2,2,2-Trifluoro-1-(6-nitro-1,2,3,4-tetrahydro-1,4-epiazano-naphthalen-9-yl)-ethanone (C12): A solution of trifluoromethanesulfonic acid (1.20 mL, 13.6 mmol) and dichloromethane (7.00 mL was cooled to 0° C. and carefully treated with a solution of HNO$_3$ (300 mL, 6.80 mmol), during which time fuming and solid formation were noted. The resultant mixture was stirred for an additional fifteen minutes at 0° C., cooled to −78° C., and treated dropwise with a solution of C11 (1.65 g, 6.80 mmol) in dry CH$_2$Cl$_2$ (10.0 mL). After stirring for 1 hour at −78° C. the mixture was warmed to 0° C. and allowed to stand for one hour at 0° C. The reaction mixture was then carefully poured into vigorously-stirred ice water, and CH$_2$Cl$_2$ was added after the ice had melted. The resultant organic phase was collected and the aqueous layer washed with CH$_2$Cl$_2$. The combined organic phases were dried over MgSO$_4$ and concentrated under reduced pressure. The resultant oily residue was purified over silica (20% EtOAc in hexanes) to provide C12 as a yellow foam (1.05 g, 3.69 mmol, 54% yield). C$_1$H$_{10}$F$_3$NO APCI m/z 286.1 (M$^-$), $^{19}$F NMR (D$_6$-DMSO) δ −71.55 ppm.

Step 3. (+/−) 1-(6-Amino-1,2,3,4-tetrahydro-1,4-epiazano-naphthalen-9-yl)-2,2,2-trifluoro-ethanone (C13): Compound C13 was prepared in a manner similar to that described for C8 in Step 2 of Example 2 except that 2,2,2-Trifluoro-1-(6-nitro-1,2,3,4-tetrahydro-1,4-epiazano-naphthalen-9-yl)-ethanone (570 mg, 1.99 mmol) was used instead of C7 to provide C13 as a tan-yellow foam (430 mg, 1.67 mmol, 84%). C$_{12}$H$_{11}$F$_3$N$_2$O LC/MS (Method F) m/z 257.1 (MH$^+$). $^1$H NMR (D$_6$-DMSO) δ 6.98 (m (F-Coupling), 1H), 6.31 (d, J=7.9 Hz, 1H), 5.15 (bs, 2H) ppm.

Step 4. Compound 5 was prepared in a manner similar to that described for 3 in Example 3 except that 1-(6-Amino-1,2,3,4-tetrahydro-1,4-epiazano-naphthalen-9-yl)-2,2,2-trifluoro-ethanone (180 mg, 0.700, 53% yield). C$_{25}$H$_{23}$F$_6$N$_7$O$_3$S HPLC r.t.=7.31 min., LC/MS (Method F) m/z 616.3 (MH$^+$).

Example 6

(+/−) N-Methyl-N-(3-{[2-(1,2,3,4-tetrahydro-1,4-epiazano-naphthalen-6-ylamino)-5-trifluoromethyl-pyrimidin-4-ylamino]-methyl}-pyridin-2-yl)-methanesulfonamide (6)

Compound 6 was prepared in a manner similar to that described for 4 in Example 4 except that 5 (8 mg, 0.0153 mmol) was used instead 3 to provide 6 as a white solid (8 mg, 0.0153 mmol, 7% yield). C$_{23}$H$_{24}$F$_3$N$_7$O$_2$S HPLC r.t.=4.80 min.; LC/MS (Method F) m/z 520.3 (MH$^+$).

Example 7

N-(3-{[2-(9-Methanesulfonyl-1,2,3,4-tetrahydro-1,4-epiazano-naphthalen-6-ylamino)-5-trifluoromethyl-pyrimidin-4-ylamino]-methyl}-pyridin-2-yl)-N-methyl-methanesulfonamide (7)

Step 1: (+/−) 6-Nitro-1,2,3,4-tetrahydro-1,4-epiazano-naphthalen (C14): Compound C14 was prepared in a manner similar to that described for 4 in Example 4 except that C12 (480 mg, 1.68 mmol) was used instead of 3 to provide C14 as a white solid (250 mg, 1.31 mmol, 78% yield). C$_{10}$H$_{10}$N$_2$O$_2$ LC/MS (Method F) m/z 191.1 (MH$^+$); $^1$H NMR (CD$_3$OD) δ 8.08 (D, J=7.9 Hz, 1H), 8.05 (s, 1H), 7.43 (d, J=7.9 Hz, 1H) ppm.

Step 2. (+/−) 9-Methanesulfonyl-6-nitro-1,2,3,4-tetrahydro-1,4-epiazano-naphthalene (C15): Compound C15 was prepared in a manner similar to that described for C7 in Step 2 of Example 2, except that C14(250 mg, 1.31 mmol) was used instead of 4-Nitro-10-aza-tricyclo[6.3.1.0$^{2.7}$]dodeca-2, 4,6-triene. The reaction provided C15 as a crystalline beige solid (350 mg, 1.30 mmol, 99% yield). C$_{11}$H$_{12}$N$_2$O$_4$S $^1$H NMR (CD$_3$OD) δ 8.24 (s, 1H), 8.19 (d, J=7.7 Hz, 1H), 7.58 (d, J=7.7 Hz, 1H), 2.48 (s, 3H) ppm.

Step 3. (+/−) 9-Methanesulfonyl-1,2,3,4-tetrahydro-1,4-epiazano-naphthalen-6-ylamine (C16): compound C16 was prepared in a manner similar to that described for C8 in Step 1 of Example 2, except that C15 (350 mg, 1.30 mmol) was used instead C7 to provide C16 as a tan solid (269 mg, 1.12 mmol, 86% yield). C$_{11}$H$_{14}$N$_2$O$_2$S GC/MS r.t.=4.72 min.; m/z 238 (MI), 210, 131 (bp); $^1$H NMR (D$_6$-DMSO) δ 6.94 (d, J=7.9 Hz, 1H), 6.55 (s, 1H), 6.29 (d, J=7.9 Hz, 1H), 5.06 (bs, 2H), 2.18 (s, 3H) ppm.

Step 3. Compound 7 was made in a manner similar to that described for 3 in Example 3, except that C16 (269 mg, 1.12 mmol) was used instead of 1-(4-Amino-10-aza-tricyclo[6.3.1.0$^{2.7}$]dodeca-2,4,6-trien-10-yl)-2,2,2-trifluoro-ethanone to provide 7 as a tan foam (0.570 mmol, 342 mg, 61% yield). $C_{24}H_{26}F_3N_2O_4S_2$ HPLC r.t.=6.43 min.

Example 9

N-(3-{[2-(9-Methanesulfonyl-1,2,3,4-tetrahydro-1,4-epiazano-naphthalen-6-ylamino)-5-trifluoromethyl-pyrimidin-4-ylamino]-methyl}-pyridin-2-yl)-N-methyl-methanesulfonamide (Enantiomer 2) (9)

Compound 7 (racemate) from Example 7 was separated on a 10×50 cm. Chiralpak AS preparatory HPLC column using a 3:2 (vol:vol) mixture of heptane/ethanol as the mobile phase at a rate of 275 mL/min. The eluent containing the slower-eluting enantiomer was concentrated under reduced pressure to provide 9 as the white foam. $C_{24}H_{26}F_3N_2O_4S_2$ Prep. HPLC r.t.=12.59 min.; LC/MS (Method F) m/z 598.2 (MH$^+$).

Example 10

1-[4-(4-Cyclopropylamino-5-trifluoromethyl-pyrimidin-2-ylamino)-10-aza-tricyclo[6.3.1.0$^{2.7}$]dodeca-2(7),3,5-trien-10-yl]-2-methoxy-ethanone (10)
(Method A)

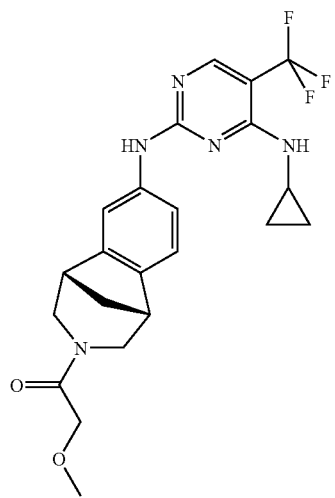

Step 1. (+/−)-2,2,2-Trifluoro-1-(4-nitro-10-aza-tricyclo[6.3.1.02.7]dodeca-2(7),3,5-trien-10-yl)-ethanone (C17): A solution of 1-(10-Aza-tricyclo[6.3.1.0$^{2.7}$]dodeca-2(7),3,5-trien-10-yl)-2,2,2-trifluoro-ethanone (49.9 g, 196 mmol) (4) (see O'Donnell et al., JOC, 2004 (69.7), 5756-59 and International Publication Nos. WO 04/063164 and WO 99/35131) and in trifluoroacetic acid (TFA) (100 mL) was cooled in an acetone/ice bath and treated drop-wise with fuming HNO$_3$ over 10 minutes. The resultant reaction mixture was stirred for 1 hour as the ice bath temperature increased to 0° C. and then for an additional 1 hour. The ice bath was removed, excess NO$_2$ was removed under a steam of nitrogen, and TFA was removed under reduced pressure. The resultant residue was poured into 300 ml ice water and extracted with 3×200 ml CH$_2$Cl$_2$. The combined organic phases were washed with saturated NaCl (1×100 ml) and saturated NaHCO$_3$ (1×100 ml). The organic phase was dried over MgSO$_4$ and passed through a 200 g plug of silica gel (230-400 mesh) eluting with CH$_2$Cl$_2$ (2000 ml). The resultant eluent was concentrated under reduced pressure to provide C17 as a pale yellow solid (55.4 g, 184 mmol, 94% yield). $^1$H NMR (400 MHz, DMSO-D6) δ ppm 2.1 (d, J=11.2 Hz, 1H) 2.3 (dd, J=10.8, 5.4 Hz, 1H) 3.2 (dd, J=12.9, 4.6 Hz, 1H) 3.4 (d, J=4.6 Hz, 2H) 3.7 (m, 1H) 3.8 (m, 1H) 4.1 (d, J=12.9 Hz, 1H) 7.5 (t, J=8.5 Hz, 1H) 8.1 (d, J=7.9 Hz, 1H) 8.2 (dd, J=10.8, 2.1 Hz, 1H) ppm.

Step 2. (+/−) 4-Nitro-10-tricyclo[6.3.1.0$^{2.7}$]dodeca-2(7),3,5-triene (C18): A solution of C17 (45.4 g, 157 mmol) in tetrahydrofuran (THF) (300 mL) was treated drop-wise with lithium hydroxide monohydrate (9.4 g, 554 mmol) in H$_2$O (75 ml) over 10 minutes. The mixture was stirred for 1 hour at 25° C. and the mixture was concentrated under reduced pressure. The resultant residue was treated with 250 ml of 1:1 (vol:vol) water saturated with NaCl: concentrated NH$_4$OH and extracted with CH$_2$Cl$_2$ (2×200 ml). The combined organic layers were dried over K$_2$CO$_3$ and concentrated under reduced pressure to provide C18 as an orange solid (32 g, 155 mmol, 99% yield). C18 was used without further purification. 1H NMR (400 MHz, DMSO-D6) δ 1.7 (d, J=0.4 Hz, 1H) 1.9 (d, J=10.4 Hz, 1H) 2.3 (m, 1H) 2.6 (dd, J=12.3, 1.9 Hz, 2H) 2.9 (m, 2H) 3.0 (d, J=13.7 Hz, 2H) 7.4 (d, J=7.9 Hz, 1H) 8.0 (s, 1H) 8.0 (dd, J=8.1, 2.3 Hz, 1H) ppm.

Step 3. (+/−)4-Nitro-10-aza-tricyclo[6.3.1.0$^{2.7}$]dodeca-2(7),3,5-triene-10-carboxylic acid tert-butyl ester (C19): To a solution of C18 (2.00 g, 9.78 mmol) in 10 mL of acetonitrile was added di-tert-butyl dicarbonate (2.12 g, 9.78 mmol), and the resultant mixture was stirred at 25° C. for 2 hours. The mixture was concentrated under reduced pressure, and resultant residue was redissolved in ethyl acetate (50 mL) and washed with saturated sodium bicarbonate (2×25 mL) and brine (2×25 mL). The combined aqueous phases were extracted with ethyl acetate (50 mL) and the combined organic phases dried over sodium sulfate and concentrated under reduced pressure. The resultant yellow residue was chromatographed on silica gel (25% EtOAc:Hexanes) and concentrated under reduced pressure to provide C19 as a colorless oil (2.7 g, 9.3 mmol, 95% yield). HPLC Rt 7.085 minutes; LC/MS (Method F) m/z 305.3 (MH$^+$); 1H NMR (400 MHz, DMSO-D6) δ ppm 1.1 (s, 9H) 1.9 (d, J=10.8 Hz, 1H) 2.2 (m, 1H) 3.1 (m, 1H) 3.2 (d, J=16.2 Hz, 3H) 3.8 (m, 2H) 7.5 (dd, J=11.4, 8.1 Hz, 1H) 8.1 (ddd, J=15.3, 8.1, 7.6 Hz, 2H) ppm.

Step 4. (+/−)4-Amino-10-aza-tricyclo[6.3.1.0$^{2.7}$]dodeca-2(7),3,5-triene-10-carboxylic acid tert-butyl ester (C20): A mixture of C19 (1.34 g, 4.27 mmol), ethanol (50 mL) and 10% Pd/C (134 mg) was charged to a Parr shaker hydrogenation vessel, and the resultant mixture was shaken under 45 psi H$_2$ for 2 hours at about 25° C. The resultant mixture was filtered through Celite® and concentrated under reduced pressure to provide C20 as a clear oil (1.2 g, 3.8 mmol, 89%). HPLC Rt 5.88; LC/MS (Method F) m/z 275.3 (MH$^+$); 1H NMR (400 MHz, DMSO-D6) δ ppm 1.2 (d, J=4.2 Hz, 9H) 1.7 (d, J=10.4 Hz, 1H) 2.0 (m, 1H) 2.9 (m, 3H) (3.1 (t, J=11.4 Hz, 1H) 3.6 (m, 2H) 4.8 (s, 2H) 6.3 (dd, J=3.9, 2.3 Hz, 1H) 6.4 (d, J=4.2 Hz, 1H) 6.8 (t, J=7.5 Hz, 1H) ppm.

Step 5. 4-(4-Chloro-5-trifluoromethyl-pyrimidin-2-ylamino)-10-aza-tricyclo[6.3.1.0$^{2.7}$]dodeca-2(7),3,5-triene-10-carboxylic acid tert-butyl ester (C21): A mixture of 5-trifluoromethyl-2,6-dichloropyrimidine (9.6 g, 44.4 mmol) and 180 mL t-BuOH/DCE (1:1) was cooled to 0° C. under a nitrogen atmosphere, treated with ZnCl$_2$ (53.3 mL, 1M in Et$_2$O, and stirred for 1 hour at 0° C. The mixture was treated dropwise with a solution of C20 (11.6 g, 42.3 mmol) in 40 ml 1:1 (vol:vol) t-BuOH/DCE and allowed to stir an additional 45 minutes at 0° C. The resultant mixture was then treated drop-wise at 0° C. with a solution of Et$_3$N (7.4 mL, 53.3 mmol) in 10 ml 1:1 (vol:vol) t-BuOH/DCE and allowed to warm to 25° C. The mixture was stirred for an additional 2 hours and concentrated under reduced pressure. The resultant green foam was dissolved in $CH_2Cl_2$, chromatographed over 500 g silica gel (230-400 mesh) eluting with 17% EtOAc/hexanes, and concentrated under reduced pressure. The result viscous pale yellow oil (17 g) was dissolved in 60 ml hexane and stirred for 2 hours, during which time crystallization occurred. The resultant solids were collected by filtration, washed with cold hexane, and dried to provide C21 as a white solid (15.3 g, 33.8 mmol, 80% yield). HPLC Rt 9.5 minutes; LC/MS (Method F) m/z 455.3 ($MH^+$); 1H NMR (400 MHz, DMSO-D6) δ ppm 1.2 (s, 9H) 1.8 (d, J=10.4 Hz, 1H) 2.1 (m, 1H) 3.0 (t, J=10.6 Hz, 1H) 3.1 (s, 1H) 3.1 (d, J=12.5 Hz, 2H) 3.7 (m, 2H) 7.2 (dd, J=11.0, 8.1 Hz, 1H) 7.4 (m, 1H) 7.5 (s, 1H) 8.7 (s, 1H) 10.6 (s, 1H) ppm.

Step 6. (+/−)-(10-Aza-tricyclo[6.3.1.0$^{2.7}$]dodeca-2(7),3,5-trien-4-yl)-(4-chloro-5-trifluoromethyl-pyrimidin-2-yl)-amine hydrochloride (C22): A solution of C21 (1.0 g, 2.2 mmol) in 12 mL HCl in 1,4-Dioxane (4N) was stirred at about 25° C. for 30 minutes during which time a white precipitate formed. The resultant solids were collected by filtration, washed with 1,4-Dioxane (2×25 mL), and dried under reduced pressure to provide C22 as a white solid (912 mg, 2.0 mmol, 91% yield). HPLC Rt 5.2 minutes; LC/MS (Method F) m/z 355.3 ($MH^+$); $^1$H NMR (400 MHz, DMSO-$d_6$) δ 1.98 (d, J=11 Hz, 2H), 2.0 (m, 2H), 2.9 (m, 4H), 3.17 (d, J=9 Hz, 3H), 3.2 (m, 4H), 7.29 (m, 2H) 7.30 (d, J=4 Hz, 1H) 7.57 (m, 2H) 7.66 (bs, 2H) 8.1 (s, 1H) 8.77 (s, 1H) 9.45 (bs, 2H) 10.75 (s, 1H) ppm.

Step 7. (+/−)-1-[4-(4-Chloro-5-trifluoromethyl-pyrimidin-2-ylamino)-10-aza-tricyclo[6.3.1.0$^{2.7}$]dodeca-2(7),3,5-trien-10-yl]-2-methoxy-ethanone (C23): A mixture of methoxyacetyl chloride (140 mg, 1.53 mmol), methoxyacetic acid (120 mg, 1.53 mmol), DIEA (1.3 mL, 7.65 mmol) and 5 mL of 1,4-dioxane was stirred for 10 minutes at 25° C. to effect in situ generation of methoxyacetic anhydride. To the preformed anhydride was added C22 (460 mg, 1.17 mmol), and the mixture stirred at 25° C. for 1 hour. The reaction mixture was then partitioned between EtOAc (10 mL) and saturated $NaHCO_3$ (10 mL) and the layers separated. The resultant organic phase was washed with brine (2×20 mL), dried over $Na_2SO_4$, and concentrated under reduced pressure. The resultant residue was purified on silica gel using a gradient 10-30% EtOAc/Hexanes to provide C23 as a white solid (480 mg, 1.12 mmol, 96% yield). HPLC Rt 6.39 minutes; LC/MS (Method F) m/z 427.8 ($MH^+$).

Step 8. Compound C23 (100 mg, 234 μmol) was treated with cyclopropyl amine (26 mg, 468 μmol) and DIEA (74 μL, 468 μmol) in 2 mL 1,4-Dioxane in a pressure vessel. The contents of the reactor were stirred at 90° C. for 1 hour, and the resultant brown solution was diluted with 5 mL EtOAc and washed with water. The organic phase was collected, concentrated under reduced pressure, and purified on silica gel (50% EtOAc/Hexanes) to provide 10 as a white solid (52.3 mg, 0.117 mmol, 50% yield). HPLC Rt 6.5 minutes; LC/MS (Method F) m/z 448.1 ($MH^+$).

Example 11

(+/−)-1-[4-(4-Cyclopropylamino-5-trifluoromethyl-pyrimidin-2-ylamino)-10-aza-tricyclo[6.3.1.0$^{2.7}$]dodeca-2(7),3,5-trien-10-yl]-2,2-difluoro-ethanone (11)

Step 1. 1-[4-(4-Chloro-5-trifluoromethyl-pyrimidin-2-ylamino)-10-aza-tricyclo[6.3.1.0$^{2.7}$]dodeca-2(7),3,5-trien-10-yl]-2,2-difluoro-ethanone (C24): A solution of C22 (1 g, 2.55 mmol) in DMF (5 mL) was treated with diisopropylethyl amine (880 μL, 5.00 mmol) and difluoroacetic acid (200 μL, 3.06 mmol) and stirred at room temperature for 5 minutes. O-(7-Azabenzotriazol-1-yl)-N,N,N',N'-tetramethyluronium hexafluorophosphate (HATU) (970 mg, 2.55 mmol) was added, and the mixture was stirred at 25° C. for 30 minutes. The mixture was poured into water (50 mL), and the resulting white precipitate was collected by filtration, washed with MeOH (20 mL), and dried under reduced pressure to provide C24 as a white powder (920 mg, 1.94 mmol, 76% yield). HPLC Rt 6.55 minutes; LC/MS (Method F) m/z 433.3, 434.6, 435.3 ($MH^+$).

Step 2. Compound 11 was prepared in a manner similar to that described for 10 in Step 8 of Example 10 except that C24 (125 mg, 289 μmol) was used instead of C23 to provide 11 as a white solid (53 mg, 116 mol, % yield). HPLC Rt 6.76; APCI m/z 454.1 ($MH^+$)

Example 12

(+/−)-1-[4-(4-Cyclopropylmethylamino-5-trifluoromethyl-pyrimidin-2-ylamino)-10-aza-tricyclo[6.3.1.0$^{2.7}$]dodeca-2(7),3,5-trien-10-yl]-2,2,2-trifluoro-ethanone (12)

Step 1. (+/−)-1-[4-(4-Chloro-5-trifluoromethyl-pyrimidin-2-ylamino)-10-aza-tricyclo[6.3.1.0$^{2.7}$]dodeca-2(7),3,5-trien-10-yl]-2-trifluoro-ethanone (C25): A suspension of C22 (1 g, 2.55 mmol) in $CHCl_3$ (5 mL) was treated with DIEA (1.33 mL, 7.65 mmol) and trifluoroacetic anhydride (500 μL, 3.06 mmol) and the resultant solution stirred at ambient temperature for 1 hour. The reaction mixture was diluted with EtOAc (5 mL), washed with saturated $NaHCO_3$ (2×10 mL) and brine (2×10 mL), dried over $Na_2SO_4$, and concentrated under reduced pressure. The resultant brown residue was purified on silica gel (30% EtOAc/Hexanes) to provide C25 as a white solid (460 mg, 102 mmol, 40% yield). HPLC Rt 7.7 minutes; APCI m/z 451.2; $^1$H NMR (400 MHz, DMSO-$d_6$) δ 1.98 (d, J=11 Hz, 1H), 2.2 (m, 1H), 3.17 (d, J=12 Hz, 2H), 3.23 (m, 2H), 3.59 (d, J=12 Hz, 1H), 3.65 (s, 1H), 4.04 (d, J=13 Hz, 1H), 7.2 (m, 1H), 7.4 (m, 1H), 7.6 (bs, 1H), 8.75 (d, J=8 Hz, 1H), 10.6 (s, 1H) ppm.

Step 2. Compound 12 was prepared in a manner similar to that described for 10 in Step 8 of Example 10 by reacting C25 (153 mg, 324 μmol) with cyclopropylmethyl amine (46 mg, 648 μmol) to provide 12 as a white solid (99 mg, 0.204 mmol, 63%). HPLC Rt 7.735; APCI m/z 486.4 ($MH^+$).

Example 13

(+/−)-$N^2$-(10-Aza-tricyclo[6.3.1.0$^{2.7}$]dodeca-2(7),3,5-trien-4-yl)-$N^4$-cyclopropyl-5-trifluoromethyl-pyrimidine-2,4-diamine dihydrochloride salt (13)

Compound 13 was prepared in a manner similar to that described for 10 in Example 10 by reacting C21 (2.0 g, 4.4 mmol) with cyclopropyl amino (410 μL, 5.9 mmol) followed by removal of the BOC group under acidic conditions using 3N MeOH hydrochloric acid to provide 13 as an off-white solid (1.89 mg, 4.22 mmol, 96% yield). LC/MS (Method F) m/z 376.3 ($MH^+$); 1H NMR (400 MHz, DMSO-D6) δ ppm 0.8 (m, 4H) 2.0 (d, J=11.2 Hz, 2H) 2.2 (d, J=5.0 Hz, 1H) 3.0 (d, J=10.4 Hz, 4H) 3.2 (t, J=9.3 Hz, 4H) 7.3 (d, J=7.9 Hz, 2H) 7.8 (s, 2H) 8.5 (s, 1H) 9.7 (s, 1H) 11.3 (s, 1H) ppm.

Example 14

(+/−)-N$^4$-Cyclopropyl-N$^2$-(10-pyridin-2-yl-10-aza-tricyclo[6.3.1.0$^{2.7}$]dodeca-2(7),3,5-trien-4-yl)-5-trifluoromethyl-pyrimidine-2,4-diamine (14)

Compound 13 (290 mg, 645 µmol) was dissolved in DMSO (2 mL) in a 15 mL screw cap pressure tube, and the resultant solution was treated with DIEA (431 µL, 2.48 mmol) and 2-fluoropyride (125 mg, 1.29 mmol). The reaction vessel was sealed and stirred at 130° C. for 14 hours. The reactor contents were cooled to 25° C., poured into H$_2$O (30 mL), and stirred for 1 hour to produce an orange, gummy residue. The H$_2$O was decanted off and the residue purified on silica gel (40% EtOAc/Hexanes) to provide 14 as an off-white powder (143 mg, 49% yield). HPLC Rt 6.57 minutes; LC/MS (Method F) m/z 453.3 (MH$^+$).

Example 15

(+/−)-[4-(4-cyclopropyl-5-trifluoromethyl-pyrimidine-2-ylamino)-10-aza-tricyclo[6.3.1.0$^{2.7}$]dodeca-2(7),3,5-trien-10-yl]pyridine-3-yl-methanone (15)

A solution of 13 (200 mg, 446 µmol) and DIEA (124 µL, 880 µmol) in 1,4-dioxane (2 mL) was treated with in one portion with nicotinoyl chloride hydrochloride (80 mg, 446 µmol). The mixture was stirred at room temperature for 4 hours and concentrated under reduced pressure. The resultant residue was purified on silica (3% CH$_3$OH/CH$_2$Cl$_2$) to provide 15 as an off-white solid (52 mg, 20% yield). HPLC Rt 5.7 minutes; LC/MS (Method F) m/z 427 (MH$^+$).

Example 16

(+/−)-1-[4-(4-Cyclopropylamino-5-trifluoromethyl-pyrimidin-2-ylamino)-10-aza-tricyclo[6.3.1.0$^{2.7}$]dodeca-2(7),3,5-trien-10-yl]-2-dimethylamino-thanone (16)

Compound 16 was prepared in a similar to that described for 15 in Example 15 by reacting 13 (150 mg, 337 µmol) with N,N-Dimethylglycine hydrochloride (127 mg, 337 µmol) to provide 16 as a white solid (62 mg, 0.135 mmol, 40% yield). LC/MS (Method F) Rt 1.4 minutes; LC/MS (Method F) m/z 461.3 (MH$^+$).

Example 17

+/−)-4-(4-Cyclopropylamino-5-trifluoromethyl-pyrimidin-2-ylamino)-10-aza-tricyclo[6.3.1.0$^{2.7}$]dodeca-2(7),3,5-triene-10-carboxylic acid ethylamide (17)

Compound 17 was prepared in a manner similar to that described for 15 in Example 15 except that ethyl isocyanate (42 µL, 337 µmol) was used instead of nicotinoyl chloride hydrochloride to provide 17 as a white solid (120 mg, 0.270 mmol, 80% yield). HPLC Rt 6.1 minutes; LC/MS (Method F) m/z 447.3.

Example 18

(+/−)-1-{4-[4-(3-Morpholin-4-yl-azetidin-1-yl)-5-trifluoromethyl-pyrimidin-2-ylamino]-10-aza-tricyclo[6.3.1.0$^{2.7}$]dodeca-2(7),3,5-trien-10-yl}-ethanone (18)

Step 1. (+/−)-1-[4-(4-Chloro-5-trifluoromethyl-pyrimidin-2-ylamino)-10-aza-tricyclo[6.3.1.0$^{2.7}$]dodeca-2(7),3,5-trien-10-yl]-ethanone (C26): Compound C26 was prepared in a manner similar to that described for 10 in Step 7 of Example 10 by reacting C22 (460 mg, 1.17 mmol) with acetic anhydride (91 µL, 1.17 mmol) to provide C26 as a light yellow solid (309 mg, 0.725 mmol, 62% yield). HPLC Rt 6.5 minutes; LC/MS (Method F) m/z 427.3 (MH$^+$); $^1$H NMR (400 MHz, DMSO-d$_6$) δ 1.65 (s, 3H), 1.84 (d, J=11 Hz, 1H), 2.18 (m, 1H), 2.86 (d, J=3 Hz, 1H), 3.127 (bs, 2H), 3.4 (d, J=6 Hz, 1H), 3.57 (d, J=12 Hz, 1H), 7.16 (dd, J=8, 8 Hz, 1H), 7.36 (d, J=8 Hz, 1H), 7.53 (d, J=19 Hz, 1H), 8.75 (s, 1H), 10.58 (s, 1H) ppm.

Step 2. 1-Azetidin-3-yl-morpholine dihydrochloride salt (C27): A sealed pressure tube was charged with 3-methanesulfonyloxy-azetidine-1-carboxylic acid tert-butyl ester (5.00 g, 19.9 mmol) (see Anderson, et al., JOC, 1972, 37, 3953), DMSO (10 mL), morpholine (5.4 g, 5937 mmol) and DIEA (3.4 mL, 19.9 mmol). The mixture was heated to 103° C. After 12 hours EtOAc (50 mL) was added and the resultant mixture filtered. The filtrate was washed with 2×100 mL water, 2×100 mL brine, dried over K$_2$CO$_3$, and concentrated. The resulting residue was purified on silica gel (75% EtOAc/Hexanes) and concentrated to provide a clear oil (2.8 g). The oil was dissolved in 1.25N HCl in MeOH and refluxed for 3 hours. The mixture was concentrated under reduced pressure and resultant residue triturated with pentane (20 mL) to provide C27 (2.0 g, 10.05 mmol, 50.5% yield). $^1$H NMR (400 MHz, DMSO-d$_6$) δ 1.91 (d, J=41 Hz, 4H), 2.93 (bs, 2H), 3.41 (bs, 3H), 4.04 (m, 3H), 4.32 (m, 4H) ppm.

Step 3. A mixture of compound C26 (200 mg, 503 µmol), DIEA (350 µL, 2.0 mmol) mixture was concentrated under reduced pressure and the resultant residue purified on silica gel (2% CH$_3$OH/CH$_2$Cl$_2$) to provide 18 as an off-white solid (120 mg, 0.236 mmol, 47% yield). LC/MS (Method F) Rt 1.7 minutes, LC/MS (Method F) m/z 503.3 (MH$^+$).

Example 19

N$^4$-Ethyl-N$^2$-(10-ethyl-10-aza-tricyclo[6.3.1.0$^{2.7}$]dodeca-2(7),3,5-trien-4-yl)-5-trifluoromethyl-pyrimidine-2,4-diamine (19)

Step 1. (+/−)-10-Ethyl-4-nitro-10-aza-tricyclo[6.3.1.0$^{2.7}$]dodeca-2(7),3,5-triene-hydroiodide salt (C28): Ethyl iodide (165 µL, 2.43 mmol) at 25° C. was added dropwise to a stirred solution of C18 (500 mg, 2.43 mmol) in acetonitrile (10 mL). The reaction mixture was allowed to stir for 12 hours at 25° C., and the resultant yellow precipitate was collected by filtration and dried to provide C28 (540 mg, 1.38 mmol, 57% yield). HPLC Rt 3.11 minutes; LC/MS (Method F) m/z 231.3 (MH$^-$); $^1$H NMR (400 MHz, DMSO-d$_6$) δ 1.04 (t, J=7 Hz, 3H), 2.09 (d, J=11 Hz, 1H), 2.23 (m, 1H), 3.04 (m, 2H), 3.35 (m, 4H), 3.51 (bs, 2H), 7.62 (d, J=8 Hz, 1H), 8.2 (m, 2H) ppm.

Step 2. (+/−)-10-Ethyl-10-aza-tricyclo[6.3.1.0$^{2.7}$]dodeca-2(7),3,5-triene-4-ylamine (C29): A Parr® shaker hydrogenation vessel was charged with C28 (1.2 g, 5.14 mmol), MeOH (15 mL), NaOH flakes (200 mg, 5.14 mmol) and 10% Pd/C (120 mg), and the contents of the reactor were shaken under 50 psi H$_2$ for 14 hours at about 25° C. The reaction mixture was filtered through Celite® and concentrated to provide C29 as a white solid. (860 mg, 83% yield). HPLC Rt 2.12 minutes; LC/MS (Method F) m/z 202.1; $^1$H NMR (400 MHz, DMSO-d6) δ ppm 0.77 (t, J=7.3 Hz, 3H) 1.49 (d, J=10.0 Hz, 1H) 2.01 (m, 1H) 2.17 (t, J=9.3 Hz, 2H) 2.23 (q, J=7.3 Hz, 2H) 2.65 (m, 2H) 2.85 (s, 2H) 4.7 (s, 2H) 6.23 (d, J=7.9 Hz, 1H) 6.34 (s, 1H) 6.71 (d, J=7.9 Hz, 1H) ppm.

Step 3. (+/−)-(4-Chloro-5-trifluoromethyl-pyrimidin-2-yl)-(10-ethyl-10-aza-tricyclo[6.3.1.0$^{2.7}$]dodeca-2(7),3,5-trien-4-yl)-amine hydrochloride salt (C30): Compound C30 was prepared in a manner similar to that described in Step 5 of Example 10 except that C29 (860 mg, 4.27 mmol) was used instead of C20 to provide the free-base form of C30 (600 mg, 1.58 mmol, 37% yield). The free-base form of C30 was dissolved in 1N HCl in MeOH (5 mL), stirred for 1 hour, and concentrated to provide C30 (718 mg, 1.58 mmol, 100% yield). LC/MS (Method F) Rt 2.4 min; LC/MS (Method F) m/z 383.2 (MH$^+$).

Step 4. A mixture of C30 (173 mg, 412 μmol), 1,4-dioxane (2 mL), DIEA (215 μL, 1.23 mmol) and 2M ethylamine in THF was stirred at 90° C. for 12 hours and concentrated. The resultant residue was purified on silica gel (6-8% CH$_3$OH/CH$_2$Cl$_2$) to provide 19 as a light yellow solid (30 mg, 18% yield). HPLC Rt 5.48 minutes; LC/MS (Method F) m/z 392.3 (MH$^+$).

Example 20

(−)-2-Methoxy-1-{4-[4-(2-methoxy-ethylamino)-5-trifluoromethyl-pyrimidin-2-ylamino]-(1R,8S)-10-aza-tricyclo[6.3.1.0$^{2.7}$]dodeca-2(7),3,5-trien-10-yl}-ethanone (20)

Step 1. (−)-4-Nitro-10-aza-tricyclo[6.3.1.0$^{2.7}$]dodeca-2(7),3,5-triene (C31): Racemic C18 (13.68 g, 67 mmol) was resolved by chiral chromatography using solution of 50/50 ethanol/heptane over a ChiralPak AD column (10 cm×50 cm), 450 ml flow rate, 6.84 g per injection. The optical rotation of each isolated enantiomer was calculated using a JASCO® polarimeter:

Peak 1: Rt=14.44 min. [α]$_D$ −12.893° (c=0.0117, CH$_2$Cl$_2$), (−)-4-Nitro-10-aza-tricyclo[6.3.1.0$^{2.7}$]dodeca-2(7),3,5-triene (C31) (6.5 g, 32.1 mmol, 96% yield)

Peak 2: Rt=20.56 min. [α]$_D$ +12.85° (c=0.0115, CH$_2$Cl$_2$), (+)-4-Nitro-10-aza-tricyclo[6.3.1.0$^{2.7}$]dodeca-2(7),3,5-triene (C32) (6.5 g, 32.1 mmol, 96% yield).

Step 2. (−)-(4-Iodo-phenyl)-(1R,8S)-(4-nitro-10-aza-tricyclo[6.3.1.0$^{2.7}$]dodeca-2(7),3,5-trien-10-yl)-methanone (C33): A mixture of C31 (1.3 g, 4.89 mmol) and 4-Iodobenzoyl chloride (1.0 g, 4.89 mmol) in MeCN (10 mL) was stirred at 25° C. for 2 hours. The resultant precipitate was collected by filtration, washed with cold MeCN (10 mL), and the dried under reduced pressure to provide (C33 as a white solid (1.35 g, 2.88 mmol, 59% yield). A 100 mg portion of C33 was recrystallized from warm ethanol. The resultant orthorhombic crystals examined by single crystal X-ray crystallography and the results confirmed the structure as depicted for C33. 1H NMR (400 MHz, DMSO-D6) δ ppm 2.0 (t, J=11.0 Hz, 1H) 2.2 (d, J=5.4 Hz, 1H) 3.1 (dd, J=12.0, 5.0 Hz, 1H) 3.2 (s, 1H) 3.4 (d, J=18.3 Hz, 1H) 4.4 (d, J=12.0 Hz, 1H) 6.6 (d, J=4.6 Hz, 2H) 7.4 (d, J=7.9 Hz, 1H) 7.5 (d, J=7.9 Hz, 1H) 7.7 (t, J=8.1 Hz, 4H) 8.0 (s, 1H) 8.1 (m, 3H) ppm. HPLC Rt 6.9 minutes; [α]$_D$$^{21}$ −59.4° (c=0.011, CH$_2$Cl$_2$); LC/MS (Method F) m/z 435 (MH$^+$).

Step 3. (−)-2-Methoxy-1-((1R,8S)-4-nitro-10-aza-tricyclo[6.3.1.0$^{2.7}$]dodeca-2(7),3,5-trien-10-yl)-ethanone (C34): Compound 34 was prepared in a manner similar to that described for C23 in Step 7 of Example 10 except that C31 (2.00 g, 9.79 mmol) was used instead of C22 to provide C34 as a white solid (1.68 g, 62% yield). $^1$H NMR (400 MHz, DMSO-D6) δ ppm 2.0 (d, J=11.2 Hz, 1H) 2.2 (d, J=5.4 Hz, 1H) 2.9 (m, 3H) 3.0 (dd, J=12.7, 3.9 Hz, 2H) 3.4 (m, 3H) 4.1 (d, J=12.5 Hz, 1H) 7.5 (dd, J=16.6, 7.9 Hz, 1H) 8.1 (m, 2H) ppm. HPLC Rt 4.56 minutes; [α]$_D$ −12.27° (c=0.010, CH$_2$Cl$_2$); LC/MS (Method F) m/z 277.3 (MH$^+$).

Step 4. (−)-1-((1R,8S)-4-Amino-10-aza-tricyclo[6.3.1.0$^{2.7}$]dodeca-2(7),3,5-trien-10-yl)-2-methoxy-ethanone (C35): Compound 35 was prepared in a manner similar to that described for C21 in Step 5 of Example 10 except that C34 (1.68 g, 6.07 mmol) was used instead of C20 to provide C35 as a white solid (1.5 g, 6 mmol, 99%). 1H NMR (400 MHz, DMSO-D6) δ ppm 1.8 (d, J=10.4 Hz, 1H) 2.1 (m, 1H) 2.8 (dd, J=11.4, 6.9 Hz, 1H) 3.0 (s, 3H) 3.0 (d, J=5.8 Hz, 2H) 3.3 (m, 1H) 3.5 (m, 1H) 3.7 (m, 2H) 4.0 (m, 1H) 4.8 (s, 2H) 6.3 (m, 1H) 6.4 (dd, J=23, 2 Hz, 1H) 6.8 (dd, J=19.9, 7.9 Hz, 1H) ppm. HPLC Rt 3.054 minutes; [α]$_D$ −11.3° (c=0.009, CH$_2$Cl$_2$); LC/MS (Method F) m/z 248.3 (MH$^+$).

Step 5. (−)-1-[4-(4-Chloro-5-trifluoromethyl-pyrimidin-2-ylamino)-(1R,8S)-10-aza-tricyclo[6.3.1.0$^{2.7}$]dodeca-2(7),3,5-trien-10-yl]-2-methoxy-ethanone (C36): A mixture of 5-trifluoromethyl-2,6-dichloropyrimidine (1.3 g, 6.12 mmol) and (1:1) (vol>vol) t-BuOH/DCE 22 mL was chilled to 0° C. under a nitrogen atmosphere and treated with ZnCl$_2$ (12.24 mL, 1M in Et$_2$O). The mixture was stirred for 1 hour at 0° C. and then treated with C35 (1.5 g, 6.12 mmol). The reactor contents were stirred for an additional 45 minutes at 0° C. then treated drop-wise with Et$_3$N (940 μL, 6.73 mmol). The reaction mixture was allowed to warm to 25° C., stirred for 2 hours, and concentrated under reduced pressure. The resultant residue was triturated with CH$_3$OH, filter, and the filtrate concentrated to dryness to provide C36 as a white solid (1.6 g, 3.06 mmol, 50% yield). HPLC Rt 6.39 minutes; LC/MS (Method F) m/z 427.8 (MH$^+$); [α]$_2$=−10.2°.

Step 6. Compound 20 was prepared in a manner similar to that described for 10 in Step 8 of Example 10 by reacting C36 (250 mg, 585 μmol) was reacted with 2-Methoxy-1-ethylamine (104 mg, 1.17 mmol) to provide 20 as a white solid (66 mg, 24% yield). MS (Method F) Rt 1.9 minutes; LC/MS (Method F) m/z 466.3 (MH$^+$).

Example 21

(+)-2-Methoxy-1-{4-[4-(2-methoxy-ethylamino)-5-trifluoromethyl-pyrimidin-2-ylamino]-(1S,8R)-10-aza-tricyclo[6.3.1.0$^{2.7}$]dodeca-2(7),3,5-trien-10-yl}-ethanone (21)

Step 1: (+)-2-Methoxy-1-((1S,8R)-4-nitro-10-aza-tricyclo[6.3.1.0$^{2.7}$]dodeca-2(7),3,5-trien-10-yl)-ethanone (C37): Compound C37 was prepared in a manner similar to that described for C34 in Step 7 of Example 10, except that C32 (2.00 g, 9.79 mmol) was used instead of C22 to provide C37 as a pale yellow solid (1.68 g, 62%). $^1$H NMR (400 MHz, DMSO-D6) δ 2.0 (d, J=11.2 Hz, 1H) 2.2 (d, J=5.4 Hz, 1H) 2.9 (m, 3H) 3.0 (dd, J=12.7, 3.9 Hz, 2H) 3.4 (m, 2H) 3.7 (m, 3H) 4.1 (d, J=12.5 Hz, 1H) 7.5 (dd, J=16.6, 7.9 Hz, 1H) 8.1 (m, 2H) ppm. HPLC Rt 4.56 minutes; LC/MS (Method F) m/z 277.3 (MH$^+$).

Step 2. (+)-1-((1S,8R)-4-Amino-10-aza-tricyclo[6.3.1.0$^{2.7}$]dodeca-2(7),3,5-trien-10-yl)-2-methoxy-ethanone (C38): Compound C38 was prepared in a manner similar to that described for C21 in Step 4 of Example 10 except that C37 (1.68 g, 6.07 mmol) was used instead of C19 to provide C38 as a white solid (1.5 g, 6.0 mmol, 99% yield). 1H NMR (400 MHz, DMSO-D6) δ ppm 1.8 (d, J=10.4 Hz, 1H) 2.8 (dd, J=11.4, 6.9 Hz, 1H) 3.0 (s, 3H) 3.0 (d, J=5.8 Hz, 2H) 3.3 (m, 1H) 3.5 (m, 1H) 3.7 (m, 2H) 4.0 (m, 1H) 4.8 (s, 2H) 6.3 (m, 1H) 6.4 (dd, J=23, 2 Hz, 1H) 6.8 (dd, J=19.9, 7.9 Hz, 1H) ppm. HPLC Rt 3.05 minutes; [α]$_D$ +12.05°; LC/MS (Method F) m/z 248.3 (MH$^+$).

Step 3. (+)-1-[4-(4-Chloro-5-trifluoromethyl-pyrimidin-2-ylamino)-(1S,8R)-10-aza-tricyclo[6.3.1.0$^{2,7}$]dodeca-2(7),3,5-trien-10-yl]-2-methoxy-ethanone (C39): Compound C39 was prepared in a manner similar to that described for C21 in Step 5 of Example 10 except that C38 (1.5 g, 6.12 mmol) was used instead of C20 to provide C39 as white solid (1.7 g, 51% yield). HPLC Rt 6.39 minutes; LC/MS (Method F) m/z 427.8 (MH$^+$); [α]$_D$=+12.04°.

Step 4. Compound 21 was prepared in a manner similar to that described for 10 in Step 8 of Example 10 by reacting C39 (250 mg, 585 μmol) with 2-Methoxy-1-ethylamine (104 mg, 1.17 mmol) to provide 21 as a white solid (110 mg, 0.234 mmol, 40% yield). LC/MS (Method F) Rt 1.9 minutes; LC/MS (Method F) m/z 466.3 (MH$^+$).

Example 22

(+/−)-N$^4$-Cyclobutyl-N$^2$-(9-methanesulfonyl-1,2,3,4-tetrahydro-1,4-epiazano-naphthalen-6-yl)-5-trifluoromethyl-pyrimidine-2,4-diamine (22)

Step 1. (+/−) 6-Nitro-1,2,3,4-tetrahydro-1,4-epiazano-naphthalene-9-carboxylic acid tert-butyl ester (C40): A solution of LiOH monohydrate (5.4 g, 128.6 mmol) in 50 ml water was added drop-wise to a solution of (+/−) 6-Nitro-1,2,3,4-tetrahydro-1,4-epiazano-naphthalene-9-trifluoroacetamide (16.65 g, 64.3 mmol) in 200 ml of THF. The resultant mixture was stirred at 25° C. for 1 hour and treated with di-t-butyldicarbonate (21.1 g, 96.5 mmol). The resultant suspension was stirred 2 hours at 25° C. and concentrated under reduced pressure. The resultant residue was then partitioned between 100 ml saturated NaCl and 3×100 ml CHCl$_3$. The combined organic layers were dried over MgSO$_4$ and concentrated under reduced pressure. The resultant orange solid was passed through a 250 g plug of silica gel (230-240 mesh) eluting with 5% EtOAc/hexanes while collecting 250 ml fractions. The fractions containing C40 were combined and concentrated to provide the racemate C40 as a pale yellow solid (14.4 g, 50.2 mmol 78%). $^1$H NMR (400 MHz, DMSO-d$_6$) δ 1.18 (m, 2H), 1.29 (s, 9H), 2.04 (m, 2H), 5.20 (m, 2H), 7.56 (m, 1H), 8.08 (m, 1H), 8.18 (m, 1H) ppm.

Step 2. A 200 g quantity (0.685 mole) of C40 was resolved using preparative chiral chromatography under the following conditions: Column: ChiralCel OJ 10×50 cm; particle size: 20 um; flow rate: 400 ml/min; detection: UV 300 nm; feed concentration: 20 mg/ml in IPA/Heptane 50/50; injection volume: 106 ml/injection; mobile phase: IPA/Heptane 15/85; run time: 17 min./injection. Injections were stacked and two fractions were collected for each injection, one for enantiomer 1 (−) isomer and the other for enantiomer 2 (+) isomer. The separation provided the following enantiomers:

93.5 g of 6-Nitro-(1S,4R)-1,2,3,4-tetrahydro-1,4-epiazano-naphthalene-9-carboxylic acid tert-butyl ester (C41) (the enantiomerically pure (−) isomer of the racemic compound C40). $^1$H NMR (400 MHz, DMSO-d$_6$) δ 1.21 (m, 2H), 1.29 (s, 9H), 2.04 (m, 2H), 5.19 (m, 2H), 7.56 (d, J=8 Hz, 1H), 8.08 (m, 1H), 8.18 (d, J=3 Hz, 1H) ppm. [α]$^D$ (CH$_2$Cl$_2$)=−14.0°.

93.5 g of 6-Nitro-(1S,4R)-1,2,3,4-tetrahydro-1,4-epiazano-naphthalene-9-carboxylic acid tert-butyl ester (C42) (the enantiomerically pure (+) isomer of the racemate C40). $^1$H NMR (400 MHz, DMSO-d$_6$) δ 1.21 (m, 2H), 1.30 (s, 9H), 2.02 (m, 2H), 5.19 (m, 2H), 7.56 (d, J=8 Hz, 1H), 8.07 (m, 1H), 8.18 (d, J=3 Hz, 1H) ppm. [α]$^D$ (CH$_2$Cl$_2$)=+12.9°.

Step 3. (+/−)-6-Amino-1,2,3,4-tetrahydro-1,4-epiazano-naphthalene-9-carboxylic acid tert-butyl ester (C43): Compound C43 was prepared in a manner similar to that described for C20 in Step 4 of Example 10 except that C40 (5.0 g, 17.2 mmol) was used instead of C19 to provide C43 as a gray solid (4.4 g, 17.0 mmol, 99% yield). $^1$H NMR (400 MHz, DMSO) δ 6.89 (d, J=7.75 Hz, 1H), 6.51 (d, J=1.56 Hz, 1H), 6.27 (dd, J=7.75 Hz, 1H), 4.94 (s, 2H), 4.84 (t, J=3 Hz, 1H), 1.92 (d, J=7.26 Hz, 2H), 1.33 (s, 9H), 1.13 (d, J=6.22 Hz, 2H); MS: 261.3 (MH+); HPLC Rt: 5.9 min.; HPLC purity: 100%.

Step 4. (+/−)-6-(4-Chloro-5-trifluoromethyl-pyrimidin-2-ylamino)-1,2,3,4-tetrahydro-1,4-epiazano-naphthalene-9-carboxylic acid tert-butyl ester (C44): Compound C44 was prepared in a manner similar to that described for C21 in Step 5 of Example 10 except that C43 (1.5 g, 5.76 mmol) was used instead of C20 to provide C44 as a white solid (2.14 g, 84%). The regiochemistry was confirmed by x-ray crystallography. $^1$HNMR (400 MHz, DMSO) δ 10.6 (s, 1H), 8.75 (s, 1H), 7.61 (s, 1H), 7.39 (dd, J=3.95 Hz, 1H), 7.25 (d, J=8.31 Hz, 1H), 4.99 (d, J=8.68 Hz, 2H), 1.97 (d, J=8.3 Hz, 2H), 1.29 (s, 9H), 1.16 (d, J=7.0 Hz, 2H). MS: 441.0/443.0 (MH+); HPLC Rt; 8.50 min; HPLC purity; 100%.

Step 5. (+/−)-6-(4-Cyclobutylamino-5-trifluoromethyl-pyrimidin-2-ylamino)-1,2,3,4-tetrahydro-1,4-epiazano-naphthalene-9-carboxylic acid tert-butyl ester (C45): Compound C44 was prepared in a manner similar to that described for 10 in Step 8 of Example 10 by reacting C44 (0.4 g, 0.9 mmol) with cyclobutyl amine (0.16 g, 2.72 mmol) to provide C45 as a white solid (2.88 g, 89%). $^1$H NMR (500 MHz, DMSO-d$_6$) δ 9.6 (s, 1H), 8.179 (s, 1H), 7.81 (s, 1H), 7.38-7.37 (m, 1H), δ 7.2 (d, J=8 Hz 1H); 7.01 (d, J=6.7 Hz, 1H), 4.985 (t, J=4 Hz, 2H), 4.616 (m, 1H), 2.28-2.14 (m, 4H), 2.01 (m, 2H), 1.71-1.62 (m, 2H), 1.33 (s, 9H), 1.20 (m, 2H); MS: 476.3 (MH+); HPLC Rt: 8.8 min; HPLC purity: 100%.

Step 6. (+/−)-N$^4$-Cyclobutyl-N$^2$-(1,2,3,4-tetrahydro-1,4-epiazano-naphthalen-6-yl)-5-trifluoromethyl-pyrimidine-2,4-diamine dihydrochloride (C46): A solution of C45 (2.73 g, 5.74 mmol) and HCl (3M in MeOH, 20 mL) was heated to 50° C. After 2 hours the mixture was concentrated under reduce pressure, diluted with EtOAc, and the resultant solid collected by filtration to provide C46 as a white solid (2.4 g, 93%). $^1$H NMR (400 MHz, DMSO-d$_6$) δ 10.9 (br, 1H), 9.6 (d, J=7.9 Hz, 1H), 9.37 (d, J=7.9 Hz, 1H), 8.39 (s, 1H), 8.39 (s, 1H), 8.10 (br, 1H), 7.77 (d, J=1 Hz, 1H), 7.52-7.50 (m, 1H), 7.42 (d, J=7.9 Hz, 1H), 6.6 (br, 1H), 5.21-5.18 (m, 2H), 4.58-4.52 (m, 1H), 2.27-2.14 (m, 6H), 1.7-1.61 (m, 2H), 1.37 (d, J=8.3 HZ, 2H); MS: 376.1 (MH+); HPLC Rt: 5.3 min; HPLC purity: 100%.

Step 7. Methanesulfonyl chloride (24 mg, 0.21 mmol) was added to a solution of C46 (75 mg, 0.17 mmol) and DIEA (65 mg, 0.5 mmol) in dichloromethane (4 mL). After 20 min the reaction mixture under reduced pressure, and the resultant residue was purified by flash column chromatography on silica gel (CH$_2$Cl$_2$/MeOH 99:1) to provide 22 as a white solid (65 mg, 86%). $^1$H NMR (500 MHz, DMSO-d$_6$) δ 9.7 (br, 1H), 8.19 (s, 1H), 7.87 (s, 1H), 7.42 (m, 1H), 7.2 (d, J=7.7 Hz, 1H), 7.03 (d, J=6.7 Hz, 1H), 5.04 (s, 2H), 4.61 (m, 1H), 2.3 (s, 3H), 2.25-2.12 (m, 6H), 1.7 (m, 2H), 1.3 (m, 2H); MS: 454.0 (MH+); HPLC Rt: 7.11 min; HPLC purity: 100%.

Example 23

(+/−)-1-[6-(4-Cyclobutylamino-5-trifluoromethyl-pyrimidin-2-ylamino)-1,2,3,4-tetrahydro-1,4-epiazano-naphthalen-9-yl]-ethanone (23)

Acetyl chloride (13.1 mg, 0.17 mmol) was added to a solution of C46 (75 mg, 0.17) and DIEA (65 mg, 0.5 mmol) in CH$_2$Cl$_2$ (4 mL). After 20 min the mixture was concentrated under reduced pressure, and the resultant residue was purified by flash column chromatography on silica gel (CH$_2$Cl$_2$/MeOH 98:2) to provide 23 as a white solid (44 mg, 107 mmol, 63%). $^1$H NMR (500 MHz, DMSO-d$_6$) δ 9.6 (br, 1H), 8.17 (s, 1H), 7.8 (m, 1H), 7.4 (m, 1H), 7.2 (m, 1H), 7.0 (m, 1H), 5.3-5.2 (m, 2H), 4.6 (m, 1H), 2.26-1.97 (m, 6H), 1.9 (s, 3H), 1.72-1.62 (m, 2H), 1.3-1.16 (m, 2H); MS: 418.1 (MH+); HPLC Rt: 6.71 min; HPLC purity: 100%.

Examples 24 to 28

The compounds of Examples 24 to 28 (Table 1) were prepared in a manner similar to that described for 23 in Example 23.

Example 29

(+/−)-[6-(4-Cyclobutylamino-5-trifluoromethyl-pyrimidin-2-ylamino)-1,2,3,4-tetrahydro-1,4-epiazano-naphthalen-9-yl]-pyrrolidin-1-yl-methanone (29)

Step 1. (+/−)-6-(4-Cyclobutylamino-5-trifluoromethyl-pyrimidin-2-ylamino)-1,2,3,4-tetrahydro-1,4-epiazano-naphthalene-9-carboxylic acid 4-nitro-phenyl ester (C47): Compound C47 was prepared in a manner similar to that described for 24 in Example 24 except that 4-Nitrophenyl chloroformate (0.45 g, 2.23 mmol) was used instead of methyl chloroformate to provide C47 as a white solid (1.0 g, 83%). $^1$H NMR (500 MHz, DMSO-d$_6$) δ 9.6 (br, 1H), 8.26-8.23 (m, 2H), 8.18 (s, 1H), 7.88 (br, 1H), 7.43 (br, 1H), 7.36 (d, J=8.8 Hz, 2H), 7.29 (d, J=7.7 Hz, 1H), 7.036 (d, J=6.7 Hz, 1H), 5.44 (br, 1H), 5.22 (br, 1H), 4.6 (m, 1H), 2.24-2.10 (m, 6H), 1.64 (br, 2H), 1.33 (br, 2H) ppm. MS: 541.4 (MH+); HPLC Rt: 8.5 min; HPLC purity: 100%.

Step 2. A solution of C47 (90 mg, 0.17 mmol), pyrrolidine (18 mg, 0.25 mmol), and DIEA (43 mg, 0.33 mmol) in DMF (2 mL) was heated to 50° C. After 2 hours the mixture was diluted with H$_2$O and extracted with EtOAc. The combined organic layers was washed with water, dried over Na$_2$SO$_4$, and concentrated under reduced pressure. The resultant residue was purified on a Biotage® flash 12S (CH$_2$Cl$_2$/MeOH 98:2) to provide 29 as a white solid (34 mg, 43%). $^1$H NMR (500 MHz, DMSO-d$_6$) δ 9.5 (br, 1H), 8.16 (s, 1H), 7.74 (s, 1H), 7.34 (m, 1H), 7.15 (d, J=8.3 Hz, 1H), 7.0 (d, J=6.7 Hz, 1H), 4.99 (s, 2H), 4.6 (br, 1H), 3.2 (br, 4H), 2.25-2.11 (m, 4H), 2.04-2.03 (m, 2H), 1.74-1.60 (m, 6H), 1.17-1.15 (m, 2H) ppm. MS: 473.5 (MH+).

Example 30

(+/−)-6-(4-Cyclobutylamino-5-trifluoromethyl-pyrimidin-2-ylamino)-1,2,3,4-tetrahydro-1,4-epiazano-naphthalene-9-carboxylic acid cyclopropylamide (30)

Step 1. Cyclopropyl-carbamic acid 4-nitro-phenyl ester (C48): 4-Nitrophenyl chloroformate (1.7 g, 8.7 mmol) was added to a solution of cyclopropylamine (0.5 g, 8.7 mmol) and DIEA (2.2 g, 17.1 mmol) in THF (25 mL). After 20 min the reaction mixture was quenched with H$_2$O and the layers separated. The aqueous layer was extracted with EtOAc, and the combined organic layers were dried over Na$_2$SO$_4$ and concentrated under reduced pressure. The resultant residue was crystallized from hexanes/EtOAc to provide C48 as a pale yellow solid (0.2 g, 0.87 mmol, 10% yield). $^1$H NMR (400 MHz, DMSO-d$_6$) δ 8.2 (m, 3H), 7.3 (m, 2H), 2.5 (m, 1H), 0.6 (m, 2H), 0.4 (m, 2H) ppm. HPLC Rt: 5.2 min; HPLC purity: 100%.

Step 2. A solution of C46 (0.1 g, 0.22 mmol), C48 (75 mg, 0.34 mmol) and DIEA (115 mg, 0.15 mL) in DMF (1 mL) was stirred at 25° C. for 2 hours. The mixture was the partitioned between EtOAc and H$_2$O, and the layers separated. The organic layer washed with water, dried over Na$_2$SO$_4$, and concentrated under reduced pressure. The resultant residue was purified on a Biotage® flash 12S (CH$_2$Cl$_2$/MeOH 99:1) to provide 30 as a white solid (73 mg, 71%). $^1$H NMR (500 MHz, DMSO-d$_6$) δ 9.5 (br, 1H), 8.17 (s, 1H), 7.74 (s, 1H), 7.3 (m, 1H), 7.15 (d, J=1 Hz, 1H), 7.0 (1, J=6.7 Hz, 1H), 6.8 (d, J=3.6 Hz, 1H), 5.08 (s, 2H), 4.6 (br, 1H), 2.4 (m, 1H), 2.28-2.13 (m, 4H), 1.9 (m, 2H), 1.7 (m, 2H), 1.1 (m, 2H), 0.5 (m, 2H), 0.3 (m, 2H) ppm. MS: 459.5 (MH+); HPLC Rt: 6.63 min; HPLC purity: 100%.

Example 31

(+/−)-1-[6-(4-Cyclobutylamino-5-trifluoromethyl-pyrimidin-2-ylamino)-1,2,3,4-tetrahydro-1,4-epiazano-naphthalen-9-yl]-2-morpholin-4-yl-ethanone (31)

Morpholine (38 mg, 0.22 mmol) was added to a solution of 28 (50 mg, 0.11 mmol) and DIEA (29 mg, 0.22 mmol) in THF (2 mL), and the resultant mixture was stirred for 2 days at about 25° C. The mixture was then partitioned between EtOAc and H$_2$O and the layers separated. The organic layer was dried over Na$_2$SO$_4$ and concentrated under reduced pressure. The resultant residue was purified on Biotage® flash 12M (CH$_2$Cl$_2$/CH$_3$OH 98:2) to provide 31 as a white solid (30 mg, 55%). $^1$H NMR (500 MHz, DMSO-d$_6$) δ 9.6 (m, 1H), 8.18 (s, 1H), 7.82 (d, J=23 Hz, 1H), 7.4 (m, 1H), 7.2 (m, 1H), 7.01 (m, 1H), 5.5 (s, 1H), 5.34 (s, 1H), 4.6 (br, 1H), 3.5 (s, 4H), 3.1-3.0 (m, 2H), 2.36-2.11 (m, 9H), 1.95 (m, 1H), 1.66 (m, 2H), 1.25 (m, 2H) ppm. MS: 503.2 (MH+); HPLC Rt: 6.3 min; HPLC purity: 100%.

Example 32

(+/−)-N$^4$-Cyclopropyl-N$^2$-(1,2,3,4-tetrahydro-1,4-epiazano-naphthalen-6-yl)-5-trifluoromethyl-pyrimidine-2,4-diamine dihydrochloride (32)

Step 1. (+/−)-6-(4-Cyclopropylamino-5-trifluoromethyl-pyrimidin-2-ylamino)-1,2,3,4-tetrahydro-1,4-epiazano-naphthalene-9-carboxylic acid tert-butyl ester (C49): Compound C49 was prepared in a manner similar to that described for C45 in Step 5 of Example 22 by reacting C44 (0.5 g, 1.13 mmol) with cyclopropyl amine (77 mg, 1.36 mmol) to provide C49 as a white solid (0.41 g, 80%). $^1$H NMR (400 MHz, DMSO-d$_6$) δ 9.6 (br, 1H), 8.15 (s, 1H), 7.94 (s, 1H), 7.52 (d, J=8 Hz, 1H), 7.15 (m, 2H), 4.92 (d, J=6 Hz, 2H), 2.8 (m, 1H), 1.95 (m, 2H), 1.28 (s, 9H), 1.14 (d, J=8 Hz, 2H), 0.74 (d, J=7 Hz, 2H), 0.65 (d, J=3 Hz, 2H) ppm. MS: 462.1 (MH+); HPLC Rt: 8.2 min; HPLC purity: 100%.

Step 2. Compound 32 was prepared in a manner similar to that described for C46 in Step 6 of Example 22 except that C49 (0.38 g, 0.83 mmol) was used instead of C45 to provide 32 as a white solid (0.36 g, 100%). $^1$H NMR (500 MHz, DMSO-d6) δ 10.8 (br, 1H), 9.47 (d, J=8 Hz, 1H), 9.31 (d, J=8 Hz, 1H), 8.4 (s, 1H), 8.03 (s, 2H), 7.7 (d, J=7 Hz, 1H), 7.42 (d, J=8 Hz, 1H), 5.22 (m, 2H), 4.8 (br, 1H), 2.9 (m, 1H), 2.2 (m, 2H), 1.4 (m, 2H), 0.83 (m, 2H), 0.74 (m, 2H) ppm. MS: 362.1 (MH+).

Example 33

(+/−)-$N^4$-Cyclopentyl-$N^2$-(1,2,3,4-tetrahydro-1,4-epiazano-naphthalen-6-yl)-5-trifluoromethyl-pyrimidine-2,4-diamine dihydrochloride (33)

Step 1. (+/−)-6-(4-Cyclopentylamino-5-trifluoromethyl-pyrimidin-2-ylamino)-1,2,3,4-tetrahydro-1,4-epiazano-naphthalene-9-carboxylic acid tert-butyl ester (C50): Compound C50 was prepared in a manner similar to that described for C44 in Step 4 of Example 22 by reacting C44 with cyclopentyl amine (119 mg, 1.35 mmol) to provide C50 as a white solid (0.38 g, 70%). $^1$H NMR (400 MHz, DMSO-$d_6$) δ 9.5 (br, 1H), 8.14 (s, 1H), 7.78 (s, 1H), 7.33 (m, 1H), 7.15 (m, 1H), 6.51 (m, 1H), 4.93 (m, 2H), 4.4 (m, 1H), 1.9 (m, 4H), 1.7 (m, 2H), 1.54 (m, 4H), 1.29 (s, 9H), 1.15 (m, 2H) ppm. MS: 490.1 (MH+); HPLC Rt: 9.1 min; HPLC purity: 100%.

Step 2. Compound 33 was prepared in a manner similar to that described for C46 in Example 22 except that C50 (341 mg, 0.697 mmol) was used instead of C45 to provide 33 as a white solid (0.32 g, 100%). $^1$H NMR (500 MHz, DMSO-$d_6$) δ 10.7 (br, 1H), 9.54 (d, J=8.3 Hz, 1H), 9.4 (d, J=7.7 Hz, 1H), 8.38 (s, 1H), 7.82 (s, 1H), 7.55 (m, 1H), 7.42 (m, 1H), 5.2 (s, 2H), 4.48 (m, 1H), 2.27 (m, 2H), 1.9 (m, 2H), 1.75-1.62 (m, 4H), 1.59-1.54 (m, 2H), 1.39 (m, 2H) ppm. MS: 390.1 (MH+).

Example 34

(+/−)-$N^4$-Methyl-$N^2$-(1,2,3,4-tetrahydro-1,4-epiazano-naphthalen-6-yl)-5-trifluoromethyl-pyrimidine-2,4-diamine dihydrochloride (34)

Step 1. (+/−)-6-(4-Methylamino-5-trifluoromethyl-pyrimidin-2-ylamino)-1,2,3,4-tetrahydro-1,4-epiazano-naphthalene-9-carboxylic acid tert-butyl ester (C51): Compound C51 was prepared in a manner similar to that described for C45 in Step 5 of Example 22 by reacting C44 (1.0 g, 2.27 mmol) with methylamine (2.0 M solution in THF, 2.2 mL, 4.54 mmol) to provide C51 as a white solid (0.85 g, 86%). $^1$H NMR (500 MHz, DMSO-$d_6$) δ 9.6 (br, 1H), 8.16 (s, 1H), 7.76 (m, 1H), 7.48 (m, 1H), 7.12 (m, 1H), 4.98 (s, 2H), 2.92 (m, 3H), 1.99 (m, 2H), 1.33 (s, 9H), 1.19 (m, 2H); MS: 436.5 (MH+) ppm. HPLC Rt: 7.7 min; HPLC purity: 100%.

Step 2. Compound 34 was prepared in a manner similar to that described for C46 in Step 6 of Example 22 except that C51 (0.85 g, 1.95 mmol) was used instead of C45 to provide 34 as a white solid (0.79 g, 99%). $^1$H NMR (500 MHz, DMSO-$d_6$) δ 11.02 (br, 1H), 9.62 (m, 1H), 9.37 (m, 1H), 8.43 (s, 1H), 8.25 (br, 1H), 7.82 (m, 1H), 7.62 (m, 1H), 7.45 (m, 1H), 5.22 (m, 2H), 2.98 (d, J=4 Hz, 3H), 2.26 (m, 2H), 1.40 (m2, H) ppm. MS: 336.5 (MH+).

Example 35

(+/−)-$N^4$-(2-Methoxy-ethyl)-N %4&-methyl-$N^2$-(1,2,3,4-tetrahydro-1,4-epiazano-naphthalen-6-yl)-5-trifluoromethyl-pyrimidine-2,4-diamine dihydrochloride (35)

Step 1. (+/−)-6-{4-[(2-Methoxy-ethyl)-methyl-amino]-5-trifluoromethyl-pyrimidin-2-ylamino}-1,2,3,4-tetrahydro-1,4-epiazano-naphthalene-9-carboxylic acid tert-butyl ester (C52): Compound C52 was prepared in a manner similar to that described for C45 in Step 5 of Example 22 by reacting C44 (1.0 g, 2.27 mmol) with (2-Methoxy-ethyl)-methyl-amine (0.4 g, 4.54 mmol) to provide C52 as a white solid (1.0 g, 89%). $^1$H NMR (500 MHz, DMSO-$d_6$) δ 9.67 (br, 1H), 8.35 (s, 1H), 7.7 (br, 1H), 7.34 (m, 1H), 7.19 (m, 1H), 4.99 (s, 2H), 3.77 (m, 2H), 3.58 (m, 2), 3.25 (s, 3H), 3.12 (s, 3H), 2.00 (m, 2H), 1.33 (s, 9H), 1.19 (m, 2H) ppm. MS: 494.5 (MH+); HPLC Rt: 8.4 min; HPLC purity: 100%.

Step 2. Compound 35 was prepared in a manner similar to that described for C46 in Step 6 of example 22 except that C52 (0.85 g, 1.95 mmol) was used instead of C45 to provide 35 as a white solid (0.95 g, 100%). $^1$H NMR (500 MHz, DMSO-$d_6$) δ 10.6 (br, 1H), 9.67 (m, 1H), 9.37 (m, 1H), 8.53 (s, 1H), 7.7 (s, 1H), 7.51 (m, 1H), 7.41 (m, 1H), 5.2 (s, 2H), 3.83 (m, 2H), 3.6 (m, 2H), 3.25 (s, 3H), 3.20 (s, 3H), 2.28 (m, 2H), 1.49 (m, 2H) ppm. MS: 349.5 (MH+).

Example 36

(+/−)-$N^4$-Ethyl-$N^2$-(1,2,3,4-tetrahydro-1,4-epiazano-naphthalen-6-yl)-5-trifluoromethyl-pyrimidine-2,4-diamine dihydrochloride (36)

Step 1. (+/−)-ethylamino-5-trifluoromethyl-pyrimidin-2-ylamino)-1,2,3,4-tetrahydro-1,4-epiazano-naphthalene-9-carboxylic acid tert-butyl ester (C53): Compound C53 was prepared in a manner similar to that described for C45 in Step 5 of Example 22 by reacting C44 (1.0 g, 2.27 mmol) with ethylamine (4.54 mmol, 2.27 mL, 2.0 M solution in THF) to provide C53 as a white solid. (0.86 g, 84%). $^1$H NMR (500 MHz, DMSO-$d_6$) δ 9.6 (br, 1H), 8.16 (s, 1H), 7.77 (s, 1H), 7.42 (m, 1H), 7.17 (m, 2H), 4.96 (m, 2H), 3.48 (m, 2H), 2.0 (m, 2H), 1.32 (s, 9H), 1.17 (m, 5H) ppm. MS: 450.5 (MH+); HPLC Rt: 8.11 min; HPLC purity: 100%.

Step 2. Compound 36 was prepared in a manner similar to that described for C46 in Step 6 of Example 22 except that C53 (0.86 g, 1.9 mmol) was used instead of C45 to provide 36 as a white solid (0.8 g, 99%). $^1$H NMR (500 MHz, DMSO-$d_6$) δ 11.0 (br, 1H), 9.64 (m, 1H), 9.38 (m, 1H), 8.44 (s, 1H), 8.2 (br, 1H), 7.8 (m, 1H), 7.58 (m, 1H), 7.44 (m, 1H), 5.23 (m, 2H), 3.5 (m, 2H), 2.28 (m, 2H), 1.39 (m, 2H), 1.17 (m, 3H) ppm. MS: 350.5 (MH+).

Example 37

(+/−)-$N^4$-(2-Methoxy-ethyl)-$N^2$-(1,2,3,4-tetrahydro-1,4-epiazano-naphthalen-6-yl)-5-trifluoromethyl-pyrimidine-2,4-diamine dihydrochloride (37)

Step 1. (+/−)-6-[4-(2-Methoxy-ethylamino)-5-trifluoromethyl-pyrimidin-2-ylamino]-1,2,3,4-tetrahydro-1,4-epiazano-naphthalene-9-carboxylic acid tert-butyl ester (C54): Compound C54 was prepared in a manner similar to that described for C45 in Step 5 of Example 22 by reacting C44 (1.0 g, 2.27 mmol) with 2-methoxyethylamine (341 mg, 4.5 mmol) to provide C54 as a white solid (1.0 g, 93%). $^1$H NMR (500 MHz, DMSO-$d_6$) δ 9.6 (br, 1H), 8.18 (s, 1H), 7.8 (br, 1H), 7.37 (m, 1H), 7.18 (m, 1H), 7.07 (m, 1H), 4.98 (s, 2H), 3.62 (m, 2H), 3.55 (m, 2H), 3.28 (s, 3H), 1.98 (m, 2H), 1.33 (s, 9H), 1.19 (m, 2H) ppm. MS: 480.5 (MH+); HPLC Rt: 7.78 min; HPLC purity: 100%.

Step 2. Compound 37 was prepared in a manner similar to that described for C46 in Step 6 of Example 22 except that C54 (1.0 g, 2.1 mmol) was used instead of C45 to provide 36 as a white solid (0.92 g, 98%). $^1$H NMR (500 MHz, DMSO-$d_6$) δ 10.5 (br, 1H), 9.4 (m, 1H), 9.3 (m, 1H), 8.3 (s, 1H), 7.85

(s, 1H), 7.56 (m, 1H), 7.41 (m, 1H), 5.2 (s, 2H), 4.3 (br, 1H), 3.63 (m, 2H), 3.52 (m, 2H), 3.27 (s, 3H), 2.25 (m, 2H), 1.40 (m, 2H) ppm. MS: 360.5 (MH+).

Example 38

(+/−)-N⁴-Isopropyl-N²-(1,2,3,4-tetrahydro-1,4-epiazano-naphthalen-6-yl)-5-trifluoromethyl-pyrimidine-2,4-diamine dihydrochloride (38)

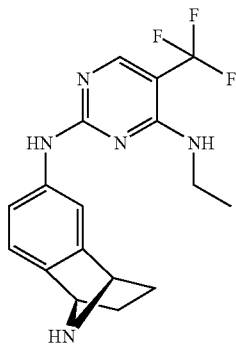

38

Step 1. (+/−)-6-(4-Isopropylamino-5-trifluoromethyl-pyrimidin-2-ylamino)-1,2,3,4-tetrahydro-1,4-epiazano-naphthalene-9-carboxylic acid tert-butyl ester (C55): Compound C55 was prepared in a manner similar to that described for C45 in Step 5 of Example 22 y reacting C44 (1.0 g, 2.27 mmol) with isopropylamine (0.27 g, 4.5 mmol) to provide C55 as a white solid (0.73 g, 69%). ¹H NMR (500 MHz, DMSO-d₆) δ 9.58 (BR, 1H), 8.17 (S, 1H), 7.73 (S, 1H), 7.41 (m, 1H), 7.19 (m, 1H), 6.47 (m, 1H), 4.9 (m, 2H), 4.4 (m, 1H), 2.0 (m, 2H), 1.33 (s, 9H), 1.23 (m, 6H), 1.2 (m, 2H) ppm. MS: 454.5 (MH+); HPLC Rt: 8.62 min; HPLC purity: 100%.

Step 2. Compound 38 was prepared in a manner similar to that described for C46 in Step 6 of Example 22 except that C55 (0.72 g, 1.55 mol) was used instead of C45 to provide 38 as a white solid (0.67 g, 99%). ¹H NMR (500 MHz, DMSO-d₆) δ 11.0 (br, 1H), 9.7 (m, 1H), 9.4 (m, 1H), 8.4 (s, 1H), 7.6 (m, 2H), 7.55 (m, 1H), 7.44 (m, 1H), 5.25 (m, 2H), 4.4 (m, 1H), 2.3 (m, 2H), 1.4 (m, 2H), 1.24 (m, 6H) ppm. MS: 364.5 (MH+).

Example 39

(+/−)-(4-Methoxy-5-trifluoromethyl-pyrimidin-2-yl)-(1,2,3,4-tetrahydro-1,4-epiazano-naphthalen-6-yl)-amine (39)

Compound 39 was prepared in a manner similar to that described for 46 in step 6 of Example 22 except that C44 (1.0 g, 2.23 mmol) was used instead of C45 to provide 39 as a white solid (0.9 g, 98%). ¹H NMR (400 MHz, DMSO-d₆) δ 10.3 (br, 1H), 9.58 (m, 1H), 9.31 (m, 1H), 8.50 (s, 1H), 7.86 (m, 1H), 7.58 (m, 1H), 7.36 (m, 1H), 5.18 (m, 2H), 4.01 (s, 3H), 2.23 (m, 2H), 1.35 (m, 2H); MS: 335.6 (MH−) ppm HPLC Rt: 4.72 min; HPLC purity: 100%.

Example 40

N⁴-Cyclobutyl-N²-(1S,4R)-(1,2,3,4-tetrahydro-1,4-epiazano-naphthalen-6-yl)-5-trifluoromethyl-pyrimidine-2,4-diamine dihydrochloride (40)

Step 1. 6-Amino-(1S,4R)-1,2,3,4-tetrahydro-1,4-epiazano-naphthalene-9-carboxylic acid tert-butyl ester (C56): Compound 56 was prepared in a manner similar to that described for C20 in Step 4 of Example 10 except that C41 (4.5 g, 15.5 mmol) was used instead of C19 to provide C56 as an off-white solid (3.95 g, 98%). ¹H NMR (400 MHz, DMSO-d₆) δ 1.10 (m, 2H), 1.29 (s, 9H), 1.89 (m, 2H), 4.81 (m, 2H), 4.95 (bs, 2H), 6.24 (m, 1H), 6.48 (m, 1H), 6.86 (m, 1H) ppm. HPLC Rt=5.95, HPLC Purity=100%. [α], C(0.1165)=−7.02°.

Step 2. 6-(4-Chloro-5-trifluoromethyl-pyrimidin-2-ylamino)-(1S,4R)-1,2,3,4-tetrahydro-1,4-epiazano-naphthalene-9-carboxylic acid tert-butyl ester (C57): Compound C57 was prepared in a manner similar to that described for C21 in Step 5 of Example 10, except that C56 (3.8 g, 14.6 mmol) was used instead of C20 to provide C57 as a white solid (4.76 g, 74%). ¹H NMR (400 MHz, DMSO-d₆) δ 1.17 (m, 2H), 1.30 (s, 9H), 1.97 (m, 2H), 4.99 (m, 2H), 7.24 (m, 1H), 7.40 (m, 1H), 7.61 (bs, 1H), 8.76 (s, 1H), 10.6 (s, 1H) ppm. HPLC Rt=8.49, HPLC Purity=100%. [α], C(0.01035)=−14.8°.

Step 3. 6-(4-Cyclobutylamino-5-trifluoromethyl-pyrimidin-2-ylamino)-(1S,4R)-1,2,3,4-tetrahydro-1,4-epiazano-naphthalene-9-carboxylic acid tert-butyl ester (C58): Compound C58 was prepared in a manner similar to that described for 10 in Step 8 of Example 12 by reacting C57 (1.1 g, 2.5 mmol) with cyclobutylamine (228 µL, 3.4 mmol) to provide of C58 as a white solid (998 mg, 84%). ¹H NMR (400 MHz, DMSO-d₆) δ 1.17 (m, 2H), 1.30 (s, 9H), 1.66 (m, 2H), 1.97 (m, 2H), 2.20 (m, 4H), 4.50 (m, 1H), 4.95 (m, 2H), 6.99 (m, 1H) 7.17 (m, 1H), 7.33 (m, 1H), 7.78 (bs, 1), 8.15 (s, 1H), 9.59 (bs, 1H) ppm. HPLC Rt=8.77, HPLC Purity=100%.

Step 4. Compound C40 was prepared in a manner similar to that described for C46 in Step 6 of Example 22 except that C58 (938 mg, 1.98 mmol) was used instead of C45 to provide 40 as a bone colored solid (911 mg, 82%). ¹H NMR (400 MHz, DMSO-d₆) δ 1.37 (m, 2H), 1.67 (m, 2H), 2.20 (m, 6H), 4.55 (m, 1H), 5.18 (m, 2H), 6.65 (bs, 1H), 7.40 (m, 1H), 7.52 (m, 1H), 7.80 (m, 1H), 7.89 (bs, 1H), 8.34 (s, 1H), 9.31 (m, 1H), 9.48 (m, 1H), 10.63 (bs, 1H) ppm. HPLC Rt=5.62, HPLC Purity=100%.

Example 41

1-[6-(4-Cyclopropylamino-5-trifluromethyl-pyrimidin-2-ylamino)-(1S,4R)-1,2,3,4-tetrahydro-1,4-epiazano-naphthalen-9-yl]-2-methylamino-ethanone (41)

Step 1. (4-Chloro-5-trifluoromethyl-pyrimidin-2-yl)-{(1S,4R)-1,2,3,4-tetrahydro-1,4-epiazano-naphthalen-6-yl}-amine dihydrochloride (C59): Compound C59 was prepared in a manner similar to that described for C22 in Step 6 of Example 10 except that C57 (1.0 g, 2.26 mmol) in 1,4-dioxane (2 mL) was used instead of C21 to provide C59 as a white solid (0.93 g, 100%). ¹H NMR (500 MHz, DMSO-d₆) δ 10.84 (s, 1H), 9.27 (br, 2H), 8.8 (s, 1H), 7.8 (s, 1H), 7.6 (m, 1H), 7.44 (m, 1H), 5.24 (m, 2H), 2.23 (m, 2H), 1.41 (m, 2H) ppm. MS: 339.4 (MH+); HPLC Rt: 4.98 min; HPLC purity: 100%.

Step 2. {2-[6-(4-Chloro-5-trifluoromethyl-pyrimidin-2-ylamino)-(1S,4R)-1,2,3,4-tetrahydro-1,4-epiazano-naphthalen-9-yl]-2-oxo-ethyl}-methyl-carbamic acid tert-butyl ester (C60): 1,3-diisopropylcarbodiimide (0.14 g, 1.1 mmol) was added to a solution of N-t-Boc-sarcosine (0.41 g, 2.20 mmol) in CH₂Cl₂ (5 mL). After 1 hour C59 (0.46 g, 1.10 mmol) was added, followed by addition of DIEA (0.43 g, 3.30 mmol). After 30 min the mixture was concentrated, and the resultant residue was partitioned between EtOAc and saturated aqueous sodium bicarbonate. The layers were separated and the aqueous layer was extracted with EtOAc. The combined organic layers were dried over Na₂SO₄ and concentrated under reduced pressure. The resultant residue was purified on Biotage® Flash 40M (hexanes/EtOAc=1:1) to provide C60 as a white solid (0.55 g, 98%). $^1$H NMR (400 MHz, DMSO-d$_6$) δ 10.65 (br, 1H), 8.7 (s, 1H), 7.6 (br, 1H), 7.39 (m, 1H), 7.26 (m, 1H), 5.4-5.34 (m, 2H), 4.02-3.94 (m, 2H), 2.7-2.67 (m, 3H), 2.92-1.92 (m, 2H), 1.34, 1.17 (rotamers) (s, s, 9H), 1.25-1.1 (m, 2H) ppm. MS: 512.4/412.3 (MH$^+$); HPLC Rt: 7.4 min; HPLC purity: 100%.

Step 3. A solution of C60 (0.1 g, 0.2 mmol), cyclopropylamine (0.23 mg, 0.40 mmol), and DIEA (78 mg, 0.60 mmol) was heated to 90° C. in a sealed tube. After 5 hours the mixture was concentrated under reduced pressure, and the resultant residue was partitioned between EtOAc and H$_2$O. The layers were separated and the organic layer was washed with water. The organic layer was then dried over Na$_2$SO$_4$ and concentrated under reduced pressure. The resultant residue was purified on Biotage® Flash 12M (hexanes/EtOAc=1:1) to provide a white solid. The solid was dissolved in CH$_2$Cl$_2$ and TFA (0.23 g, 2.0 mmol) was added. After 20 min the mixture was concentrated under reduced pressure. The resultant residue was dissolved in EtOAc and washed with saturated aqueous NaHCO$_3$ and H$_2$O. The organic layer was dried over Na$_2$SO$_4$ and concentrated under reduced pressure to provide 41 as a white solid (60 mg, 70%). $^1$H NMR (500 MHz, DMSO-d$_6$) δ 9.71 (br, 1H), 8.18 (s, 1H), 7.99 (m, 1H), 7.57 (m, 1H), 7.19 (m, 2H), 5.34 (m, 2H), 3.32-3.12 (m, 3H), 2.85 (m, 1H), 2.2 (s, 3H), 2.06-1.93 (m, 2H), 1.23 (m, 2H), 0.80 (m, 2H), 0.68 (m, 2H) ppm. MS: 433.0 (MH+); HPLC Rt: 5.0 min; HPLC purity: 100%.

Example 42

N-{2-[6-(4-Cyclopropylamino-5-trifluoromethyl-pyrimidin-2-ylamino)-(1S,4R)-1,2,3,4-tetrahydro-1,4-epiazano-naphthalen-9-yl]-2-oxo-ethyl}-N-methyl-acetamide (42)

Acetic anhydride (12 mg, 0.12 mmol) was added to a solution of 41 (50 mg, 0.12 mmol) and DIEA (45 mg, 0.35 mmol) in THF (5 mL). After 20 min the mixture was concentrated under reduced pressure, and the resultant residue was purified on Biotage® Flash 12M (CH$_2$Cl$_2$/CH3OHl=98:2) to provide 42 as a white solid (38 mg, 69%). $^1$H NMR (500 MHz, DMSO-d$_6$) δ 9.7 (br, 1H), 8.18 (s, 1H), 8.01 (m, 1H), 7.59 (m, 1H), 7.2 (m, 2H), 5.36-5.29 (m, 2H), 4.01 (m, 2H), 2.89, 2.69 (s, s, 3H), 2.85 (BR, 1H), 20.9-1.9 (M, 2H), 1.98 (S, 3H), 1.2 (M, 2H), 0.8 (M, 2H), 0.68 (M, 2H) ppm. MS: 475.0 (MH+); HPLC Rt: 5.54 min; HPLC purity: 100%.

Example 43

1-[6-(4-Cyclobutylamino-5-trifluoromethyl-pyrimidin-2-ylamino)-(1S,4R)-1,2,3,4-tetrahydro-1,4-epiazano-naphthalen-9-yl]-2-methylamino-ethanone (43)

Step 1. {2-[6-(4-Cyclobutylamino-5-trifluoromethyl-pyrimidin-2-ylamino)-(1S,4R)-1,2,3,4-tetrahydro-1,4-epiazano-naphthalen-9-yl]-2-oxo-ethyl}-methyl-carbamic acid tert-butyl ester (C61): Compound C61 was prepared in a manner similar to that described for C60 in Example 41 by reacting 40 (0.1 mg, 0.223 mmol) and N-methyl-N-t-Boc-sarcosine (84 mg g, 0.45 mmol) to provide C61 as a white solid (0.1 g, 98%). $^1$H NMR (500 MHz, DMSO-d$_6$) δ 9.6 (br, 1H), 8.2 (s, 1H), 7.8 (br, 1H), 7.4 (m, 1H), 7.2 (m, 1H), 7.02 (m, 1H), 5.34 (m, 2H), 4.6 (br, 1H), 4.0 (m, 1H), 3.86 (m, 1H), 2.6 (m, 3H), 2.25-1.9 (m, 6H), 1.7 (m, 2H), 1.37, 1.2 (rotamers) (m, 9H), 1.3 (m, 2H); MS: 547.5/447.4 (MH+); HPLC Rt: 7.7 min; HPLC purity 100%.

Step 2. TFA (0.15 g, 1.3 mmol) was added to a solution of C61 (0.18 g, 0.33 mmol) in CH$_2$Cl$_2$ (5 mL). After 1 hour the mixture was concentrated, the resultant residue partitioned between EtOAc and saturated aqueous NaHCO$_3$, and the layers separated. The organic layer was washed with H$_2$O, dried over Na$_2$SO$_4$, and concentrated under reduced pressure to provide 43 as a white solid (0.12 g, 82%). $^1$H NMR (500 MHz, DMSO-d$_6$) δ 9.61 (br, 1H), 8.18 (s, 1H), 7.6 (m, 1H), 7.3 (m, 1H), 7.2 (m, 1H), 7.0 (m, 1H), 5.3 (m, 2H), 4.6 (br, 1H), 3.28 (m, 2H), 2.25-1.95 (m, 6H), 2.2 (s, 3H), 1.6 (m, 2H), 1.2 (m, 2H) ppm. MS: 447.4 (MH+); HPLC Rt: 5.5 min; HPLC purity: 100%.

Example 44

N-{2-[6-(4-Cyclobutylamino-5-trifluoromethyl-pyrimidin-2-ylamino)-(1S,4R)-1,2,3,4-tetrahydro-1,4-epiazano-naphthalen-9-yl]-2-oxo-ethyl}-methyl-acetamide (44)

Compound 44 was prepared in a manner similar to that described for 42 in Example 42 except that 40 (70 mg, 0.16 mmol) was used instead of 41 to provide 44 as an off-white solid (60 mg, 78%). $^1$H NMR (500 MHz, DMSO-d$_6$) δ 9.6 (br, 1H), 8.18 (s, 1H), 7.8 (m, 1H), 7.4 (m, 1H), 7.2 (m, 1H), 7.0 (m, 1H), 5.36 (m, 2H), 4.6 (br, 1H), 4.1 (m, 1H), 4.0 (m, 1H), 2.9, 2.7 (rotamers) (s, s, 3H), 2.2 (m, 6H), 1.99 (m, 3H), 1.69 (m, 2H), 1.2 (m, 2H); MS: 489.0 (MH+) ppm. HPLC Rt: 6.0 min; HPLC purity: 100%.

Example 45

N-{2-[6-(4-Cyclobutylamino-5-trifluoromethyl-pyrimidin-2-ylamino)-(1S,4R)-1,2,3,4-tetrahydro-1,4-epiazano-naphthalen-9-yl]-2-oxo-ethyl}-acetamide (45)

Step 1. N-{2-[6-(4-Chloro-5-trifluoromethyl-pyrimidin-2-ylamino)-(1S,4R)-1,2,3,4-tetrahydro-1,4-epiazano-naphthalen-9-yl]-2-oxo-ethyl}-acetamide (C62):

Method A. Compound C62 was prepared in a manner similar to that described for C60 in Example 41 by reacting C59 (0.92 mg, 2.23 mmol) and N-acetylglycine (0.6 g, 2.25 mmol) to provide C62 as an off-white solid (0.54 g, 55%). $^1$H NMR (500 MHz, DMSO-d$_6$) δ 10.68 (m, 1H), 8.79 (s, 1H), 8.03 (br, 1H), 7.68 (br, 1H), 7.4 (m, 1H), 7.3 (m, 1H), 5.48-5.36 (m, 2H), 3.93 (m, 1H), 3.73 (m, 1H), 2.12 (m, 1H), 1.95 (m, 1H), 1.82 (s, 3H), 1.28-1.11 (m, 2H) ppm. MS: 442.0/439.9 (MH+); HPLC Rt: 5.6 min; HPLC purity: 100%.

Method B. As an alternative, compound C62 can be prepared adding a solution of C41 (37.9 g, 0.13 mmol) in methanol (38 mL) to a solution of thionyl chloride (47.4 mL, 0.650 mol, 5 eq) in methanol (380 mL) under nitrogen at 25° C., mixed for 18 hours, and concentrated under reduced pressure to provide 6-Nitro-1,2,3,4-tetrahydro-1,4-epiazano-naphthalene HCl (C113) as a solid (33.1 g, 0.145 mol, 112% yield (excess yield due to residual methanol)):

A mixture of n-acetyl glycine (3.26 g, 0.027 mol, 0.97 eq) and acetonitrile (50 mL) was cooled to 0° C. and treated dropwise with N-methyl morpholine (3.03 mL, 0.028 mol, 1 eq). After 2 hours the mixture was treated with solid C113 (5.00 g, 0.028 mol), and the reaction mixture was allowed to warm to room temperature. After about 18 hours the mixture was filtered, concentrated to approximately half the volume, and treated with water with stirring. The resultant mixture was filtered and concentrated under reduced pressure to provide N-[2-((1S,4R)-6-Nitro-1,2,3,4-tetrahydro-1,4-epiazano-naphthalen-9-yl)-2-oxo-ethyl]-acetamide (CAB) (5.30 g, 0.018 mol, 83% yield).

Compound C114 (4.2 g, 0.015 mol), 10% palladium on carbon 50% water wet (400 mg), and ethanol (40 mL) were charged to a Parr reactor, and the contents of the reactor were treated with 50 PSI of hydrogen at 40° C. After 1 hour the mixture was filtered through celite at 40° C. and concentrated to dryness to provide N-[2-((1S,4R)-6-Amino 1,2,3,4-tetrahydro-1,4-epiazano-naphthalen-9-yl)-2-oxo-ethyl]-acetamide (C115) (3.43 g, 0.013 mol, 91% yield).

A mixture of C115 (0.44 g, 17 mmol), zinc dibromide (0.43 g, 18 mmol, 1.1 eq) t-butanol (1.3 mL), and dichloroethane (1.32 mL) was stirred at room temperature for 30 minutes. The mixture was then treated with 2,4-dichloro-5-trifluoromethylpyrimidine (0.42 g, 18 mmol 1.1 eq) followed by triethylamine (0.26 mL, 18 mmol, 1.1 eq). After 3 hours the mixture was concentrated, and the resultant residue was triturated with hexanes overnight. The resultant solids were collected y filtration to provide C62 (0.33 g, 075 mmol, 44% yield).

Step 2. Compound 45 was prepared in a manner similar to that described in Step 8 of Example 10 by reacting C62 (0.10 g, 0.23 mmol) with cyclobutyl amine (32 mg, 0.45 mmol) to provide 45 as a white solid (39 mg, 62%). $^1$H NMR (400 MHz, DMSO-$d_6$) δ 9.6 (br, 1H), 8.15 (s, 1H), 8.0 (m, 1H), 7.78 (m, 1H), 7.37 (m, 1H), 7.19 (m, 1H), 7.0 (m, 1H), 5.39-5.3 (m, 2H), 4.6 (m, 1H), 3.9-3.8 (m, 1H), 3.7-3.6 (m, 1H), 2.21-2.0 (m, 5H)), 1.9-1.8 (m, 1H), 1.8 (s, 3H), 1.67-1.63 (m, 2H), 1.2-1.1 (m, 2H) ppm. HPLC Rt: 8.82 min; HPLC purity: 100%.

Example 46

N$^4$-Isopropyl-N$^2$-{(1S,4R)-1,2,3,4-tetrahydro-1,4-epiazano-naphthalen-6-yl}-5-trifluoromethyl-pyrimidine-2,4-diamine dihydrochloride (46)

Step 1. 6-(4-Isopropylamino-5-trifluoromethyl-pyrimidin-2-ylamino)-(1S,4R)-1,2,3,4-tetrahydro-1,4-epiazano-naphthalene-9-carboxylic acid tert-butyl ester (C63): Compound C63 was prepared in a manner similar to that described for C58 in Step 3 of Example 40 except that isopropylamine (0.16 g, 2.27 mmol) was used instead of cyclobutylamine to provide C63 as an off-white solid (0.78 g, 74%). $^1$H NMR (400 MHz, DMSO-$d_6$) δ 9.5 (br, 1H), 8.14 (s, 1H), 7.69 (s, 1H), 7.37 (m, 1H), 7.15 (m, 1H), 6.44 (m, 1H), 4.94 (m, 2H), 4.4 (m, 1H), 1.9 (m, 2H), 1.29 (s, 9H), 1.2 (m, 6H), 1.1 (m, 2H); MS: 464.6 (MH+) ppm. HPLC Rt: 8.6 min; HPLC purity: 100%.

Step 2. Compound 46 was prepared in a manner similar to that described for 40 in Step 4 of Example 40 except that C63 (70 mg, 0.16 mmol) was used instead of C58 to provide 46 as a white solid (0.73 g, 99%). $^1$H NMR (500 MHz, DMSO-$d_6$) δ 10.8 (br, 1H), 9.62 (m, 1H), 9.36 (m, 1H), 8.4 (s, 1H), 7.7 (s, 1H), 7.6 (br, 1H), 7.5 (m, 1H), 7.43 (m, 1H), 5.23 (m, 2H), 4.4 (m, 1H), 4.4 (br, 1H), 2.27 (m, 2H), 1.39 (m, 2H), 1.24 (m, 6H) ppm. MS: 364.5 (MH+).

Example 47

N$^4$-Ethyl-N$^2$-{(1S,4R)-1,2,3,4-tetrahydro-1,4-epiazano-naphthalen-6-yl}-5-trifluoromethyl-pyrimidine-2,4-diamine dihydrochloride (47)

Step 1. 6-(4-Ethylamino-5-trifluoromethyl-pyrimidin-2-ylamino)-(1S,4R)-1,2,3,4-tetrahydro-1,4-epiazano-naphthalene-9-carboxylic acid tert-butyl ester (C64): Compound C64 was prepared in a manner similar to that described for C58 in Step 3 of Example 40 except that ethylamine (2.0 M solution in tetrahydrofuran, 2.27 mL, 4.5 mmol) was used instead of cyclobutylamine to provide C64 as a white solid (1.0 g, 98%). $^1$H NMR (500 MHz, DMSO-$d_6$) δ 9.6 (br, 1H), 8.16 (s, 1H), 7.7 (s, 1H), 7.42 (m, 1H), 7.18 (m, 2H), 4.97 (m, 2H), 3.48 (m, 2H), 1.99 (m, 2H), 1.32 (s, 9H), 1.17 (m, 5H); MS: 450.5 (MH+) ppm. HPLC Rt: 8.0 min; HPLC purity: 100%.

Step 2. Compound 47 was prepared in a manner similar to that described for 40 in Step 4 of Example 40 except that C64 (1.0 g, 2.22 mmol) was used instead of C58 to provide 47 as a white solid (0.87 g, 93%). $^1$H NMR (500 MHz, DMSO-$d_6$) δ 10.8 (br, 1H), 9.55 (m, 1H), 9.35 (m, 1H), 8.4 (s, 1H), 8.21 (br, 1H), 7.81 (m, 1H), 7.58 (m, 1H), 7.43 (m, 1H), 5.22 (m, 2H), 3.5 (m, 2H), 2.26 (m, 2H), 1.4 (m, 2H), 1.17 (m, 3H); MS: 350.5 (MH+).

Example 48

2-Amino-1-[6-(4-ethylamino-5-trifluoromethyl-pyrimidin-2-ylamino)-(1S,4R)-1,2,3,4-tetrahydro-1,4-epiazano-naphthalen-9-yl]-ethanone (48)

Compound 48 was prepared in a manner similar to that described for 43 in Step 2 of Example 43 by reacting 47 (0.15 g, 0.35 mmol) with tert-Butoxycarbonylamino-acetic acid (0.12 g, 0.71 mmol) to provide 48 as an amber solid (45 mg, 31%). $^1$H NMR (500 MHz, DMSO-$d_6$) δ 9.6 (br, 1H), 8.16 (s, 1H), 7.78 (m, 1H), 7.44 (m, 1H), 7.2 (m, 2H), 5.32 (m, 2H), 3.4 (m, 2H), 3.32 (m, 2H), 3.17 (m, 2H), 2.06-1.94 (m, 2H), 1.23-1.17 (m, 5H); MS: 407.0 (MH+) ppm. HPLC Rt: 4.7 min; HPLC purity: 100%.

Example 49

N$^4$-Propyl-N$^2$-{(1S,4R)-1,2,3,4-tetrahydro-1,4-epiazano-naphthalen-6-yl}-5-trifluoromethyl-pyrimidine-2,4-diamine dihydrochloride (49)

Step 1. 6-(4-Propylamino-5-trifluoromethyl-pyrimidin-2-ylamino)-(1S,4R)-1,2,3,4-tetrahydro-1,4-epiazano-naphthalene-9-carboxylic acid tert-butyl ester (C65): Compound C65 was prepared in a manner similar to that described for C58 in Step 3 of Example 40 except that propylamine (0.2 g, 3.4 mmol) was used instead of cyclobutyl amine to provide C65 as a white solid (1.0 g, 2.27 mmol). $^1$H NMR (500 MHz, DMSO-$d_6$) δ 9.6 (br, 1H), 8.15 (s, 1H), 7.78 (s, 1H), 7.41 (m, 1H), 7.19 (m, 2H), 4.97 (m, 2H), 3.39 (m, 2H), 1.98 (m, 2H), 1.6 (m, 2H), 1.32 (s, 9H), 1.17 (m, 2H), 0.91 (m, 3H); MS: 463.5 (MH+) ppm. HPLC Rt: 8.35 min; HPLC purity: 100%.

Step 2. Compound 49 was prepared in a manner similar to that described for 40 in Step 4 of Example 40 except that C65 (0.96 g, 2.1 mmol) was used instead of C58 to provide 49 as an off-white solid (0.88 g, 98%). $^1$H NMR (500 MHz, DMSO-$d_6$) δ 11.0 (br, 1H), 9.62 (m, 1H), 9.37 (m, 1H), 8.43 (s, 1H), 8.3 (br, 1H), 7.7 (s, 1H), 7.61 (m, 1H), 7.44 (m, 1H), 5.2 (s, 2H), 3.42 (m, 2H), 2.28 (m, 2H), 1.60 (m, 2H), 1.4 (m, 2H), 0.89 (m, 3H) ppm. MS: 364.5 (MH+).

Example 50

N$^4$-(2-Methoxy-ethyl)-N$^2$-[(1S,4R)-1,2,3,4-tetrahydro-1,4-epiazano-naphthalen-6-yl]-5-trifluoromethyl-pyrimidine-2,4-diamine dihydrochloride (50)

Step 1. 6-[4-(2-Methoxy-ethylamino)-5-trifluoromethyl-pyrimidin-2-ylamino]-(1S,4R)-1,2,3,4-tetrahydro-1,4-epiazano-naphthalene-9-carboxylic acid tert-butyl ester (C66):

Compound C66 was prepared in a manner similar to that described for C58 in Step 3 of Example 40 except that 2-methoxyethylamine (256 mg, 3.4 mmol) was used instead of cyclobutylamine to provide C66 as a pale syrup (1.02 g, 94%). $^1$H NMR (500 MHz, DMSO-d$_6$) δ 9.6 (br, 1H), 8.18 (s, 1H), 7.8 (br, 1H), 7.37 (m, 1H), 7.17 (m, 1H), 7.07 (m, 1H), 4.98 (s, 2H), 3.6 (m, 2H), 3.51 (m, 2H), 3.28 (s, 3H), 1.99 (m, 2H), 1.33 (s, 9H), 1.19 (m, 2H); MS: 480.5 (MH+); HPLC Rt: 7.76 min; HPLC purity: 100%.

Step 2. Compound 50 was prepared in a manner similar to that described for 40 in Step 4 of Example 40 except that C66 (1.0 g, 2.08 mmol) was used instead of C58 to provide 50 as an off-white solid (0.88 g, 94%). $^1$H NMR (500 MHz, DMSO-d$_6$) δ 10.8 (br, 1H), 9.57 (m, 1H), 9.36 (m, 1H), 8.4 (s, 1H), 8.07 (br, 1H), 7.82 (s, 1H), 7.56 (m, 1H), 7.41 (m, 1H), 5.2 (s, 2H), 3.62 (m, 2H), 3.52 (m, 2H), 3.27 (s, 3H), 2.27 (m, 2H), 1.4 (m, 2H) ppm. MS: 380.5 (MH+).

Example 51

N$^4$-Cyclobutyl-N$^2$-(1R,4S)-(1,2,3,4-tetrahydro-1,4-epiazano-naphthalen-6-yl)-5-trifluoromethyl-pyrimidine-2,4-diamine dihydrochloride salt (51)

Step 1. 6-Amino-(1R,4S)-1,2,3,4-tetrahydro-1,4-epiazano-naphthalene-9-carboxylic acid tert-butyl ester (C67): Compound C67 was prepared in a manner similar to that described for C20 in Step 4 of Example 10 except that C42 (4.5 g, 15.5 mmol) was used instead of C19 to provide C67 as an off-white solid (3.59 g, 89%). $^1$H NMR (400 MHz, DMSO-d$_6$) δ 1.10 (m, 2H), 1.29 (s, 9H), 1.89 (m, 2H), 4.81 (m, 2H), 4.95 (bs, 2H), 6.24 (m, 1H), 6.48 (m, 1H), 6.86 (m, 1H) ppm. [α], C(0.01165)=+5.82°.

Step 2. 6-(4-Chloro-5-trifluoromethyl-pyrimidin-2-ylamino)-(1R,4S)-1,2,3,4-tetrahydro-1,4-epiazano-naphthalene-9-carboxylic acid tert-butyl ester C(68): Compound C68 was prepared in a manner similar to that described for C21 in Step 5 of Example 10 except that C67 (3.4 g, 13.1 mmol) was used instead of C20 to provide C68 as a white solid (4.68 g (81%). $^1$H NMR (400 MHz, DMSO-d$_6$) δ 1.17 (m, 2H), 1.30 (s, 9H), 1.97 (m, 2H), 5.00 (m, 2H), 7.24 (m, 1H), 7.40 (m, 1H), 7.61 (bs, 1H), 8.75 (s, 1H), 10.6 (s, 1H) ppm. HPLC Rt=8.49, HPLC Purity=100%. [α], C(0.01015)=+14.1°.

Step 3. 6-(4-Cyclobutylamino-5-trifluoromethyl-pyrimidin-2-ylamino)-(1R,4S)-1,2,3,4-tetrahydro-1,4-epiazano-naphthalene-9-carboxylic acid tert-butyl ester (C69): Compound C69 was prepared in a manner similar to that described for C45 in Step 5 of Example 22 except that C68 (1.1 g, 2.5 mmol) was used instead of C44 to provide C69 as a white solid (1.17 g, 98%). $^1$H NMR (400 MHz, DMSO-d$_6$) δ 1.17 (m, 2H), 1.30 (s, 9H), 1.66 (m, 2H), 1.97 (m, 2H), 2.20 (m, 4H), 4.50 (m, 1H), 4.95 (m, 2H), 6.99 (m, 1H), 7.17 (m, 1H), 7.33 (m, 1H), 7.78 (bs, 1), 8.15 (s, 1H), 9.59 (bs, 1H) ppm. HPLC Rt=8.78, HPLC Purity=100%.

Step 4. Compound 51 was prepared in a manner similar to that described for C46 in Step 6 of Example 22 except that C69 (938 mg, 1.98 mmol) was used instead of C45 to provide 51 as a bone colored solid (1.08 g, >100%). $^1$H NMR (400 MHz, DMSO-d$_6$) δ 1.38 (m, 2H), 1.66 (m, 2H), 2.22 (m, 6H), 4.58 (m, 1H), 5.19 (m, 2H), 7.05 (bs, 1), 7.39 (m, 1H), 7.52 (m, 1H), 7.70 (bs, 1H), 7.81 (s, 1H), 8.32 (s, 1H), 9.29 (m, 1H), 9.42 (m, 1H), 10.25 (bs, 1H) ppm. [α], C(0.0059) CH$_2$Cl$_2$=−8.3°. HPLC Rt=5.10, HPLC Purity=100%.

Example 52

N$^4$-Cyclopropyl-N$^2$-(1R,4S)-(1,2,3,4-tetrahydro-1,4-epiazano-naphthalen-6-yl)-5-trifluoromethyl-pyrimidine-2,4-diamine-dihydrochloride (52)

Compound 52 was prepared in a manner similar to that described for C45 and C46 in Steps 5 and 6, respectively, of Example 22 by reacting C68 (2.0 g, 4.5 mmol) with cyclopropylamine (425 µL, 6.1 mmol) followed by treatment with methanoic HCl to provide 52 as a white solid (1.95 g, 99%). $^1$H NMR (400 MHz, DMSO-d$_6$) δ 0.70 (m, 2H), 0.79 (m, 2H), 1.36 (m, 2H), 2.23 (m, 2H), 2.87 (m, 1), 5.18 (m, 2H), 5.82 (bs, 1H), 7.38 (m, 1H), 7.67 (m, 1H), 7.93 (bs, 1H), 8.01 (m, 1H), 8.34 (s, 1H), 9.26 (m, 1H), 9.42 (m, 1H), 10.65 (bs, 1H) ppm. HPLC Rt=4.70, HPLC Purity=100%.

Examples 53 to 87

Examples 53 to 87 (Table 1) were prepared according to the methods described in Example 23 or 52.

Example 88

N-(2-{6-[4-(2-Methoxy-ethylamino)-5-trifluoromethyl-pyrimidin-2-ylamino]-(1R,4S)-1,2,3,4-tetrahydro-1,4-epiazano-naphthalen-9-yl}-2-oxo-ethyl)-acetamide methanesulfonic acid salt (88)

A suspension of N-acetylglycine (182 mg, 1.56 mmol) in 10 ml of CH$_2$Cl$_2$ was treated with diisopropylcarbodiimide (eDIC) (140 µL, 0.9 mmol) under nitrogen atmosphere and the mixture stirred for 1 hour at 25° C. The resultant suspension was treated with 57 (300 mg, 0.664 mmol) followed by DIEA (787 µL, 4.52 mmol) stirred overnight at 25° C. The mixture was concentrated under reduced pressure, and the resultant residue was partitioned between 1×25 ml EtOAc and 3×20 ml 50% saturated NaHCO$_3$. The organic layer was dried over Na$_2$SO$_4$ and concentrated under reduced pressure. The resultant pasty solid was dissolved in 3 ml isopropanol, treated with methanesulfonic acid (43 µL, 0.664 mmol), and concentrated. The resultant pale from was suspended in 10 ml EtOAc and the mixture was stirred at 65° C. for 1 hour. The resultant fine white solid was collected, washed with Et$_2$O, and dried. The solid was titrated with warm EtOAc a second time to remove residual diisopropyl urea to provide 88 as a white solid (302 mg, 79%). HPLC Rt=4.98, HPLC Purity=100%. MS for C$_{22}$H$_{25}$F$_3$N$_6$O$_3$: [M+J]=479.2.

Example 89

N-{2-[6-(4-Cyclobutylamino-5-trifluoromethyl-pyrimidin-2-ylamino)-(1R,4S)-1,2,3,4-tetrahydro-1,4-epiazano-naphthalen-9-yl]-2-oxo-ethyl}-acetamide methanesulfonic acid salt (89)

Compound 89 was prepared in a manner similar to that described for 88 in Example 88 by reacting 51 (500 mg, 1.13 mmol) and N-acetylglycine (311 mg, 2.65 mol) to provide 89 as a white solid (490 mg, 76%). HPLC Rt=5.84, HPLC Purity=100%. MS for C$_{23}$H$_{25}$F$_3$N$_6$O$_2$: [M+H]=475.3.

Example 90

N-{2-[6-(4-Ethylamino-5-trifluoromethyl-pyrimidin-2-ylamino)-(1S,4R)-1,2,3,4-tetrahydro-1,4-epiazano-naphthalen-9-yl]-2-oxo-ethyl}-N-methyl-acetamide hydrochloride salt (90)

Step 1. N-{2-[6-(4-Chloro-5-trifluoromethyl-pyrimidin-2-ylamino)-(1S,4R)-1,2,3,4-tetrahydro-1,4-epiazano-naphthalen-9-yl]-2-oxo-ethyl}-N-methyl-acetamide (C70): A solution of C60 (0.37 g, 0.73) in HCl (4.0 M in 1,4-dioxane, 5 mL) was stirred at 25° C. for 20 min and concentrated. The resultant white solid was dissolved in $CH_2Cl_2$ (5 mL), and treated with acetic anhydride (75 mg, 0.73 mmol) and DIEA (0.28 g, 2.19 mmol). After 20 min the reaction was quenched with water, layers were separated, and the aqueous layer extracted with EtOAc. The combined organic layers were dried over $Na_2SO_4$ and concentrated to provide C70 (as a white solid (0.27 g, 82%). MS: 454.0 (MH+); HPLC Rt: 5.84 min; HPLC purity: 100%.

Step 2. Compound C70 (125 mg, 0.276 mmol) was combined with ethylamine (96 μL, 0.52 mmol) and DIEA (250 μL, 1.44 mmol) in 3 ml of dioxane in a 15 ml screw top pressure tube under nitrogen atmosphere. The mixture was warmed to 90° C., stirred for 4 hours, and cooled to 25° C. The mixture was diluted with 10 ml $CHCl_3$ to dissolve suspended solids, and the solution was concentrated under reduced pressure. The resultant residue was chromatographed over 15 g silica gel (230-400 mesh) eluting with 4% MeOH/$CH_2Cl_2$ while collecting 9 ml fractions. The fractions containing 90 were combined and concentrated. The resultant white foam (132 mg) was dissolved in 3 ml EtOAc and treated with 0.35 ml 1N HCl in $Et_2O$. The solids were collected and dried to provide 90 an off-white solid (110 mg, 80%). HPLC Rt=5.46, HPLC Purity=100%. MS for $C_{22}H_{25}F_3N_6O_2$: [M+H]=463.3.

Example 91

6-(4-Cyclobutylamino-5-trifluoromethyl-pyrimidin-2-ylamino)-(1S,4R)-1,2,3,4-tetrahydro-1,4-epiazano-naphthalene-9-carboxylic acid methyl ester (91)

Compound 91 was prepared in a manner similar to that described for 24 in Example 24 by reacting 40 (140 mg, 0.313 mmol) and methyl chloroformate (26 μL, 0.340 mmol) to provide 91 as a white solid (101 mg, 74%). $^1$H NMR (400 MHz, DMSO-$d_6$) δ 1.18 (m, 2H), 1.64 (m, 2H), 2.05 (m, 2H), 2.21 (m, 4H), 3.49 (s, 3H), 4.58 (m, 1H), 5.05 (s, 2H), 6.98 (m, 1H), 7.18 (m, 1H), 7.35 (m, 1H), 7.77 (m, 1H), 8.15 (s, 1H), 9.57 (s, 1H) ppm. HPLC Rt=7.66, HPLC Purity=100%.

Example 92

6-(4-Cyclobutylamino-5-trifluoromethyl-pyrimidin-2-ylamino)-(1R,4S)-1,2,3,4-tetrahydro-1,4-epiazano-naphthalene-9-carboxylic acid methyl ester (92)

Compound 92 was prepared in a manner similar to that described for 24 in Example 24 by reacting 51 (140 mg, 0.313 mmol) and methyl chloroformate (26 μL, 0.340 mmol) to provide 92 as a white solid (58 mg, 37%). $^1$H NMR (400 MHz, DMSO-$d_6$) δ 1.18 (m, 2H), 1.64 (m, 2H), 2.05 (m, 2H), 2.21 (m, 4H), 3.49 (s, 3H), 4.58 (m, 1H), 5.05 (s, 2H), 6.98 (m, 1H), 7.18 (m, 1H), 7.35 (m, 1H), 7.77 (m, 1H), 8.15 (s, 1H), 9.57 (s, 1H) ppm. HPLC Rt=7.66, HPLC Purity=100%.

Example 93

$N^4$-Cyclobutyl-$N^2$-(9-methanesulfonyl-(1R,4S)-1,2,3,4-tetrahydro-1,4-epiazano-naphthalen-6-yl)-5-trifluoromethyl-pyrimidine-2,4-diamine (93)

Compound 93 was prepared in a manner similar to that described for 22 in Example 22 by reacting 40 (140 mg, 0.313 mmol) and methanesulfonyl chloride (26 μL, 0.340 mmol) to provide 93 as a white solid (61 mg, 43%). $^1$H NMR (400 MHz, DMSO-$d_6$) δ 1.26 (m, 2H), 1.65 (m, 2H), 2.22 (m, 6H), 2.26 (m, 3H), 4.58 (m, 1H), 5.01 (S, 2H), 7.01 (m, 1H), 7.23 (m, 1H), 7.38 (m, 1H), 7.84 (m, 1H), 8.16 (s, 1H), 9.64 (bs, 1H) ppm. HPLC Rt=7.11, HPLC Purity=100%.

Example 94

$N^4$-Cyclobutyl-$N^2$-(9-methanesulfonyl-(1S,4R)-1,2,3,4-tetrahydro-1,4-epiazano-naphthalen-6-yl)-5-trifluoromethyl-pyrimidine-2,4-diamine (94)

Compound 94 was prepared in a manner similar to that described for 22 in Example 22 by reacting 51 (140 mg, 0.313 mmol) and methanesulfonyl chloride (26 μL, 0.340 mmol) to provide 94 as a white solid (61 mg, 43%). $^1$H NMR (400 MHz, DMSO-$d_6$) δ 1.26 (m, 2H), 1.65 (m, 2H), 2.22 (m, 6H), 2.26 (m, 3H), 4.58 (m, 1H), 5.01 (S, 2H), 7.01 (m, 1H), 7.23 (m, 1H), 7.38 (m, 1H), 7.84 (m, 1H), 8.16 (s, 1H), 9.64 (bs, 1H) ppm. HPLC Rt=7.11, HPLC Purity=100%.

Example 95

(+/−)-1-[6-(4-Isopropylamino-5-trifluoromethyl-pyrimidin-2-ylamino)-1,2,3,4-tetrahydro-1,4-epiazano-naphthalen-9-yl]-ethanone (95)

Step 1. 6-Nitro-1,2,3,4-tetrahydro-1,4-epiazano-naphthalene hydrochloride (C71): A solution of C40 (3.67 g, 12.6 mmol) in HCl (1.25 M in MeOH, 10 mL) was heated to 50° C. for 30 min and concentrated to provide C71 as a pink solid (2.84 g, 100%). $^1$H NMR (400 MHz, DMSO-$d_6$) δ 9.89-9.71 (br, 2H), 8.31 (d, J=2.07 Hz, 1 Hz), 8.22 (ss, J=2.07, 8.31 Hz, 1H), 7.71 (d, J=8.3 Hz, 1H), 5.34 (t, J=3 Hz, 2H), 2.35-2.24 (m, 2H), 1.46-1.33 (m, 2H); $^{13}$C NMR (100 MHz, DMSO-$d_6$) δ 148.0, 147.8, 142.6, 124.8, 123.0, 117.3, 60.7, 23.9 ppm.

Step 2. (+/−)-1-(6-Nitro-1,2,3,4-tetrahydro-1,4-epiazano-naphthalen-9-yl)-ethanone (C72): Acetic anhydride (2.1 g, 20.5 mmol) was added to a solution of C71 (3.0 g, 15.8 mmol) in EtOAc (30 mL). After 30 min the white precipitate formed. The solids were isolated by filtration to provide C72 (as a white solid (3.3 g, 90%). $^1$H NMR (500 MHz, DMSO-$d_6$) δ 8.21 (d, J=6.5 Hz, 1H), 8.11 (d, J=7.7 Hz, 1H), 7.61-7.58 (m, 1H), δ 5.54-5.51 (m, 2H), 2.17-2.12 (m, 1H), 2.03-1.96 (m, 1H), 1.93 (s, 3H), 1.35-1.18 (m, 2H) ppm. HPLC Rt: 4.58 min; HPLC Purity: 100%. MS: 232.3 (MH−) ppm.

Step 3. (+/−)-1-(6-Amino-1,2,3,4-tetrahydro-1,4-epiazano-naphthalen-9-yl)-ethanone (C73): A suspension of C72 (3.3 g, 14.2 mmol) in EtOH (100 mL) was shaken over 10% Pd/C (0.33 g) with hydrogen at 45 psi and at about 25° C. After 2 hours the mixture was filtered thru diatomaceous earth, and the filtrate was concentrated to provide C73 as a white solid (2.83 g, 97%). $^1$H NMR (500 MHz, DMSO-$d_6$) δ 6.90 (d, J=7.7 Hz, 1H), 6.53 (br, 1H), 6.28 (d, J=7.3 Hz, 1H), 5.75-5.10 (m, 2H), 4.97 (br, 2H), 1.99-1.95 (m, 2H), 1.87 (s, 3H), 1.23-1.18 (m, 1H), 1.13-1.10 (m, 1H); HPLC Rt: 3.0 min; HPLC purity: 100%. MS: 203.2 (MH+) ppm.

Step 4. (+/31 )-1-[6-(4-Chloro-5-trifluoromethyl pyrimidin-2-ylamino)-1,2,3,4-tetrahydro-1,4-epiazano-naphthalen-9-yl]-ethanone (C74): $ZnCl_2$ (1.0 M in $Et_2O$, 30.3 mL, 30.3 mmol) was added drop-wise to a solution of 2,4-dichloro-5-(trifluoromethyl)pyrimidine (5.5 g, 25.2 mmol) in t-BuOH/DCE (1:1 (vol:vol), 200 mL) at 0° C. After 1 hour C73 (1.5 g, 5.76 mmol) was added followed by drop-wise addition of TEA (27.7 mmol, 3.8 mL). After 2 hours the mixture was concentrated under reduced pressure, and the resultant residue was partitioned between EtOAc and water. The layers were separate and the organic layer was washed with water. The organic layer was then dried over $Na_2SO_4$ and concentrated under reduced pressure. The resultant residue was crystallized from EtOAc/hexanes to provide C74 as a white solid (6.15 g, 64%). The regiochemistry was confirmed by x-ray crystallography. $^1$H NMR (500 MHz, DMSO-$d_6$) δ 10.6 (d, J=10.3 Hz, 1H), 8.78 (s, 1H), 7.68-7.65 (br, 1H), 7.44-7.41 (m, 1H), 7.9 (d, J=8.3 Hz, 1H), 5.37-5.31 (m, 2H), 2.1-2.05 (m, 1H), 1.98-1.93 (m, 1H), 1.9 (d, J=3.6 Hz, 3H), 1.3-1.21 (m, 1H), 1.20-1.15 (m, 1H) ppm. HPLC Rt: 6.4 min; HPLC purity: 100%. MS: 383.4 (MH+).

Step 5. A solution of C74 (0.15 g, 0.39 mmol), isopropyl amine (28 mg, 0.47 mmol) and DIEA (0.1 g, 0.78) mmol in 1,4-dioxane (2 mL) was heated to 90° C. for 1 hour. The reaction mixture was then concentrated under reduced pressure. The resultant residue was partitioned between EtOAc and $H_2O$ and the layers were separated. The organic layer was washed with $H_2O$, dried over $Na_2SO_4$, and concentrated under reduced pressure. The resultant residue was crystallized from EtOAc to provide 95 as a white solid (90 mg, 56%). $^1$H NMR (500 MHz, DMSO-$d_6$) δ 9.58 (br, 1H), 8.17 (s, 1H), 7.74 (d, J=6 Hz, 1H), 7.26 (d, J=8 Hz, 1H), 7.2 (d, J=8 Hz, 1H), 6.46 (d, J=8 Hz, 1H), 5.30-5.26 (m, 2H), 4.46-4.43 (m, 1H), 2.08-2.03 (m, 1H), 1.96-1.92 (m, 1H), 1.9 (s, 3H), 1.29-1.14 (m, 8H) ppm. HPLC Rt: 6.55 min; HPLC purity: 100%. MS: 406.3 (MH+).

Example 96

(+/−)-6-[4-(1-Ethylcarbamoyl-azetidin-3-ylamino)-5-trifluoromethyl-pyrimidin-2-ylamino]-1,2,3,4-tetrahydro-1,4-epiazano-naphthalene-9-carboxylic acid ethylamide (96)

Step 1. (+/−)-3-[2-(9-Acetyl-1,2,3,4-tetrahydro-1,4-epiazano-naphthalen-6-ylamino)-5-trifluoromethyl-pyrimidin-4-ylamino]-azetidine-1-carboxylic acid tert-butyl ester (C88): A solution of C74 (2.47 g, 6.81 mmol) and 1,4-dioxane (15 mL) was treated with DIEA (2.36 mL, 13.62 mmol) followed by addition of 3-Amino-azetidine-1-carboxylic acid tert-butyl ester (1.4 g, 8.18 mmol). The mixture was heated to 90° C. and stirred for 12 hours. The mixture was diluted with EtOAc (25 mL) and $H_2O$ (25 ml) to form a biphasic mixture. The organic phase was collected, dried over $Na_2SO_4$, and concentrated under reduced pressure. The resultant yellow residue was purified on silica gel (60% EtOAc/hexanes) to provide C88 as a white solid (3.0 g, 85%). 1H NMR (400 MHz, DMSO-D6) δ ppm 1.2 (m, 2H) 1.3 (s, 9H), 1.9 (m, 4H) 2.0 (m, 1H) 3.9 (m, 2H) 4.0 (d, J=17.0 Hz, 2H) 4.7 (d, J=5.8 Hz, 1H) 5.3 (m, 2H) 7.2 (d, J=7.5 Hz, 1H) 7.3 (m, 1H) 7.4 (d, J=5.4 Hz, 1H) 7.7 (s, 1H) 8.2 (s, 1H) 9.6 (s, 1H) ppm. HPLC Rt=6.55 minutes. LC/MS (Method F) m/z 519 (MH+).

Step 2. (+/−)-N4-Azetidin-3-yl-N2-(1,2,3,4-tetrahydro-1,4-epiazano-naphthalen-6-yl)-5-trifluoromethyl-pyrimidine-2,4-diamine dihydrochloride (C89): Compound C88 (2.72 g, 5.25 mmol) and 3N HCl in MeOH (15 mL) were combined, and the mixture refluxed 12 hours. The mixture was concentrated under reduced pressure and dried under vacuum to provide C89 as a white solid (2.33 g, 99%). HPLC Rt=2.92 minutes. LC/MS (Method F) m/z 377 (MH+).

Step 3. C89 (125 mg, 254 μMol) and 1,4-dioxane (1 mL) were combined, and the mixture was treated with ethyl isocyanate (36 mg, 508 μMol) and DIEA (176 μL, 1.01 mmol). The mixture was stirred at 25° C. for 15 hours, diluted with EtOAc (4 mL), and partitioned with $H_2O$ (3×4 mL). The organic phase was collected, dried over $Na_2SO_4$, concentrated. The resultant residue was purified on silica gel (5% $CH_3OH/CH_2Cl_2$) to provide 96 as a yellow solid (35 mg, 26% yield). HPLC Rt=4.92 minutes. LC/MS (Method F) m/z 519 (MH+).

Example 97

(+/−)-3-[2-(9-Acetyl-1,2,3,4-tetrahydro-1,4-epiazano-naphthalen-6-ylamino)-5-trifluoro methyl-pyrimidin-4-ylamino]-azetidine-1-carboxylic acid isopropyl-amide (97)

Step 1. 1-{6-[4-(Azetidin-3-ylamino)-5-trifluoromethyl-pyrimidin-2-ylamino]-1,2,3,4-tetrahydro-1,4-epiazano-naphthalen-9-yl}-ethanone trifluoroacetate salt (C90): Compound C74 (1.5 g, 2.89 mmol) and 15 mL of 20% TFA in $CHCl_3$ were reacted for 15 hours at about 25° C. and concentrated to provide C90 as a viscous brown oil (1.5 g, 98% yield). 1H NMR (400 MHz, DMSO-D6) δ 1.2 (m, 2H) 1.9 (m, 4H) 2.0 (m, 1H) 3.9 (m, 2H) 4.0 (d, J=17.0 Hz, 2H) 4.7 (d, J=5.8 Hz, 1H) 5.3 (m, 2H) 7.2 (d, J=7.5 Hz, 1H) 7.3 (m, 1H) 7.4 (d, J=5.4 Hz, 1H) 7.7 (s, 1H) 8.2 (s, 1H) 9.6 (s, 1H) ppm. HPLC Rt 3.9 minutes. LC/MS (Method F) m/z 419 (MH$^+$).

Step 2. A mixture of C90 (208 mg, 400 μmol), 1,4-dioxane (1 mL), DIEA (140 μL, 800 μmol) and isopropyl isocyanate (60 mg) was stirred at 25° C. for 2 hours. The mixture was diluted with 4 mL EtOAc and washed with saturated $NaHCO_3$ (2×4 mL) and brine (2×4 mL). The organic phase was collected, dried over $Na_2SO_4$, and concentrated to provide 97 as an off-white solid (50 mg, 25% yield). LC/MS (Method F) Rt=2.0 minutes. LC/MS (Method F) m/z 504.3 (MH$^+$).

Example 98

(+/−)-3-[2-(9-Acetyl-1,2,3,4-tetrahydro-1,4-epiazano-naphthalen-6-ylamino)-5-trifluoromethyl-pyrimidin-4-ylamino]-azetidine-1-carboxylic acid ethyl ester (98)

Compound 98 was prepared in a manner similar to that described for 97 in Step 2 of Example 97 by reacting C90 (208 mg, 400 μmol) 1,4-dioxane (1 mL), DIEA (140 μL, 800 μmol) and ethyl chloroformate (28 μL, 800 μmol) to provide 98 as an off-white solid (50 mg, 25% yield). HPLC Rt=5.78 minutes. LC/MS (Method F) m/z 491.3 (MH$^+$).

Example 99

(+/−)-1-[6-(4-Cyclobutyloxy-5-trifluoromethyl-pyrimidin-2-ylamino)-1,2,3,4-tetrahydro-1,4-epiazano-naphthalen-9-yl]-ethanone (99)

Compound C74 (125 mg, 326 μmol) was treated with DIEA (113 μL, 652 μmol) and cyclobutanol (47 mg, 652 μmol) and the neat mixture heated to 130° C. for 16 hours. The mixture was cooled to 25° C., diluted with EtOAc (5 mL), and washed with H$_2$O (2×5 mL). The organic phase was dried over Na$_2$SO$_4$ and purified on silica gel (30% EtOAc/Hexanes) to provide 99 as a tan solid (38 mg, 28% yield). HPLC Rt 7.1 minutes. LC/MS (Method F) m/z 419.2 (MH$^+$).

Example 100

(−)-(4-Ethylsulfanyl-5-trifluoromethyl-pyrimidin-2-yl)-(1S,4R)-(1,2,3,4-tetrahydro-1,4-epiazano-naphthalen-6-yl)-amine hydrochloride salt (100)

Step 1. (−)-6-(4-Ethylsulfanyl-5-trifluoromethyl-pyrimidin-2-ylamino)-(1S,4R)-1,2,3,4-tetrahydro-1,4-epiazano-naphthalene-9-carboxylic acid tert-butyl ester (C91): A flame dried sealed pressure tube was charged with 1,4-dioxane (5 mL) and C57 (700 mg, 1.59 mmol). The mixture was then treated with ethanol (118 mg, 1.9 mmol) followed by addition of a 60% sodium hydride dispersion in mineral oil (82 mg, 2.06 mmol). The mixture was then stirred at 50° C. for 1.5 hours, diluted with EtOAc (10 mL), and washed with saturated NH$_4$Cl (2×10 mL) and brine (2×10 mL). The organic phase was collected, dried over Na$_2$SO$_4$, and concentrated. The resultant residue was purified on silica gel (20% EtOAc/Hexanes) to provide C91 as a white solid (730 mg, 98% yield). 1H NMR (400 MHz, DMSO-D6) 1.2 (m, 3H) 1.27 (m, 2H) 1.3 (m, 9H) 2.0 (d, J=7.5 Hz, 2H) 3.2 (q, J=7.1 Hz, 2H) 5.0 (s, 2H) 7.2 (d, J=7.9 Hz, 1H) 7.3 (d, J=7.5 Hz, 1H) 7.7 (s, 1H) 8.4 (s, 1H) 10.1 (s, 1H) ppm. HPLC Rt=9.0 minutes; LC/MS (Method F) m/z 467.3 (MH$^+$).

Step 2. A mixture of C91 (730 mg, 1.56 mmol) and 4N HCl in 1,4-dioxane was stirred at 25° C. for 1 hour during which time a yellow precipitate. The solids were collected by filtration, washed with 1,4-dioxane, and dried under reduced pressure to provide 100 as a yellow solid (554 mg, 95%). $^1$H NMR (400 MHz, DMSO-D6) 1.3 (t, J=7.3 Hz, 3H) 1.4 (d, J=9.6 Hz, 2H) 2.2 (d, J=9.1 Hz, 2H) 3.2 (q, J=7.3 Hz, 2H) 5.2 (d, J=14.1 Hz, 2H) 7.4 (d, J=7.9 Hz, 1H) 7.5 (d, J=7.9 Hz, 1H) 7.8 (s, 1H) 8.5 (s, 1H) 9.3 (s, 1H) 9.4 (s, 1H) 10.3 (s, 1H) ppm. HPLC Rt=6.6 minutes. LC/MS (Method F) m/z 367.3 (MH$^+$).

Example 101

(−)-1-[6-(4-Ethylsulfanyl-5-trifluoromethyl-pyrimidin-2-ylamino)-(1S,4R)-1,2,3,4-tetrahydro-1,4-epiazano-naphthalen-9-yl]-ethanone (101)

A suspension of 100 (250 mg, 620 μmol) and CH$_2$Cl$_2$ (5 mL) was treated with DIEA (270 μL, 1.55 mmol) followed by addition of acetic anhydride (126 μL, 1.24 mmol). The mixture was stirred at 25° C. for 1 hour and concentrated under reduced pressure. The resultant residue was purified on silica gel (20% EtOAc/Hexanes) to provide 101 as a white solid (110 mg, 43% yield). HPLC Rt=7.0 minutes. LC/MS (Method F) m/z 409.3 (MH$^+$).

Example 102

N$^4$-((1R,2R)-2-Dimethylamino-cyclopentyl)-N$^2$-[(1R,4S)1,2,3,4-tetrahydro-1,4-epiazano-naphthalen-6-yl]-5-trifluoromethyl-pyrimidine-2,4-diamine (102)

Step 1. (1R,4S)-6-[4-((1R,2R)-2-Dimethylamino-cyclopentylamino)-5-trifluoromethyl-pyrimidin-2-ylamino]-1,2,3,4-tetrahydro-1,4-epiazano-naphthalene-9-carboxylic acid tert-butyl ester (C92): Compound C68 (1.83 g, 4.15 mmol) was added to a suspension of C93 (918 mg, 4.56 mmol) and Na$_2$CO$_3$ (2.20 g, 20.74 mmol) in 1-Methyl-2-pyrrolidinone (30 ml, anhydrous). The mixture was stirred at 70° C. for 16 hours, cooled, and poured into ice water (150 mL). The precipitate was removed by filtration, washed with water, and air dried. The resultant white solid was purified by flash column chromatography (eluted with CHCl$_3$/MeOH/NH$_4$OH, 90:9:1) to provide C92 as a foamy white solid (1.9 g, 86%). LC/MS (Method F) Rt 1.8 min, HPLC purity (254 nM, >95%) M+H=533.5.

Step 2. HCl (g) was bubbled through EtOAc (10 mL) until fuming was noted. The resultant solution was added to a solution of C92 (1.9 g, 3.57 mmol) in EtOH (10 ml), absolute) and the mixture stirred at 25° C. for about 14 hours. The mixture was concentrated under reduced pressure to provide 102 as an off-white solid (1.67 g, 3.30 mmol). LC/MS (Method F) Rt 1.0 min HPLC purity (254 nm, 90%). M+H=433.5.

Example 103

1-{6-[4-((1R,2R)-2-Dimethylamino-cyclopentylamino)-5-trifluoromethyl-pyrimidin-2-ylamino]-(1R,4S)-1,2,3,4-tetrahydro-1,4-epiazano-naphthalen-9-yl}-ethanone dihydrochloride salt (103)

A suspension of compound 102 (1.67 g, 3.30 mmol) in CH$_2$Cl$_2$ (30 mL) was treated with TEA (2.30 mL), 16.52 mmol) and acetic anhydride and stirred at 25° C. for 1 hour. The mixture was diluted with CH$_2$Cl$_2$ and washed with H$_2$O, NaHCO$_3$ (sat. aq.), and brine. The organic layer was collected, dried over Na$_2$SO$_4$, and concentrated to provide a foam. $^1$H NMR (400 mHz, CD$_3$OD) δ 1.29-1.49, 1.5-1.8, 1.95-2.3, 2.25, 2.65-2.9, 4.6-4.7, 5.3-5.35, 5.45-5.50, 7.21-7.26, 7.31-7.37, 7.69-7.73, 8.1 LC/MS (Method F) Rt 2.2 min HPLC Purity (254 nm, >95%) M+H=475.4. The foam was converted to the dihydrochloride salt by method described in Step 2 of Example 2 to provide 103 as a white powder (1.7 g, 94%). LC/MS (Method F) Rt 1.5 min, HPLC purity >90%, M+H=475.3.

Example 104

N$^4$-((1R,2R)-2-Dimethylamino-cyclopentyl)-N$^2$-(1,2,3,4-tetrahydro-1,4-epiazano-naphthalen-6-yl)-5-trifluoromethyl-pyrimidine-2,4-diamine (104)

Step 1. 6-[4-((1R,2R)-2-Dimethylamino-cyclopentylamino)-5-trifluoromethyl-pyrimidin-2-ylamino]-1,2,3,4-tetrahydro-1,4-epiazano-naphthalene-9-carboxylic acid tert-butyl ester (C94): Compound C94 was prepared in a manner similar to that described for C92 in Step 1 of Example 102 by reacting C44 (200 mg, 0.45 mmol) and (1R,2R)—N,N-Dimethyl-cyclopentane-1,2-diamine (63 mg, 0.49 mmol) to provide C94 as a mixture of diastereomers in the form of a tan solid (193 mg, 80%). LC/MS (Method F) Rt 2.17 min HPLC Purity (254 nm, °90%) M+H=533.3.

Step 2. Compound 104 was prepared in a manner similar to that described for 102 in Step 2 of Example 102 except that C94 (90 mg, 1.69 mmol) was used instead of C92. Purification by preparative HPLC provided 104 as a mixture of diastereomers in the form of a white solid (55 mg, 75% yield). LC/MS (Method F) Rt 1.2 min HPLC purity (254 nm, >95%). M+H=433.3.

Example 105

1-{6-[4-((1R,2R)-2-Dimethylamino-cyclopentylamino)-5-trifluoromethyl-pyrimidin-2-ylamino]-1,2,3,4-tetrahydro-1,4-epiazano-naphthalen-9-yl}-ethanone (105)

Compound 105 was prepared in a manner similar to that described for 103 in Example 103 except that 104 (50 mg, 0.12 mmol) was used instead of 102. Purification by flash chromatography (Biotage) eluting with $CH_2Cl_2$/MeOH/NH4OH provided 105 as a mixture of diastereomers in the form of a clear glass (25 mg, 44% yield). $^1H$ NMR (400 mHz, $CD_3OD$) 1.2-1.5, 1.5-1.8, 2.0-2.2, 2.0, 2.25, 2.8-2.9, 4.6-4.7, 5.3-5.4, 5.4-5.5, 7.2, 7.3-7.4, 7.7, 8.1, LC/MS (Method F) Rt 1.1 min HPLC purity (254 nm, >95%). M+H=475.3.

Example 106

$N^4$-((1R,2R)-2-Dimethylamino-cyclopentyl)-$N^2$-(9-methanesulfonyl-1,2,3,4-tetrahydro-1,4-epiazano-naphthalen-6-yl)-5-trifluoromethyl-pyrimidine-2,4-diamine (106)

A solution of 104 (50 mg, 0.12 mmol) in DMF (1 mL) was treated with TEA (64 mL, 0.14 mmol) and methanesulfonyl chloride (11 mL, 0.14 mmol) and stirred at 25° C. for 3 hours. The mixture was poured into $H_2O$ and extracted with EtOAc. The combined organic layers were washed with water and brine, dried over $Na_2SO_4$, and concentrated under reduced pressure. The resultant residue was purified via flash column chromatography (Biotage) to provide 106 as a mixture of diastereomers in the form of a clear glass (25 mg, 44% yield). LC/MS (Method F) Rt 1.6 min HPLC Purity (254 nm, >95%). M+H=511.2.

Example 107

$N^4$-((1R,2R)-2-Dimethylamino-cyclopentyl)-$N^2$-(1S,4R)-1,2,3,4-tetrahydro-1,4-epiazano-naphthalen-6-yl-5-trifluoromethyl-pyrimidine-2,4-diamine (107)

Step 1. (1S,4R)-6-[4-((1R,2R)-2-Dimethylamino-cyclopentylamino)-5-trifluoromethyl-pyrimidin-2-ylamino]-1,2,3,4-tetrahydro-1,4-epiazano-naphthalene-9-carboxylic acid tert-butyl ester (C95): Compound C95 was prepared in a manner similar to that described for C92 in Step 1 of Example 102 except that C57 (200 mg, 0.45 mmol) was used instead of C68 to provide C95 as a mixture of diastereomers in the form of a tan solid (126 mg, 52.5%). LC/MS (Method F) Rt 1.8 min, HPLC Purity (254 nm, >90%). M+H=533.3.

Step 2. Compound 107 was prepared in a manner similar to that described for 102 in Step 2 of Example 102 except that C95 (126 mg, 0.236 mmol) was used instead of C92 to provide 107 as a mixture of diastereomers in the form of a white solid (125 mg, >100%). LC/MS (Method F) Rt<0.9, M+H=433.3.

Example 108

1-{(1S,4R)-6-[4-((1R,2R)-2-Dimethylamino-cyclopentylamino)-5-trifluoromethyl-pyrimidin-2-ylamino]-1,2,3,4-tetrahydro-1,4-epiazano-naphthalen-9-yl}-ethanone dihydrochloride salt (108)

Compound 108 was prepared in a manner similar to that described for 103 in Example 103 except that 107 (125 mg, 0.288 mmol) was used instead of 102. Purification by flash chromatography (Biotage) eluting with $CH_2Cl_2$/NH4OH provided an off-white foam. The foam was converted to the dihydrochloride salt by the method described in Step 2 of Example 102 to provide 108 as a white solid (121 mg, 77%). $^1H$ NMR (400 mHz, dmso-d6) 1.1-1.3, 1.5-1.8, 1.8-2.2, 2.6-2.8, 3.8-4.0, 4.6-4.8, 5.3-5.4, 7.2-7.4, 7.6, 7.8, 8.3 ppm. LC/MS (Method F) Rt 1.5 min, HPLC purity (254 nm, >95%). M+H=475.2.

Example 109

N-{(1R,2R)-2-[2-(1,2,3,4-Tetrahydro-1,4-epiazano-naphthalen-6-ylamino)-5-trifluoromethyl-pyrimidin-4-ylamino]-cyclopentyl}-acetamide (109)

Step 1. ((1R,2R)-2-Amino-cyclopentyl-carbamic acid benzyl ester (C96): Compound C96 was prepared in a manner similar to that described for 103 in Example 103, except that ((1R,2R)-2-Benzyloxycarbonylamino-cyclopentyl)-carbamic acid tert-butyl ester (100 mg, 0.299 mmol) was used instead of 102 to provide C96 as a white solid (92 mg, 100%).

Step 2. ((1R,2R)-2-Acetylamino-cyclopentyl)-carbamic acid benzyl ester (C97): Compound C97 was prepared in a manner similar to that described for 103 in Example 103, except that C96 (92 mg, 0.299 mmol) was used instead of 102 to provide C97 as a white solid (82 mg, 100%). LC/MS (Method F) Rt 1.8 min HPLC purity (245 nm, >95%). M+H=277.3.

Step 3. N-((1R,2R)-2-Amino-cyclopentyl)-acetamide (C98): A mixture of C97 (82 mg, 0.3 mmol), MeOH and palladium on Carbon (10%, catalytic) was shaken on Parr® shaker at 45 psi $H_2$ for 16 hours at about 25° C. The mixture was filtered through celite and the solids washed with copious amounts of MeOH. The combined filtrates were concentrated under reduced pressure to provide C98 as an off-white solid (40 mg, 94%).

Step 4. 6-[4-((1R,2R)-2-Acetylamino-cyclopentylamino)-5-trifluoromethyl-pyrimidin-2-ylamino]-1,2,3,4-tetrahydro-1,4-epiazano-naphthalene-9-carboxylic acid tert-butyl ester (C99): Compound C99 was prepared in a manner similar to that described for 102 in Step 2 of Example 102 except that C44 (144 mg, 0.321 mmol) was used instead of C92 to provide C99 as a mixture of diastereomers in the form of a tan solid (55 mg, 36%). LC/MS (Method F) Rt 2.6 min HPLC purity (254 nm, >95%) M+H=547.3.

Step 5. Compound 109 was prepared in a manner similar to that described for 102 in Step 2 of Example 102 by cleaving C99 (55 mg, 0.100 mmol) with HCl to provide 109 as a mixture of diastereomers in the form of a white solid (50 mg, 96%). LC/MS (Method F) Rt 1.0 min, HPLC purity (254 nm, >95%). M+H=447.3.

Example 110

N-{(1R,2R)-2-[2-(9-Acetyl-1,2,3,4-tetrahydro-1,4-epiazano-naphthalen-6-ylamino)-5-trifluoromethyl-pyrimidin-4-ylamino]-cyclopentyl}-acetamide (110)

Compound 110 was prepared in a manner similar to that described for 103 in Example 103, except that 109 (50 mg, 0.096 mmol) was used instead of 102 to provide 110 as a mixture of diastereomers in the form of a white solid (37 mg, 78%). LC/MS (Method F) Rt 1.8 min, HPLC purity (254 nm, >93%). M+H=489.4.

Example 111

N-{(1R,2R)-2-[2-(1,2,3,4-Tetrahydro-1,4-epiazano-naphthalen-6-ylamino)-5-trifluoromethyl-pyrimidin-4-ylamino]-cyclohexyl}-acetamide (111)

Step 1. N-((1R,2R)-2-Amino-cyclohexyl)-acetamide (C100): A solution of (1R,2R)-1,2-Cyclohexanediamine (10.0 g, 87.9 mmol) and ethyl acetamidate (11.0 g, 88.8 mmol) in EtOH (350 mL) was refluxed for 18 hour under a dry nitrogen atmosphere. The reaction mixture was cooled to 25° C. and concentrated. The resultant white solid was dissolved in 1:1 (vol:vol) mixture of EtOH/H$_2$O, buffered to pH=7, and refluxed for 2 days. The mixture was cooled to about 25° C., and 12 N HCl was added with cooling and stirring. The resultant viscous oil was re-dissolved in 50 mL of MeOH and stirred at about 25° C. for 1 hours. The resultant mixture was filtered and concentrated. The resultant foamy solid was triturated with Et$_2$O overnight. The resulting solids were collected by filtration, washed with Et$_2$O (3×50 mL), and dried under reduced pressure to provide C100 as a solid having a purity of about 80%. (17.2 g). Compound C100 was used without further purification LC/MS (Method F) Rt 0.3 min, M+H=157.1, M (calc) 156.13.

Step 2. 6-[4-((1R,2R)-2-Acetylamino-cyclohexylamino)-5-trifluoromethyl-pyrimidin-2-ylamino]-1,2,3,4-tetrahydro-1,4-epiazano-naphthalene-9-carboxylic acid tert-butyl ester (C101): Compound C101 was prepared in a manner similar to that described for C92 in Step 1 of Example 102 by reacting C44 (100 mg, 0.223 mmol) and C100 (49 mg, 0.250 mmol) to provide C101 as a mixture of diastereomers in the form of a white solid (91 mg, 0.163%). LC/MS (Method F) Rt 2.8 min, HPLC purity (254 nm, >85%). M+H=561.4.

Step 3. Compound 111 was prepared in a manner similar to that described for 102 in Step 2 of Example 102 except that C101 (91 mg, 73 mmol) was used instead of C92 to provide 111 as a mixture of diastereomers in the form of yellow solid (92 mg, 100%). LC/MS (Method F) Rt 1.2 min, HPLC purity (254 nm, >95%), M+H=461.3.

Example 112

N$^4$-((1R,2R)-2-Dimethylamino-cyclohexyl)-N$^2$-(9-methyl-1,2,3,4-tetrahydro-1,4-epiazano-naphthalen-6-yl)-5-trifluoromethyl-pyrimidine-2,4-diamine (112)

A solution of 111 (38 mg, 0.08 mmol) and MP-Carbonate (xs) (polymer-supported carbonate) in MeOH (2 mL, anhydrous) was stirred at 25° C. for 2 hours. The resultant mixture was filtered and the solids washed with MeOH. The combined filtrates were added to paraformaldehyde (7 mg, 0.08 mmol), and the resultant solution stirred at 25° C. for 3 hours. The solution was treated with NaBH$_4$ (9 mg, 0.23 mmol), stirred at about 25° C. for 16 hours, and concentrated under reduced pressure The resultant residue was purified via flash chromatography (eluted with CH$_2$Cl$_2$/MeOH/NH$_4$OH) to provide 112 as a mixture of diastereomers in the form of a white solid (6 mg, 17%). LC/MS (Method F) Rt 1.0 min, HPLC purity (254 nm, >95%). M+H=447.4.

Example 113

N-{(1R,2R)-2-[2-(9-Methanesulfonyl-1,2,3,4-tetrahydro-1,4-epiazano-naphthalen-6-ylamino)-5-trifluoromethyl-pyrimidin-4-ylamino]cyclohexyl}-acetamide (113)

Compound 113 was prepared in a manner similar to that described for 106 in Example 106 except that 111 (30 mg, 0.056 mmol) was used instead of 104 to provide 113 as a mixture of diastereomer in the form of a white solid (21 mg, 71%). LC/MS (Method F) Rt 2.0 min, HPLC purity (254 nm, 92%). M+H=525.3.

Example 114

6-[4-(1,3-Dihydro-pyrrolo[3,4-c]pyridin-2-yl)-5-trifluoromethyl-pyrimidin-2-ylamino]-1,2,3,4-tetrahydro-1,4-epiazano-naphthalene-9-carboxylic acid tert-butyl ester (114)

Step 1. 6-[4-(1,3-Dihydro-pyrrolo[3,4-c]pyridin-2-yl)-5-trifluoromethyl-pyrimidin-2-ylamino]-1,2,3,4-tetrahydro-1,4-epiazano-naphthalene-9-carboxylic acid tert-butyl ester (C103): Compound C103 was prepared in a manner similar to that described for C92 in Step 1 of Example 102 by reacting C44 (105 mg, 0.234 mol) and (1R,2R)—N,N-Dimethyl-cyclopentane-1,2-diamine (C102) (see U.S. Pat. No. 5,371,090) (28 g, 0.234) to provide C103 as a white solid (108 mg, 88%). LC/MS (Method F) Rt 2.8 min, HPLC Purity (254 nm, 84%). M+H=525.4.

Step 2. Compound 114 was prepared in a manner similar to that described for C92 in Step 1 of Example 102, except that C103 (108 mg, 0.206 mmol) was used instead of C68 to provide to provide 114 as a white solid (105 mg, 96%). LC/MS (Method F) Rt 1.8 min (polar method) HPLC Purity (254 nm, 95%). M+H=425.3.

Example 115

1-{6-[4-(1,3-Dihydro-pyrrolo[3,4-c]pyridin-2-yl)-5-trifluoromethyl-pyrimidin-2-ylamino]-1,2,3,4-tetrahydro-1,4-epiazano-naphthalen-9}-ethanone (115)

Compound 115 was prepared in a manner similar to that described for 103 in Example 103, except that 114 (105 mg, 0.196 mmol) was used instead of 102 to provide 115 as a white solid (65 mg, 71%). LC/MS (Method F) Rt 1.9 min, HPLC purity (245 nm, >95%). M+H=467.3.

Example 116

N$^4$-((1R,2R)-2-Morpholin-4-yl-cyclopentyl)-N$^2$-(1,2,3,4-tetrahydro-1,4-epiazano-naphthalen-6-yl)-5-trifluoromethyl-pyrimidine-2,4-diamine (116)

Step 1. 6-[4-((1R,2R)-2-Morpholin-4-yl-cyclopentylamino)-5-trifluoromethyl-pyrimidin-2-ylamino]-1,2,3,4-tetrahydro-1,4-epiazano-naphthalene-9-carboxylic acid tert-butyl ester (C104): Compound C104 was prepared in a manner similar to that described for C92 in Step 1 of Example 102, except that 2-Morpholin-4-yl-cyclopentylamine (38 mg, 0.223 mmol) was used instead of C68 to react with C44 (100 mg, 0.223 mmol) to provide to provide C104 as a mixture of diastereomers in the form of a white solid (130 mg, 100%). LC/MS (Method F) Rt 1.9 min, HPLC purity (254 nm, 95%). M+H=575.5.

Step 2. Compound 116 was prepared in a manner similar to that described for 102 in Step 2 of Example 102, except that C104 (130 mg, 0.223 mmol) was used instead of C92 to provide to provide 116 as a mixture of diastereomers in the form of a white solid (13 mg, 10%). LC/MS (Method F) Rt 0.8 min, HPLC purity (254 nm, >95%). M+H=475.3.

Example 117

1-[6-(4-Ethylamino-5-methyl-pyrimidin-2-ylamino)-(1S,4R)-1,2,3,4-tetrahydro-1,4-epiazano-naphthalen-9-yl]-ethanone (117)

Step 1. 6-Nitro-(1S,4R)-1,2,3,4-tetrahydro-1,4-epiazano-naphthalene hydrochloride (C105): A mixture of C41 (2.50 g, 8.61 mmol) and 4 N hydrogen chloride in 1,4-dioxane (100 mL, 400 mmol) was stirred at 25° C. for 40 min. The mixture was concentrated, and the resultant residue dried under reduced pressure to provide C105 as a brown syrup ((1.99 g, 100%). $^1$H NMR (500 MHz, DMSO-$d_6$) δ 9.68 (br s, 2H), 8.36 (d, J=1.5 Hz, 1H), 8.26 (dd, J=8.0, 2.0 Hz, 1H), 7.76 (d, J=8.5 Hz, 1H), 5.38 (s, 2H), 3.36 (s, 2H), 2.32 (m, 2H), 1.45 (m, 2H).

Step 2. 1-(6-Nitro-(1S,4R)-1,2,3,4-tetrahydro-1,4-epiazano-naphthalen-9-yl)-ethanone (C106): A mixture of C105 (1.99 g, 8.61 mmol) and DIEA (2.22 g, 17.2 mmol) in $CH_2Cl_2$ (110 mL) was treated with acetyl chloride (1.01 g, 12.9 mmol) and stirred at 25° C. overnight. The reaction mixture was diluted with $CH_2Cl_2$ (100 mL) and washed with saturated aqueous $NaHCO_3$ (150 mL) then brine (150 mL). The organic layer was collected, dried over $Na_2SO_4$, filtered, and concentrated to dryness to provide C106 as a brown syrup (1.82 g, 91%). $^1$H NMR (500 MHz, $CDCl_3$) δ 8.13 (m, 2H), 7.41 (m, 1H), 5.66 (m, 1H), 5.21 (m, 1H), 2.21 (m, 2H), 2.04 (m, 3H), 1.40 (m, 2H).

Step 3. 1-(6-Amino-(1S,4R)-1,2,3,4-tetrahydro-1,4-epiazano-naphthalen-9-yl)-ethanone (C107): A mixture of C106 (1.82 g, 7.84 mmol) and 10% palladium on carbon (0.750 g, 50% water by wt.) in MeOH (55 mL) was shaken under an atmosphere of hydrogen (50 psi) for 1.5 hours at 25° C. The reaction mixture was then filtered through diatomaceous earth and the filtrated concentrated to dryness to provide C107 as a white solid (1.60 g, 100%). $^1$H NMR (500 MHz, $CDCl_3$) δ 7.00 (m, 1H), 6.62 (dd, J=14.0, 2.0 Hz, 1H), 6.44 (m, 1H), 5.44 (m, 1H), 4.97 (m, 1H), 3.65 (br s, 2H), 2.06 (m, 2H), 1.99 (m, 3H), 1.40 (m, 1H), 1.29 (m, 1H).

Step 4. A mixture of C107 (0.196 g, 0.969 mmol), (2-Chloro-5-methyl-pyrimidin-4-yl)-ethylamine (0.166 g, 0.969 mmol), tris(dibenzylidineacetone) dipalladium(0) (0.088 g, 0.097 mmol) and 2-(dicyclohexylphosphino) biphenyl (0.034 g, 0.097 mmol) in THF (1 mL) was treated with a 1 M solution of lithium bis(trimethylsilyl) amide in THF (2.13 mL, 2.13 mmol). The resultant mixture was heated in a microwave reactor at 140° C. for 20 min. The mixture was then cooled to room temperature, diluted with MeOH (2 mL), and concentrated to dryness. The resultant residue was purified by preparatory HPLC followed by chromatography (silica, 1:9 MeOH/EtOAc). The eluents containing 117 were combined and concentrated. The resultant residue was hydrolyzed from acetonitrile/water to provide 117 as a white solid (0.134 g, 41%). HPLC (Method B1) Rt=4.21, HPLC Purity=100%. MS for $C_{19}H_{23}N_5O$: [M+H]=388.

Examples 118 to 125

The compounds of Examples 118 to 125 (Table 1) were prepared in a manner similar to that described for 117 in Step 4 of Example 117.

Example 126

1-[6-(4-Ethylamino-5-fluoro-pyrimidin-2-ylamino)-(1S,4R)-1,2,3,4-tetrahydro-1,4-epiazano-naphthalen-9-yl]-ethanone (126)

Step 1. (2-Chloro-5-fluoro-pyrimidin-4-yl)-ethylamine (C108): A mixture of 2,4-dichloro-5-fluoro-pyrimidine (4.95 g, 29.6 mmol), DIEA (7.64 g, 59.2 mmol) and a 2.0 M solution of $EtNH_2$ in MeOH (14.8 mL, 29.6 mmol) was stirred at 50° C. in a sealed vessel for 20 hours. The reaction mixture was then cooled to 25° C. and concentrated. The resultant residue was dissolved in EtOAc (200 mL) and washed with $H_2O$ (150 mL) and brine (150 mL). The organic phase was dried over $Na_2SO_4$ and concentrated under reduced pressure. The resultant residue was titrated with hexanes to provide C108 as an off-white solid (4.02 g, 77%). MP: 56-58° C. $^1$H NMR (500 MHz, $CDCl_3$) δ 7.86 (d, J=3.0 Hz, 1H), 5.20 (br s, 1H), 3.57 (m, 1H), 1.29 (t, J=7.5 Hz, 3H) ppm.

Step 2. A mixture of C107 (0.200 g, 1.00 mmol), C108 (0.187 g, 1.00 mmol), tris(dibenzylidineacetone) dipalladium (0) (0.090 g, 0.100 mmol) and 2-(dicyclohexylphosphino) biphenyl (0.035 g, 0.100 mmol) in THF (1 mL) was stirred for 1 min at 25° C. A 1 M solution of lithium bis(trimethylsilyl) amide in THF (2.20 mL, 2.20 mmol) was added, and the mixture was heated in a microwave reactor at 140° C. for 20 min. The resulting mixture was then cooled to room temperature, diluted with MeOH (2 mL), and concentrated to dryness. The resultant residue was purified by chromatography (silica, 1:1 EtOAc/hexanes to EtOAc) then preparative HPLC to provide 126 as a white solid (0.112 g, 33%). MP: 201-203° C. $^1$H NMR) 500 MHz, $CDCl_3$) δ 7.66 (m, 1H), 7.65 (d, J=1.3 Hz, 1H), 7.23 (m, 1H), 7.15 (m, 1H), 6.80 (d, J=3.1 Hz, 1H), 5.52 (m, 1H), 5.04 (m, 1H), 4.91 (br s, 1H), 3.53 (m, 2H), 2.09 (m, 2H), 2.00 (s, 3H), 1.43 (m, 1H), 1.29 (m, 4H) ppm.

Example 127

1-[6-(5-Fluoro-4-isopropylamino-pyrimidin-2-ylamino)-(1S,4R)-1,2,3,4-tetrahydro-1,4-epiazano-naphthalen-9-yl]-ethanone (127)

Step 1. (2-Chloro-5-fluoro-pyrimidin-4-yl)-isopropylamine (C109): A mixture of 2,4-dichloro-5-fluoro-pyrimidine (5.01 g, 30.0 mmol), DIEA (7.93 g, 60 mmol) and isopropylamine (1.77 g, 30.0 mmol) in EtOH (15 mL) was stirred at 50° C. in a sealed vessel for 21 hours. The mixture was then cooled to 25° C. and concentrated. The resultant residue was dissolved in EtOAc (200 mL) and washed with $H_2O$ (200 mL) and brine (200 mL). The organic phase was dried over $Na_2SO_4$ and concentrated under reduced pressure. The resultant residue was purified by chromatography (silica, hexanes to 3:1 $CH_2Cl_2$/hexanes) to provide C109 as a yellow solid (4.67 g, 82%). MP: 55-57° C. $^1$H NMR (500 MHz, $CDCl_3$) δ 7.85 (d, J=3.0 Hz, 1H), 5.31 (br s, 1H), 3.34 (m, 1H), 1.29 (d, J=6.5 Hz, 6H) ppm.

Step 2. Compound 127 was prepared in a manner similar to that described for 126 in Step 2 of Example 126 except that C109 (0.199 g, 1.0 mmol) was used instead of C108 to provide 127 as a white solid (0.138 g, 39%). HPLC (Method B1) Rt=3.81, HPLC Purity=99%. MS for $C_{19}H_{22}FIN_5O$: [M+H] =356.

Example 128

1-[6-(4-Cyclopropylamino-5-fluoro-pyrimidin-2-ylamino)-(1S,4R)-1,2,3,4-tetrahydro-1,4-epiazano-naphthalen-9-yl]-ethanone (128)

Step 1. (2-Chloro-5-fluoro-pyrimidin-4-yl)-cyclopropylamine (C110): A mixture of 2,4-dichloro-5-fluoro-pyrimidine (4.96 g, 29.7 mmol), DIEA (7.64 g, 59.4 mmol) and cyclopropylamine (1.69 g, 29.7 mmol) in EtOH (15 mL) was stirred at 50° C. in a sealed vessel for 25 hours. The mixture was cooled to 25° C. and concentrated. The resultant residue was dissolved in EtOAc (200 mL) and washed with $H_2O$ (150 mL) and brine (150 mL). The organic phase was collected, dried over $Na_2SO_4$, and concentrated under reduced pressure, The resultant residue was titrated with hexanes to provide C110 as an off-white solid (4.97 g, 89%). MP: 83-85° C. $^1$H NMR (500 MHz, $CDCl_3$) δ 7.89 (m, 1H), 5.42 (br s, 1H), 2.90 (m, 1H), 0.93 (m, 2H), 0.63 (m, 2H) ppm.

Step 2. Compound 128 was prepared in a manner similar to that described for 126 in Step 2 of Example 126 except that C110 (0.197 g, 1.0 mmol) was used instead of C108 to provide 128 as a white solid (0.033 g, 8%). HPLC (Method B1) Rt=10.1, HPLC Purity=85%. MS for $C_{19}H_{20}FIN_5O$: [M+H]=354.

Example 129

1-[6-(4-Cyclobutylamino-5-fluoro-pyrimidin-2-ylamino)-(1S,4R)-1,2,3,4-tetrahydro-1,4-epiazano-naphthalen-9-yl]-ethanone (129)

Step 1. (2-Chloro-5-fluoro-pyrimidin-4-yl)-cyclobutylamine (C111): A mixture of 2,4-dichloro-5-fluoro-pyrimidine (4.89 g, 29.3 mmol), DIEA (7.79 g, 58.6 mmol) and cyclobutylamine (2.08 g, 29.3 mmol) in EtOH (15 mL) was stirred at 50° C. in a sealed vessel for 21 hours. The mixture was then cooled to 25° C. and concentrated. The resultant residue was dissolved in EtOAc (200 mL) and washed with $H_2O$ (200 mL) and brine (200 mL). The organic phase was collected, dried over $Na_2SO_4$, and concentrated under reduced pressure. The resultant residue was purified by chromatography (silica, hexanes to 3:1 $CH_2Cl_2$/hexanes) to provide C111 as a yellow solid (4.57 g, 82%). MP: 63-65° C. $^1$H NMR (500 MHz, $CDCl_3$) δ 7.87 (m, 1H), 5.33 (br s, 1H), 4.61 (m, 1H), 2.46 (m, 2H), 1.96 (m, 2H), 1.81 (m, 2H) ppm.

Step 2. Compound 129 was prepared in a manner similar to that described for 126 in Step 2 of Example 126 except that C111 (0.210 g, 1.0 mmol) was used instead of C108 to provide 129 as a off-white solid (0.125 g, 38%). HPLC (Method B1) Rt=11.1, HPLC Purity=99%. MS for $C_{20}H_{22}FIN_5O$: [M+H]=368.

Examples 130 to 355

Examples 130 to 355 (Table 2) were prepared by specific methods of the previously described examples or by methods known to those skilled in the art.

Example 356

(+/−)-1-[6-(4-Cyclobutylamino-5-trifluoromethyl-pyrimidin-2-ylamino)-1,2,3,4-tetrahydro-1,4-epiazano-naphthalen-9-yl]-propan-2-one (356)

A solution of C46 (92 mg, 0.22 mmol), chloro-2-propanone (25 mg, 0.27 mmole) and DIEA (115 mg, 0.89 mmol) in DMF (2 mL) was stirred at 29° C. for 12 hours. The reaction mixture was partitioned between EtOAc and $H_2O$ and the layers separated. The organic layer was collected, washed with water, dried over $Na_2SO_4$, and concentrated and concentrated under reduced pressure. Purification of the resultant residue on Biotage® Flash 12S($CH_2Cl_2/CH_3OH$=99:1) provide 356 as a brown solid (50 mg, 52%). $^1$H NMR (500 MHz, DMSO-$d_6$) δ 9.5 (s, 1H), 8.2 (s, 1H), 7.7 (s, 1H), 7.3 (m, 1H), 7.1 (d, J=8 Hz, 1H), 7.0 (d, J=7 Hz, 1H), 4.6 (br, 1H), 4.17 (t, J=4 Hz, 2H), 2.95 (m, 2H), 2.2 (m, 2H), 2.15 (m, 2H), 2.01 (s, 3H), 1.90 (m, 2H), 1.7-1.6 (m, 2H), 1.09 (m, 2H) ppm. MS: 432.5 (MH+).

Example 357

(+/−)-[6-(4-Cyclobutylamino-5-trifluoromethyl-pyrimidin-2-ylamino)-1,2,3,4-tetrahydro-1,4-epiazano-naphthalen-9-yl]-acetic acid dihydrochloride (357)

Step 1. (+/−)-[6-(4-Cyclobutylamino-5-trifluoromethyl-pyrimidin-2-ylamino)-1,2,3,4-tetrahydro-1,4-epiazano-naphthalen-9-yl]-acetic acid tert-butyl ester (C112): Bromoacetic acid tert-butyl ester (0.48 g, 2.45 mmol) was added to a solution of C46 (1.0 g, 2.23 mmol) and DIEA (0.86 g, 6.7 mmol) in THF (10 mL) and DMF (10 mL). After 2 hours the reaction mixture was partitioned between EtOAc and $H_2O$ and the layer separated. The organic layer was collected, and the aqueous layer was extracted with EtOAc. The combined organic layers were washed with $H_2O$, dried over $Na_2SO_4$, and concentrated under reduced pressure. Purification of the resultant residue on Biotage® Flash 40M ($CH_2Cl_2/CH_3OH$=97:3) provided C112 as a white solid (0.93 g, 85%). $^1$H NMR (400 MHz, DMSO-$d_6$) δ 9.54 (br, 1H), 8.14 (s, 1H), 7.7 (s, 1H), 7.3 (m, 1H), 7.12 (d, J=8 Hz, 1H), 6.9 (m, 1H), 4.5 (br, 1H), 4.2 (t, J=4 Hz, 2H), 2.7 (m, 2H), 2.18-2.12 (m, 4H), 1.97 (m, 2H), 1.67-1.58 (m, 2H), 1.33 (s, 9H), 1.0 (m, 2H); MS: 490.3 (MH+).

Step 2. A solution of HCl (4N in dioxane, 10 mL) and C112 (0.19 g, 0.388 mmol) was stirred at about 25° C. for 4 hours. The mixture was then concentrated to provide 357 as a white solid (0.19 g, 100%). $^1$H NMR (400 MHz, DMSO-$d_6$) δ 1.63 (br, 1H), 8.3 (s, 1H), 7.87 (m, 1H), 7.81 (br, 1H), 7.6 (m, 1H), 7.5 (m, 1H), 5.3 (m, 2H), 4.5 (m, 1H), 4.0 (s, 1H), 3.6 (m, 2H), 2.4 (m, 2H), 2.1 (m, 4H), 1.7 (m, 2H), 1.47 (m, 2H) ppm. HPLC Rt: 4.72 min; HPLC purity: 100% MS: 432.2 (MH+).

Example 361

(+/−)-2-[6-(4-Cyclobutylamino-5-trifluoromethyl-pyrimidin-2-ylamino)-1,2,3,4-tetrahydro-1,4-epiazano-naphthalen-9-yl]-N-methyl-acetamide (358)

A solution of 357 (0.19 g, 0.37 mmol) in thionyl chloride (0.22 g, 1.86 mmol) was heated to 50° C. After 2 hours the mixture was concentrated and the residue was dissolved in THF (5 mL). The resultant solution was treated with DIEA (0.15 g, 1.12 mmol) and methylamine (2.0 M in THF, 0.37 mL, 0.75 mmol) were added and stirred for 2 hours at about 25° C. The reaction mixture was quenched with water and extracted with EtOAc. The organic layer was dried over Na₂SO₄ and concentrated under reduced pressure. Purification of the resultant residue on Biotage® Flash 12S (CH₂Cl₂/CH₃OH=98:2) provided 358 as a brown solid (45 mg, 27%). ¹H NMR (500 MHz, DMSO-d₆) δ 9.6 (br, 1H), 8.1 (s, 1H), 7.7 (s, 1H), 7.6 (br, 1H), 7.4 (d, J=7.7 Hz, 1H), 7.19 (d, J=7.7 Hz, 1H), 7.05 (d, J=6 Hz, 1H), 4.6 (br, 1H), 4.2 (br, 2H), 2.7 (br, 2H), 2.6 (d, J=5 Hz, 3H), 2.24-2.11 (m, 6H), 1.64-1.60 (m, 2H), 1.15 (br, 2H) ppm. HPLC Rt: 5.6 min; HPLC purity: 100%. MS: 447.3 (MH+).

Examples 359 to 362

Examples 359 to 362 (Table 3) were prepared in a manner similar to that described for 356 in Example 356.

Example 367-417

Examples 363-417 (Table 4) were prepared by the general method described below.

A solution of the appropriate aryl chloride (0.2 mmol), the appropriate amine (0.3 mmol), and DIEA (0.4 mmol) in 1,4-dioxane (1 mL) was shaken at 90° C. overnight. The reaction mixture was concentrated and the resultant residue dissolved in DCE (2 mL). The resultant solution was treated with polystyrene benzaldehyde resin (2 eq.) and shaken overnight. The mixture was filtered and concentrated. The resultant residue was dissolved in DMSO (1 mL), filtered and concentrated to provide the products.

Example 418

5-Chloro-N⁴-cyclobutyl-N²-9-methanesulfonyl-1,2,3,4-tetrahydro-1,4-epiazano-naphthalen-6-yl)-pyrimidine-2,4-diamine trifluoroacetic acid salt (418)

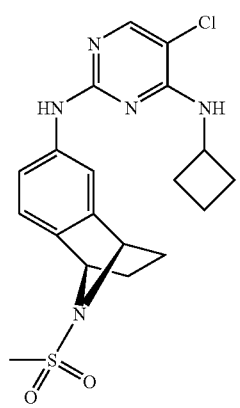

418

2,4,5-trichloro-pyrimidine (0.5 M in DMSO) cyclobutyl amine (0.5 M in DMSO, 160 μL) and DIEA (neat, 30 μL) were added to an 8-ml reaction vial. The vial was capped and the contents shaken at 25° C. for 22 h. The reaction mixture was concentrated in Genevac to provide 4-cyclobutylamino-2,5-dichloro-pyrimidine. The solid was treated with C16 (0.5 M in DMSO, 160 μL), concentrated in Genevac, and the resultant residue treated with EtOAc (160 ul). The vial was capped and the contents shaken at 75° C. for 22.5 hours. The reaction mixture was then concentrated in Genevac. The resultant crude product was dissolved in DMSO and purified by HPLC to provide 418 (11.9 mg, 35%). APCI LCMS: Retention time: 3.00 min (Method A), Observed mass: 419.99 [M+H].

Examples 419-482

Examples 419-482 (Table 5) were in a manner similar t that described for 421 in Example 421.

Examples 483-490

Examples 483-490 (Table 6) were prepared by the general procedure described below.

Compound C74 (1 mL, 0.05 M in NMP, 50 μmol), azetidine-3-carboxylic acid (300 μL, 0.5M in NMP, 150 μmol) and neat DIEA to were added to an 8-ml vial, and the contents of the vial were shaken at 80° C. overnight. The mixture was concentrated in Genevac, and the contents of the vial treated with DCE (3 mL) and a saturated NH₄Cl solution (2 mL). The vials were vortexed and centrifuged and the top layer (2 mL) was removed. to waste. Add saturated solution of NaHCO₃ (2 mL) was added to the vial. The vial was vortexed and centrifuged, and 2700 uL portion was removed from the mixture and transferred to a clean vial. The contents of the clean vial were concentrated to provide the crude product. LC/MS (Method F) product: Rt=1.96 s. Exact mass 447.1. The contents of vial were treated with the appropriate amine (0.5 M in DMF, 200 μL), HBTU (0.25 M in DMF, 400 μL) and neat DIPEA (50 μL) and shaken at 25° C. overnight. The crude product was dissolved in DCE, washed with a saturated solution of NH₄Cl and a saturated solution of NaHCO₃, and concentrated. The resultant residue was then purified by HPLC to provide product.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

All patents, applications, publications, test methods, literature, and other materials cited herein are hereby incorporated by reference in their entireties.

TABLE 1

Examples 24 to 28, 53 to 87 and 118-125.

| Ex. | IUPAC Name | Reagents | Prep. Method | Yield, % | Analytical |
|---|---|---|---|---|---|
| 24 | (+/−)-6-(4-Cyclobutylamino-5-trifluoromethyl-pyrimidin-2-ylamino)-1,2,3,4-tetrahydro-1,4-epiazano-naphthalene-9-carboxylic acid methyl ester | C46 and methyl chloroformate | 23 | 81 | ¹H NMR(400 MHz, DMSO-d₆) δ 9.5(s, 1H), 8.14(s, 1H), 7.7(d, J=1.2 Hz, 1H), 7.34(m, 1H), 7.18(d, 1H), 6.97(d, J=6.6 Hz, 1H), 5.0(s, 2H), 4.58(m, 1H), 3.49(s, 3H), |

TABLE 1-continued

Examples 24 to 28, 53 to 87 and 118-125.

| Ex. | IUPAC Name | Reagents | Prep. Method | Yield, % | Analytical |
|---|---|---|---|---|---|
| | | | | | 2.24-2.08(m, 4H), 2.07-1.95(m, 2H), 1.7-1.58(m, 2H), 1.19-1.1(m, 2H); MS: 434.3(MH+); HPLC Rt: 7.65 min; HPLC purity: 100%. |
| 25 | (+/−)-6-(4-Cyclobutylamino-5-trifluoromethyl-pyrimidin-2-ylamino)-1,2,3,4-tetrahydro-1,4-epiazano-naphthalene-9-carboxylic acid isopropyl-amide | C46 and isopropyl isocyanate | 23 | 64 | $^1$H NMR(500 MHz, DMSO-d$_6$) δ 9.6(s, 1H), 8.17(s, 1H), 7.74(s, 1H), 7.36(m, 1H), 7.15(d, J=7.7 Hz, 1H), 7.01(d, J=6.7 Hz, 1H), 6.54(d, J=7.7 Hz, 1H), 5.1(s, 2H), 4.6(m, 1H), 3.6(m, 1H), 2.27-2.13(m, 4H), 1.96(m, 2H), 1.6(m, 2H), 1.14(d, J=7.3 Hz, 2H), 0.98(d, J=6.7 Hz, 6H); MS: 461.5(MH+); HPLC Rt: 6.95 min; HPLC purity: 100%. |
| 26 | (+/−)-1-[6-(4-Cyclobutylamino-5-trifluoromethyl-pyrimidin-2-ylamino)-1,2,3,4-tetrahydro-1,4-epiazano-naphthalen-9-yl]-2-methyl-propan-1-one | C46 and ethyl isocyanate | 23 | 51 | $^1$H NMR(500 MHz, DMSO-d$_6$) δ 9.6(br, 1H), 8.1(s, 1H), 7.8(s, 1H), 7.39(t, J=7.7 Hz, 1H), 7.21(d, J=7.7 Hz, 1H), 7.0(d, J=6.7 Hz, 1H), 5.4(m, 1H), 5.3(m, 1H), 4.6(br, 1H), 2.7(m, 1H), 2.27-2.06(m, 5H), 1.95(m, 1H), 1.65(m, 2H), 1.3(m, 1H), 1.2(m, 1H), 1.0(m, 3H), 0.85(m, 3H) ppm. MS: 446.5(MH+); HPLC Rt: 7.3 min; HPLC purity: 100%. |
| 27 | (+/−)-Cyclobutyl-[6-(4-cyclobutylamino-5-trifluoromethyl-pyrimidin-2-ylamino)-1,2,3,4-tetrahydro-1,4-epiazano-naphthalen-9-yl]-methanone | C46 and cyclobutyl carbonyl chloride | 23 | 65 | $^1$H NMR(500 MHz, DMSO-d$_6$) δ 9.6(br, 1H), 8.18(s, 1H), 8.79(d, J=9.3 Hz, 1H), 7.38(d, J=8.3 Hz, 1H), 7.2(m, 1H), 7.01(d, J=6.9 Hz, 1H), 5.3(m, 1H), 5.2(m, 1H), 4.6(br, 1H), 3.26(m, 1H), 2.26-1.84(m, 12H), 1.7(m, 2H), 1.26(m, 2H) ppm. MS: 458.5(MH+); HPLC Rt: 7.64 min; HPLC purity: 100%. |
| 28 | (+/−)-2-Chloro-1-[6-(4-cyclobutylamino-5-trifluoromethyl-pyrimidin-2-ylamino)-1,2,3,4-tetrahydro-1,4-epiazano-naphthalen-9-yl]-ethanone | C46 and chloroacetic anhydride | 23 | 85 | $^1$H NMR(500 MHz, DMSO-d$_6$) δ 9.6(br, 1H), 8.18(s, 1H), 7.83(s, 1H), 7.42(m, 1H), 7.2(m, 1H), 7.02(d, J=6.7 Hz, 1H), 5.4(m, 1H), 5.37(m, 1H), 4.6(m, 1H), 4.3(m, 2H), 2.25-2.1(m, 5H), 1.98(m, 1H), 1.70(m, 2H), 1.29(m, 2H) ppm. MS: 452.4(MH+); HPLC Rt: 7.0 min; HPLC purity: 100%. |
| 53 | N4-Methyl-N2-(1S,4R)-(1,2,3,4-tetrahydro-1,4-epiazano-naphthalen-6-yl)-5-trifluoromethyl-pyrimidine-2,4-diamine dihydrochloride | C57 and methylamine | 52 | 99 | HPLC Rt=4.04, HPLC Purity=100%. MS for C$_{16}$H$_{16}$F$_3$N$_6$: [M+H]=336.1. |
| 54 | N4-Bicyclo[1.1.1]pent-1-yl-N2(1S,4R)-(1,2,3,4-tetrahydro-1,4-epiazano-naphthalen-6-yl)-5-trifluoromethyl-pyrimidine-2,4-diamine dihydrochloride | C57 and 1-aminobicyclo-1.1.1-pentane hydrochloride | 52 | 68 | HPLC Rt=5.61, HPLC Purity=100%. MS for C$_{20}$H$_{20}$F$_3$N$_6$: [M+H]=388.3. |
| 55 | N4-Methyl-N2-(1R,4S)-(1,2,3,4-tetrahydro-1,4-epiazano-naphthalen-6-yl)-5-trifluoromethyl-pyrimidine-2,4-diamine dhydrochloride salt | C68 and methylamine | 52 | 99 | $^1$H NMR (400 MHz, CD$_3$OD) δ 1.61(m, 2H), 2.38(m, 2H), 3.07(s, 3H), 5.28(m, 2H), 7.55(m, 1H), 7.78(m, 1H), 8.23(s, 1H) ppm. HPLC Rt=4.04, HPLC Purity=100%. MS for C$_{16}$H$_{16}$F$_3$N$_5$: [M+H]=336.1. |
| 56 | N4-Ethyl-N2-(1R,4S)-(1,2,3,4-tetrahydro-1,4-epiazano-naphthalen-6-yl)-5-trifluoromethyl-pyrimidine-2,4-diamine dihydrochloride salt | C68 and ethylamine | 52 | 95 | HPLC Rt=4.53, HPLC Purity=100%. MS for C$_{17}$H$_{18}$F$_3$N$_5$: [M+H]=350.1. |
| 57 | N4-(2-Methoxy-ethyl)-N2-(1R,4S)-(1,2,3,4-tetrahydro-1,4-epiazano-naphthalen-6-yl)-5-trifluoromethyl-pyrimidine-2,4-diamine dihydrochloride salt | C68 and 2-methoxyethylamine | 52 | 98 | HPLC Rt=4.51, HPLC Purity=100%. MS for C$_{17}$H$_{18}$F$_3$N$_8$: [M+H]=380.1. |
| 58 | N4-Cyclopropyl-N2-(1S,4R)-(1,2,3,4-tetrahydro-1,4-epiazano-naphthalen-6-yl)-5-trifluoromethyl-pyrimidine-2,4-diamine dihydrochloride | C57 and cyclopropylamine | 52 | 99 | $^1$H NMR(400 MHz, DMSO-d$_6$) δ 0.70(m, 2H), 0.79(m, 2H), 1.37(m, 2H), 2.21(m, 2H), 2.86(m, 1), 5.18(m, 2H), 6.01(bs, 1H), 7.38(m, 1H), 7.68(m, 1H), 7.95(bs, 1H), 8.01(m, 1H), 8.35(s, 1H), 9.27(m, 1H), 9.44(m, 1H), 10.65(bs, 1H) ppm. HPLC Rt=4.62, HPLC Purity=100%. |
| 59 | 6-(4-Cyclobutylamino-5-trifluoromethyl-pyrimidin-2-ylamino)-(1S,4R)-1,2,3,4-tetrahydro-1,4-epiazano-naphthalene-9-carboxylic acid ethylamide | 40 and ethyl isocyanate | 23 | 99 | $^1$H NMR(400 MHz, DMSO-d$_6$) δ 0.90(t, J=7 Hz, 3H), 1.11(m, 2H), 1.66(m, 2H), 2.14(m, 4H), 1.93(m, 2H), 2.91(m, 2H), 4.58(m, 1H), 5.06(s, 2H), 6.76(t, J=6 Hz, 1H), 6.97(d, J=7 Hz, 1H), 7.12(d, J=8 Hz, 1H), 7.32(q, J=2 Hz, 8 Hz, 1H), 7.71(d, J=2 Hz, 1H), 8.14(s, 1H), 9.54(s, 1H) ppm. HPLC Rt=6.64, HPLC Purity=100%. |
| 60 | 6-(4-Cyclopropylamino-5-trifluoromethyl-pyrimidin-2-ylamino)-(1S,4R)-1,2,3,4-tetrahydro-1,4-epiazano-naphthalene-9-carboxylic acid isopropyl-amide hydrochloride salt | 58 and isopropyl isocyanate | 23 | 91 | HPLC Rt=6.44, HPLC Purity=100%. MS for C$_{22}$H$_{25}$F$_3$N$_6$O: [M+H]=447.3. |

TABLE 1-continued

Examples 24 to 28, 53 to 87 and 118-125.

| Ex. | IUPAC Name | Reagents | Prep. Method | Yield, % | Analytical |
|---|---|---|---|---|---|
| 61 | 6-(4-Cyclobutylamino-5-trifluoromethyl-pyrimidin-2-ylamino)-(1R,4S)-1,2,3,4-tetrahydro-1,4-epiazano-naphthalene-9-carboxylic acid ethylamide | 51 and ethyl isocyanate | 23 | 69 | $^1$H NMR(400 MHz, DMSO-$d_6$) δ 0.90(t, J=7 Hz, 3H), 1.11(m, 2H), 1.66(m, 2H), 1.95(m, 2H), 2.15(m, 4H), 2.91(m, 2H), 4.58(m, 1H), 5.06(s, 2H), 6.76(t, J=6 Hz, 1H), 6.97(d, J=7 Hz, 1H), 7.12(d, J=8 Hz, 1H), 7.32(q, J=2 Hz, 8 Hz, 1H), 7.71(d, J=2 Hz, 1H), 8.14(s, 1H), 9.54(s, 1H) ppm. HPLC Rt=6.64, HPLC Purity=100%. |
| 62 | 6-(4-Cyclopropylamino-5-trifluoromethyl-pyrimidin-2-ylamino)-(1R,4S)-1,2,3,4-tetrahydro-1,4-epiazano-naphthalene-9-carboxylic acid isopropy-amide mesylate salt | 52 and isopropyl isocyanate | 23 | 97 | $^1$H NMR(400 MHz, CD$_3$OD) δ 0.78(m, 2H), 0.09(m, 2H), 1.06(m, 6H), 1.27(m, 2H), 2.12(m, 2H), 2.71(s, 3H), 2.93(bs, 1H), 3.29(m, 1H), 5.20(s, 2H), 7.32(m, 2H), 7.85(m, 1H), 8.17(m, 1H) ppm. HPLC Rt=6.45, HPLC Purity=100%. |
| 63 | 6-(4-Cyclobutylamino-5-trifluoromethyl-pyrimidin-2-ylamino)-(1R,4S)-1,2,3,4-tetrahydro-1,4-epiazano-naphthalene-9-carboxylic acid isopropyl-amide hydrochloride salt. | 51 and isopropyl isocyanate | 23 | 97 | HPLC Rt=6.45, HPLC Purity=100%. MS for $C_{23}H_{27}F_3N_6O$: [M+H]=461.4. |
| 64 | 6-(4-Ethylamino-5-trifluoromethyl-pyrimidin-2-ylamino)-(1R,4S)-1,2,3,4-tetrahydro-1,4-epiazano-naphthalene-9-carboxylic acid isopropyl-amide hydrochloride salt | 56 (140 mg, 0.331 mmol) and isopropyl isocyanate | 23 | 99 | HPLC Rt=6.08, HPLC Purity=100%. MS for $C_{21}H_{25}F_3N_6O$: [M+H]=435.3 |
| 65 | 6-[4-(2-Methoxy-ethylamino)-5-trifluoromethyl-pyrimidin-2-ylamino]-(1R,4S)-1,2,3,4-tetrahydro-1,4-epiazano-naphthalene-9-carboxylic acid isopropyl-amide hydrochloride salt | 57 and isopropyl isocyanate | 23 | 97 | HPLC Rt=6.98, HPLC Purity=100%. MS for $C_{22}H_{27}F_3N_6O_2$: [M+H]=465.4 |
| 66 | 1-[6-(4-Cyclopropylamino-5-trifluoromethyl-pyrimidin-2-ylamino)-(1S,4R)-1,2,3,4-tetrahydro-1,4-epiazano-naphthalen-9-yl]-ethanone | 58 and acetic anhydride | 23 | 72 | $^1$H NMR(400 MHz, DMSO-$d_6$) δ 0.65(m, 2H), 0.76(m, 2H), 1.23(m, 2H), 1.87(m, 4H), 2.02(m, 1H), 2.82(bs, 1H), 5.24(m, 2H), 7.16(m, 2H), 7.54(m, 1H), 7.95(m, 1H), 8.15(s 1H), 9.67(s, 1H) ppm. HPLC Rt=6.10, HPLC Purity=100%. |
| 67 | 2-Chloro-1-[6-(4-cyclopropylamino-5-trifluoromethyl-pyrimidin-2-ylamino)-(1S,4R)-1,2,3,4-tetrahydro-1,4-epiazano-naphthalen-9-yl]-ethanone | 58 and chloroacetic anyhdride | 23 | 60 | $^1$H NMR(400 MHz, CD$_3$OD) δ 0.78(m, 2H), 0.89(m 2H), 1.39(m, 2H), 2.13(m, 1H), 2.28(m, 1H), 2.94(bs, 1H), 4.16(s, 2H), 5.51(m, 2H), 7.4(bs, 2H), 7.69(bs, 1H), 8.16(bs, 1H) ppm. HPLC Rt=6.50, HPLC Purity=100%. |
| 68 | 1-[6-(4-Cyclopropylamino-5-trifluoromethyl-pyrimidin-2-ylamino)-(1S,4R)-1,2,3,4-tetrahydro-1,4-epiazano-naphthalen-9-yl]-2,2-dimethyl-propan-1-one hydrochloride salt | 58 and pivalic anhydride | 23 | 89 | $^1$H NMR(400 MHz, DMSO-$d_6$) δ 0.71(m, 2H), 0.79(m, 2H), 1.06(s, 9H), 1.16(m, 2H), 2.00(m, 2H), 2.90(m, 1H), 5.49(m, 2H), 7.26(m, 1H), 7.47(m, 1H), 7.80(m, 1H), 8.08(bs, 1H), 8.34(bs, 1H), 10.53(bs, 1H) ppm. HPLC Rt=7.26, HPLC Purity=100%. MS for $C_{22}H_{24}F_3N_5O$: [M+H]=446.3. |
| 69 | 1-[6-(4-Cyclopropylamino-5-trifluoromethyl-pyrimidin-2-ylamino)-(1S,4R)-1,2,3,4-tetrahydro-1,4-epiazano-naphthalen-9-yl]-2-methyl-propan-1-one. | 58 and isobutyl anhydride | 23 | 89 | HPLC Rt=6.73, HPLC Purity=100%. MS for $C_{22}H_{24}F_3N_5O$: [M+H]=432.6. |
| 70 | 1-[6-(4-Cyclopropylamino-5-trifluoromethyl-pyrimidin-2-ylamino)-(1S,4R)-1,2,3,4-tetrahydro-1,4-epiazano-naphthalen-9-yl]-3-methyl-butan-1-one hydrochloride salt | 58 and isovaleric anyhydride | 23 | 91 | HPLC Rt=7.09, HPLC Purity=100%. MS for $C_{23}H_{26}F_3N_6O$: [M+H]=446.3 |
| 71 | 1-[6-(4-Methylamino-5-trifluoromethyl-pyrimidin-2-ylamino)-(1S,4R)-1,2,3,4-tetrahydro-1,4-epiazano-naphthalen-9-yl]-ethanone | 53 (120 mg, 0.35 mmol) and acetic anhydride | 23 | 62 | $^1$H NMR(400 MHz, DMSO-$d_6$) δ 1.14(m, 1H), 1.24(m, 1H), 1.87(m, 4H), 2.03(m, 1H), 2.47(m, 3H), 5.27(m, 2H), 7.09(bs, 1H), 7.15(m, 1H), 7.46(m, 1H), 7.75(m, 1H), 8.13(m, 1H), 9.59(bs, 1H) ppm. HPLC Rt=5.57, HPLC Purity=100%. |
| 72 | 1-{6-[4-(Bicyclo[1.1.1]pent-1-ylamino)-5-trifluoromethyl-pyrimidin-2-ylamino]-(1S,4R)-1,2,3,4-tetrahydro-1,4-epiazano-naphthalen-9-yl}-ethanone hydrochloride salt | 54 and acetic anhydride | 23 | 67 | HPLC Rt=6.73, HPLC Purity=100%. MS for $C_{22}H_{22}F_3N_5O$: [M+H]=430.3 |
| 73 | 1-[6-(4-Cyclopropylamino-5-trifluoromethyl-pyrimidin-2-ylamino)-(1S,4R)-1,2,3,4-tetrahydro-1,4-epiazano-naphthalen-9-yl]-2-methoxy-ethanone hydrochloride salt | 58 and methoxyacetic anyhydride | 23 | 89 | HPLC Rt=6.06, HPLC Purity=100%. MS for $C_{21}H_{22}F_3N_5O_2$: [M+H]=434.3 |
| 74 | Cyclobutyl-[6-(4-cyclopropylamino-5-trifluoromethyl-pyrimidin-2-ylamino)-(1S,4R)-1,2,3,4-tetrahydro-1,4-epiazano-naphthalen-9-yl]-methanone | 58 and cyclobutane-carboxylic anhydride | 23 | 89 | HPLC Rt=7.06, HPLC Purity=100% MS for $C_{23}H_{24}F_3N_5O$: [M+H]=444.3 |

TABLE 1-continued

Examples 24 to 28, 53 to 87 and 118-125.

| Ex. | IUPAC Name | Reagents | Prep. Method | Yield, % | Analytical |
|---|---|---|---|---|---|
| 75 | 1-[6-(4-Cyclobutylamino-5-trifluoromethyl-pyrimidin-2-ylamino)-(1R,4S)-1,2,3,4-tetrahydro-1,4-epiazano-naphthalen-9-yl]-2-dimethylamino-ethanone | 51 and N,N-dimethylamino-acetyl chloride hydrochloride | 23 | 17 | $^1$H NMR(400 MHz, DMSO-d$_6$) δ 1.20(4, 4H), 1.66(m, 2H), 2.10(m, 10H), 2.99(m, 2H), 4.58(m, 1H), 5.30(m, 1H), 5.44(m, 1H), 7.00(m, 1H), 7.18(m, 1H), 7.34(m, 1H), 7.78(m 1H), 8.15(s, 1H), 9.58(bs, 1H) ppm. HPLC Rt=5.71, HPLC Purity=100% |
| 76 | (5-Bromo-thiophen-2-yl)-[6-(4-cyclobutylamino-5-trifluoromethyl-pyrimidin-2-ylamino)-(1R,4S)-1,2,3,4-tetrahydro-1,4-epiazano-naohthalen-9-yl]-methanone | 51 and 5-bromothiophene-carbonyl chloride | 23 | 17 | $^1$H NMR(400 MHz, DMSO-d$_6$) δ 1.27(m, 2H), 1.66(m, 2H), 2.17(m, 6H), 4.56(m, 1H), 5.23(m, 2H), 6.98(m, 1H), 7.21(m, 1H), 7.28(m, 1H), 7.35(m, 1H), 7.48(m, 1H), 7.82(s, 1H), 8.15(s, 1H), 9.60(bs, 1H) ppm. HPLC Rt=8.63, HPLC Purity=100%. |
| 77 | 1-[6-(4-Cyclobutylamino-5-trifluoromethyl-pyrimidin-2-ylamino)-(1R,4S)-1 2,3,4-tetrahydro-1,4-epiazano-naphthalen-9-yl]-ethanone | 51 and acetyl chloride | 23 | 56 | $^1$H NMR(400 MHz, DMSO-D$_6$) δ 0.82(m, 1H), 1.24(m, 3H), 1.64(m, 2H), 1.88(s, 3H), 2.22(m, 4H), 4.59(m, 1H), 5.26(m, 2H), 6.98(m, 1H), 7.18(m, 1H), 7.36(m, 1H), 7.76(m, 1H), 8.15(s, 1H), 9.58(s, 1H) ppm. HPLC Rt=6.72, HPLC Purity=100%. |
| 78 | 1-[6-(4-Cyclobutylamino-5-trifluoromethyl-pyrimidin-2-ylamino)-(1R,4S)-1,2,3,4-tetrahydro-1,4-epiazano-naphthalen-9-yl]-2-methoxy-ethanone hydrochloride salt | 51 and methoxyacetic anhydride | 23 | 97 | HPLC Rt=6.65, HPLC Purity=100%. MS for $C_{17}H_{18}F_3N_5$: [M+H]=448.3. |
| 79 | 1-[6-(4-Cyclocpropylamino-5-trifluoromethyl-pyrimidin-2-ylamino)-(1R,4S)-1,2,3,4-tetrahydro-1,4-epiazano-naphthalen-9-yl]-ethanone | 52 and acetic anhydride | 23 | 62 | $^1$H NMR(400 MHz, DMSO-d$_6$) δ 0.66(m, 2H), 0.77(m, 2H), 1.24(m, 2H), 1.87(m, 4H), 2.02(m, 1H), 2.82(bs, 1H), 5.23(m, 2H), 7.16(m 2H), 7.54(m, 1H), 7.95(m, 1H), 8.15(s, 1H), 9.67(s, 1H) ppm. HPLC Rt=6.10, HPLC Purity=100%. |
| 80 | 1-[6-(4-Cyclopropylamino-5-trifluoromethyl-pyrimidin-2-ylamino)-(1R,4S)-1,2,3,4-tetrahydro-1,4-epiazano-naphthalen-9-yl]-2-methoxy-ethanone hydrochloride salt | 52 and methoxyacetic anhydride | 23 | 93 | $^1$H NMR(400 MHz, DMSO-d$_6$) δ 0.71(m, 2H), 0.78(m, 2H), 1.23(m, 2H), 1.92(m, 1H), 2.05(m 1H), 2.85(m, 1H), 3.19(s, 3H), 3.97(m, 2H), 5.36(m, 2H), 5.80(bs, 1H), 7.25(m, 1H), 7.48(m, 1H), 7.85(m, 1H), 7.96(bs, 1H), 8.30(s, 1H), 10.40(bs, 1H) ppm. HPLC Rt=6.01, HPLC Purity=100%. |
| 81 | 1-[6-(4-Cyclopropylamino-5-trifluoromethyl-pyrimidin-2-ylamino)-(1R,4S)-1,2,3,4-tetrahydro-1,4-epiazano-naphthalen-9-yl]-2-methyl-propan-1-one hydrochloride salt | 52 and isobutyric anhydride | 23 | 94 | HPLC Rt=6.73, HPLC Purity=100%. MS for $C_{22}H_{24}F_3N_5O$: [M+H]=432.2 |
| 82 | Cyclopropyl-[6-(4-(cyclopropylamino-5-trifluoromethyl-pyrimidin-2-ylamino)-(1R,4S)-1,2,3,4-tetrahydro-1,4-epiazano-naphthalen-9-yl]-methanone hydrochloride salt | 52 and cyclopropane carboxylic anyhydride | 23 | 93 | HPLC Rt=6.64, HPLC Purity=100%. MS for $C_{22}H_{22}F_3N_5O$: [M+H]=430.2 |
| 83 | 1-[6-(4-Ethylamino-5-trifluoromethyl-pyrimidin-2-ylamino)-(1R,4S)-(1,2,3,4-tetrahydro-1,4-epiazano-naphthalen-9-yl]2-methoxy-ethanone hydrochloride salt | 53 and methoxyacetic anyhydride | 23 | 99 | HPLC Rt=5.99, HPLC Purity=100%. MS for $C_{20}H_{22}F_3N_5O_2$: [M+H]=422.3 |
| 84 | 2-Methoxy-1-{6-[4-(2-methoxy-ethylamino)-5-trifluoromethyl-pyrimidin-2-ylamino]-(1R,4S)-1,2,3,4-tetrahydro-1,4-epiazano-naphthalen-9-yl}-ethanone hydrochloride salt | 57 and methoxyacetic anhydride | 23 | 99 | HPLC Rt=5.99, HPLC Purity=100%. MS for $C_{22}H_{24}F_3N_5O$: [M+H]=422.3 |
| 85 | 2-Methoxy-1-[6-(4-methylamino-5-trifluoromethyl-pyrimidin-2-ylamino)-(1R,4S)-1,2,3,4-tetrahydro-1,4-epiazano-naphthalen-9-yl]-ethanone | 55 and methoxyacetic anhydride | 23 | 65 | HPLC Rt=5.47, HPLC Purity=100%. MS for $C_{18}H_{20}F_3N_5O_2$: [M+H]=408.1 |
| 86 | 1-[6-(4-Methylamino-5-trifluoromethyl-pyrimidin-2-ylamino)-(1R,4S)-1,2,3,4-tetrahydro-1,4-epiazano-naphthalen-9-yl]-ethanone | 55 (120 mg, 0.35 mmol) and acetic anhydride | 23 | 70 | $^1$H NMR(400 MHz, DMSO-d$_6$) δ 1.24(m, 2H), 1.87(m, 4H), 2.02(m, 1H), 2.90(m, 3H), 5.27(m, 2H), 7.10(m, 1H), 7.16(m, 1H), 7.46(m, 1H), 7.75(m, 1H), 8.13(s, 1H), 9.59(bs, 1H) ppm. HPLC Rt=5.55, HPLC Purity=100% |
| 87 | Cyclopropyl-[6-(4-methylamino-5-trifluoromethyl-pyrimidin-2-ylamino)-(1R,4S)-1,2,3,4-tetrahydro-1,4-epiazano-naphthalen-9-yl]-methanone hydrochloride salt | 55 and cyclopropane carboxylic anhydride | 23 | 48 | HPLC Rt=6.12, HPLC Purity=100%. MS for $C_{20}H_{20}F_3N_5O$: [M+H]=404.2 |
| 118 | 1-[6-(4-isopropylamino-5-methyl-pyrimidin-2-ylamino)-(1S,4R)-1,2,3,4-tetrahydro-1,4-epiazano-naphthalen-9-yl]-ethanone | C107 and (2-Chloro-5-methyl-pyrimidin-4-yl)-isopropylamine | 117 (Step 4) | 45 | HPLC(Method B1) Rt=10.7, HPLC Purity=100%. MS for $C_{20}H_{25}N_5O$: [M+H]=352 |
| 119 | 1-[6-(4-cyclopropylamino-5-methyl-pyrimidin-2-ylamino)-(1S,4R)-1,2,3,4-tetrahydro-1,4-epiazano-naphthalen-9-yl]-ethanone | C107 and (2-Chloro-5-methyl-pyrimidin-4-yl)-cyclopropylamine | 117 (Step 4) | 20 | MP: 108-112° C. MS for $C_{20}H_{23}N_5O$: [M+H]=350 |

TABLE 1-continued

Examples 24 to 28, 53 to 87 and 118-125.

| Ex. | IUPAC Name | Reagents | Prep. Method | Yield, % | Analytical |
|---|---|---|---|---|---|
| 120 | 1-[6-(4-cyclobutylamino-5-methyl-pyrimidin-2-ylamino)-(1S,4R)-1,2,3,4-tetrahydro-1,4-epiazano-naphthalen-9-yl]-ethanone | C107 and (2-Chloro 5-methyl-pyrimidin-4-yl)-cyclobutylamine | 117 (Step 4 | 45 | HPLC(Method B1) Rt=11.0, HPLC Purity=100%. MS for $C_{21}H_{25}N_5O$: [M+H]=365 |
| 121 | 1-[6-(4-ethylamino-5-chloro-pyrimidin-2-ylamino)-(1S,4R)-1,2,3,4-tetrahydro-1,4-epiazano-naphthalen-9-yl]-ethanone | C107 and (2,5-dichloro-pyrimidinyl-4-yl)ethylamine | 117 (Step 4 | 27 | HPLC(Method B1) Rt=9.72, HPLC Purity=100%. MS for $C_{18}H_{20}ClN_5O$: [M+H]=352 |
| 122 | 1-[6-(4-isopropylamino-5-chloro-pyrimidin-2-ylamino)-(1S,4R)-1,2,3,4-tetrahydro-1,4-epiazano-naphthalen-9-yl]-ethanone | C107 and (2,5-dichloro-pyrimidin-4-yl)-isopropylamine | 117 (Step 4 | 23 | HPLC(Method B1) Rt=9.72, HPLC Purity=100%. MS for $C_{18}H_{20}ClN_5O$: [M+H]=352 HPLC(Method B1) Rt=10.7, HPLC Purity=100%. MS for $C_{19}H_{22}ClN_5O$: [M+H]=372 |
| 123 | 1-[6-(4-cyclopropylamino-5-chloro-pyrimidin-2-ylamino)-(1S,4R)-1,2,3,4-tetrahydro-1,4-epiazano-naphthalen-9-yl]-ethanone | C107 and (2,5-Dichloro-pyrimidin-4-yl)-cyclopropylamine | 117 (Step 4 | 26 | HPLC(Method B1) Rt=10.3, HPLC Purity=100%. MS for $C_{19}H_{20}ClN_5O$: [M+H]=370 |
| 124 | 1-[6-(4-cyclobutylamino-5-chloro-pyrimidin-2-ylamino)-(1S,4R)-1,2,3,4-tetrahydro-1,4-epiazano-naphthalen-9-yl]-ethanone | C107 and (2,5-Dichloro-pyrimidin-4-yl)-cyclobutylamine | 117 (Step 4 | 7 | HPLC(Method A1) Rt=8.99, HPLC Purity=100%. MS for $C_{30}H_{22}ClN_5O$: [M+H]=384 |
| 125 | 1-[6-4-methylamino-5-chloro-pyrimidin-2-ylamino)-(1S,4R)-1,2,3,4-tetrahydro-1,4-epiazano-naphthalen-9-yl]-ethanone | C107 and [(2,5-Dichloro-pyrimidin-4-yl)-methylamine | 117 (Step 4 | 25 | HPLC(Method B1) Rt=4.18, HPLC Purity=100%. MS for $C_{17}H_{18}ClN_5O$: [M+H]=344 |

TABLE 2

Examples 130-355.

| Ex. | Compound | Prep. Method | MS | HPLC Rf (min) | Purity (HPLC), % | HPLC Method |
|---|---|---|---|---|---|---|
| 130 | (+/−)-1-[4-(4-Cyclopropylamino-5-trifluoromethyl-pyrimidin-2-ylamino)-10-aza-tricyclo[6.3.1.0$^{2,7}$]dodeca-2(7),3,5-trien-10-yl]-2,2,2-trifluoro-ethanone | 12 | 472.4 | 7.42 | 100 | E |
| 131 | (+/−)-1-[4-(4-Ethylamino-5-trifluoromethyl-pyrimidin-2-ylamino)-10-aza-tricyclo[6.3.1.0$^{2,7}$]dodeca-2(7),3,5-trien-10-yl]-2,2,2-trifluoro-ethanone | 12 | 460.4 | 7.35 | 100 | E |
| 132 | 1-[4-(4-Cyclobutylamino-5-trifluoromethyl-pyrimidin-2-ylamino)-10-aza-(1S,8R)tricyclo[6.3.1.0$^{2,7}$]dodeca-2,4,6-trien-10-yl]-2-methoxy-ethanone | 20 | 462.2 | | | F |
| 133 | (+/−)-1-{4-[4-(Cyclopropylmethyl-amino)-5-trifluoromethyl-pyrimidin-2-ylamino]-10-aza-tricyclo[6.3.1.0$^{2,7}$]dodeca-2(7),3,5-trien-10-yl}-2,2,2-trifluoro-ethanone | 12 | 486.4 | 7.73 | 100 | E |
| 134 | 1-[4-(4-Ethylamino-5-trifluoromethyl-pyrimidin-2-ylamino)-10-aza-(1S,8R)tricyclo[6.3.1.0$^{2,7}$]dodeca-2,4,6-trien-10-yl]-2-methoxy-ethanone | 20 | 436.19 | | | F |
| 135 | 2-Methoxy-1-[4-(4-propylamino-5-trifluoromethyl-pyrimidin-2-ylamino)-10-aza-(1S,8R)tricyclo[6.3.1.0$^{2,7}$]dodeca-2,4,6-trien-10-yl]-ethanone | 20 | 450.2 | | | F |
| 136 | 1-[4-(4-Isopropylamino-5-trifluoromethyl-pyrimidin-2-ylamino)-10-aza-(1S,8R)tricyclo[6.3.1.0$^{2,7}$]dodeca-2,4,6-trien-10-yl]-2-methoxy-ethanone | 20 | 450.2 | | | F |
| 137 | 2-Methoxy-1-{4-[4-(2-methoxy-ethylamino)-5-trifluoromethyl-pyrimidin-2-ylamino]-10-aza-(1S,8R)tricyclo[6.3.1.0$^{2,7}$]dodeca-2,4,6-trien-10-yl}-ethanone | 20 | 466.2 | | | F |
| 138 | 1-[4-(4-Cyclopropylamino-5-trifluoromethyl-pyrimidin-2-ylamino)-10-aza-(1S,8R)tricyclo[6.3.1.0$^{2,7}$]dodeca-2,4,6-trien-10-yl]-2-methoxy-ethanone | 20 | 448.19 | | | F |
| 139 | 1-[4-(4-Cyclobutylamino-5-trifluoromethyl-pyrimidin-2-ylamino)-10-aza-(1S,8R)tricyclo[6.3.1.0$^{2,7}$]dodeca-2,4,6-trien-10-yl]-2-methoxy-ethanone | 20 | 462.2 | | | F |
| 140 | N-{2-[4-(4-Ethylamino-5-trifluoromethyl-pyrimidin-2-ylamino)-10-aza-(1S,8R)tricyclo[6.3.1.0$^{2,7}$]dodeca-2,4,6-trien-10-yl]-2-oxo-ethyl}-acetamide | 20 | 463.2 | | | F |
| 141 | N-{2-Oxo-2-[4-(4-propylamino-5-trifluoromethyl-pyrimidin-2-ylamino)-10-aza-(1S,8R)tricyclo[6.3.1.0$^{2,7}$]dodeca-2,4,6-trien-10-yl]-ethyl}-acetamide | 20 | 477.21 | | | F |
| 142 | N-{2-[4-(4-Isopropylamino-5-trifluoromethyl-pyrimidin-2-ylamino)-10-aza-(1S,8R)tricyclo[6.3.1.0$^{2,7}$]dodeca-2,4,6-trien-10-yl]-2-oxo-ethyl}-acetamide | 20 | 477.21 | | | F |
| 143 | (+/−)-N$^4$-Cyclopropyl-N$^2$-(10-pyridin-2-yl-10-aza-tricyclo[6.3.1.0$^{2,7}$]dodeca-2(7),3,5-trien-4-yl)-5-trifluoromethyl-pyrimidine-2,4-diamine | 14 | 453.19 | 6.57 | 100 | E |
| 144 | (+/−)-1-[4-(4-Cyclopropylamino-5-trifluoromethyl-pyrimidin-2-ylamino)-10-aza-tricyclo[6.3.1.0$^{2,7}$]dodeca-2(7),3,5-trien-10-yl]-2,2-difluoro-ethanone | 11 | 454.16 | 6.76 | 100 | E |
| 145 | (+/−)-1-[4-(4-Ethylamino-5-trifluoromethyl-pyrimidin-2-ylamino)-10-aza-tricyclo[6.3.1.0$^{2,7}$]dodeca-2(7),3,5-trien-10-yl]-2,2-difluoro-ethanone | 11 | 442.16 | 6.67 | 100 | E |
| 146 | (+/−)-1-{4-[4-(Cyclopropylmethyl-amino)-5-trifluoromethyl-pyrimidin-2-ylamino]-10-aza-tricyclo[6.3.1.0$^{2,7}$]dodeca-2(7),3,5-trien-10-yl}-2,2-difluoro-ethanone | 11 | 468.17 | 7.1 | 100 | E |
| 147 | N-(2-{(1S,8R)-4-[4-(2-Methoxy-ethylamino)-5-trifluoromethyl-pyrimidin-2-ylamino]-10-aza-tricyclo[6.3.1.0$^{2,7}$]dodeca-2,4,6-trien-10-yl}-2-oxo-ethyl)-acetamide | 20 | 493.21 | | | F |

TABLE 2-continued

Examples 130-355.

| Ex. | Compound | Prep. Method | MS | HPLC Rf (min) | Purity (HPLC), % | HPLC Method |
|---|---|---|---|---|---|---|
| 148 | N-{2-[(1S,8R)-4-(4-Cyclopropylamino-5-trifluoromethyl-pyrimidin-2-ylamino)-10-aza-tricyclo[6.3.1.0$^{2,7}$]dodeca-2,4,6-trien-10-yl]-2-oxo-ethyl}-acetamide | 20 | 475.2 | | | F |
| 149 | N-{2-[4-(4-Ethylamino-5-trifluoromethyl-pyrimidin-2-ylamino)-10-aza-(1R,8S)tricyclo[6.3.1.0$^{2,7}$]dodeca-2,4,6-trien-10-yl]-2-oxo-ethyl}-acetamide | 20 | 463.2 | | | F |
| 150 | N-{2-Oxo-2-[4-(4-propylamino-5-trifluoromethyl-pyrimidin-2-ylamino)-10-aza-(1R,8S)tricyclo[6.3.1.0$^{2,7}$]dodeca-2,4,6-trien-10-yl]-ethyl}-acetamide | 20 | 477.21 | | | F |
| 151 | N-{2-[4-(4-Isopropylamino-5-trifluoromethyl-pyrimidin-2-ylamino)-10-aza-(1R,8S)tricyclo[6.3.1.0$^{2,7}$]dodeca-2,4,6-trien-10-yl]-2-oxo-ethyl}-acetamide | 20 | 477.21 | | | F |
| 152 | N-(2-{4-[4-(2-Methoxy-ethylamino)-5-trifluoromethyl-pyrimidin-2-ylamino]-10-aza-(1R,8S)tricyclo[6.3.1.0$^{2,7}$]dodeca-2,4,6-trien-10-yl}-2-oxo-ethyl)-acetamide | 20 | 493.21 | | | F |
| 153 | N-{2-[4-(4-Cyclopropylamino-5-trifluoromethyl-pyrimidin-2-ylamino)-10-aza-(1R,8S)tricyclo[6.3.1.0$^{2,7}$]dodeca-2,4,6-trien-10-yl]-2-oxo-ethyl}-acetamide | 20 | 475.2 | | | F |
| 154 | N-{2-[4-(4-Cyclobutylamino-5-trifluoromethyl-pyrimidin-2-ylamino)-10-aza-(1R,8S)tricyclo[6.3.1.0$^{2,7}$]dodeca-2,4,6-trien-10-yl]-2-oxo-ethyl}-acetamide | 20 | 489.21 | | | F |
| 155 | (+/−)-4-(4-Cyclopropylamino-5-trifluoromethyl-pyrimidin-2-ylamino)-10-aza-tricyclo[6.3.1.0$^{2,7}$]dodeca-2(7),3,5-triene-10-carboxylic acid ethylamide | 17 | 447.2 | 6.1 | 100 | E |
| 156 | (+/−)-1-[4-(4-Cyclopropylamino-5-trifluoromethyl-pyrimidin-2-ylamino)-10-aza-tricyclo[6.3.1.0$^{2,7}$]dodeca-2(7),3,5-trien-10-yl]-ethanone | 23 | 418.18 | 6.1 | 100 | E |
| 157 | (+/−)-1-[4-(4-Cyclopropylamino-5-trifluoromethyl-pyrimidin-2-ylamino)-10-aza-tricyclo[6.3.1.0$^{2,7}$]dodeca-2(7),3,5-trien-10-yl]-2-methoxy-ethanone | 10 | 448.19 | 6 | 100 | E |
| 158 | (+/−)-1-[4-(4-Cyclobutylamino-5-trifluoromethyl-pyrimidin-2-ylamino)-10-aza-tricyclo[6.3.1.0$^{2,7}$]dodeca-2(7),3,5-trien-10-yl]-ethanone | 23 | 432.19 | 6.8 | 100 | E |
| 159 | (+/−)-1-(4-{4-[(1-Hydroxy-cyclobutylmethyl)-amino]-5-trifluoromethyl-pyrimidin-2-ylamino}-10-aza-tricyclo[6.3.1.0$^{2,7}$]dodeca-2(7),3,5-trien-10-yl)-ethanone | 23 | 462.2 | 6 | 100 | E |
| 160 | 1-{4-[4-(3-Morpholin-4-yl-azetidin-1-yl)-5-trifluoromethyl-pyrimidin-2-ylamino]-10-aza-tricyclo[6.3.1.0$^{2,7}$]dodeca-2(7),3,5-trien-10-yl}-ethanone | 23 | 503.23 | 5.6 | 100 | E |
| 161 | (+/−)-1-[4-(4-Hydroxy-5-trifluoromethyl-pyrimidin-2-ylamino)-10-aza-tricyclo[6.3.1.0$^{2,7}$]dodeca-2(7),3,5-trien-10-yl]-ethanone | 23 | 379.13 | | 100 | F |
| 162 | (+/−)-1-[4-(4-Methylamino-5-trifluoromethyl-pyrimidin-2-ylamino)-10-aza-tricyclo[6.3.1.0$^{2,7}$]dodeca-2(7),3,5-trien-10-yl]-ethanone | 23 | 392.16 | 5.5 | 100 | E |
| 163 | (+/−)-4-(4-Methylamino-5-trifluoromethyl-pyrimidin-2-ylamino)-10-aza-tricyclo[6.3.1.0$^{2,7}$]dodeca-2(7),3,5-triene-10-carboxylic acid isopropylamide | 17 | 435.2 | 6.1 | 100 | E |
| 164 | 1-[4-(4-Ethylamino-5-trifluoromethyl-pyrimidin-2-ylamino)-10-aza-(1R,8S)tricyclo[6.3.1.0$^{2,7}$]dodeca-2,4,6-trien-10-yl]-2-methoxy-ethanone | 20 | 436.19 | | | F |
| 165 | 2-Methoxy-1-[4-(4-propylamino-5-trifluoromethyl-pyrimidin-2-ylamino)-10-aza-(1R,8S)tricyclo[6.3.1.0$^{2,7}$]dodeca-2,4,6-trien-10-yl]-ethanone | 20 | 450.2 | | | F |
| 166 | 1-[4-(4-Isopropylamino-5-trifluoromethyl-pyrimidin-2-ylamino)-10-aza-(1R,8S)tricyclo[6.3.1.0$^{2,7}$]dodeca-2,4,6-trien-10-yl]-2-methoxy-ethanone | 20 | 450.2 | | | F |
| 167 | 2-Methoxy-1-{4-[4-(2-methoxy-ethylamino)-5-trifluoromethyl-pyrimidin-2-ylamino]-10-aza-(1R,8S)tricyclo[6.3.1.0$^{2,7}$]dodeca-2,4,6-trien-10-yl}-ethanone | 20 | 466.2 | | | F |
| 168 | 1-[4-(4-Cyclopropylamino-5-trifluoromethyl-pyrimidin-2-ylamino)-10-aza-(1R,8S)tricyclo[6.3.1.0$^{2,7}$]dodeca-2,4,6-trien-10-yl]-2-methoxy-ethanone | 20 | 448.19 | | | F |
| 169 | (+/−)-1-[4-(4-Cyclopropylamino-5-trifluoromethyl-pyrimidin-2-ylamino)-10-aza-tricyclo[6.3.1.0$^{2,7}$]dodeca-2(7),3,5-trien-10-yl]-2-methyl-propan-1-one | 69 | 446.21 | 6.2 | 100 | E |
| 170 | (+/−)-[4-(4-Cyclopropylamino-5-trifluoromethyl-pyrimidin-2-ylamino)-10-aza-tricyclo[6.3.1.0$^{2,7}$]dodeca-2(7),3,5-trien-10-yl]-pyridin-3-yl-methanone | 15 | 481.19 | 6.6 | 100 | E |
| 171 | (+/−)-1-[4-(4-Ethylamino-5-trifluoromethyl-pyrimidin-2-ylamino)-10-aza-tricyclo[6.3.1.0$^{2,7}$]dodeca-2(7),3,5-trien-10-yl]-ethanone | 23 | 406.18 | 6.11 | 100 | E |
| 172 | (+/−)-1-{4-[4-(Cyclopropylmethyl-amino)-5-trifluoromethyl-pyrimidin-2-ylamino]-10-aza-tricyclo[6.3.1.0$^{2,7}$]dodeca-2(7),3,5-trien-10-yl}-ethanone | 23 | 432.19 | 6.55 | 100 | E |
| 173 | (+/−)-N$^4$-Ethyl-N$^2$-(10-ethyl-10-aza-tricyclo[6.3.1.0$^{2,7}$]dodeca-2(7),3,5-trien-4-yl)-5-trifluoromethyl-pyrimidine-2,4-diamine | 19 | 392.2 | 5.48 | 100 | E |
| 174 | (+/−)-N$^4$-Cyclobutyl-N$^2$-(10-ethyl-10-aza-tricyclo[6.3.1.0$^{2,7}$]dodeca-2(7),3,5-trien-4-yl)-5-trifluoromethyl-pyrimidine-2,4-diamine | 19 | 418.21 | | | F |
| 175 | (+/−)-N$^4$-Cyclopropyl-N$^2$-(10-ethyl-10-aza-tricyclo[6.3.1.0$^{2,7}$]dodeca-2(7),3,5-trien-4-yl)-5-trifluoromethyl-pyrimidine-2,4-diamine | 19 | 404.2 | 5.43 | 100 | E |
| 176 | (+/−)-1-[6-(4-Piperidin-1-yl-5-trifluoromethyl-pyrimidin-2-ylamino)-1,2,3,4-tetrahydro-1,4-epiazano-naphthalen-9-yl]-ethanone | 95 | 432.2 | 7.48 | 100 | E |
| 177 | (+/−)-1-[6-(4-Cyclohexylamino-5-trifluoromethyl-pyrimidin-2-ylamino)-1,2,3,4-tetrahydro-1,4-epiazano-naphthalen-9-yl]-ethanone | 95 | 446.3 | 7.60 | 100 | E |
| 178 | (+/−)-1-[6-(4-Isopropylamino-5-trifluoromethyl-pyrimidin-2-ylamino)-1,2,3,4-tetrahydro-1,4-epiazano-naphthalen-9-yl]-ethanone | 95 | 406.3 | 6.60 | 100 | E |
| 179 | (+/−)-1-[6-(4-Dimethylamino-5-trifluoromethyl-pyrimidin-2-ylamino)-1,2,3,4-tetrahydro-1,4-epiazano-naphthalen-9-yl]-ethanone | 95 | 392.3 | 6.30 | 100 | E |
| 180 | (+/−)-1-[6-(4-Methylamino-5-trifluoromethyl-pyrimidin-2-ylamino)-1,2,3,4-tetrahydro-1,4-epiazano-naphthalen-9-yl]-ethanone | 95 | 378.3 | 5.60 | 100 | E |
| 181 | (+/−)-1-{6-[4-(2-Morpholin-4-yl-ethylamino)-5-trifluoromethyl-pyrimidin-2-ylamino]-1,2,3,4-tetrahydro-1,4-epiazano-naphthalen-9-yl}-ethanone | 95 | 477.3 | 4.20 | 100 | E |
| 182 | (+/−)-1-{6-[4-(3-Morpholin-4-yl-propylamino)-5-trifluoromethyl-pyrimidin-2-ylamino]-1,2,3,4-tetrahydro-1,4-epiazano-naphthalen-9-yl}-ethanone | 95 | 491.3 | 4.24 | 100 | E |
| 183 | (+/−)-1-[6-(4-Azetidin-1-yl-5-trifluoromethyl-pyrimidin-2-ylamino)-1,2,3,4-tetrahydro-1,4-epiazano-naphthalen-9-yl]-ethanone | 95 | 404.3 | 6.50 | 100 | E |

TABLE 2-continued

Examples 130-355.

| Ex. | Compound | Prep. Method | MS | HPLC Rf (min) | Purity (HPLC), % | HPLC Method |
|---|---|---|---|---|---|---|
| 184 | (+/−)-1-[6-(4-Pyrrolidin-1-yl-5-trifluoromethyl-pyrimidin-2-ylamino)-1,2,3,4-tetrahydro-1,4-epiazano-naphthalen-9-yl]-ethanone | 95 | 417.4 | 6.90 | 100 | E |
| 185 | (+/−)-1-[6-(4-Morpholin-4-yl-5-trifluoromethyl-pyrimidin-2-ylamino)-1,2,3,4-tetrahydro-1,4-epiazano-naphthalen-9-yl]-ethanone | 95 | 434.3 | 5.90 | 100 | E |
| 186 | (+/−)-1-{6-[4-(4-Methyl-piperazin-1-yl)-5-trifluoromethyl-pyrimidin-2-ylamino]-1,2,3,4-tetrahydro-1,4-epiazano-naphthalen-9-yl}-ethanone | 95 | 447.3 | 4.10 | 100 | E |
| 187 | (+/−)-1-{6-[4-(3-(S)-Hydroxy-pyrrolidin-1-yl)-5-trifluoromethyl-pyrimidin-2-ylamino]-1,2,3,4-tetrahydro-1,4-epiazano-naphthalen-9-yl}-ethanone | 95 | 434.3 | 5.10 | 100 | E |
| 188 | (+/−)-1-{6-[4-(2-(R)-Hydroxymethyl-pyrrolidin-1-yl)-5-trifluoromethyl-pyrimidin-2-ylamino]-1,2,3,4-tetrahydro-1,4-epiazano-naphthalen-9-yl}-ethanone | 95 | 448.3 | 5.70 | 100 | E |
| 189 | (+/−)-1-{6-[4-(2-(S)-Hydroxymethyl-pyrrolidin-1-yl)-5-trifluoromethyl-pyrimidin-2-ylamino]-1,2,3,4-tetrahydro-1,4-epiazano-naphthalen-9-yl}-ethanone | 95 | 448.3 | 5.70 | 100 | E |
| 190 | (+/−)-1-{6-[4-(2-(R)-Methoxymethyl-pyrrolidin-1-yl)-5-trifluoromethyl-pyrimidin-2-ylamino]-1,2,3,4-tetrahydro-1,4-epiazano-naphthalen-9-yl}-ethanone | 95 | 462.3 | 6.90 | 100 | E |
| 191 | (+/−)-1-{6-[4-(2-(S)-Methoxymethyl-pyrrolidin-1-yl)-5-trifluoromethyl-pyrimidin-2-ylamino]-1,2,3,4-tetrahydro-1,4-epiazano-naphthalen-9-yl}-ethanone | 95 | 462.3 | 6.90 | 100 | E |
| 192 | (+/−)-1-{6-[4-(3-(S)-Morpholin-4-yl-pyrrolidin-1-yl)-5-trifluoromethyl-pyrimidin-2-ylamino]-1,2,3,4-tetrahydro-1,4-epiazano-naphthalen-9-yl}-ethanone | 95 | 503.3 | 5.30 | 100 | E |
| 193 | (+/−)-1-{6-[4-(3-Pyrrolidin-1-yl-azetidin-1-yl)-5-trifluoromethyl-pyrimidin-2-ylamino]-1,2,3,4-tetrahydro-1,4-epiazano-naphthalen-9-yl}-ethanone | 95 | 473.3 | 4.40 | 100 | E |
| 194 | (+/−)-N-{1-[2-(9-Acetyl-1,2,3,4-tetrahydro-1,4-epiazano-naphthalen-6-ylamino)-5-trifluoromethyl-pyrimidin-4-yl]-azetidin-3-yl}-acetamide | 95 | 461.3 | 4.84 | 100 | E |
| 195 | (+/−)-1-{6-[4-(1-Acetyl-azetidin-3-ylamino)-5-trifluoromethyl-pyrimidin-2-ylamino]-1,2,3,4-tetrahydro-1,4-epiazano-naphthalen-9-yl}-ethanone | 95 | 461.3 | 4.70 | 100 | E |
| 196 | (+/−)-1-[6-(4-Propylamino-5-trifluoromethyl-pyrimidin-2-ylamino)-1,2,3,4-tetrahydro-1,4-epiazano-naphthalen-9-yl]-ethanone | 95 | 406.5 | 6.40 | 100 | E |
| 197 | (+/−)-(9-Methanesulfonyl-1,2,3,4-tetrahydro-1,4-epiazano-naphthalen-6-yl)-(4-morpholin-4-yl-5-trifluoromethyl-pyrimidin-2-yl)-amine | 95 | 468.2 | 6.50 | 100 | E |
| 198 | (+/−)-(9-Methanesulfonyl-1,2,3,4-tetrahydro-1,4-epiazano-naphthalen-6-yl)-[4-(3-(S)-morpholin-4-yl-pyrrolidin-1-yl)-5-trifluoromethyl-pyrimidin-2-yl]-amine | 93 | 539.3 | 5.97 | 100 | E |
| 199 | (+/−)-$N^2$-(9-Methanesulfonyl-1,2,3,4-tetrahydro-1,4-epiazano-naphthalen-6-yl)-$N^4,N^4$-dimethyl-5-trifluoromethyl-pyrimidine-2,4-diamine | 93 | 428.2 | 6.80 | 100 | E |
| 200 | (+/−)-(4-Azetidin-1-yl-5-trifluoromethyl-pyrimidin-2-yl)-(9-methanesulfonyl-1,2,3,4-tetrahydro-1,4-epiazano-naphthalen-6-yl)-amine | 93 | 440.2 | 6.90 | 100 | E |
| 201 | (+/−)-(9-Methanesulfonyl-1,2,3,4-tetrahydro-1,4-epiazano-naphthalen-6-yl)-(4-pyrrolidin-1-yl-5-trifluoromethyl-pyrimidin-2-yl)-amine | 93 | 454.2 | 7.30 | 100 | E |
| 202 | (+/−)-(9-Methanesulfonyl-1,2,3,4-tetrahydro-1,4-epiazano-naphthalen-6-yl)-(4-piperidin-1-yl-5-trifluoromethyl-pyrimidin-2-yl)-amine | 93 | 468.2 | 7.80 | 100 | E |
| 203 | (+/−)-(9-Methanesulfonyl-1,2,3,4-tetrahydro-1,4-epiazano-naphthalen-6-yl)-[4-(4-methyl-piperazin-1-yl)-5-trifluoromethyl-pyrimidin-2-yl]-amine | 93 | 483.2 | 4.60 | 100 | E |
| 204 | (+/−)-1-[2-(9-Methanesulfonyl-1,2,3,4-tetrahydro-1,4-epiazano-naphthalen-6-ylamino)-5-trifluoromethyl-pyrimidin-4-yl]-pyrrolidin-3-(S)-ol | 93 | 470.2 | 5.70 | 100 | E |
| 205 | (+/−)-(9-Methanesulfonyl-1,2,3,4-tetrahydro-1,4-epiazano-naphthalen-6-yl)-[4-(2-(R)-methoxymethyl-pyrrolidin-1-yl)-5-trifluoromethyl-pyrimidin-2-yl]-amine | 93 | 498.2 | 7.40 | 100 | E |
| 206 | (+/−)-(9-Methanesulfonyl-1,2,3,4-tetrahydro-1,4-epiazano-naphthalen-6-yl)-[4-(2-(S)-methoxymethyl-pyrrolidin-1-yl)-5-trifluoromethyl-pyrimidin-2-yl]-amine | 93 | 498.2 | 7.40 | 100 | E |
| 207 | (+/−)-$N^4$-Cyclohexyl-$N^2$-(9-methanesulfonyl-1,2,3,4-tetrahydro-1,4-epiazano-naphthalen-6-yl)-5-trifluoromethyl-pyrimidine-2,4-diamine | 95 | 482.2 | 7.80 | 100 | E |
| 208 | (+/−)-$N^2$-(9-Methanesulfonyl-1,2,3,4-tetrahydro-1,4-epiazano-naphthalen-6-yl)-$N^3$-(3-morpholin-4-yl-propyl)-5-trifluoromethyl-pyrimidine-2,4-diamine | 93 | 527.3 | 4.80 | 100 | E |
| 209 | (+/−)-$N^4$-Isopropyl-N2-(9-methanesulfonyl-1,2,3,4-tetrahydro-1,4-epiazano-naphthalen-6-yl)-5-trifluoromethyl-pyrimidine-2,4-diamine | 95 | 442.2 | 7.00 | 100 | E |
| 210 | (+/−)-$N^2$-(9-Methanesulfonyl-1,2,3,4-tetrahydro-1,4-epiazano-naphthalen-6-yl)-$N^2$-methyl-5-trifluoromethyl-pyrimidine-2,4-diamine | 93 | 414.2 | 6.10 | 100 | E |
| 211 | (+/−)-{1-[2-(9-Methanesulfonyl-1,2,3,4-tetrahydro-1,4-epiazano-naphthalen-6-ylamino)-5-trifluoromethyl-pyrimidin-4-yl]-pyrrolidin-2-(R)-yl}-methanol | 93 | 484.2 | 6.20 | 100 | E |
| 212 | (+/−)-{1-[2-(9-Methanesulfonyl-1,2,3,4-tetrahydro-1,4-epiazano-naphthalen-6-ylamino)-5-trifluoromethyl-pyrimidin-4-yl]-pyrrolidin-2-(S)-yl}-methanol | 93 | 484.2 | 6.20 | 100 | E |
| 213 | (+/−)-(9-Methanesulfonyl-1,2,3,4-tetrahydro-1,4-epiazano-naphthalen-6-yl)-[4-(3-(S)-methoxymethyl-morpholin-4-yl)-5-trifluoromethyl-pyrimidin-2-yl]-amine | 93 | 512.2 | 6.60 | 100 | E |
| 214 | (+/−)-N-{1-[2-(9-Methanesulfonyl-1,2,3,4-tetrahydro-1,4-epiazano-naphthalen-6-ylamino)-5-trifluoromethyl-pyrimidin-4-yl]-azetidin-3-yl}-acetamide | 93 | 497.2 | 5.30 | 100 | E |
| 215 | (+/−)-1-{3-(9-Methanesulfonyl-1,2,3,4-tetrahydro-1,4-epiazano-naphthalen-6-ylamino)-5-trifluoromethyl-pyrimidin-4-ylamino]-azetidin-1-yl}-ethanone | 93 | 497.2 | 5.14 | 100 | E |
| 216 | N-{2-[6-(4-Cyclopropylamino-5-trifluoromethyl-pyrimidin-2-ylamino)-(1S,4R)-1,2,3,4-tetrahydro-1,4-epiazano-naphthalen-9-yl]-2-oxo-ethyl}-acetamide | 45 | 461.1 | 5.33 | 100 | E |
| 217 | N-{2-[6-(4-Isopropylamino-5-trifluoromethyl-pyrimidin-2-ylamino)-(1S,4R)-1,2,3,4-tetrahydro-1,4-epiazano-naphthalen-9-yl]-2-oxo-ethyl}-acetamide | 45 | 463.2 | 5.64 | 100 | E |
| 218 | N-{2-Oxo-2-[6-(4-propylamino-5-trifluoromethyl-pyrimidin-2-ylamino)-(1S,4R)-1,2,3,4-tetrahydro-1,4-epiazano-naphthalen-9-yl]-ethyl}-acetamide | 45 | 463.2 | 5.59 | 100 | E |
| 219 | N-(2-{6-[4-(2-Methoxy-ethylamino)-5-trifluoromethyl-pyrimidin-2-ylamino]-(1S,4R)-1,2,3,4-tetrahydro-1,4-epiazano-naphthalen-9-yl}-2-oxo-ethyl)-acetamide | 45 | 479.2 | 4.97 | 100 | E |

TABLE 2-continued

Examples 130-355.

| Ex. | Compound | Prep. Method | MS | HPLC Rf (min) | Purity (HPLC), % | HPLC Method |
|---|---|---|---|---|---|---|
| 220 | 1-(6-{4-[(1-Isopropyl-1H-pyrazol-4-ylmethyl)-methyl-amino]-5-trifluoromethyl-pyrimidin-2-ylamino}-1,4-dimethyl-(1S,4R)-1,2,3,4-tetrahydro-1,4-epiazano-naphthalen-9-yl)-ethanone | 95 | 500.4 | 8.26 | 100 | E |
| 221 | 1-(1,4-Dimethyl-6-{4-[methyl-(2-phenoxy-ethyl)-amino]-5-trifluoromethyl-pyrimidin-2-ylamino}-(1S,4R)-1,2,3,4-tetrahydro-1,4-epiazano-naphthalen-9-yl)-ethanone | 95 | 498.4 | 9.43 | 100 | E |
| 222 | 4-{1-[2-(9-Acetyl-1,4-dimethyl-(1S,4R)-1,2,3,4-tetrahydro-1,4-epiazano-naphthalen-6-ylamino)-5-trifluoromethyl-pyrimidin-4-yl]-azetidin-3-yloxy}-benzonitrile | 95 | 565.3 | 8.88 | 100 | E |
| 223 | N-{1-[2-(9-Acetyl-1,4-dimethyl-(1S,4R)-1,2,3,4-tetrahydro-1,4-epiazano-naphthalen-6-ylamino)-5-trifluoromethyl-pyrimidin-4-yl]-pyrrolidin-3-yl}-N-ethyl-acetamide | 95 | 503.3 | 7.14 | 100 | E |
| 224 | 3-[2-(9-Acetyl-1,4-dimethyl-(1S,4R)-1,2,3,4-tetrahydro-1,4-epiazano-naphthalen-6-ylamino)-5-trifluoromethyl-pyrimidin-4-ylamino]-cyclopentanecarboxylic acid cyclopropylamide | 95 | 515.3 | 7.19 | 100 | E |
| 225 | 3-[2-(9-Acetyl-(1R,4S)-1,2,3,4-tetrahydro-1,4-epiazano-naphthalen-6-ylamino)-5-trifluoromethyl-pyrimidin-4-ylamino]-cyclohexanecarboxylic acid cyclopropylamide | 95 | 529.3 | 7.30 | 100 | E |
| 226 | 1-[2-(9-Acetyl-(1R,4S)-1,2,3,4-tetrahydro-1,4-epiazano-naphthalen-6-ylamino)-5-trifluoromethyl-pyrimidin-4-yl]-piperidine-3-carboxylic acid isopropyl-amide | 95 | 517.3 | 7.56 | 100 | E |
| 227 | 1-[2-(9-Acetyl-(1R,4S)-1,2,3,4-tetrahydro-1,4-epiazano-naphthalen-6-ylamino)-5-trifluoromethyl-pyrimidin-4-yl]-piperidine-3-carboxylic acid cyclopropylamide | 95 | 515.3 | 7.20 | 100 | E |
| 228 | 2-[2-(9-Acetyl-(1R,4S)-1,2,3,4-tetrahydro-1,4-epiazano-naphthalen-6-ylamino)-5-trifluoromethyl-pyrimidin-4-ylamino]-cyclohexanecarboxylic acid isopropyl-amide | 95 | 531.3 | 8.25 | 100 | E |
| 229 | 2-[2-(9-Acetyl-(1R,4S)-1,2,3,4-tetrahydro-1,4-epiazano-naphthalen-6-ylamino)-5-trifluoromethyl-pyrimidin-4-ylamino]-cyclohexanecarboxylic acid cyclopropylamide | 95 | 529.3 | 7.68 | 100 | E |
| 230 | (+/−)-[6-(4-Cyclobutylamino-5-trifluoromethyl-pyrimidin-2-ylamino)-1,2,3,4-tetrahydro-1,4-epiazano-naphthalen-9-yl]-phenyl-methanone | 28 | 480.5 | 7.80 | 100 | E |
| 231 | (+/−)-1-[6-(4-Cyclobutylamino-5-trifluoromethyl-pyrimidin-2-ylamino)-1,2,3,4-tetrahydro-1,4-epiazano-naphthalen-9-yl]-2,2-dimethyl-propan-1-one | 28 | 460.6 | 7.80 | 100 | E |
| 232 | (+/−)-1-[6-(4-Cyclobutylamino-5-trifluoromethyl-pyrimidin-2-ylamino)-1,2,3,4-tetrahydro-1,4-epiazano-naphthalen-9-yl]-3-methyl-butan-1-one | 28 | 460.5 | 7.60 | 100 | E |
| 233 | (+/−)-1-[6-(4-Cyclobutylamino-5-trifluoromethyl-pyrimidin-2-ylamino)-1,2,3,4-tetrahydro-1,4-epiazano-naphthalen-9-yl]-butan-1-one | 28 | 446.5 | 7.40 | 100 | E |
| 234 | (+/−)-1-[6-(4-Cyclobutylamino-5-trifluoromethyl-pyrimidin-2-ylamino)-1,2,3,4-tetrahydro-1,4-epiazano-naphthalen-9-yl]-2-phenyl-ethanone | 28 | 494.5 | 7.70 | 100 | E |
| 235 | (+/−)-[6-(4-Cyclobutylamino-5-trifluoromethyl-pyrimidin-2-ylamino)-1,2,3,4-tetrahydro-1,4-epiazano-naphthalen-9-yl]-pyridin-4-yl-methanone | 28 | 481.5 | 6.80 | 100 | E |
| 236 | 1-[6-(4-Propylamino-5-trifluoromethyl-pyrimidin-2-ylamino)-(1S,4R)-1,2,3,4-tetrahydro-1,4-epiazano-naphthalen-9-yl]-ethanone | 28 | 406.5 | 6.45 | 100 | E |
| 237 | 1-[6-(4-Isopropylamino-5-trifluoromethyl-pyrimidin-2-ylamino)-(1S,4R)-1,2,3,4-tetrahydro-1,4-epiazano-naphthalen-9-yl]-ethanone | 28 | 406.5 | 6.53 | 100 | E |
| 238 | 1-[6-(4-Cyclobutylamino-5-trifluoromethyl-pyrimidin-2-ylamino)-(1S,4R)-1,2,3,4-tetrahydro-1,4-epiazano-naphthalen-9-yl]-ethanone | 28 | 418.5 | 6.70 | 100 | E |
| 239 | 1-[6-(4-Ethylamino-5-trifluoromethyl-pyrimidin-2-ylamino)-(1S,4R)-1,2,3,4-tetrahydro-1,4-epiazano-naphthalen-9-yl]-ethanone | 28 | 392.5 | 6.00 | 100 | E |
| 240 | 1-{6-[4-(2-Methoxy-ethylamino)-5-trifluoromethyl-pyrimidin-2-ylamino]-(1S,4R)-1,2,3,4-tetrahydro-1,4-epiazano-naphthalen-9-yl}-ethanone | 28 | 422.5 | 5.61 | 100 | E |
| 241 | 1-{6-[4-(2-Methoxy-ethylamino)-5-trifluoromethyl-pyrimidin-2-ylamino]-(1S,4R)-1,2,3,4-tetrahydro-1,4-epiazano-naphthalen-9-yl}-2-methyl-propan-1-one | 28 | 450.5 | 6.33 | 100 | E |
| 242 | 2-Methyl-1-[6-(4-methylamino-5-trifluoromethyl-pyrimidin-2-ylamino)-(1S,4R)-1,2,3,4-tetrahydro-1,4-epiazano-naphthalen-9-yl]-propan-1-one | 28 | 406.5 | 6.24 | 100 | E |
| 243 | 2-Methyl-1-[6-(4-propylamino-5-trifluoromethyl-pyrimidin-2-ylamino)-(1S,4R)-1,2,3,4-tetrahydro-1,4-epiazano-naphthalen-9-yl]-propan-1-one | 28 | 434.5 | 7.08 | 100 | E |
| 244 | 1-[6-(4-Ethylamino-5-trifluoromethyl-pyrimidin-2-ylamino)-(1S,4R)-1,2,3,4-tetrahydro-1,4-epiazano-naphthalen-9-yl]-2-methyl-propan-1-one | 28 | 420.5 | 6.70 | 100 | E |
| 245 | 1-[6-(4-Isopropylamino-5-trifluoromethyl-pyrimidin-2-ylamino)-(1S,4R)-1,2,3,4-tetrahydro-1,4-epiazano-naphthalen-9-yl]-2-methyl-propan-1-one | 28 | 434.5 | 7.20 | 100 | E |
| 246 | 1-[6-(4-Cyclobutylamino-5-trifluoromethyl-pyrimidin-2-ylamino)-(1S,4R)-1,2,3,4-tetrahydro-1,4-epiazano-naphthalen-9-yl]-2-methyl-propan-1-one | 28 | 446.5 | 7.30 | 100 | E |
| 247 | (+/−)-Cyclobutyl-[6-(4-cyclobutylamino-5-trifluoromethyl-pyrimidin-2-ylamino)-1,2,3,4-tetrahydro-1,4-epiazano-naphthalen-9-yl]-methanone | 28 | 458.5 | 7.63 | 100 | E |
| 248 | (+/−)-[6-(4-Cyclobutylamino-5-trifluoromethyl-pyrimidin-2-ylamino)-1,2,3,4-tetrahydro-1,4-epiazano-naphthalen-9-yl]-cyclopropyl-methanone | 28 | 444.5 | 7.20 | 100 | E |
| 249 | (+/−)-1-[6-(4-Cyclobutylamino-5-trifluoromethyl-pyrimidin-2-ylamino)-1,2,3,4-tetrahydro-1,4-epiazano-naphthalen-9-yl]-2-methoxy-ethanone | 29 | 448.5 | 6.61 | 100 | E |
| 250 | (+/−)-[6-(4-Cyclobutylamino-5-trifluoromethyl-pyrimidin-2-ylamino)-1,2,3,4-tetrahydro-1,4-epiazano-naphthalen-9-yl]-cyclohexyl-methanone | 29 | 486.5 | 8.18 | 100 | E |
| 251 | (+/−)-1-[6-(4-Cyclobutylamino-5-trifluoromethyl-pyrimidin-2-ylamino)-1,2,3,4-tetrahydro-1,4-epiazano-naphthalen-9-yl]-2-cyclopentyl-ethanone | 29 | 486.5 | 8.23 | 100 | E |

TABLE 2-continued

Examples 130-355.

| Ex. | Compound | Prep. Method | MS | HPLC Rf (min) | Purity (HPLC), % | HPLC Method |
|---|---|---|---|---|---|---|
| 252 | (+/−)-[6-(4-Cyclobutylamino-5-trifluoromethyl-pyrimidin-2-ylamino)-1,2,3,4-tetrahydro-1,4-epiazano-naphthalen-9-yl]-cyclopentyl-methanone | 29 | 472.5 | 7.90 | 100 | E |
| 253 | (+/−)-1-[6-(4-Cyclobutylamino-5-trifluoromethyl-pyrimidin-2-ylamino)-1,2,3,4-tetrahydro-1,4-epiazano-naphthalen-9-yl]-propan-1-one | 29 | 432.5 | 7.00 | 100 | E |
| 254 | 2-Methoxy-1-[6-(4-methylamino-5-trifluoromethyl-pyrimidin-2-ylamino)-(1S,4R)-1,2,3,4-tetrahydro-1,4-epiazano-naphthalen-9-yl]-ethanone | 29 | 408.5 | 5.52 | 100 | E |
| 255 | 2-Methoxy-1-{6-[4-(2-methoxy-ethylamino)-5-trifluoromethyl-pyrimidin-2-ylamino]-(1S,4R)-1,2,3,4-tetrahydro-1,4-epiazano-naphthalen-9-yl}-ethanone | 29 | 452.5 | 5.60 | 100 | E |
| 256 | 2-Methoxy-1-[6-(4-propylamino-5-trifluoromethyl-pyrimidin-2-ylamino)-(1S,4R)-1,2,3,4-tetrahydro-1,4-epiazano-naphthalen-9-yl]-ethanone | 29 | 436.5 | 6.36 | 100 | E |
| 257 | 1-[6-(4-Ethylamino-5-trifluoromethyl-pyrimidin-2-ylamino)-(1S,4R)-1,2,3,4-tetrahydro-1,4-epiazano-naphthalen-9-yl]-2-methoxy-ethanone | 29 | 422.5 | 5.90 | 100 | E |
| 258 | 1-[6-(4-Cyclobutylamino-5-trifluoromethyl-pyrimidin-2-ylamino)-(1S,4R)-1,2,3,4-tetrahydro-1,4-epiazano-naphthalen-9-yl]-2-methoxy-ethanone | 29 | 448.5 | 6.60 | 100 | E |
| 259 | Cyclopropyl-[6-(4-methylamino-5-trifluoromethyl-pyrimidin-2-ylamino)-(1S,4R)-1,2,3,4-tetrahydro-1,4-epiazano-naphthalen-9-yl]-methanone | 29 | 404.5 | 6.15 | 100 | E |
| 260 | Cyclopropyl-{6-[4-(2-methoxy-ethylamino)-5-trifluoromethyl-pyrimidin-2-ylamino]-(1S,4R)-1,2,3,4-tetrahydro-1,4-epiazano-naphthalen-9-yl}-methanone | 29 | 448.5 | 6.20 | 100 | E |
| 261 | Cyclopropyl-[6-(4-propylamino-5-trifluoromethyl-pyrimidin-2-ylamino)-(1S,4R)-1,2,3,4-tetrahydro-1,4-epiazano-naphthalen-9-yl]-methanone | 29 | 432.5 | 7.00 | 100 | E |
| 262 | Cyclopropyl-[6-(4-ethylamino-5-trifluoromethyl-pyrimidin-2-ylamino)-(1S,4R)-1,2,3,4-tetrahydro-1,4-epiazano-naphthalen-9-yl]-methanone | 29 | 418.5 | 6.60 | 100 | E |
| 263 | [6-(4-Cyclobutylamino-5-trifluoromethyl-pyrimidin-2-ylamino)-(1S,4R)-1,2,3,4-tetrahydro-1,4-epiazano-naphthalen-9-yl]-cyclopropyl-methanone | 29 | 444.5 | 7.21 | 100 | E |
| 264 | Cyclopropyl-[6-(4-isopropylamino-5-trifluoromethyl-pyrimidin-2-ylamino)-(1S,4R)-1,2,3,4-tetrahydro-1,4-epiazano-naphthalen-9-yl]-methanone | 29 | 432.5 | 7.06 | 100 | E |
| 265 | 1-[6-(4-Isopropylamino-5-trifluoromethyl-pyrimidin-2-ylamino)-(1S,4R)-1,2,3,4-tetrahydro-1,4-epiazano-naphthalen-9-yl]-2-methoxy-ethanone | 29 | 436.5 | 6.48 | 100 | E |
| 266 | [6-(4-Cyclobutylamino-5-trifluoromethyl-pyrimidin-2-ylamino)-(1R,4S)-1,2,3,4-tetrahydro-1,4-epiazano-naphthalen-9-yl]-cyclopropyl-methanone | 29 | 444.4 | 7.22 | 100 | E |
| 267 | Cyclopropyl-{6-[4-(2-methoxy-ethylamino)-5-trifluoromethyl-pyrimidin-2-ylamino]-(1R,4S)-1,2,3,4-tetrahydro-1,4-epiazano-naphthalen-9-yl}-methanone | 29 | 448.4 | 6.26 | 100 | E |
| 268 | (+/−)-6-(4-Cyclobutylamino-5-trifluoromethyl-pyrimidin-2-ylamino)-1,2,3,4-tetrahydro-1,4-epiazano-naphthalene-9-carboxylic acid ethylamide | 25 | 447.5 | 6.60 | 100 | E |
| 269 | (+/−)-6-(4-Cyclobutylamino-5-trifluoromethyl-pyrimidin-2-ylamino)-1,2,3,4-tetrahydro-1,4-epiazano-naphthalene-9-carboxylic acid isopropyl-amide | 25 | 461.5 | 6.95 | 100 | E |
| 270 | (+/−)-6-(4-Cyclobutylamino-5-trifluoromethyl-pyrimidin-2-ylamino)-1,2,3,4-tetrahydro-1,4-epiazano-naphthalene-9-carboxylic acid cyclopentylamide | 25 | 487.5 | 7.42 | 100 | E |
| 271 | (+/−)-6-(4-Cyclobutylamino-5-trifluoromethyl-pyrimidin-2-ylamino)-1,2,3,4-tetrahydro-1,4-epiazano-naphthalene-9-carboxylic acid tert-butyl-amide | 25 | 475.5 | 7.55 | 100 | E |
| 272 | 6-(4-Methylamino-5-trifluoromethyl-pyrimidin-2-ylamino)-(1S,4R)-1,2,3,4-tetrahydro-1,4-epiazano-naphthalene-9-carboxylic acid isopropyl-amide | 25 | 421.5 | 5.95 | 100 | E |
| 273 | 6-(4-Ethylamino-5-trifluoromethyl-pyrimidin-2-ylamino)-(1S,4R)-1,2,3,4-tetrahydro-1,4-epiazano-naphthalene-9-carboxylic acid isopropyl-amide | 25 | 435.5 | 6.35 | 100 | E |
| 274 | 6-(4-Cyclobutylamino-5-trifluoromethyl-pyrimidin-2-ylamino)-(1S,4R)-1,2,3,4-tetrahydro-1,4-epiazano-naphthalene-9-carboxylic acid isopropyl-amide | 25 | 461.5 | 6.95 | 100 | E |
| 275 | 6-(4-Propylamino-5-trifluoromethyl-pyrimidin-2-ylamino)-(1S,4R)-1,2,3,4-tetrahydro-1,4-epiazano-naphthalene-9-carboxylic acid isopropyl-amide | 25 | 449.4 | 6.73 | 100 | E |
| 276 | 6-(4-Isopropylamino-5-trifluoromethyl-pyrimidin-2-ylamino)-(1S,4R)-1,2,3,4-tetrahydro-1,4-epiazano-naphthalene-9-carboxylic acid isopropyl-amide | 25 | 449.3 | 6.80 | 100 | E |
| 277 | 6-[4-(2-Methoxy-ethylamino)-5-trifluoromethyl-pyrimidin-2-ylamino]-(1S,4R)-1,2,3,4-tetrahydro-1,4-epiazano-naphthalene-9-carboxylic acid isopropyl-amide | 25 | 465.4 | 6.06 | 100 | E |
| 278 | 6-(4-Methylamino-5-trifluoromethyl-pyrimidin-2-ylamino)-(1S,4R)-1,2,3,4-tetrahydro-1,4-epiazano-naphthalene-9-carboxylic acid ethylamide | 25 | 407.5 | 5.60 | 100 | E |
| 279 | 6-[4-(2-Methoxy-ethylamino)-5-trifluoromethyl-pyrimidin-2-ylamino]-(1S,4R)-1,2,3,4-tetrahydro-1,4-epiazano-naphthalene-9-carboxylic acid ethylamide | 25 | 451.5 | 5.70 | 100 | E |
| 280 | 6-(4-Propylamino-5-trifluoromethyl-pyrimidin-2-ylamino)-(1S,4R)-1,2,3,4-tetrahydro-1,4-epiazano-naphthalene-9-carboxylic acid ethylamide | 25 | 435.5 | 6.37 | 100 | E |
| 281 | 6-(4-Cyclobutylamino-5-trifluoromethyl-pyrimidin-2-ylamino)-(1S,4R)-1,2,3,4-tetrahydro-1,4-epiazano-naphthalene-9-carboxylic acid ethylamide | 25 | 447.5 | 6.62 | 100 | E |
| 282 | 6-(4-Isopropylamino-5-trifluoromethyl-pyrimidin-2-ylamino)-(1S,4R)-1,2,3,4-tetrahydro-1,4-epiazano-naphthalene-9-carboxylic acid ethylamide | 25 | 435.5 | 6.47 | 100 | E |
| 283 | (+/−)-[6-(4-Cyclobutylamino-5-trifluoromethyl-pyrimidin-2-ylamino)-1,2,3,4-tetrahydro-1,4-epiazano-naphthalen-9-yl]-pyrrolidin-1-yl-methanone | 26 | 473.5 | | | E |
| 284 | (+/−)-6-(4-Cyclobutylamino-5-trifluoromethyl-pyrimidin-2-ylamino)-1,2,3,4-tetrahydro-1,4-epiazano-naphthalene-9-carboxylic acid dimethylamide | 26 | 447.5 | 7.14 | 100 | E |
| 285 | (+/−)-Azetidin-1-yl-[6-(4-cyclobutylamino-5-trifluoromethyl-pyrimidin-2-ylamino)-1,2,3,4-tetrahydro-1,4-epiazano-naphthalen-9-yl]-methanone | 26 | 459.5 | 7.07 | 100 | E |
| 286 | (+/−)-6-(4-Cyclobutylamino-5-trifluoromethyl-pyrimidin-2-ylamino)-1,2,3,4-tetrahydro-1,4-epiazano-naphthalene-9-carboxylic acid methylamide | 26 | 433.5 | 6.30 | 100 | E |
| 287 | (+/−)-[6-(4-Cyclobutylamino-5-trifluoromethyl-pyrimidin-2-ylamino)-1,2,3,4-tetrahydro-1,4-epiazano-naphthalen-9-yl]-(4-ethyl-piperazin-1-yl)-methanone | 26 | 516.5 | 6.03 | 100 | E |

TABLE 2-continued

Examples 130-355.

| Ex. | Compound | Prep. Method | MS | HPLC Rf (min) | Purity (HPLC), % | HPLC Method |
|---|---|---|---|---|---|---|
| 288 | (+/−)-[6-(4-Cyclobutylamino-5-trifluoromethyl-pyrimidin-2-ylamino)-1,2,3,4-tetrahydro-1,4-epiazano-naphthalen-9-yl]-morpholin-4-yl-methanone | 26 | 489.5 | 6.92 | 100 | E |
| 289 | (+/−)-6-(4-Cyclobutylamino-5-trifluoromethyl-pyrimidin-2-ylamino)-1,2,3,4-tetrahydro-1,4-epiazano-naphthalene-9-carboxylic acid diethylamide | 26 | 475.5 | 7.90 | 100 | E |
| 290 | (+/−)-[6-(4-Cyclobutylamino-5-trifluoromethyl-pyrimidin-2-ylamino)-1,2,3,4-tetrahydro-1,4-epiazano-naphthalen-9-yl]-thiomorpholin-4-yl-methanone | 26 | 505.5 | 7.70 | 100 | E |
| 291 | (+/−)-6-(4-Cyclobutylamino-5-trifluoromethyl-pyrimidin-2-ylamino)-1,2,3,4-tetrahydro-1,4-epiazano-naphthalene-9-carboxylic acid cyclobutylamide | 26 | 473.5 | 7.13 | 100 | E |
| 292 | (+/−)-1-[6-(4-Cyclobutylamino-5-trifluoromethyl-pyrimidin-2-ylamino)-1,2,3,4-tetrahydro-1,4-epiazano-naphthalen-9-yl]-2-morpholin-4-yl-ethanone | 31 | 503.2 | 6.30 | 100 | E |
| 293 | (+/−)-1-[6-(4-Cyclobutylamino-5-trifluoromethyl-pyrimidin-2-ylamino)-1,2,3,4-tetrahydro-1,4-epiazano-naphthalen-9-yl]-2-methylamino-ethanone | 31 | 447.5 | | | |
| 294 | (+/−)-2-Azetidin-1-yl-1-[6-(4-cyclobutylamino-5-trifluoromethyl-pyrimidin-2-ylamino)-1,2,3,4-tetrahydro-1,4-epiazano-naphthalen-9-yl]-ethanone | 31 | 473.5 | 5.66 | 100 | E |
| 295 | (+/−)-1-[6-(4-Cyclobutylamino-5-trifluoromethyl-pyrimidin-2-ylamino)-1,2,3,4-tetrahydro-1,4-epiazano-naphthalen-9-yl]-2-pyrrolidin-1-yl-ethanone | 31 | 487.5 | 6.00 | 100 | E |
| 296 | (+/−)-1-[6-(4-Cyclobutylamino-5-trifluoromethyl-pyrimidin-2-ylamino)-1,2,3,4-tetrahydro-1,4-epiazano-naphthalen-9-yl]-2-(4-ethyl-piperazin-1-yl)-ethanone | 31 | 530.6 | 5.50 | 100 | E |
| 297 | (+/−)-2-tert-Butylamino-1-[6-(4-cyclobutylamino-5-trifluoromethyl-pyrimidin-2-ylamino)-1,2,3,4-tetrahydro-1,4-epiazano-naphthalen-9-yl]-ethanone | 31 | 489.5 | 6.20 | 100 | E |
| 298 | (+/−)-1-[6-(4-Cyclobutylamino-5-trifluoromethyl-pyrimidin-2-ylamino)-1,2,3,4-tetrahydro-1,4-epiazano-naphthalen-9-yl]-2-isopropylamino-ethanone | 31 | 475.5 | 5.80 | 100 | E |
| 299 | (+/−)-1-[6-(4-Cyclobutylamino-5-trifluoromethyl-pyrimidin-2-ylamino)-1,2,3,4-tetrahydro-1,4-epiazano-naphthalen-9-yl]-2-ethylamino-ethanone | 31 | 461.5 | 5.60 | 100 | E |
| 300 | (+/−)-1-[6-(4-Cyclobutylamino-5-trifluoromethyl-pyrimidin-2-ylamino)-1,2,3,4-tetrahydro-1,4-epiazano-naphthalen-9-yl]-2-(1,1-dioxo-1$I%6&-thiomorpholin-4-yl)-ethanone | 31 | 551.5 | 6.20 | 100 | E |
| 301 | (+/−)-1-[6-(4-Cyclobutylamino-5-trifluoromethyl-pyrimidin-2-ylamino)-1,2,3,4-tetrahydro-1,4-epiazano-naphthalen-9-yl]-2-thiomorpholin-4-yl-ethanone | 31 | 519.5 | 7.10 | 100 | E |
| 302 | (+/−)-1-[6-(4-Cyclobutylamino-5-trifluoromethyl-pyrimidin-2-ylamino)-1,2,3,4-tetrahydro-1,4-epiazano-naphthalen-9-yl]-2-diethylamine-ethanone | 31 | 489.5 | 6.00 | 100 | E |
| 303 | (1R,4S)-1-[6-(4-Cyclobutylamino-5-trifluoromethyl-pyrimidin-2-ylamino)-1,2,3,4-tetrahydro-1,4-epiazano-naphthalen-9-yl]-2-methylamino-ethanone | 31 | 447.5 | 5.45 | 100 | E |
| 304 | 1-[6-(4-Ethylamino-5-trifluoromethyl-pyrimidin-2-ylamino)-1,2,3,4-tetrahydro-1,4-epiazano-naphthalen-9-yl]-2,2-difluoro-ethanone | 11 | 428.14 | | | F |
| 305 | 2,2-Difluoro-1-[6-(4-propylamino-5-trifluoromethyl-pyrimidin-2-ylamino)-(1S,4R)-1,2,3,4-tetrahydro-1,4-epizano-naphthalen-9-yl]-ethanone | 11 | 442.16 | | | F |
| 306 | 2,2-Difluoro-1-[6-(4-isopropylamino-5-trifluoromethyl-pyrimidin-2-ylamino)-(1S,4R)-1,2,3,4-tetrahydro-1,4-epiazano-naphthalen-9-yl]-ethanone | 11 | 442.16 | | | F |
| 307 | 2,2-Difluoro-1-{6-[4-(2-methoxy-ethylamino)-5-trifluoromethyl-pyrimidin-2-ylamino]-(1S,4R)-1,2,3,4-tetrahydro-1,4-epiazano-naphthalen-9-yl}-ethanone | 11 | 458.15 | | | F |
| 308 | 1-[6-(4-Cyclopropylamino-5-trifluoromethyl-pyrimidin-2-ylamino)-(1S,4R)-1,2,3,4-tetrahydro-1,4-epiazano-naphthalen-9-yl]-2,2-difluoro-ethanone | 11 | 440.14 | | | F |
| 309 | 1-[6-(4-Cyclobutylamino-5-trifluoromethyl-pyrimidin-2-ylamino)-(1S,4R)-1,2,3,4-tetrahydro-1,4-epiazano-naphthalen-9-yl]-2,2-difluoro-ethanone | 11 | 454.16 | | | F |
| 310 | 2-Fluoro-1-[6-(4-Ethylamino-5-trifluoromethyl-pyrimidin-2-ylamino)-(1R,4S)-1,2,3,4-tetrahydro-1,4-epiazano-naphthalen-9-yl]-ethanone | 23 | 410.15 | | | F |
| 311 | 1-[6-(4-Amino-5-trifluoromethyl-pyrimidin-2-ylamino)-1,2,3,4-tetrahydro-1,4-epiazano-naphthalen-9-yl]-ethanone | 95 | 364.4 | 5 | 100 | E |
| 312 | 1-(6-{4-[(1-Hydroxy-cyclobutylmethyl)-amino]-5-trifluoromethyl-pyrimidin-2-ylamino}-1,2,3,4-tetrahydro-1,4-epiazano-naphthalen-9-yl)-ethanone | 95 | 448.4 | 5.2 | 100 | E/F |
| 313 | 1-[6-(4-Methylamino-5-trifluoromethyl-pyrimidin-2-ylamino)-1,2,3,4-tetrahydro-1,4-epizano-naphthalen-9-yl]-ethanone | 95 | 378.15 | 4.5 | 100 | E |
| 314 | 1-(6-{4-[(1-Hydroxy-cyclopentylmethyl)-amino]-5-trifluoromethyl-pyrimidin-2-ylamino}-1,2,3,4-tetrahydro-1,4-epiazano-naphthalen-9-yl)-ethanone | 95 | 462.2 | 5.4 | 100 | E/F |
| 315 | 1-[6-(4-Pyrrolidin-1-yl-5-trifluoromethyl-pyrimidin-2-ylamino)-1,2,3,4-tetrahydro-1,4-epiazano-naphthalen-9-yl]-ethanone | 95 | 418.18 | 5.42 | 100 | E |
| 316 | 1-[6-(4-Cyclopentyloxy-5-trifluoromethyl-pyrimidin-2-ylamino)-1,2,3,4-tetrahydro-1,4-epiazano-naphthalen-9-yl]-ethanone | 99 | 433.18 | 7.6 | 100 | E |
| 317 | 2,2-Difluoro-1-[6-(4-{[(S)-1-(tetrahydro-furan-2-yl)methyl]-amino}-5-trifluoromethyl-pyrimidin-2-ylamino)-(1S,4R)-1,2,3,4-tetrahydro-1,4-epiazano-naphthalen-9-yl]-ethanone | 11 | 484.17 | | | F |
| 318 | 2,2-Difluoro-1-[6-(4-{[(R)-1-(tetrahydro-furan-2-yl)methyl]-amino}-5-trifluoromethyl-pyrimidin-2-ylamino)-(1S,4R)-1,2,3,4-tetrahydro-1,4-epiazano-naphthalen-9-yl]-ethanone | 11 | 484.17 | | | F |
| 319 | 1-[6-(4-Ethylamino-5-trifluoromethyl-pyrimidin-2-ylamino)-(1S,4R)-1,2,3,4-tetrahydro-1,4-epiazano-naphthalen-9-yl]-2,2,2-trifluoro-ethanone | 12 | 446.13 | | | F |
| 320 | 2,2,2-Trifluoro-1-[6-(4-propylamino-5-trifluoromethyl-pyrimidin-2-ylamino)-(1S,4R)-1,2,3,4-tetrahydro-1,4-epiazano-naphthalen-9-yl]-ethanone | 12 | 460.15 | | | F |
| 321 | 2,2,2-Trifluoro-1-[6-(4-isopropylamino-5-trifluoromethyl-pyrimidin-2-ylamino)-(1S,4R)-1,2,3,4-tetrahydro-1,4-epiazano-naphthalen-9-yl]-ethanone | 12 | 460.15 | | | F |
| 322 | 2,2,2-Trifluoro-1-{6-[4-(2-methoxy-ethylamino)-5-trifluoromethyl-pyrimidin-2-ylamino]-(1S,4R)-1,2,3,4-tetrahydro-1,4-epiazano-naphthalen-9-yl}-ethanone | 12 | 476.14 | | | F |

TABLE 2-continued

Examples 130-355.

| Ex. | Compound | Prep. Method | MS | HPLC Rf (min) | Purity (HPLC), % | HPLC Method |
|---|---|---|---|---|---|---|
| 323 | 1-[6-(4-Cyclopropylamino-5-trifluoromethyl-pyrimidin-2-ylamino)-(1S,4R)-1,2,3,4-tetrahydro-1,4-epiazano-naphthalen-9-yl]-2,2,2-trifluoro-ethanone | 12 | 458.13 | | | F |
| 324 | 1-[6-(4-Cyclobutylamino-5-trifluoromethyl-pyrimidin-2-ylamino)-(1S,4R)-1,2,3,4-tetrahydro-1,4-epiazano-naphthalen-9-yl]-2,2,2-trifluoro-ethanone | 12 | 472.15 | | | F |
| 325 | 2-Fluoro-1-{6-[4-(2-methoxy-ethylamino)-5-trifluoromethyl-pyrimidin-2-ylamino]-(1R,4S)-1,2,3,4-tetrahydro-1,4-epiazano-naphthalen-9-yl}-ethanone | 23 | 440.16 | | | F |
| 326 | 1-{6-[4-(1,3-Dihydro-pyrrolo[3,4-c]pyridin-2-yl)-5-trifluoromethyl-pyrimidin-2-ylamino]-(1S,4R)-1,2,3,4-tetrahydro-1,4-epiazano-naphthalen-9-yl}-ethanone | 95 | 467.17 | 6.14 | 100 | E |
| 327 | 2-Fluoro-1-[6-(4-Ethylamino-5-trifluoromethyl-pyrimidin-2-ylamino)-(1S,4R)-1,2,3,4-tetrahydro-1,4-epiazano-naphthalen-9-yl]-ethanone | 23 | 410.15 | | | F |
| 328 | N-(2-{6-[4-(1,3-Dihydro-pyrrolo[3,4-c]pyridin-2-yl)-5-trifluoromethyl-pyrimidin-2-ylamino]-(1S,4R)-1,2,3,4-tetrahydro-1,4-epiazano-naphthalen-9-yl}-2-oxo-ethyl)-acetamide | 95 | 524.19 | 5.34 | 100 | E |
| 329 | 1-[6-(4-Phenylsulfanyl-5-trifluoromethyl-pyrimidin-2-ylamino)-(1S,4R)-1,2,3,4-tetrahydro-1,4-epiazano-naphthalen-9-yl]-ethanone | 100 | 457.3 | 8.15 | 100 | E |
| 330 | 3-[2-(9-Acetyl-1,2,3,4-tetrahydro-1,4-epiazano-naphthalen-6-ylamino)-5-trifluoromethyl-pyrimidin-4-ylamino]-azetidine-1-carboxylic acid ethylamide | 97 | 490.3 | 5.6 | 100 | E |
| 331 | 1-{6-[4-(Cyclopentylmethyl-amino)-5-trifluoromethyl-pyrimidin-2-ylamino]-1,2,3,4-tetrahydro-1,4-epiazano-naphthalen-9-yl}-ethanone | 95 | 446.3 | 7.4 | 100 | E |
| 332 | 1-{6-[4-(Cyclopropylmethyl-amino)-5-trifluoromethyl-pyrimidin-2-ylamino]-1,2,3,4-tetrahydro-1,4-epiazano-naphthalen-9-yl}-ethanone | 95 | 418.3 | 6.4 | 100 | E |
| 333 | 1-[6-(4-Ethylamino-5-trifluoromethyl-pyrimidin-2-ylamino)-1,2,3,4-tetrahydro-1,4-epiazano-naphthalen-9-yl]-ethanone | 95 | 392.4 | 5.96 | 100 | E |
| 334 | 1-{6-[4-(3-Morpholin-4-yl-azetidin-1-yl)-5-trifluoromethyl-pyrimidin-2-ylamino]-1,2,3,4-tetrahydro-1,4-epiazano-naphthalen-9-yl}-ethanone | 18 | 489.3 | 5.4 | 100 | E |
| 335 | 1-[6-(4-{[(S)-1-(Tetrahydro-furan-2-yl)methyl]-amino}-5-trifluoromethyl-pyrimidin-2-ylamino)-1,2,3,4-tetrahydro-1,4-epiazano-naphthalen-9-yl]-ethanone | 95 | 448.3 | 5.92 | 100 | E |
| 336 | 2-Fluoro-1-[6-(4-propylamino-5-trifluoromethyl-pyrimidin-2-ylamino)-(1S,4R)-1,2,3,4-tetrahydro-1,4-epiazano-naphthalen-9-yl]-ethanone | 23 | 424.17 | | | F |
| 337 | 2-Fluoro-1-[6-(4-isopropylamino-5-trifluoromethyl-pyrimidin-2-ylamino)-(1S,4R)-1,2,3,4-tetrahydro-1,4-epiazano-naphthalen-9-yl]-ethanone | 23 | 424.17 | | | F |
| 338 | 2-Fluoro-1-{6-[4-(2-methoxy-ethylamino)-5-trifluoromethyl-pyrimidin-2-ylamino]-(1S,4R)-1,2,3,4-tetrahydro-1,4-epiazano-naphthalen-9-yl}-ethanone | 23 | 440.16 | | | F |
| 339 | 2-Fluoro-1-{6-[4-Cyclopropylamino-5-trifluoromethyl-pyrimidin-2-ylamino]-(1S,4R)-1,2,3,4-tetrahydro-1,4-epiazano-naphthalen-9-yl}-ethanone | 23 | 422.15 | | | F |
| 340 | 2-Fluoro-1-{6-[4-Cyclobutylamino-5-trifluoromethyl-pyrimidin-2-ylamino]-(1S,4R)-1,2,3,4-tetrahydro-1,4-epiazano-naphthalen-9-yl}-ethanone | 23 | 436.17 | | | F |
| 341 | (+/−)-$N^4$-Cyclopropyl-$N^2$-(9-methanesulfonyl-1,2,3,4-tetrahydro-1,4-epiazano-naphthalen-6-yl)-5-trifluoromethyl-pyrimidine-2,4-diamine | 93 | 440.0 | | | |
| 342 | (+/−)-1-[6-(4-Cyclopropylamino-5-trifluoromethyl-pyrimidin-2-ylamino)-1,2,3,4-tetrahydro-1,4-epiazano-naphthalen-9-yl]-ethanone | 23 | 404.2 | | | |
| 343 | (+/−)-$N^4$-Cyclopentyl-$N^2$-(9-methanesulfonyl-1,2,3,4-tetrahydro-1,4-epiazano-naphthalen-6-yl)-5-trifluoromethyl-pyrimidine-2,4-diamine | 93 | 468.0 | | | |
| 344 | (+/−)-1-[6-(4-Cyclopentylamino-5-trifluoromethyl-pyrimidin-2-ylamino)-1,2,3,4-tetrahydro-1,4-epiazano-naphthalen-9-yl]-ethanone | 23 | 432.2 | | | |
| 345 | (+/−)-1-[6-(4-Cyclobutylamino-5-trifluoromethyl-pyrimidin-2-ylamino)-1,2,3,4-tetrahydro-1,4-epiazano-naphthalen-9-yl]-2-dimethylamino-ethanone | 23 | 461.3 | | | |
| 346 | (+/−)-Acetic acid 2-[6-(4-cyclobutylamino-5-trifluoromethyl-pyrimidin-2-ylamino)-1,2,3,4-tetrahydro-1,4-epiazano-naphthalen-9-yl]-2-oxo-ethyl ester | 23 | 476.3 | | | |
| 347 | (+/−)-Acetic acid 2-[6-(4-cyclobutylamino-5-trifluoromethyl-pyrimidin-2-ylamino)-1,2,3,4-tetrahydro-1,4-epiazano-naphthalen-9-yl]-1,1-dimethyl-2-oxo-ethyl ester | 23 | 504.5 | | | |
| 348 | N-{2-[6-(4-Ethylamino-5-trifluoromethyl-pyrimidin-2-ylamino)-(1S,4R)-1,2,3,4-tetrahydro-1,4-epiazano-naphthalen-9-yl]-2-oxo-ethyl}-acetamide | 45 | 449.1 | 5.21 | 100 | E |
| 349 | N-{2-[6-(4-Methylamino-5-trifluoromethyl-pyrimidin-2-ylamino)-(1S,4R)-1,2,3,4-tetrahydro-1,4-epiazano-naphthalen-9-yl]-2-oxo-ethyl}-acetamide | 45 | 435.0 | 4.84 | 100 | E |
| 350 | (+/−)-N-{2-[6-(4-Cyclobutylamino-5-trifluoromethyl-pyrimidin-2-ylamino)-1,2,3,4-tetrahydro-1,4-epiazano-naphthalen-9-yl]-2-oxo-ethyl}-acetamide | 45 | 475.5 | 5.81 | 100 | E |
| 351 | (+/−)-{2-[6-(4-Cyclobutylamino-5-trifluoromethyl-pyrimidin-2-ylamino)-1,2,3,4-tetrahydro-1,4-epiazano-naphthalen-9-yl]-2-oxo-ethyl}-carbamic acid tert-butyl ester | 45 | 533.5/433.5 | 7.40 | 100 | E |
| 352 | 1-{6-[4-(2-Methoxy-ethylamino)-5-trifluoromethyl-pyrimidin-2-ylamino]-(1S,4R)-1,2,3,4-tetrahydro-1,4-epiazano-naphthalen-9-yl}-2-methylamino-ethanone | 41 | 451.0 | 4.67 | 100 | E |
| 353 | 1-[6-(4-Ethylamino-5-trifluoromethyl-pyrimidin-2-ylamino)-(1S,4R)-1,2,3,4-tetrahydro-1,4-epiazano-naphthalen-9-yl]-2-methylamino-ethanone | 41 | 421.0 | 4.94 | 100 | E |
| 354 | 1-[6-(4-Isopropylamino-5-trifluoromethyl-pyrimidin-2-ylamino)-(1S,4R)-1,2,3,4-tetrahydro-1,4-epiazano-naphthalen-9-yl]-2-methylamino-ethanone | 41 | 435.0 | 5.30 | 100 | E |
| 355 | 2-Methylamino-1-[6-(4-propylamino-5-trifluoromethyl-pyrimidin-2-ylamino)-(1S,4R)-1,2,3,4-tetrahydro-1,4-epiazano-naphthalen-9-yl]-ethanone | 41 | 435.0 | 5.28 | 100 | E |

TABLE 3

Examples 359-362.

| Ex. | Compound | Prep. Method | MS | HPLC Rf (min) | Purity (HPLC), % | HPLC Method |
|---|---|---|---|---|---|---|
| 359 | (+/−)-1-[6-(4-Cyclobutylamino-5-trifluoromethyl-pyrimidin-2-ylamino)-1,2,3,4-tetrahydro-1,4-epiazano-naphthalen-9-yl]-3,3-dimethyl-butan-2-one | 359 | 474.4 | 7.02 | 100 | E |
| 360 | (+/−)-2-[6-(4-Cyclobutylamino-5-trifluoromethyl-pyrimidin-2-ylamino)-1,2,3,4-tetrahydro-1,4-epiazano-naphthalen-9-yl]-1-phenyl-ethanone | 359 | 494.3 | 7.30 | 100 | E |
| 361 | (+/−)-2-[6-(4-Cyclobutylamino-5-trifluoromethyl-pyrimidin-2-ylamino)-1,2,3,4,-tetrahydro-1,4-epiazano-naphthalen-9-yl]-N,N-dimethyl-acetamide | 359 | 461.4 | 5.77 | 100 | E |
| 362 | (+/−)-2-[6-(4-Cyclobutylamino-5-trifluoromethyl-pyrimidin-2-ylamino)-1,2,3,4-tetrahydro-1,4-epiazano-naphthalen-9-yl]-acetamide | 359 | 433.3 | 5.27 | 100 | E |

TABLE 4

Examples 363-417.

| Ex. | Compound | MS | Purity (HPLC), % | Purity (ELSD), % | Ret. Time (min.) | HPLC Method |
|---|---|---|---|---|---|---|
| 363 | (+/−)-N-(3-{[2-(9-Ethyl-1,2,3,4-tetrahydro-1,4-epiazano-naphthalen-6-ylamino)-5-trifluoromethyl-pyrimidin-4-ylamino]-methyl}-6-methyl-pyridin-2-yl)-N-methyl-methanesulfonamide | 562.46 | 89 | 95 | 2.58 | G |
| 364 | (+/−)-$N^2$-(9-Ethyl-1,2,3,4-tetrahydro-1,4-epiazano-naphthalen-6-yl)-$N^4$-(2-methoxy-ethyl)-5-trifluoromethyl-pyrimidine-2,4-diamine | 518.38 | 86 | 100 | 2.43 | G |
| 365 | (+/−)-N-(3-{[2-(9-Methanesulfonyl-1,2,3,4-tetrahydro-1,4-epiazano-naphthalen-6-ylamino)-5-trifluoromethyl-pyrimidin-4-ylamino]-methyl}-6-methyl-pyridin-2-yl)-N-methyl-methanesulfonamide | 547.43 | 80 | 92 | 2.52 | G |
| 366 | (+/−)-$N^4$-(9-Methanesulfonyl-1,2,3,4-tetrahydro-1,4-epiazano-naphthalen-6-yl)-$N^4$-(2-methoxy-ethyl)-5-trifluoromethyl-pyrimidine-2,4-diamine | 548.43 | 94 | 93 | 2.49 | G |
| 367 | (+/−)-N-(3-{[2-(9-Acetyl-1,2,3,4-tetrahydro-1,4-epiazano-naphthalen-6-ylamino)-5-trifluoromethyl-pyrimidin-4-ylamino]-methyl}-6-methyl-pyridin-2-yl)-N-methyl-methanesulfonamide | 561.49 | 85 | 94 | 2.70 | G |
| 368 | (+/−)-1-{6-[4-(2-Methoxy-ethylamino)-5-trifluoromethyl-pyrimidin-2-ylamino]-1,2,3,4-tetrahydro-1,4-epiazano-naphthalen-9-yl}-ethanone | 561.49 | 83 | 90 | 2.73 | G |
| 369 | (+/−)-6-(4-{[2-(Methanesulfonyl-methyl-amino)-6-methyl-pyridin-3-ylmethyl]-amino}-5-trifluoromethyl-pyrimidin-2-ylamino)-1,2,3,4-tetrahydro-1,4-epiazano-naphthalene-9-carboxylic acid methyl ester | 408.49 | 89 | 94 | 2.28 | G |
| 370 | (+/−)-6-[4-(2-Methoxy-ethylamino)-5-trifluoromethyl-pyrimidin-2-ylamino]-1,2,3,4,-tetrahydro-1,4-epiazano-naphthalene-9-carboxylic acid methyl ester | 448.46 | 95 | 100 | 2.34 | G |
| 371 | (+/−)-$N^2$-(9-Ethyl-1,2,3,4-tetrahydro-1,4-epiazano-naphthalen-6-yl)-$N^4$-(3-methanesulfonyl-benzyl)-5-trifluoromethyl-pyrimidine-2,4-diamine | 422.47 | 83 | 96 | 2.41 | G |
| 372 | (+/−)-4-[2-(9-Ethyl-1,2,3,4-tetrahydro-1,4-epiazano-naphthalen-6-ylamino)-5-trifluoromethyl-pyrimidin-4-ylamino]-cyclohexanol | 461.47 | 95 | 98 | 2.12 | G |
| 373 | (+/−)-4-[2-(9-Methanesulfonyl-1,2,3,4-tetrahydro-1,4-epiazano-naphthalen-6-ylamino)-5-trifluoromethyl-pyrimidin-4-ylamino]-cyclohexanol | 449.33 | 96 | 95 | 2.26 | G |
| 374 | (+/−)-1-{6-[4-(3-Methanesulfonyl-benzylamino)-5-trifluoromethyl-pyrimidin-2-ylamino]-1,2,3,4-tetrahydro-1,4-epiazano-naphthalen-9-yl}-ethanone | 456.38 | 84 | 97 | 2.22 | G |
| 375 | (+/−)-1-{6-[4-(4-Hydroxy-cyclohexylamino)-5-trifluoromethyl-pyrimidin-2-ylamino]-1,2,3,4-tetrahydro-1,4-epiazano-naphthalen-9-yl}-ethanone | 416.46 | 82 | 98 | 2.46 | G |
| 376 | (+/−)-6-[4-(4-Hydroxy-cyclohexylamino)-5-trifluoromethyl-pyrimidin-2-ylamino]-1,2,3,4-tetrahydro-1,4-epiazano-naphthalene-9-carboxylic acid ethylamide | 568.35 | 95 | 100 | 2.92 | G |
| 377 | (+/−)-6-[4-(3-Methanesulfonyl-benzylamino)-5-trifluoromethyl-pyrimidin-2-ylamino]-1,2,3,4-tetrahydro-1,4-epiazano-naphthalene-9-carboxylic acid methyl ester | 597.38 | 94 | 92 | 3.06 | G |
| 378 | (+/−)-6-[4-(4-Hydroxy-cyclohexylamino)-5-trifluoromethyl-pyrimidin-2-ylamino]-1,2,3,4-tetrahydro-1,4-epiazano-naphthalene-9-carboxylic acid methyl ester | 598.37 | 100 | 100 | 2.99 | G |
| 379 | (+/−)-$N^2$-(9-Ethyl-1,2,3,4-tetrahydro-1,4-epiazano-naphthalen-6-yl)-$N^4$-(2-methoxy-1-methyl-ethyl)-5-trifluoromethyl-pyrimidine-2,4-diamine | 611.44 | 81 | 100 | 3.28 | G |
| 380 | (+/−)-N-(3-{[2-(9-Methanesulfonyl-1,2,3,4-tetrahydro-1,4-epiazano-naphthalen-6-ylamino)-5-trifluoromethyl-pyrimidin-4-ylamino]-methyl}-phenyl)-N-methyl-methanesulfonamide | 599.37 | 100 | 100 | 3.04 | G |
| 381 | (+/−)-$N^2$-(9-Methanesulfonyl-1,2,3,4-tetrahydro-1,4-epiazano-naphthalen-6-yl)-$N^4$-(2-methoxy-1-methyl-ethyl)-5-trifluoromethyl-pyrimidine-2,4-diamine | 615.40 | 89 | 100 | 3.16 | G |
| 382 | (+/−)-N-(3-{[2-(9-Acetyl-1,2,3,4-tetrahydro-1,4-epiazano-naphthalen-6-ylamino)-5-trifluoromethyl-pyrimidin-4-ylamino]-methyl}-phenyl)-N-methyl-methanesulfonamide | 458.36 | 100 | 100 | 2.80 | G |

TABLE 4-continued

Examples 363-417.

| Ex. | Compound | MS | Purity (HPLC), % | Purity (ELSD), % | Ret. Time (min.) | HPLC Method |
|---|---|---|---|---|---|---|
| 383 | (+/−)-1-{6-[4-(2-Methoxy-1-methyl-ethylamino)-5-trifluoromethyl-pyrimidin-2-ylamino]-1,2,3,4-tetrahydro-1,4-epiazano-naphthalen-9-yl}-ethanone | 498.36 | 96 | 97 | 2.72 | G |
| 384 | (+/−)-6-{4-[3-(Methanesulfonyl-methyl-amino)-benzylamino]-5-trifluoromethyl-pyrimidin-2-ylamino}-1,2,3,4-tetrahydro-1,4-epiazano-naphthalene-9-carboxylic acid ethylamide | 472.35 | 100 | 100 | 2.98 | G |
| 385 | (+/−)-6-[4-(2-Methoxy-1-methyl-ethylamino)-5-trifluoromethyl-pyrimidin-2-ylamino]-1,2,3,4-tetrahydro-1,4-epiazano-naphthalene-9-carboxylic acid methyl ester | 499.40 | 71 | 74 | 2.68 | G |
| 386 | (+/−)-N-(3-{[2-(9-Ethyl-1,2,3,4-tetrahydro-1,4-epiazano-naphthalene-6-ylamino)-5-trifluoromethyl-pyrimidin-4-ylamino]-methyl}-pyridin-2-yl)-N-methyl-methanesulfonamide | 506.33 | 100 | 100 | 2.66 | G |
| 387 | (+/−)-$N^4$-(1-Ethyl-pyrrolidin-2-ylmethyl)-$N^2$-(9-ethyl-1,2,3,4-tetrahydro-1,4-epiazano-naphthalen-6-yl)-5-trifluoromethyl-pyrimidine-2,4-diamine | 466.34 | 100 | 100 | 3.10 | G |
| 388 | (+/−)-N-(3-{[2-(9-Methanesulfonyl-1,2,3,4-tetrahydro-1,4-epiazano-naphthalen-6-ylamino)-5-trifluoromethyl-pyrimidin-4-ylamino]-methyl}-pyridin-2-yl)-N-methyl-methanesulfonamide | 576.44 | 100 | 100 | 2.86 | G |
| 389 | (+/−)-$N^4$-(1-Ethyl-pyrrolidin-2-ylmethyl)-$N^2$-(9-methanesulfonyl-1,2,3,4-tetrahydro-1,4-epiazano-naphthalen-6-yl)-5-trifluoromethyl-pyrimidine-2,4-diamine | 532.39 | 91 | 97 | 2.70 | G |
| 390 | (+/−)-N-(3-{[2-(9-Acetyl-1,2,3,4-tetrahydro-1,4-epiazano-naphthalen-6-ylamino)-5-trifluoromethyl-pyrimidin-4-ylamino]-methyl}-pyridin-2-yl)-N-methyl-methanesulfonamide | 561.42 | 94 | 97 | 2.83 | G |
| 391 | (+/−)-1-(6-{4-[(1-Ethyl-pyrrolidin-2-ylmethyl)-amino]-5-trifluoromethyl-pyrimidin-2-ylamino}-1,2,3,4-tetrahydro-1,4-epiazano-naphthalen-9-yl)-ethanone | 562.41 | 92 | 100 | 2.74 | G |
| 392 | (+/−)-6-(4-{[2-(Methanesulfonyl-methyl-amino)-pyridin-3-ylmethyl]-amino}-5-trifluoromethyl-pyrimidin-2-ylamino)-1,2,3,4-tetrahydro-1,4-epiazano-naphthalene-9-carboxylic acid ethylamide | 575.20 | 100 | 100 | 2.99 | G |
| 393 | (+/−)-6-(4-{[2-(Methanesulfonyl-methyl-amino)-pyridin-3-ylmethyl]-amino}-5-trifluoromethyl-pyrimidin-2-ylamino)-1,2,3,4-tetrahydro-1,4-epiazano-naphthalene-9-carboxylic acid methyl ester | 563.40 | 95 | 97 | 2.78 | G |
| 394 | (+/−)-N-(2-{[2-(9-Ethyl-1,2,3,4-tetrahydro-1,4-epiazano-naphthalen-6-ylamino)-5-trifluoromethyl-pyrimidin-4-ylamino]-methyl}-5-methyl-phenyl)-N-methyl-methanesulfonamide | 422.40 | 97 | 100 | 2.58 | G |
| 395 | (+/−)-N-(2-{[2-(9-Acetyl-1,2,3,4-tetrahydro-1,4-epiazano-naphthalen-6-ylamino)-5-trifluoromethyl-pyrimidin-4-ylamino]-methyl}-5-methyl-phenyl)-N-methyl-methanesulfonamide | 449.39 | 96 | 95 | 2.42 | G |
| 396 | (+/−)-6-{4-[2-(Methanesulfonyl-methyl-amino)-4-methyl-benzylamino]-5-trifluoromethyl-pyrimidin-2-ylamino}-1,2,3,4-tetrahydro-1,4-epiazano-naphthalene-9-carboxylic acid ethylamide | 470.37 | 100 | 100 | 2.46 | G |
| 397 | (+/−)-N-(2-{[2-(9-Ethyl-1,2,3,4-tetrahydro-1,4-epiazano-naphthalen-6-ylamino)-5-trifluoromethyl-pyrimidin-4-ylamino]-methyl}-3-methyl-phenyl)-N-methyl-methanesulfonamide | 590.12 | 73 | 84 | 2.90 | G |
| 398 | (+/−)-2-{[2-(9-Ethyl-1,2,3,4-tetrahydro-1,4-epiazano-naphthalen-6-ylamino)-5-trifluoromethyl-pyrimidin-4-yl]-methyl-amino}-N,N-dimethyl-acetamide | 591.44 | 79 | 79 | 2.79 | G |
| 399 | (+/−)-N-(2-{[2-(9-Methanesulfonyl-1,2,3,4-tetrahydro-1,4-epiazano-naphthalen-6-ylamino)-5-trifluoromethyl-pyrimidin-4-ylamino]-methyl}-3-methyl-phenyl)-N-methyl-methanesulfonamide | 604.51 | 85 | 90 | 3.07 | G |
| 400 | (+/−)-N-(2-{[2-(9-Acetyl-1,2,3,4-tetrahydro-1,4-epiazano-naphthalen-6-ylamino)-5-trifluoromethyl-pyrimidin-4-ylamino]-methyl}-3-methyl-phenyl)-N-methyl-methanesulfonamide | 592.43 | 92 | 97 | 2.88 | G |
| 401 | (+/−)-6-{4-[2-(Methanesulfonyl-methyl-amino)-6-methyl-benzylamino]-5-trifluoromethyl-pyrimidin-2-ylamino}-1,2,3,4-tetrahydro-1,4-epiazano-naphthalene-9-carboxylic acid methyl ester | 465.42 | 42 | 42 | 2.67 | G |
| 402 | (+/−)-N-(3-{[2-(9-Ethyl-1,2,3,4-tetrahydro-1,4-epiazano-naphthalen-6-ylamino)-5-trifluoromethyl-pyrimidin-4-ylamino]-methyl}-pyrazin-2-yl)-N-methyl-methanesulfonamide | 478.44 | 29 | 31 | 2.49 | G |
| 403 | (+/−)-$N^2$-(9-Ethyl-1,2,3,4-tetrahydro-1,4-epiazano-naphthalen-6-yl)-$N^4$-(2-methanesulfonyl-ethyl)-5-trifluoromethyl-pyrimidine-2,4-diamine | 492.43 | 44 | 36 | 2.54 | G |
| 404 | (+/−)-N-(3-{[2-(9-Methanesulfonyl-1,2,3,4-tetrahydro-1,4-epiazano-naphthalen-6-ylamino)-5-trifluoromethyl-pyrimidin-4-ylamino]-methyl}-pyrazin-2-yl)-N-methyl-methanesulfonamide | 499.40 | 47 | 36 | 2.53 | G |
| 405 | (+/−)-$N^4$-(2-Methanesulfonyl-ethyl)-$N^2$-(9-methanesulfonyl-1,2,3,4-tetrahydro-1,4-epiazano-naphthalen-6-yl)-5-trifluoromethyl-pyrimidine-2,4-diamine | 459.42 | 80 | 84 | 2.94 | G |
| 406 | (+/−)-N-(3-{[2-(9-Acetyl-1,2,3,4-tetrahydro-1,4-epiazano-naphthalen-6-ylamino)-5-trifluoromethyl-pyrimidin-4-ylamino]-methyl}-pyrazin-2-yl)-N-methyl-methanesulfonamide | 592.43 | 88 | 100 | 3.22 | G |
| 407 | (+/−)-1-{6-[4-(2-Methanesulfonyl-ethylamino)-5-trifluoromethyl-pyrimidin-2-ylamino]-1,2,3,4-tetrahydro-1,4-epiazano-naphthalen-9-yl}-ethanone | 548.38 | 97 | 100 | 3.04 | G |

TABLE 4-continued

Examples 363-417.

| Ex. | Compound | MS | Purity (HPLC), % | Purity (ELSD), % | Ret. Time (min.) | HPLC Method |
|---|---|---|---|---|---|---|
| 408 | (+/−)-6-(4-{[3-(Methanesulfonyl-methyl-amino)-pyrazin-2-ylmethyl]-amino}-5-trifluoromethyl-pyrimidin-2-ylamino)-1,2,3,4-tetrahydro-1,4-epiazano-naphthalene-9-carboxylic acid ethylamide | 577.44 | 90 | 100 | 3.17 | G |
| 409 | (+/−)-6-(4-{[3-(Methanesulfonyl-methyl-amino)-pyrazin-2-ylmethyl]-amino}-5-trifluoromethyl-pyrimidin-2-ylamino)-1,2,3,4-tetrahydro-1,4-epiazano-naphthalene-9-carboxylic acid methyl ester | 591.44 | 88 | 100 | 3.33 | G |
| 410 | (+/−)-6-[4-(2-Methanesulfonyl-ethylamino)-5-trifluoromethyl-pyrimidin-2-ylamino]-1,2,3,4-tetrahydro-1,4-epiazano-naphthalene-9-carboxylic acid methyl ester | 591.44 | 87 | 100 | 3.39 | G |
| 411 | (+/−)-N-(3-{[2-(9-Ethyl-1,2,3,4-tetrahydro-1,4-epiazano-naphthalen-6-ylamino)-5-trifluoromethyl-pyrimidin-4-ylamino]-methyl}-4-fluoro-phenyl)-N-methyl-methanesulfonamide | 579.15 | 100 | 100 | 3.12 | G |
| 412 | (+/−)-$N^4$-Bicyclo[1.1.1]pent-1-yl-$N^2$-(9-ethyl-1,2,3,4-tetrahydro-1,4-epiazano-naphthalen-6-yl)-5-trifluoromethyl-pyrimidine-2,4-diamine | 595.40 | 96 | 100 | 3.25 | G |
| 413 | (+/−)-N-(4-Fluoro-3-{[2-(9-methanesulfonyl-1,2,3,4-tetrahydro-1,4-epiazano-naphthalen-6-ylamino)-5-trifluoromethyl-pyrimidin-4-ylamino]-methyl}-phenyl)-N-methyl-methanesulfonamide | 438.40 | 100 | 100 | 2.95 | G |
| 414 | (+/−)-$N^4$-Bicyclo[1.1.1]pent-1-yl-$N^2$-(9-methanesulfonyl-1,2,3,4-tetrahydro-1,4-epiazano-naphthalen-6-yl)-5-trifluoromethyl-pyrimidine-2,4-diamine | 478.42 | 96 | 98 | 2.84 | G |
| 415 | (+/−)-6-{4-[2-Fluoro-5-(methanesulfonyl-methyl-amino)-benzylamino]-5-trifluoromethyl-pyrimidin-2-ylamino}-1,2,3,4-tetrahydro-1,4-epiazano-naphthalene-9-carboxylic acid ethylamide | 465.41 | 96 | 100 | 2.73 | G |
| 416 | (+/−)-6-{4-[2-Fluoro-5-(methanesulfonyl-methyl-amino)-benzylamino]-5-trifluoromethyl-pyrimidin-2-ylamino}-1,2,3,4-tetrahydro-1,4-epiazano-naphthalene-9-carboxylic acid methyl ester | 486.33 | 100 | 100 | 2.80 | G |
| 417 | (+/−)-6-[4-(Bicyclo[1.1.1]pent-1-ylamino)-5-trifluoromethyl-pyrimidin-2-ylamino]-1,2,3,4-tetrahydro-1,4-epiazano-naphthalene-9-carboxylic acid methyl ester | 446.41 | 100 | 100 | 3.25 | G |

TABLE 5

Examples 419-482.

| Ex. | IUPAC Name | MS | Retention Time (min) | HPLC Method |
|---|---|---|---|---|
| 419 | (+/−)-$N^4$-cyclobutyl-6,7-dimethoxy-$N^2$-[9-(methylsulfonyl)-1,2,3,4-tetrahydro-1,4-epiazano-naphthalen-6-yl]quinazoline-2,4-diamine | 496.06 | 2.86 | A |
| 420 | (+/−)-$N^4$-cyclobutyl-$N^2$-[9-(methylsulfonyl)-1,2,3,4-tetrahydro-1,4-epiazano-naphthalen-6-yl]quinazoline-2,4-diamine | 436.00 | 2.97 | A |
| 421 | (+/−)-$N^4$-cyclobutyl-6,7-difluoro-$N^2$-[9-(methylsufonyl)-1,2,3,4-tetrahydro-1,4-epiazano-naphthalen-6-yl]quinazoline-2,4-diamine | 472.03 | 3.28 | A |
| 422 | (+/−)-$N^4$-cyclobutyl-7,8-dimethoxy-$N^2$-[9-(methylsulfonyl)-1,2,3,4-tetrahydro-1,4-epiazano-naphthalen-6-yl]quinazoline-2,4-diamine | 496.04 | 2.95 | A |
| 423 | (+/−)-$N^4$-cyclobutyl-5-methyl-N2-[9-(methylsulfonyl)-1,2,3,4-tetrahydro-1,4-epiazano-naphthalen-6-yl]pyrimidine-2,4-diamine | 400.03 | 2.73 | A |
| 424 | (+/−)-$N^4$-cyclobutyl-$N^2$-[9-(methylsulfonyl)-1,2,3,4-tetrahydro-1,4-epiazano-naphthalen-6-yl]-6,7-dihydrothieno[3,2-d]pyrimidine-2,4-diamine | 444.12 | 2.87 | A |
| 425 | (+/−)-$N^4$-cyclobutyl-5,6-dimethyl-$N^2$-[9-(methylsulfonyl)-1,2,3,4-tetrahydro-1,4-epiazano-naphthalen-6-yl]pyrimidine-2,4-diamine | 413.95 | 2.88 | A |
| 426 | (+/−)-$N^4$-cyclobutyl-$N^2$-[9-(methylsulfonyl)-1,2,3,4-tetrahydro-1,4-epiazano-naphthalen-6-yl]-6,7-dihydro-5H-cyclopenta[d]pyrimidine-2,4-diamine | 425.98 | 2.89 | A |
| 427 | (+/−)-$N^4$-cyclobutyl-$N^2$-[9-(methylsulfonyl)-1,2,3,4-tetrahydro-1,4-epiazano-naphthalen-6-yl]-5,6,7,8-tetrahydroquinazoline-2,4-diamine | 440.04 | 3.13 | A |
| 428 | (+/−)-$N^4$-cyclobutyl-5-ethyl-$N^2$-[9-(methylsulfonyl)-1,2,3,4-tetrahydro-1,4-epiazano-naphthalen-6-yl]pyrimidine-2,4-diamine | 414.00 | 2.92 | A |
| 429 | (+/−)-5-chloro-$N^4$-cyclobutyl-$N^2$-[9-(methylsulfonyl)-1,2,3,4-tetrahydro-1,4-epiazano-naphthalen-6-yl]pyrimidine-2,4-diamine | 419.99 | 3.00 | A |
| 430 | (+/−)-$N^4$-cyclobutyl-$N^2$-[9-(methylsulfonyl)-1,2,3,4-tetrahydro-1,4-epiazano-naphthalen-6-yl]pyrimidine-2,4-diamine | 386.02 | 2.56 | A |
| 431 | (+/−)-$N^2$-[9-acetyl-1,2,3,4-tetrahydro-1,4-epiazano-naphthalen-6-yl]-$N^4$-cyclopropyl-5-fluoropyrimidine-2,4-diamine | 354.21 | 1.84 | B |
| 432 | (+/−)-$N^2$-[9-acetyl-1,2,3,4-tetrahydro-1,4-epiazano-naphthalen-6-yl]-$N^4$-cyclopropyl-5-methylpyrimidine-2,4-diamine | 350.27 | 1.96 | B |
| 433 | (+/−)-$N^2$-[9-acetyl-1,2,3,4-tetrahydro-1,4-epiazano-naphthalen-6-yl]-$N^4$-cyclopropyl-5-ethylpyrimidine-2,4-diamine | 364.22 | 2.14 | B |
| 434 | (+/−)-$N^2$-[9-acetyl-1,2,3,4-tetrahydro-1,4-epiazano-naphthalen-6-yl]-$N^4$-cyclobutylpyrimidine-2,4-diamine | 350.22 | 2.06 | B |

TABLE 5-continued

Examples 419-482.

| Ex. | IUPAC Name | MS | Retention Time (min) | HPLC Method |
|-----|------------|-----|----------------------|-------------|
| 435 | (+/−)-N$^2$-[9-acetyl-1,2,3,4-tetrahydro-1,4-epiazano-naphthalen-6-yl]-N$^4$-cyclobutyl-5-fluoropyrimidine-2,4-diamine | 368.23 | 2.04 | B |
| 436 | (+/−)-N$^2$-[9-acetyl-1,2,3,4-tetrahydro-1,4-epiazano-naphthalen-6-yl]-N$^4$-cyclobutyl-5-methylpyrimidine-2,4-diamine | 364.22 | 2.17 | B |
| 437 | (+/−)-N$^2$-[9-acetyl-1,2,3,4-tetrahydro-1,4-epiazano-naphthalen-6-yl]-N$^4$-cyclobutyl-5-ethylpyrimidine-2,4-diamine | 378.27 | 2.35 | B |
| 438 | (+/−)-N$^2$-[9-acetyl-1,2,3,4-tetrahydro-1,4-epiazano-naphthalen-6-yl]-N$^4$-cyclopentylpyrimidine-2,4-diamine | 364.24 | 2.23 | B |
| 439 | (+/−)-N$^2$-[9-acetyl-1,2,3,4-tetrahydro-1,4-epiazano-naphthalen-6-yl]-N$^4$-cyclopentyl-5-fluoropyrimidine-2,4-diamine | 382.24 | 2.19 | B |
| 440 | (+/−)-N$^2$-[9-acetyl-1,2,3,4-tetrahydro-1,4-epiazano-naphthalen-6-yl]-N$^4$-cyclopentyl-5-methylpyrimidine-2,4-diamine | 378.25 | 2.35 | B |
| 441 | (+/−)-N$^2$-[9-acetyl-1,2,3,4-tetrahydro-1,4-epiazano-naphthalen-6-yl]-N$^4$-cyclopentyl-5-ethylpyrimidine-2,4-diamine | 392.3 | 2.54 | B |
| 442 | (+/−)-N$^2$-[9-acetyl-1,2,3,4-tetrahydro-1,4-epiazano-naphthalen-6-yl]-N$^4$-isopropylpyrimidine-2,4-diamine | 338.24 | 1.96 | B |
| 443 | (+/−)-N$^2$-[9-acetyl-1,2,3,4-tetrahydro-1,4-epiazano-naphthalen-6-yl]-5-fluoro-N$^4$-isopropylpyrimidine-2,4-diamine | 356.24 | 1.93 | B |
| 444 | (+/−)-N$^2$-[9-acetyl-1,2,3,4-tetrahydro-1,4-epiazano-naphthalen-6-yl]-N$^4$-isopropyl-5-methylpyrimidine-2,4-diamine | 352.25 | 2.08 | B |
| 445 | (+/−)-N$^2$-[9-acetyl-1,2,3,4-tetrahydro-1,4-epiazano-naphthalen-6-yl]-5-ethyl-N$^4$-isopropylpyrimidine-2,4-diamine | 366.26 | 2.25 | B |
| 446 | (+/−)-trans-4-[(2-{[9-acetyl-1,2,3,4-tetrahydro-1,4-epiazano-naphthalen-6-yl]amino}-5-fluoropyrimidin-4-yl)amino]cyclohexanol | 412.25 | 1.58 | B |
| 447 | (+/−)-trans-4-[(2-{[9-acetyl-1,2,3,4-tetrahydro-1,4-epiazano-naphthalen-6-yl]amino}-5-methylpyrimidin-4-yl)amino]cyclohexanol | 408.29 | 1.70 | B |
| 448 | (+/−)-trans-4-[(2-{[9-acetyl-1,2,3,4-tetrahydro-1,4-epiazano-naphthalen-6-yl]amino}-5-ethylpyrimidin-4-yl)amino]cyclohexanol | 422.29 | 1.86 | B |
| 449 | (+/−)-N$^2$-[9-acetyl-1,2,3,4-tetrahydro-1,4-epiazano-naphthalen-6-yl]-N$^4$-(cyclopropylmethyl)pyrimidine-2,4-diamine | 350.23 | 2.04 | B |
| 450 | (+/−)-N$^2$-[9-acetyl-1,2,3,4-tetrahydro-1,4-epiazano-naphthalen-6-yl]-N$^4$-(cyclopropylmethyl)-5-methylpyrimidine-2,4-diamine | 364.23 | 2.14 | B |
| 451 | (+/−)-N$^2$-[9-acetyl-1,2,3,4-tetrahydro-1,4-epiazano-naphthalen-6-yl]-5-chloro-N$^4$-cyclobutylpyrimidine-2,4-diamine | 384.15 | 2.17 | B |
| 452 | (+/−)-N$^2$-[9-acetyl-1,2,3,4-tetrahydro-1,4-epiazano-naphthalen-6-yl]-5-chloro-N$^4$-cyclopentylpyrimidine-2,4-diamine | 398.22 | 2.36 | B |
| 453 | (+/−)-N$^2$-[9-acetyl-1,2,3,4-tetrahydro-1,4-epiazano-naphthalen-6-yl]-5-chloro-N$^4$-isopropylpyrimidine-2,4-diamine | 372.18 | 2.07 | B |
| 454 | (+/−)-trans-4-[(2-{[9-acetyl-1,2,3,4-tetrahydro-1,4-epiazano-naphthalen-6-yl]amino}-5-chloropyrimidin-4-yl)amino]cyclohexanol | 428.22 | 1.70 | B |
| 455 | (+/−)-N$^2$-[9-acetyl-1,2,3,4-tetrahydro-1,4-epiazano-naphthalen-6-yl]-5-chloro-N$^4$-(cyclopropylmethyl)pyrimidine-2,4-diamine | 384.22 | 2.14 | B |
| 456 | (+/−)-N$^2$-[9-acetyl-1,2,3,4-tetrahydro-1,4-epiazano-naphthalen-6-yl]-N$^4$-[3-(3,5-dimethyl-1H-pyrazol-1-yl)propyl]-5-fluoropyrimidine-2,4-diamine | 450.28 | 2.91 | C |
| 457 | (+/−)-{1-[(2-{[9-acetyl-1,2,3,4-tetrahydro-1,4-epiazano-naphthalen-6-yl]amino}-5-fluoropyrimidin-4-yl)amino]cyclopentyl}methanol | 412.24 | 2.77 | C |
| 458 | (+/−)-N$^2$-[9-acetyl-1,2,3,4-tetrahydro-1,4-epiazano-naphthalen-6-yl]-5-fluoro-N$^4$-[2-(5-methyl-4H-1,2,4-triazol-3-yl)ethyl]pyrimidine-2,4-diamine | 423.25 | 2.07 | C |
| 459 | (+/−)-N$^2$-[9-acetyl-1,2,3,4-tetrahydro-1,4-epiazano-naphthalen-6-yl]-5-fluoro-N$^4$-(2-methoxy-1-methylethyl)pyrimidine-2,4-diamine | 386.25 | 2.79 | C |
| 460 | (+/−)-9-acetyl-N-{5-fluoro-4-[(2S)-2-(methoxymethyl)pyrrolidin-1-yl]pyrimidin-2-yl}-1,2,3,4-tetrahydro-1,4-epiazano-naphthalen-6-amine | 412.24 | 3.28 | C |
| 461 | (+/−)-9-acetyl-N-{4-[(3aS,6aR)-1,1-dioxidohexahydro-5H-pyrrolo[3,4-d]isothiazol-5-yl]-5-fluoropyrimidin-2-yl}-1,2,3,4-tetrahydro-1,4-epiazano-naphthalen-6-amine | 459.19 | 2.50 | C |
| 462 | (+/−)-N$^2$-[9-acetyl-1,2,3,4-tetrahydro-1,4-epiazano-naphthalen-6-yl]-5-fluoro-N$^4$-[(1S)-2-methoxy-1-methylethyl]pyrimidine-2,4-diamine | 386.25 | 2.80 | C |
| 463 | (+/−)-N$^2$-[9-acetyl-1,2,3,4-tetrahydro-1,4-epiazano-naphthalen-6-yl]-5-fluoro-N$^4$-{3-[methyl(phenyl)amino]propyl}pyrimidine-2,4-diamine | 461.28 | 3.64 | C |
| 464 | (+/−)-9-acetyl-N-{5-fluoro-4-[3-(methylsulfonyl)pyrrolidin-1-yl]pyrimidin-2-yl}-1,2,3,4-tetrahydro-1,4-epiazano-naphthalen-6-amine | 446.18 | 2.55 | C |
| 465 | (+/−)-N$^2$-[9-acetyl-1,2,3,4-tetrahydro-1,4-epiazano-naphthalen-6-yl]-N$^4$-cyclohexyl-N4-[2-(dimethylamino)ethyl]-5-fluoropyrimidine-2,4-diamine | 467.33 | 3.65 | C |
| 466 | (+/−)-N$^2$-[9-acetyl-1,2,3,4-tetrahydro-1,4-epiazano-naphthalen-6-yl]-5-fluoro-N$^4$-[(1R,2S)-2-(methoxymethyl)cyclopentyl]pyrimidine-2,4-diamine | 426.25 | 3.37 | C |
| 467 | (+/−)-N$^2$-[9-acetyl-1,2,3,4-tetrahydro-1,4-epiazano-naphthalen-6-yl]-N$^4$-bicyclo[1.1.1]pent-1-yl-5-fluoropyrimidine-2,4-diamine | 380.2 | 3.20 | C |
| 468 | (+/−)-N$^2$-[9-acetyl-1,2,3,4-tetrahydro-1,4-epiazano-naphthalen-6-yl]-5-fluoro-N$^4$-[1-(2,2,2-trifluoroethyl)piperidin-4-yl]pyrimidine-2,4-diamine | 479.24 | 3.32 | C |
| 469 | (+/−)-(3S)-1-(2-{[9-acetyl-1,2,3,4-tetrahydro-1,4-epiazano-naphthalen-6-yl]amino}-5-fluoropyrimidin-4-yl)piperidine-3-carboxamide | 425.23 | 2.45 | C |
| 470 | (+/−)-N$^2$-[9-acetyl-1,2,3,4-tetrahydro-1,4-epiazano-naphthalen-6-yl]-5-chloro-N$^4$-[3-(3,5-dimethyl-1H-pyrazol-1-yl)propyl]pyrimidine-2,4-diamine | 466.24 | 3.12 | C |

TABLE 5-continued

Examples 419-482.

| Ex. | IUPAC Name | MS | Retention Time (min) | HPLC Method |
|---|---|---|---|---|
| 471 | (+/−)-N$^2$-[9-acetyl-1,2,3,4-tetrahydro-1,4-epiazano-naphthalen-6-yl]-N$^4$-[(3R)-1-benzylpyrrolidin-3-yl]-5-chloropyrimidine-2,4-diamine | 489.24 | 3.58 | C |
| 472 | (+/−)-N$^2$-[9-acetyl-1,2,3,4,-tetrahydro-1,4-epiazano-naphthalen-6-yl]-5-chloro-N$^2$-[2-(5-methyl-4H-1,2,4-triazol-3-yl)ethyl]pyrimidine-2,4-diamine | 439.21 | 2.27 | C |
| 473 | (+/−)-N$^2$-[9-acetyl-1,2,3,4-tetrahydro-1,4-epiazano-naphthalen-6-yl]-5-chloro-N$^4$-(2-methoxy-1-methylethyl)pyrimidine-2,4-diamine | 402.19 | 3.12 | C |
| 474 | (+/−)-9-acetyl-N-{5-chloro-4-[(2S)-2-(methoxymethyl)pyrrolidin-1-yl]pyrimidin-2-yl}-1,2,3,4-tetrahydro-1,4-epiazano-naphthalen-6-amine | 428.22 | 3.52 | C |
| 475 | (+/−)-9-acetyl-N-{5-chloro-4-[(3aS,6aR)-1,1-dioxidohexahydro-5H-pyrrolo[3,4-d]isothiazol-5-yl]pyrimidin-2-yl}-1,2,3,4-tetrahydro-1,4-epiazano-naphthalen-6-amine | 475.16 | 2.70 | C |
| 476 | (+/−)-N$^2$-[9-acetyl-1,2,3,4-tetrahydro-1,4-epiazano-naphthalen-6-yl]-5-chloro-N$^4$-[(1S)-2-methoxy-1-methylethyl]pyrimidine-2,4-diamine | 402.18 | 3.11 | C |
| 477 | (+/−)-N$^2$-[9-acetyl-1,2,3,4-tetrahydro-1,4-epiazano-naphthalen-6-yl]-5-chloro-N$^4$-{3-[methyl(phenyl)amino]propyl}pyrimidine-2,4-diamine | 477.25 | 3.86 | C |
| 478 | (+/−)-9-acetyl-N-{5-chloro-4-[3-(methylsulfonyl)pyrrolidin-1-yl]pyrimidin-2-yl}-1,2,3,4-tetrahydro-1,4-epiazano-naphthalen-6-amine | 462.17 | 2.76 | C |
| 479 | (+/−)-N$^2$-[9-acetyl-1,2,3,4-tetrahydro-1,4-epiazano-naphthalen-6-yl]-5-chloro-N$^4$-[(1R,2S)-2-(methoxymethyl)cyclopentyl]pyrimidine-2,4-diamine | 442.23 | 3.76 | C |
| 480 | (+/−)-N$^2$-[9-acetyl-1,2,3,4-tetrahydro-1,4-epiazano-naphthalen-6-yl]-N$^4$-bicyclo[1.1.1]pent-1-yl-5-chloropyrimidine-2,4-diamine | 396.19 | 3.45 | C |
| 481 | (+/−)-N$^2$-[9-acetyl-1,2,3,4-tetrahydro-1,4-epiazano-naphthalen-6-yl]-5-chloro-N$^4$-[1-(2,2,2-trifluoroethyl)piperidin-4-yl]pyrimidine-2,4-diamine | 495.22 | 3.58 | C |
| 482 | (+/−)-(3S)-1-(2-{[9-acetyl-1,2,3,4-tetrahydro-1,4-epiazano-naphthalen-6-yl]amino}-5-chloropyrimidin-4-yl)piperidine-3-carboxamide | 441.21 | 2.67 | C |

TABLE 6

Examples 483-490.

| Ex. | IUPAC Name | MS | Retention Time (min) | HPLC Method |
|---|---|---|---|---|
| 483 | (+/−)-9-acetyl-N-[4-(3-{[(2S)-2-(methoxymethyl)pyrrolidin-1-yl]carbonyl}azetidin-1-yl)-5-(trifluoromethyl)pyrimidin-2-yl]-1,2,3,4-tetrahydro-1,4-epiazano-naphthalen-6-amine | 544.241 | 2.00 | D |
| 484 | (+/−)-1-[2-{[9-acetyl-1,2,3,4-tetrahydro-1,4-epiazano-naphthalen-6-yl]amino}-5-(trifluoromethyl)pyrimidin-4-yl]-N-[(1S)-2-methoxy-1-methylethyl]azetidine-3-carboxamide | 518.225 | 1.67 | D |
| 485 | (+/−)-1-[2-{[9-acetyl-1,2,3,4-tetrahydro-1,4-epiazano-naphthalen-6-yl]amino}-5-(trifluoromethyl)pyrimidin-4-yl]-N-(2-methoxyethyl)azetidine-3-carboxamide | 504.21 | 1.74 | D |
| 486 | (+/−)-1-[2-{[9-acetyl-1,2,3,4-tetrahydro-1,4-epiazano-naphthalen-6-yl]-amino}-5-(trifluoromethyl)pyrimidin-4-yl]-N-cyclobutylazetidine-3-carboxamide | 500.215 | 1.99 | D |
| 487 | (+/−)-1-[2-{[9-acetyl-1,2,3,4-tetrahydro-1,4-epiazano-naphthalen-6-yl]amino}-5-(trifluoromethyl)pyrimidin-4-yl]-N-cyclopropylazetidine-3-carboxamide | 486.199 | 1.82 | D |
| 488 | (+/−)-9-acetyl-N-{4-[3-(morpholin-4-ylcarbonyl)azetidin-1-yl]-5-(trifluoromethyl)pyrimidin-2-yl}-1,2,3,4-tetrahydro-1,4-epiazano-naphthalen-6-amine | 516.21 | 2.19 | D |
| 489 | (+/−)-1-[2-{[9-acetyl-1,2,3,4-tetrahydro-1,4-epiazano-naphthalen-6-yl]amino}-5-(trifluoromethyl)pyrimidin-4-yl]-N,N-dimethylazetidine-3-carboxamide | 474.199 | 1.79 | D |
| 490 | (+/−)-1-[2-{[9-acetyl-1,2,3,4-tetrahydro-1,4-epiazano-naphthalen-6-yl]amino}-5-(trifluoromethyl)pyrimidin-4-yl]-N-(cyclopropylmethyl)azetidine-3-carboxamide | 500.215 | 1.97 | D |

What is claimed is:

1. A compound selected from the group consisting of:

1-[6-(4-Cyclobutylamino-5-trifluoromethyl-pyrimidin-2-ylamino)-(1S,4R)-1,2,3,4-tetrahydro-1,4-epiazano-naphthalen-9-yl]-2-hydroxy-ethanone, 2-Amino-1-[6-(4-cyclobutylamino-5-trifluoromethyl-pyrimidin-2-ylamino)-(1S,4R)-1,2,3,4-tetrahydro-1,4-epiazano-naphthalen-9-yl]-ethanone, 1-[6-(5-Chloro-4-cyclobutylamino-pyrimidin-2-ylamino)-(1S,4R)-1,2,3,4-tetrahydro-1,4-epiazano-naphthalen-9-yl]-ethanone, N-{2-[6-(4-Cyclobutylamino-5-trifluoromethyl-pyrimidin-2-ylamino)-(1S,4R)-1,2,3,4-tetrahydro-1,4-epiazano-naphthalen-9-yl]-2-oxo-ethyl}-acetamide, 6-(4-Cyclobutylamino-5-trifluoromethyl-pyrimidin-2-ylamino)-(1S,2R)-1,2,3,4-tetrahydro-1,4-epiazano-naphthalene-9-carboxylic acid ethyl-amide, 1-[6-(4-Cyclobutylamino-5-trifluoromethyl-pyrimidin-2-ylamino)-(1S,4R)-1,2,3,4-tetrahydro-1,4-epiazano-naphthalen-9-yl]-2-methoxy-ethanone,

[6-(4-Cyclobutylamino-5-trifluoromethyl-pyrimidin-2-ylamino)-(1S,4R)-1,2,3,4-tetrahydro-1,4-epiazano-naphthalen-9-yl]-cyclopropyl-methanone, 1-[6-(4-Cyclobutylamino-5-trifluoromethyl-pyrimidin-2-ylamino)-(1S,4R)-1,2,3,4-tetrahydro-1,4-epiazano-naphthalen-9-yl]-ethanone, N4-Cyclobutyl-N2-[(1S,4R)-1,2,3,4-tetrahydro-1,4-epiazano-naphthalen-6-yl]-5-trifluoromethyl-pyrimidine-2,4-diamine, (+/−)-1-[6-(4-Cyclopropylamino-5-trifluoromethyl-pyrimidin-2-ylamino)-1,2,3,4-tetrahydro-1,4-epiazano-naphthalen-9-yl]-ethanone,
1-[6-(4-Cyclopropylamino-5-methyl-pyrimidin-2-ylamino)-(1S,4R)-1,2,3,4-tetrahydro-1,4-epiazano-naphthalen-9-yl]-ethanone,
1-[6-(4-Cyclopropylamino-5-fluoro-pyrimidin-2-ylamino)-(1S,4R)-1,2,3,4-tetrahydro-1,4-epiazano-naphthalen-9-yl]-ethanone,
1-[6-(4-Ethylamino-5-methyl-pyrimidin-2-ylamino)-(1S,4R)-1,2,3,4-tetrahydro-1,4-epiazano-naphthalen-9-yl]-ethanone,
1-[6-(4-Ethylamino-5-fluoro-pyrimidin-2-ylamino)-(1S,4R)-1,2,3,4-tetrahydro-1,4-epiazano-naphthalen-9-yl]-ethanone,
1-[6-(4-ethylamino-5-chloro-pyrimidin-2-ylamino)-(1S,4R)-1,2,3,4-tetrahydro-1,4-epiazano-naphthalen-9-yl]-ethanone,
1-{6-[5-Fluoro-4-((S)-2-methoxymethyl-pyrrolidin-1-yl)-pyrimidin-2-ylamino]-(1S,4R)-1,2,3,4-tetrahydro-1,4-epiazano-naphthalen-9-yl}-ethanone,
N4-Cyclobutyl-N2-[(1R,4S)-1,2,3,4-tetrahydro-1,4-epiazano-naphthalen-6-yl]-5-trifluoromethyl-pyrimidine-2,4-diamine,
1-[6-(4-Cyclobutylamino-5-methyl-pyrimidin-2-ylamino)-(1R,4S)-1,2,3,4-tetrahydro-1,4-epiazano-naphthalen-9-yl]-ethanone,
1-[6-(4-Cyclobutylamino-5-fluoro-pyrimidin-2-ylamino)-(1R,4S)-1,2,3,4-tetrahydro-1,4-epiazano-naphthalen-9-yl]-ethanone,
N-{2-[6-(4-Cyclobutylamino-5-trifluoromethyl-pyrimidin-2-ylamino)-(1R,4S)-1,2,3,4-tetrahydro-1,4-epiazano-naphthalen-9-yl]-2-oxo-ethyl}-acetamide,
[6-(4-Cyclobutylamino-5-trifluoromethyl-pyrimidin-2-ylamino)-(1R,4S)-1,2,3,4-tetrahydro-1,4-epiazano-naphthalen-9-yl]-acetic acid methyl ester,
[6-(4-Cyclobutylamino-5-trifluoromethyl-pyrimidin-2-ylamino)-(1R,4S)-1,2,3,4-tetrahydro-1,4-epiazano-naphthalen-9-yl]-(R)-pyrrolidin-2-yl-methanone,
[6-(4-Cyclobutylamino-5-trifluoromethyl-pyrimidin-2-ylamino)-(1R,4S)-1,2,3,4-tetrahydro-1,4-epiazano-naphthalen-9-yl]-cyclopropyl-methanone,
1-[6-(4-Cyclobutylamino-5-trifluoromethyl-pyrimidin-2-ylamino)-(1R,4S)-1,2,3,4-tetrahydro-1,4-epiazano-naphthalen-9-yl]-2-methoxy-ethanone,
6-(4-Cyclobutylamino-5-trifluoromethyl-pyrimidin-2-ylamino)-(1R,4S)-1,2,3,4-tetrahydro-1,4-epiazano-naphthalene-9-carboxylic acid isopropyl-amide,
1-[6-(4-Cyclobutylamino-5-trifluoromethyl-pyrimidin-2-ylamino)-(1R,4S)-1,2,3,4-tetrahydro-1,4-epiazano-naphthalen-9-yl]-2-methylamino-ethanone,
1-[6-(5-Chloro-4-cyclobutylamino-pyrimidin-2-ylamino)-(1R,4S)-1,2,3,4-tetrahydro-1,4-epiazano-naphthalen-9-yl]-ethanone,
1-[6-(4-Cyclobutylamino-5-fluoro-pyrimidin-2-ylamino)-(1R,4S)-1,2,3,4-tetrahydro-1,4-epiazano-naphthalen-9-yl]-ethanone,
1-[6-(4-Cyclobutylamino-5-ethyl-pyrimidin-2-ylamino)-(1R,4S)-1,2,3,4-tetrahydro-1,4-epiazano-naphthalen-9-yl]-ethanone,
1-[6-(4-Cyclobutylamino-5-methyl-pyrimidin-2-ylamino)-(1R,4S)-1,2,3,4-tetrahydro-1,4-epiazano-naphthalen-9-yl]-ethanone,
N4-Cyclopropyl-N2-(1R,4S)-1,2,3,4-tetrahydro-1,4-epiazano-naphthalen-6-yl-5-trifluoromethyl-pyrimidine-2,4-diamine,
N4-Cyclopropyl-N2-[(1R,4S)-9-methanesulfonyl-1,2,3,4-tetrahydro-1,4-epiazano-naphthalen-6-yl]-5-trifluoromethyl-pyrimidine-2,4-diamine,
1-[6-(4-Cyclopropylamino-5-trifluoromethyl-pyrimidin-2-ylamino)-(1R,4S)-1,2,3,4-tetrahydro-1,4-epiazano-naphthalen-9-yl]-2-methoxy-ethanone,
(+/−)-1-{6-[4-(2-Methoxy-ethylamino)-5-trifluoromethyl-pyrimidin-2-ylamino]-1,2,3,4-tetrahydro-1,4-epiazano-naphthalen-9-yl}-ethanone,
(+/−)-2-[6-(4-Cyclobutylamino-5-trifluoromethyl-pyrimidin-2-ylamino)-1,2,3,4-tetrahydro-1,4-epiazano-naphthalen-9-yl]-N,N-dimethyl-acetamide,
(+/−)-N-{2-[6-(4-Cyclobutylamino-5-trifluoromethyl-pyrimidin-2-ylamino)-1,2,3,4-tetrahydro-1,4-epiazano-naphthalen-9-yl]-2-oxo-ethyl}-acetamide, and pharmaceutically acceptable salts thereof of each of the foregoing compounds.

2. A compound of the following formula

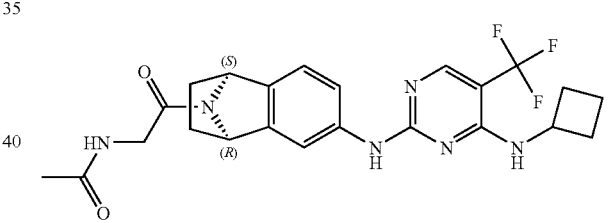

which is N-{2-[6-(4-cyclobutylamino-5-trifluoromethyl-pyrimidin-2-ylamino)-(1S,4R)-1,2,3,4-tetrahydro-1,4-epiazano-naphthalen-9-yl]-2-oxo-ethyl}-acetamide or a pharmaceutically acceptable salt thereof.

3. A pharmaceutical composition comprising a compound or salt according to claim 2, and a pharmaceutically acceptable carrier.

* * * * *